(12) United States Patent
Mulder et al.

(10) Patent No.: US 11,660,319 B2
(45) Date of Patent: May 30, 2023

(54) COMPOSITIONS COMPRISING BACTERIAL STRAINS

(71) Applicant: 4D Pharma Research Limited, Aberdeen (GB)

(72) Inventors: Imke Elisabeth Mulder, Aberdeen (GB); Anna Ettorre, Aberdeen (GB); Suaad Ahmed, Aberdeen (GB); Parthena Fotiadou, Aberdeen (GB); Samantha Yuille, Aberdeen (GB); Joseph Roby Iringan Urcia, Aberdeen (GB); Helene Savignac, Aberdeen (GB)

(73) Assignee: 4D Pharma Research Limited, Aberdeen (GB)

( * ) Notice: Subject to any disclaimer, the term of this patent is extended or adjusted under 35 U.S.C. 154(b) by 0 days.

(21) Appl. No.: 16/713,911

(22) Filed: Dec. 13, 2019

(65) Prior Publication Data
US 2020/0215126 A1 Jul. 9, 2020

Related U.S. Application Data

(63) Continuation of application No. PCT/EP2018/065903, filed on Jun. 14, 2018.

(30) Foreign Application Priority Data

| Jun. 14, 2017 | (GB) | 1709468 |
| Jun. 15, 2017 | (GB) | 1709534 |
| Aug. 10, 2017 | (GB) | 1712851 |
| Mar. 9, 2018 | (GB) | 1803826 |
| Apr. 11, 2018 | (GB) | 1805989 |
| Apr. 11, 2018 | (GB) | 1805990 |
| Apr. 11, 2018 | (GB) | 1805991 |
| Apr. 25, 2018 | (GB) | 1806779 |
| Apr. 25, 2018 | (GB) | 1806780 |

(51) Int. Cl.
| *A01N 63/00* | (2020.01) |
| *A61K 35/74* | (2015.01) |
| *A61K 9/19* | (2006.01) |
| *A61K 9/00* | (2006.01) |
| *C12N 1/20* | (2006.01) |
| *A61K 45/06* | (2006.01) |
| *C12R 1/01* | (2006.01) |

(52) U.S. Cl.
CPC ............ *A61K 35/74* (2013.01); *A61K 9/006* (2013.01); *A61K 9/0019* (2013.01); *A61K 9/0031* (2013.01); *A61K 9/0043* (2013.01); *A61K 9/19* (2013.01); *C12N 1/205* (2021.05); *A61K 45/06* (2013.01); *C12R 2001/01* (2021.05)

(58) Field of Classification Search
CPC .................................................. A61K 35/74
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,138,498 A | 2/1979 | Das |
| 4,275,149 A | 6/1981 | Litman et al. |
| 4,277,437 A | 7/1981 | Maggio |
| 4,366,241 A | 12/1982 | Tom et al. |
| 4,683,202 A | 7/1987 | Mullis |
| 4,816,567 A | 3/1989 | Cabilly et al. |
| 5,589,168 A | 12/1996 | Allen et al. |
| 5,599,795 A | 2/1997 | McCann et al. |
| 5,674,707 A | 10/1997 | Hintz et al. |
| 5,741,665 A | 4/1998 | Kato et al. |
| 5,925,657 A | 7/1999 | Seed et al. |
| 5,951,977 A | 9/1999 | Nisbet et al. |
| 6,348,452 B1 | 2/2002 | Brown et al. |
| 6,468,964 B1 | 10/2002 | Rowe et al. |
| 6,635,260 B1 * | 10/2003 | Gerding .......... G01N 33/56911 424/247.1 |
| 6,645,530 B1 | 11/2003 | Borody |
| 6,652,866 B1 | 11/2003 | Hertha |
| 7,011,826 B1 | 3/2006 | Rowe et al. |
| 7,101,565 B2 | 9/2006 | Monte |
| 7,485,325 B2 | 2/2009 | Swain |
| 7,625,704 B2 | 12/2009 | Fredricks et al. |
| 7,749,494 B2 | 7/2010 | Renaud et al. |
| 7,998,474 B2 | 8/2011 | Kelly |
| 8,197,805 B2 | 6/2012 | Lin et al. |
| 8,287,932 B2 | 10/2012 | Rosales et al. |
| 8,460,648 B2 | 6/2013 | Borody |
| 8,557,233 B2 | 10/2013 | MacSharry et al. |
| 9,011,834 B1 | 4/2015 | McKenzie et al. |
| 9,314,489 B2 | 4/2016 | Kelly et al. |

(Continued)

FOREIGN PATENT DOCUMENTS

| CA | 2768301 A1 | 1/2011 |
| CA | 3016911 A1 | 9/2017 |

(Continued)

OTHER PUBLICATIONS

Jan. 17, 2019 Notice of Allowance for U.S. Appl. No. 15/803,721.
Dec. 21, 2018 Notice of Allowance U.S. Appl. No. 15/700,700.
Jan. 30, 2019 Notice of Corrected Allowability for U.S. Appl. No. 15/803,721.
Jan. 30, 2019 Final Rejection for U.S. Appl. No. 15/842,635.
Feb. 1, 2019 Non-Final Office Action U.S. Appl. No. 16/040,356.
Mar. 4, 2019 Final Office Action for U.S. Appl. No. 15/704,245.
4d Pharma Plc: "Clinical Update—RNS—London Stock Exchange", Jul. 19, 2016.

(Continued)

*Primary Examiner* — Albert M Navarro
(74) *Attorney, Agent, or Firm* — Wilson Sonsini Goodrich & Rosati

(57) ABSTRACT

The invention provides compositions comprising commensal bacterial strains and organic acids and the uses thereof in the treatment of diseases.

19 Claims, 55 Drawing Sheets

Specification includes a Sequence Listing.

(56) References Cited

U.S. PATENT DOCUMENTS

| | | |
|---|---|---|
| 9,371,510 B2 | 6/2016 | Moore |
| 9,376,473 B2 | 6/2016 | Gleiberman et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,839,655 B2 | 12/2017 | Mulder et al. |
| 9,855,302 B2 | 1/2018 | Gajewski et al. |
| 9,937,211 B2 | 4/2018 | Kelly et al. |
| 9,974,815 B2 | 5/2018 | Mulder et al. |
| 9,987,311 B2 | 6/2018 | Mulder et al. |
| 10,046,015 B2 | 8/2018 | Mulder et al. |
| 10,058,574 B2 | 8/2018 | Grant et al. |
| 10,080,772 B2 | 9/2018 | Crouzet et al. |
| 10,086,020 B2 | 10/2018 | Bernalier-Donadille et al. |
| 10,086,021 B2 | 10/2018 | Jeffery et al. |
| 10,086,022 B2 | 10/2018 | Bernalier-Donadille et al. |
| 10,086,023 B2 | 10/2018 | Bernalier-Donadille et al. |
| 10,183,046 B2 | 1/2019 | Kelly |
| 10,226,489 B2 | 3/2019 | Patterson et al. |
| 10,391,130 B2 | 8/2019 | Grant et al. |
| 2003/0147858 A1 | 8/2003 | Renaud et al. |
| 2004/0005304 A1 | 1/2004 | Brudnak |
| 2004/0005348 A1* | 1/2004 | Vincent ............... A23K 10/18 536/123 |
| 2004/0106564 A1 | 6/2004 | Nilius et al. |
| 2004/0120963 A1 | 6/2004 | Ushida et al. |
| 2004/0170617 A1 | 9/2004 | Finegold |
| 2006/0062774 A1 | 3/2006 | Davis et al. |
| 2006/0073161 A1 | 4/2006 | Breton |
| 2006/0115465 A1 | 6/2006 | Macfarlane et al. |
| 2007/0167423 A1 | 7/2007 | Bergauer et al. |
| 2007/0219270 A1 | 9/2007 | Bruggeman |
| 2007/0258953 A1 | 11/2007 | Duncan et al. |
| 2007/0286913 A1 | 12/2007 | Swain et al. |
| 2008/0069861 A1 | 3/2008 | Brown et al. |
| 2008/0206212 A1 | 8/2008 | McMahon et al. |
| 2008/0206380 A1 | 8/2008 | Ushida et al. |
| 2008/0260906 A1 | 10/2008 | Stojanovic |
| 2008/0299098 A1 | 12/2008 | Se et al. |
| 2009/0217401 A1 | 8/2009 | Korman et al. |
| 2010/0028449 A1 | 2/2010 | Prakash et al. |
| 2010/0047209 A1 | 2/2010 | Stanton et al. |
| 2010/0247489 A1 | 9/2010 | Saur-Brosch |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1 | 12/2010 | Renaud et al. |
| 2011/0053829 A1 | 3/2011 | Baumhof et al. |
| 2011/0086011 A1 | 4/2011 | Kasper et al. |
| 2011/0280840 A1 | 11/2011 | Blaser et al. |
| 2012/0020943 A1 | 1/2012 | Lin |
| 2012/0107279 A1 | 5/2012 | Arigoni et al. |
| 2012/0207726 A1* | 8/2012 | Lipkin ..................... A61P 1/00 424/93.41 |
| 2012/0315249 A1* | 12/2012 | Olmstead ............... A61K 45/06 424/93.3 |
| 2013/0022575 A1 | 1/2013 | Cassity |
| 2013/0130988 A1 | 5/2013 | Blareau et al. |
| 2013/0195802 A1 | 8/2013 | Moore |
| 2013/0280724 A1 | 10/2013 | Ramadan et al. |
| 2013/0316032 A1 | 11/2013 | Itoh et al. |
| 2013/0336931 A1 | 12/2013 | Wadstroem et al. |
| 2014/0037716 A1 | 2/2014 | Nowill et al. |
| 2014/0056852 A1 | 2/2014 | Guglielmetti et al. |
| 2014/0112897 A1 | 4/2014 | Pyne et al. |
| 2014/0147425 A1 | 5/2014 | Henn et al. |
| 2014/0154218 A1 | 6/2014 | Kohno et al. |
| 2014/0179770 A1 | 6/2014 | Zhang et al. |
| 2014/0193464 A1 | 7/2014 | Lin et al. |
| 2014/0199281 A1 | 7/2014 | Henn et al. |
| 2014/0227227 A1 | 8/2014 | Qin et al. |
| 2014/0275233 A1 | 9/2014 | Heiman |
| 2014/0328803 A1 | 11/2014 | McKenzie et al. |
| 2014/0335131 A1 | 11/2014 | Mazmanian et al. |
| 2014/0341921 A1 | 11/2014 | Honda et al. |
| 2014/0363397 A1 | 12/2014 | Allen-Vercoe et al. |
| 2015/0044173 A1 | 2/2015 | Jones et al. |
| 2015/0071957 A1 | 3/2015 | Kelly et al. |
| 2015/0104418 A1 | 4/2015 | Flint et al. |
| 2015/0132264 A1 | 5/2015 | Kelly et al. |
| 2015/0284781 A1 | 10/2015 | Klumpp et al. |
| 2016/0058804 A1 | 3/2016 | Jones et al. |
| 2016/0067188 A1 | 3/2016 | Cade et al. |
| 2016/0119425 A1 | 4/2016 | Nagashima |
| 2016/0184370 A1 | 6/2016 | McKenzie et al. |
| 2016/0193258 A1 | 7/2016 | Berry et al. |
| 2016/0199424 A1 | 7/2016 | Berry et al. |
| 2016/0199425 A1 | 7/2016 | Lue |
| 2016/0223553 A1 | 8/2016 | Sears et al. |
| 2016/0235792 A1 | 8/2016 | Berry et al. |
| 2016/0243175 A1 | 8/2016 | Bushman et al. |
| 2016/0271188 A1 | 9/2016 | Berry et al. |
| 2017/0049828 A1 | 2/2017 | Kim et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0319634 A1 | 11/2017 | Grant et al. |
| 2017/0326202 A1 | 11/2017 | Kelly |
| 2017/0354695 A1 | 12/2017 | Grant et al. |
| 2017/0354697 A1 | 12/2017 | Schneider et al. |
| 2017/0360856 A1 | 12/2017 | Grant et al. |
| 2017/0368110 A1 | 12/2017 | Grant et al. |
| 2018/0072778 A1 | 3/2018 | Kelly et al. |
| 2018/0078585 A1 | 3/2018 | Mulder et al. |
| 2018/0078587 A1 | 3/2018 | Crott et al. |
| 2018/0133265 A1 | 5/2018 | Stevenson |
| 2018/0207207 A1 | 7/2018 | Bernalier-Donadille et al. |
| 2018/0207208 A1 | 7/2018 | Jeffery et al. |
| 2018/0214496 A1 | 8/2018 | Bernalier-Donadille |
| 2018/0221421 A1 | 8/2018 | Bernalier-Donadille |
| 2018/0250346 A1 | 9/2018 | Mulder et al. |
| 2018/0271918 A1 | 9/2018 | Kelly et al. |
| 2018/0344780 A1 | 12/2018 | Grant et al. |
| 2018/0369292 A1 | 12/2018 | Bernalier-Donadille et al. |
| 2018/0369293 A1 | 12/2018 | Jeffery et al. |
| 2019/0000892 A1 | 1/2019 | Mulder et al. |
| 2019/0008908 A1 | 1/2019 | Crouzet et al. |
| 2019/0015459 A1 | 1/2019 | Grant et al. |
| 2019/0099458 A1 | 4/2019 | Grant et al. |
| 2019/0134108 A1 | 5/2019 | Patterson et al. |
| 2019/0134109 A1 | 5/2019 | Mulder et al. |
| 2019/0151380 A1 | 5/2019 | Grant et al. |
| 2019/0247448 A1 | 8/2019 | Grant et al. |
| 2019/0255123 A1 | 8/2019 | Jeffery et al. |

FOREIGN PATENT DOCUMENTS

| | | |
|---|---|---|
| CN | 1863540 A | 11/2006 |
| CN | 1917946 A | 2/2007 |
| CN | 1954066 A | 4/2007 |
| CN | 101590081 A | 12/2009 |
| CN | 101596216 A | 12/2009 |
| CN | 101914452 A | 12/2010 |
| CN | 102304483 A | 1/2012 |
| CN | 102408998 A | 4/2012 |
| CN | 102031235 B | 7/2012 |
| CN | 102093967 B | 1/2013 |
| CN | 102905558 A | 1/2013 |
| CN | 102940652 A | 2/2013 |
| CN | 201180025408 | 2/2013 |
| CN | 102373172 B | 3/2013 |
| CN | 103037876 A | 4/2013 |
| CN | 103142656 A | 6/2013 |
| CN | 103146620 A | 6/2013 |
| CN | 103156888 A | 6/2013 |
| CN | 103652322 A | 3/2014 |
| CN | 103781487 A | 5/2014 |
| CN | 103820363 A | 5/2014 |
| CN | 103849590 A | 6/2014 |
| CN | 103865846 A | 6/2014 |
| CN | 103930117 A | 7/2014 |

(56) References Cited

FOREIGN PATENT DOCUMENTS

| | | |
|---|---|---|
| CN | 103981115 A | 8/2014 |
| CN | 103981117 A | 8/2014 |
| CN | 104160014 A | 11/2014 |
| CN | 104195075 A | 12/2014 |
| CN | 103509741 B | 2/2015 |
| CN | 102940652 B | 3/2015 |
| CN | 104415060 A | 3/2015 |
| CN | 104435000 A | 3/2015 |
| CN | 103037876 B | 4/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| CN | 104560820 A | 4/2015 |
| CN | 201410522408 | 4/2015 |
| CN | 105112333 A | 12/2015 |
| CN | 103820363 B | 2/2016 |
| CN | 103865846 B | 3/2016 |
| CN | 105555286 A | 5/2016 |
| CN | 105979952 A | 9/2016 |
| CN | 105982919 A | 10/2016 |
| CN | 106890196 A | 6/2017 |
| DE | 19826928 A1 | 12/1999 |
| DE | 10206995 A1 | 9/2003 |
| EP | 0120516 A2 | 10/1984 |
| EP | 0238023 A2 | 9/1987 |
| EP | 0433299 A1 | 6/1991 |
| EP | 0449375 A2 | 10/1991 |
| EP | 0581171 A1 | 2/1994 |
| EP | 0778778 A1 | 6/1997 |
| EP | 0888118 A1 | 1/1999 |
| EP | 1141235 A2 | 10/2001 |
| EP | 1227152 A1 | 7/2002 |
| EP | 1383514 A1 | 1/2004 |
| EP | 1389464 A1 | 2/2004 |
| EP | 1448995 A1 | 8/2004 |
| EP | 1481681 A1 | 12/2004 |
| EP | 1765391 A1 | 3/2007 |
| EP | 1675481 B1 | 11/2008 |
| EP | 1997499 A1 | 12/2008 |
| EP | 1997905 A1 | 12/2008 |
| EP | 1997906 A1 | 12/2008 |
| EP | 1997907 A1 | 12/2008 |
| EP | 2044436 A2 | 4/2009 |
| EP | 2103226 A1 | 9/2009 |
| EP | 2133088 A3 | 1/2010 |
| EP | 1280541 B2 | 3/2010 |
| EP | 2236598 A1 | 10/2010 |
| EP | 2286832 A1 | 2/2011 |
| EP | 2308498 A1 | 4/2011 |
| EP | 2217253 B1 | 6/2011 |
| EP | 1940243 B1 | 8/2011 |
| EP | 2359838 A1 | 8/2011 |
| EP | 1855550 B1 | 10/2011 |
| EP | 1871400 B1 | 10/2011 |
| EP | 2436275 A1 | 4/2012 |
| EP | 2124972 B1 | 6/2012 |
| EP | 1773361 B2 | 9/2012 |
| EP | 1945234 B1 | 12/2012 |
| EP | 2323493 B8 | 12/2012 |
| EP | 2323494 B8 | 12/2012 |
| EP | 1629850 B2 | 5/2013 |
| EP | 2203551 B1 | 8/2013 |
| EP | 2140771 B1 | 12/2013 |
| EP | 2687227 A1 | 1/2014 |
| EP | 2179028 B1 | 8/2014 |
| EP | 2650002 A4 | 8/2014 |
| EP | 2164349 B1 | 9/2014 |
| EP | 2134835 B1 | 10/2014 |
| EP | 2810652 A2 | 12/2014 |
| EP | 2305838 B1 | 1/2015 |
| EP | 2832859 A1 | 2/2015 |
| EP | 3804737 A1 | 4/2021 |
| ES | 2408279 A2 | 6/2013 |
| JP | S5557520 A | 4/1980 |
| JP | H08259450 A | 10/1996 |
| JP | 2003261453 A | 9/2003 |
| JP | 2005097280 A | 4/2005 |
| JP | 2006265212 A | 10/2006 |
| JP | 2007504131 A | 3/2007 |
| JP | 2007084533 A | 4/2007 |
| JP | 2007116991 A | 5/2007 |
| JP | 2008195635 A | 8/2008 |
| JP | 2009507023 A | 2/2009 |
| JP | 2010246523 A | 11/2010 |
| JP | 5031249 B2 | 9/2012 |
| JP | 2013005759 A | 1/2013 |
| JP | 5183848 B2 | 4/2013 |
| JP | 2013527240 A | 6/2013 |
| JP | 2013201912 A | 10/2013 |
| JP | 5557520 B2 | 7/2014 |
| JP | 2014196260 A | 10/2014 |
| JP | 2014534957 A | 12/2014 |
| JP | 2015500792 A | 1/2015 |
| JP | 5710876 B2 | 4/2015 |
| JP | 5792105 B2 | 10/2015 |
| JP | 2017222601 A | 12/2017 |
| KR | 100468522 B1 | 1/2005 |
| KR | 20100128168 A | 12/2010 |
| KR | 1020100128168 | 12/2010 |
| KR | 101017448 B1 | 2/2011 |
| KR | 101057357 B1 | 8/2011 |
| KR | 20130021764 A | 3/2013 |
| KR | 101250463 B1 | 4/2013 |
| KR | 20140023568 A | 2/2014 |
| KR | 20140037544 A | 3/2014 |
| KR | 20140061328 A | 5/2014 |
| KR | 101426276 B1 | 8/2014 |
| KR | 20160131237 | 11/2016 |
| KR | 20160131237 A | 11/2016 |
| KR | 101745084 B1 | 6/2017 |
| PL | 229020 B1 | 5/2018 |
| RU | 2078815 C1 | 5/1997 |
| TW | I417054 B | 12/2013 |
| WO | WO-8807865 A1 | 10/1988 |
| WO | WO-9117243 A1 | 11/1991 |
| WO | WO-9611014 A1 | 4/1996 |
| WO | WO-9720577 A1 | 6/1997 |
| WO | WO-9730717 A1 | 8/1997 |
| WO | WO-9735956 A1 | 10/1997 |
| WO | WO-9843081 A1 | 10/1998 |
| WO | WO-9855131 A1 | 12/1998 |
| WO | WO-9857631 A1 | 12/1998 |
| WO | WO-9919459 A1 | 4/1999 |
| WO | WO-9942568 A1 | 8/1999 |
| WO | WO-9945955 A1 | 9/1999 |
| WO | WO-0116120 A1 | 3/2001 |
| WO | WO-0158275 A2 | 8/2001 |
| WO | WO-0185187 A1 | 11/2001 |
| WO | WO-0193904 A1 | 12/2001 |
| WO | WO-0207741 A1 | 1/2002 |
| WO | WO-0242328 A2 | 5/2002 |
| WO | WO-02070670 A1 | 9/2002 |
| WO | WO-02085933 A1 | 10/2002 |
| WO | WO-02094296 A1 | 11/2002 |
| WO | WO-03010297 A1 | 2/2003 |
| WO | WO-03022255 A2 | 3/2003 |
| WO | WO-03045317 A2 | 6/2003 |
| WO | WO-03046580 A1 | 6/2003 |
| WO | WO-03053220 A2 | 7/2003 |
| WO | WO-2004003235 A3 | 6/2004 |
| WO | WO-2004085628 A1 | 10/2004 |
| WO | WO-2005007834 A1 | 1/2005 |
| WO | WO-2005023179 A2 | 3/2005 |
| WO | WO-2005030133 A2 | 4/2005 |
| WO | WO-2005032567 A2 | 4/2005 |
| WO | WO-2005058335 A1 | 6/2005 |
| WO | WO-2005032567 A3 | 7/2005 |
| WO | WO-2005093049 A1 | 10/2005 |
| WO | WO-2005107381 A2 | 11/2005 |
| WO | WO-2005121130 A2 | 12/2005 |
| WO | WO-2006012586 A2 | 2/2006 |

(56) References Cited

FOREIGN PATENT DOCUMENTS

| | | |
|---|---|---|
| WO | WO-2006033949 A1 | 3/2006 |
| WO | WO-2006033950 A1 | 3/2006 |
| WO | WO-2006033951 A1 | 3/2006 |
| WO | WO-2006102350 A1 | 9/2006 |
| WO | WO-2006102536 A2 | 9/2006 |
| WO | WO-2006091103 A3 | 10/2006 |
| WO | WO-2006110406 A2 | 10/2006 |
| WO | WO-2006130205 A1 | 12/2006 |
| WO | WO-2007027761 A2 | 3/2007 |
| WO | WO-2007056218 A2 | 5/2007 |
| WO | WO-2007064732 A1 | 6/2007 |
| WO | WO-2007064749 A1 | 6/2007 |
| WO | WO-2007098371 A2 | 8/2007 |
| WO | WO-2007136719 A2 | 11/2007 |
| WO | WO-2007140230 A3 | 2/2008 |
| WO | WO-2008031438 A3 | 5/2008 |
| WO | WO-2008055702 A1 | 5/2008 |
| WO | WO-2008055703 A2 | 5/2008 |
| WO | WO-2008064489 A1 | 6/2008 |
| WO | WO-2008073148 A2 | 6/2008 |
| WO | WO-2008076696 A2 | 6/2008 |
| WO | WO-2008053444 A3 | 7/2008 |
| WO | WO-2008083157 A2 | 7/2008 |
| WO | WO-2008134450 A2 | 11/2008 |
| WO | WO-2008153377 A1 | 12/2008 |
| WO | WO-2009027753 A1 | 3/2009 |
| WO | WO-2009030481 A1 | 3/2009 |
| WO | WO-2009055362 A1 | 4/2009 |
| WO | WO-2009059284 A2 | 5/2009 |
| WO | WO-2009072889 A1 | 6/2009 |
| WO | WO-2009079564 A2 | 6/2009 |
| WO | WO-2009043856 A3 | 7/2009 |
| WO | WO-2009080862 A1 | 7/2009 |
| WO | WO-2009100331 A2 | 8/2009 |
| WO | WO-2009116864 A1 | 9/2009 |
| WO | WO-2009128949 A2 | 10/2009 |
| WO | WO-2009138220 A1 | 11/2009 |
| WO | WO-2009149149 A1 | 12/2009 |
| WO | WO-2009151315 A1 | 12/2009 |
| WO | WO-2009154463 A2 | 12/2009 |
| WO | WO-2009156301 A1 | 12/2009 |
| WO | WO-2010002241 A1 | 1/2010 |
| WO | WO-2010036876 A2 | 4/2010 |
| WO | WO-2010037402 A1 | 4/2010 |
| WO | WO-2010037408 A1 | 4/2010 |
| WO | WO-2010037539 A1 | 4/2010 |
| WO | WO-2010048481 A1 | 4/2010 |
| WO | WO-2010063601 A1 | 6/2010 |
| WO | WO-2010081126 A3 | 9/2010 |
| WO | WO-2010129839 A1 | 11/2010 |
| WO | WO-2010130659 A1 | 11/2010 |
| WO | WO-2010130660 A1 | 11/2010 |
| WO | WO-2010130662 A1 | 11/2010 |
| WO | WO-2010130663 A1 | 11/2010 |
| WO | WO-2010130697 A1 | 11/2010 |
| WO | WO-2010130699 A1 | 11/2010 |
| WO | WO-2010130700 A1 | 11/2010 |
| WO | WO-2010130701 A1 | 11/2010 |
| WO | WO-2010130702 A1 | 11/2010 |
| WO | WO-2010130704 A1 | 11/2010 |
| WO | WO-2010130710 A1 | 11/2010 |
| WO | WO-2010130713 A1 | 11/2010 |
| WO | WO-2010/143940 A1 | 12/2010 |
| WO | WO-2010139531 A1 | 12/2010 |
| WO | WO-2010142504 A1 | 12/2010 |
| WO | WO-2010143961 A1 | 12/2010 |
| WO | WO-2010147714 A1 | 12/2010 |
| WO | WO-2010133475 A3 | 1/2011 |
| WO | WO-2011000620 A1 | 1/2011 |
| WO | WO-2011000621 A1 | 1/2011 |
| WO | WO-2011005756 A1 | 1/2011 |
| WO | WO-2010133472 A3 | 2/2011 |
| WO | WO-2011020748 A1 | 2/2011 |
| WO | WO-2011036539 A1 | 3/2011 |
| WO | WO-2011043654 A1 | 4/2011 |
| WO | WO-2011044208 A1 | 4/2011 |
| WO | WO-2011058535 A1 | 5/2011 |
| WO | WO-2011068398 A1 | 6/2011 |
| WO | WO-2011075138 A1 | 6/2011 |
| WO | WO-2011096808 A1 | 8/2011 |
| WO | WO-2011096809 A1 | 8/2011 |
| WO | WO-2011110918 A1 | 9/2011 |
| WO | WO-2011121379 A1 | 10/2011 |
| WO | WO-2011149335 A1 | 12/2011 |
| WO | WO-2011152566 A2 | 12/2011 |
| WO | WO-2011153226 A2 | 12/2011 |
| WO | WO-2011157816 A1 | 12/2011 |
| WO | WO-2012012874 A1 | 2/2012 |
| WO | WO-2012016287 A2 | 2/2012 |
| WO | WO-2012024638 A2 | 2/2012 |
| WO | WO-2011153226 A3 | 3/2012 |
| WO | WO-2012055408 A1 | 5/2012 |
| WO | WO-2012062780 A1 | 5/2012 |
| WO | WO-2012071380 A1 | 5/2012 |
| WO | WO-2012076739 A1 | 6/2012 |
| WO | WO-2012105312 A1 | 8/2012 |
| WO | WO-2012122478 A1 | 9/2012 |
| WO | WO-2012140636 A1 | 10/2012 |
| WO | WO-2012142605 A1 | 10/2012 |
| WO | WO-2012145491 A2 | 10/2012 |
| WO | WO-2012158517 A1 | 11/2012 |
| WO | WO-2012165843 A2 | 12/2012 |
| WO | WO-2012170478 A2 | 12/2012 |
| WO | WO-2013005836 A1 | 1/2013 |
| WO | WO-2013008039 A1 | 1/2013 |
| WO | WO-2013008102 A2 | 1/2013 |
| WO | WO-2013037068 A1 | 3/2013 |
| WO | WO-2013050792 A1 | 4/2013 |
| WO | WO-2013053836 A1 | 4/2013 |
| WO | WO-2013054001 A1 | 4/2013 |
| WO | WO-2013063849 A1 | 5/2013 |
| WO | WO-2013080561 A1 | 6/2013 |
| WO | WO-2013124725 A1 | 8/2013 |
| WO | WO-2013144701 A1 | 10/2013 |
| WO | WO-2013153358 A1 | 10/2013 |
| WO | WO-2013154725 A1 | 10/2013 |
| WO | WO-2013171515 A1 | 11/2013 |
| WO | WO-2013175038 A1 | 11/2013 |
| WO | WO-2013181694 A1 | 12/2013 |
| WO | WO-2013182038 A1 | 12/2013 |
| WO | WO-2014001368 A1 | 1/2014 |
| WO | WO-2014019271 A1 | 2/2014 |
| WO | WO-2014020004 A1 | 2/2014 |
| WO | WO-2014032108 A1 | 3/2014 |
| WO | WO-2014036182 A2 | 3/2014 |
| WO | WO-2014043593 A2 | 3/2014 |
| WO | WO-2014053608 A1 | 4/2014 |
| WO | WO-2014064359 A1 | 5/2014 |
| WO | WO-2014067976 A1 | 5/2014 |
| WO | WO-2014070014 A1 | 5/2014 |
| WO | WO-2014070225 A1 | 5/2014 |
| WO | WO-2014075745 A1 | 5/2014 |
| WO | WO-2014078911 A1 | 5/2014 |
| WO | WO-2014082050 A1 | 5/2014 |
| WO | WO-2014093622 A2 | 6/2014 |
| WO | WO-2014093635 A1 | 6/2014 |
| WO | WO-2014093655 A2 | 6/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014130540 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014167338 A1 | 10/2014 |
| WO | WO-2014182966 A1 | 11/2014 |
| WO | WO-2014200334 A1 | 12/2014 |
| WO | WO-2014201037 A2 | 12/2014 |
| WO | WO-2015003001 A1 | 1/2015 |
| WO | WO-2015006355 A2 | 1/2015 |

(56) References Cited

FOREIGN PATENT DOCUMENTS

| WO | WO-2015013214 A2 | 1/2015 |
|---|---|---|
| WO | WO-2015017625 A1 | 2/2015 |
| WO | WO-2015021936 A1 | 2/2015 |
| WO | WO-201503305 A1 | 3/2015 |
| WO | WO-2015038731 A1 | 3/2015 |
| WO | WO-2015057151 A1 | 4/2015 |
| WO | WO-2015077794 A1 | 5/2015 |
| WO | WO-2015095241 A2 | 6/2015 |
| WO | WO-2015077794 A4 | 7/2015 |
| WO | WO-2015156419 A1 | 10/2015 |
| WO | WO-2015156519 A1 | 10/2015 |
| WO | WO-2015168534 A1 | 11/2015 |
| WO | WO-2015169944 A1 | 11/2015 |
| WO | WO-2015095241 A4 | 12/2015 |
| WO | WO-2016019505 A1 | 2/2016 |
| WO | WO-2016019506 A1 | 2/2016 |
| WO | WO-2016033439 A2 | 3/2016 |
| WO | WO-2016036615 A1 | 3/2016 |
| WO | WO-2016057671 A1 | 4/2016 |
| WO | WO-2016065324 A1 | 4/2016 |
| WO | WO-2016069795 A2 | 5/2016 |
| WO | WO-2016069801 A1 | 5/2016 |
| WO | WO-2016070151 A1 | 5/2016 |
| WO | WO-2016086161 A1 | 6/2016 |
| WO | WO-2016086205 A2 | 6/2016 |
| WO | WO-2016086206 A1 | 6/2016 |
| WO | WO-2016086208 A1 | 6/2016 |
| WO | WO-2016086209 A1 | 6/2016 |
| WO | WO-2016086210 A1 | 6/2016 |
| WO | WO-2016102950 A1 | 6/2016 |
| WO | WO-2016102951 A1 | 6/2016 |
| WO | WO-2016118730 A1 | 7/2016 |
| WO | WO-2016139217 A1 | 9/2016 |
| WO | WO-2016149449 A1 | 9/2016 |
| WO | WO-2016149687 A1 | 9/2016 |
| WO | WO-2016203218 A1 | 12/2016 |
| WO | WO-2016203220 A1 | 12/2016 |
| WO | WO-2017031371 A1 | 2/2017 |
| WO | WO-2017079450 A1 | 5/2017 |
| WO | WO-2017085205 A1 | 5/2017 |
| WO | WO-2017091753 A1 | 6/2017 |
| WO | WO-2017091783 A2 | 6/2017 |
| WO | WO-2017091783 A3 | 7/2017 |
| WO | WO-2017122197 A1 | 7/2017 |
| WO | WO-2017148596 A1 | 9/2017 |
| WO | WO-2017160711 A1 | 9/2017 |
| WO | WO-2018011594 A1 | 1/2018 |
| WO | WO-2018047106 A1 | 3/2018 |
| WO | WO-2018094190 A2 | 5/2018 |
| WO | WO-2018/112365 A2 | 6/2018 |
| WO | WO-2018112363 | 6/2018 |
| WO | WO-2018112363 A1 | 6/2018 |
| WO | WO-2018112365 A2 | 6/2018 |
| WO | WO-2018215782 A1 | 11/2018 |
| WO | WO-2018229189 A1 | 12/2018 |
| WO | WO-2018229216 A1 | 12/2018 |
| WO | WO-2018229236 A2 | 12/2018 |
| WO | WO-2019010255 A1 | 1/2019 |
| WO | WO-2019215345 A1 | 11/2019 |
| WO | WO-2020120714 A1 | 6/2020 |

OTHER PUBLICATIONS

4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].

Abel and Zukin, "Epigenetic targets of HDAC inhibition in neurodegenerative and psychiatric disorders", 2008, Current Opinion Pharmacology, 2008. 8(1): 57-64.

Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.

Alenghat, Theresa et al., "Histone deacetylase 3 coordinates commensal-bacteria-dependent intestinal homeostasis",2013, Nature, 504: 153-157.

Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006.

Altschul et al. 'Basic local alignment search tool.' Journal of Molecular Biology. 1990, vol. 215, No. 3, pp. 403-410.

"Amedei, A. et al. Multiple sclerosis: the role of cytokines in pathogenesis and in therapies. Int J Mol Sci. Oct. 19, 2012;13(10):13438-60. doi: 10.3390/ijms131013438."

Aminov et al. Molecular diversity, cultivation, and improved detection by fluorescent in situ hybridization of a dominant group of human gut bacteria related to *Roseburia* spp. or *Eubacterium rectale*. Applied and environmental microbiology. 2006, vol. 72, No. 9, pp. 6371-6376.

An et al. (1985) "New cloning vehicles for transformation of higher plants," EMBO J. 4:277-284.

An et al. (1988) "Binary Vectors," Plant Molecular Biology Manual. A3:1-19.

An et al. Transformation of Tobacco, Tomato, Potato, and *Arabiodopsis thaliana* Using a Binary Ti Vector System,Plant Physiol. May 1986; 81:301-305.

Angiolilli, Chiara et al., "Hisone deacetylase 3 regulates the inflammatory gene expression programme of rheumatoid arthritis fibroblast-like synoviocytes", Ann Rheum Dis, 2017, 76: 277-285.

Anonymous: "4D pharma's Blautix for Irritable Bowel Syndrome shows positive impact—pharmaceutical daily news", Dec. 13, 2016.

Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sept. 8, 2011:DOI:10.1152.ajpg.00167.2011.

Archer et al. (1997) "The Molecular Biology of Secreted Enzyme Production by Fungi," Critical Reviews Biotechnology. 17(4):273-306.

Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.

Atarashi et al. Induction of colonic regulatory T cells by indigenous *Clostridium* species. Science 331(6015):337-341 (2011).

Atarashi et al., Th17 Cell Induction by Adhesion of Microbes to Intestinal Epithelial Cells. Cell, vol. 163, No. 2, Oct. 8, 2015. pp. 367-380.

Atarashi, et al., Treg induction by a rationally selected mixture of Clostridia strains from the human microbiota. Supplementary Information. Nature 500, 232-236 (Aug. 8, 2013) doi:10.1038/nature12331.

Atarashi, K. et al., Treg induction by a rationally selected mixture of Clostridia strains from the human microbiota. Nature. 2013; 500(7461):232-236.

ATCC Catalog, https://www.atcc.org/search_results.aspx?dsNav=Ntk:primarysearch%7cbacteroides+thetaiotaomicron%7c3%7c,Ny:true,ro:0,N:1000552&searchterms=bacteroides+thetaiotaomicron&redir=1, Accessed on May 2, 2018.

Auriel, E. et al., "Chapter 38—Nonsteroidal anti-inflammatory drugs exposure and the central nerous system", 2014, Handbook of Clinical Neurology 119, 577-584.

Ausubel et al. (1999) Short Protocols in Molecular Biology. 4th edition, pp. 7-58 to 7-60, and Chapter 18. pp. 18-1 to 18-23.

Awadel-Kariem, Mustafa et al., First report of Parabacteroides goldsteinii bacteraemia in a patient with complicated intra-abdominal infection, Anaerobe, vol. 16, Issue 3, Jun. 2010, pp. 223-225.

Azad, M.B. et al., Probiotic supplementation during pregnancy or infancy for the prevention of asthma and wheeze: systematic review and meta-analysis BMJ 2013; 347 :f6471.

Aziz et al. The RAST Server: rapid annotations using subsystems technology. BMC Genomics. 2008, vol. 9, No. 1, pp. 75.

(56) References Cited

OTHER PUBLICATIONS

Aziz, R.K., Bartels, D., Best, A.A., DeJongh, M., Disz, T., Edwards, R.A., et al. (2008). The RAST Server: Rapid Annotations using Subsystems Technology. BMC Genomics 9, 75. doi: 10.1186/1471-2164-9-75.

Bagge, et al., Diversity of spore-forming bacteria in cattle manure, slaughterhouse waste and samples from biogas plants. Journal of applied microbiology. 2010;109: 1549-1565.

Balato, et al., Effects of adalimumab therapy in adult subjects with moderate-to-severe psoriasis on Th17 pathway. (2014) J Eur Acad Dermatol Venereol. 28(8):1016-24.

Banfield, J. & Murphy, K.R., Non-Th2, Late-onset, non-allergic asthma. Copd & Asthma for NPs, A peer-reviewed newsletter, Aug. 2016; 14: 8 Pages.

Baraczka, Krisztina et al ,"Changes in dopamine and 3,4-dihydroxyphenylacetic acid (DOPAC) levels in human cerebrospinal fluid after L-dopa and deprenyl administration", J Neural Transmission, 1983, 58(3-4):299-304.

Barcenilla, et al. Phylogenetic relationships of butyrate-producing bacteria from the human gut. Appl Environ Microbiol. Apr. 2000. 66(4):1654-61.

Barry, et al., Criteria for Disksusceptibility tests and quality control guidelines for the cefoperazone-sulbactam combination, Journal of clinical microbiology, Jan. 1988;26(1):13-17.

Beaucage, et al. Deoxynucleoside phosphoramidites—A new class of key intermediates for deoxypolynucleotide synthesis. Tetrahedron Letters, vol. 22, 1981, pp. 1859-1869.

Beggs (1978) "Transformation of yeast by a replicating hybrid plasmid," Nature. 275:104-109.

Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.

Berg et al. (1996) "Enterocolitis and colon cancer in interleukin-10-deficient mice are associated with aberrant cytokine production and CD4(+) TH1-like responses," The Journal of Clinical Investigation. 98(4):1010-1020.

Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.

Berger, S. Gideon guide to medically important bacteria. Gideon E-book Series. 2017 edition. 4 pages.

Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen Helicobacter pylori. Infect Immun 74(1), 425-434. doi: 10.1128/IAI.74.1.425-434.2006.

Bernalier, A., et al., "Diversity of H2/C02-utilizing acetogenic Bacteria from Feces of Non-Methane-Producing Humans", Current Microbiology vol. 33 (Aug. 1996), pp. 94-99, Springer-Vertag New York Inc., USA.

Bernalier et al., "Acetogenesis from H02 and C0-2 By Methane and Non-Methane-Producing Human Colonic Bacterial Communities" Fems Microbiology Ecology, vol. 19. No. 3. 1996. pp. 193-202. XP000979130.

Bernalier et al. *Ruminococcus hydrogenotrophicus* sp. nov., a new H2/CO2-utilizing acetogenic bacterium isolated from human feces. 1996 Arch. Microbiol. 166 (3), 176-183.

Bertram, J. et al. Establishment of a cloned line of Lewis lung carcinoma cells adapted to cell culture. (1980) Cancer let. 11:63-73.

Blandino, G., Fazio, D., DiMarco, R. Probiotics: Overview of microbiological and immunological characteristics (2008). Expert Review of Anti-Infective Therapy, 6 (4), pp. 497-508.

Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.

Born, P., et al., English Abstract "Carbohydrate substitutes: comparalive study of intestinal absorption of fructose, sorbitol and xylitol", "Zuckeraustauschstoffe: Vergleichende Untersuchung zur intestinalen Resorption von Fructose, Sorbit und Xylit", Medizinische Klinik 89, Technischen Universitat Munchen (Munich) Nov. 15, 1994; 89 (11): 575-8 (Article in German), Urban & Vogel, Munich, Germany.

Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.

Bottacini, et al., Comparative genomics of the Bifidobacterium brevetaxon. BMC Genomics, 2014; 15:170. DOI:10.1186/1471-1471-2164-15-170.

Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/s41598-018-28919-4.

Bottacini, F., O'Connell Motherway, M., Kuczynski, J., O'Connell, K.J., Serafini, F., Duranti, S., et al. (2014). Comparative genomics of the Bifidobacterium breve taxon. BMC Genomics 15(1), 170. doi: 10.1186/1471-2164-15-170.

Bourassa, Megan W et al. "Butyrate, neuroepigenetics and the gut microbiome: Can a high fiber diet improve brain health?." Neuroscience letters vol. 625 (2016): 56-63. doi:10.1016/j.neulet.2016.02.009.

Brand et al., Collagen-induced arthritis, 2007; Protocol 2(5):1269-1275.

Brasel et al. (2000) "Generation of murine dendritic cells from ftl3-ligand-supplemented bone marrow cultures," Blood. 96(9):3029-3039.

Bravo, Javier A. et al., "Ingestion of Lactobacillus strain regulates emotional behavior and central GABA receptor expression in a mouse via the vagus nerve", PNAS Sep. 20, 2011 108 (38) 16050-16055; https://doi.org/10.1073/pnas.1102999108.

Bressa, et al., Differences in gut microbiota profile between women with active lifestyle and sedentary women. Plos One, 2017; 12(2): 1-20.

Brook, I., Clinical Review: Bacteremia caused by anaerobic bacteria in children. Critical Care 6(3): 7 pages (2002).

Bry et al. A model of host-microbial interactions in an open mammalian ecosystem. Science 273(5280):1380-1383 (1996).

Budd and Nicholls, "Mitochondria in the life and death of neurons", 1998, Essays in Biochemistry, 33:43-52.

Buffie et al., Precision microbiome restoration of bile acid-mediated resistance to Clostridium difficile. Nature, 517(7533):205-208 (2015).

Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.

Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.

"Campeau, J.L. et al., Intestinal Epithelial Cells Modulate Antigen-Presenting Cell Responses to Bacterial DNA. Infectionand Immunity. Aug. 2012; 80(8): 2632-2644."

Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292.

Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07.

Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0.

Candela, M., Centanni M Fau-Fiori, J., Fiori J Fau-Biagi, E., Biagi E Fau-Turroni, S., Turroni S Fau-Orrico, C., Orrico C Fau-Bergmann, S., et al. (2010). DnaK from *Bifidobacterium animalis* subsp. *lactis* is a surface-exposed human plasminogen receptor upregulated in response to bile salts. Microbiology 156(6), 1609-1618.

(56) References Cited

OTHER PUBLICATIONS

Carlson, Greg C. "Glutamate receptor dysfunction and drug targets across models of autism spectrum disorders." Pharmacology, biochemistry, and behavior vol. 100,4 (2012): 850-4. doi:10.1016/j.pbb.2011.02.003.
Caruthers, et al. New chemical methods for synthesizing polynucleotides. Nucleic Acids Symp Ser. 1980;(7):215-23.
Carvalho et al. (Jan. 2011) "TLR5 activation induces secretory interleukin-1 receptor antagonist (sIl-1 Ra) and reduces inflammasome-associated tissue damage," Nature. 4(1):102-111.
Casey et al. 'Isolation and characterization of anti-*Salmonella* lactic acid bacteria from the porcine gastrointestinal tract'. Letters in Applied Microbiology. 2004, vol. 39, No. 5, pp. 431-438.
Caspi, P.R. Experimental autoimmune uveoretinitis in the rat and mouse. Curr Protoc Immunol. May 2003;Chapter15:Unit 15.6. doi: 10.1002/0471142735.im1506s53.
Cekanaviciute, et al., Gut bacteria from multiple sclerosis patients modulate human T cells and exacerbate symptoms in mouse models. PNAS. Jun. 30, 2017; 1-6.
Cereghino et al. (2000) "Heterologous protein expression in the methylotrophic yeast *Pichia pastoris*," FEMS Microbiol Review. 24(1):45-66.
Charriot, et al., Future treatment for asthma, Eur Respir Rev 2016; 25: 77-92.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages.
Chevreux et al. 'Genome sequence assembly using trace signals and additional sequence information.' German Conference on Bioinformatics. 1999.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages.
Choi, Kieun et al., "In Situ Biphasic Extractive Fermentation for Hexanoic Acid Production from Sucrose by Megasphaera elsdenii NCIMB 702410", 2013, Apply Biochem Biotechnol, 171 (5), 1094-1107.
Choji Kaneuchi et al., "Clostridium coccoides, a New Species from the Feces of Mice", International Journal of Systematic Bacteriology, vol. 26, No. 4, Oct. 1976, p. 482-486.
Chothia et al. The relation between the divergence of sequence and structure in proteins. EMBO Journal. 1986, 5(4):823-826.
Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111.
Christmann, et al., Human seroreactivity to gut microbiota antigens. J Allergy Clin Immunol 136(5):1378-1386; available online May 23, 2015.
Christou (1994) "Genetic engineering of crop legumes and cereals: current status and recent advances," Agro-Food Industry Hi-Tech. pp. 17-27.
Chung et al. 'Microbiota-stimulated immune mechanisms to maintain gut homeostasis.' Current Opinion in Immunology. 2010, vol. 22, No. 4, pp. 455-460.
Cintas LM, Casaus MP, Herranz C, Nes IF, Hernandez PE. Review: bacteriocins of lactic acid bacteria (2001). Food Sci Technol 7(4):281-305.
Claesson, et al. Gut microbiota composition correlates with diet and health in the elderly. 2012. Nature, 488, 178-184.
Clarridge III, J.E. Impact of 16S rRNA gene sequence analysis for identification of bacteria on clinical microbiology and infectious diseases (2004). Clinical Microbiology Reviews, 17 (4), pp. 840-862.
Clinical Trials for Thetanix, EU Clinical Trials Register, Date of commencement of clinical trial: Oct. 16, 2015. Available at: https://clinicaltrialsregister.eu/ctr-search/search?query=Thetanix.
Coakley M et al.: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para. of the right-hand col.
Colin, et al., GIC-1001, A Clinical Stage, Orally Administered Colonic Analgesic Drug Proposed as a Cost-Effective Alternative to I.V. Sedation Used in Colonoscopy. Canadian Digestive Diseases Week, 2014; 2 pages.
Collins, M.D., et al., Enterococcus avium nom. rev., comb. nov.; E. casseliflavus nom. rev., comb. nov.; E. durans nom. rev., comb. nov.; E. gallinarum comb. nov.; and E. malodoratus sp. nov. (1984) Int J Syst Evol Microbiol. 34: 220-223.
Constantinescu, Cris S et al. "Experimental autoimmune encephalomyelitis (EAE) as a model for multiple sclerosis (MS)." British journal of pharmacology vol. 164,4 (2011): 1079-106. doi:10.1111/j.1476-5381.2011.01302.x.
Constantinescu et al. Experimental autoimmune encephalomyelitis (EAE) as a model for multiple sclerosis (MS). 2011. Br J Pharmacol. 164(4):1079-1106.
Co-pending U.S. Appl. No. 15/359,144, filed Nov. 22, 2016.
Co-pending U.S. Appl. No. 15/916,205, filed Mar. 8, 2018.
Co-pending U.S. Appl. No. 16/206,250, filed Nov. 30, 2018.
Co-pending U.S. Appl. No. 16/240,644, filed Jan. 4, 2019.
Corsetti A. et al., "Antimould activity of sourdough lactic acid bacteria: identification of a mixture of organic acids produced by Lactobacillus sanfrancisco CB1", 1998 Appl Microbiol Biotechnol, 50(2), 253-6.
Cotter, P.O., Hill, C., Ross, R.P. Food microbiology: Bacteriocins: Developing im1ate immunity for food (2005). Nature Reviews Microbiology, 3 (10), pp. 777-788.
Coughenour LL et al., "A new device for the rapid measurement of impaired motor function in mice", Pharmacol Biochem Behav. Mar. 1977;6(3):351-3.
Crawley, Jacqueline N. "Translational animal models of autism and neurodevelopmental disorders." Dialogues in clinical neuroscience vol. 14,3 (2012): 293-305.
Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.
Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.
Cryan JF and Mombereau C., "In search of a depressed mouse: utility of models for studying depression-related behavior in genetically modified mice", Mol Psychiatry. Apr. 2004;9(4):326-57.
Cryan, John F, and Timothy G Dinan. "More than a gut feeling: the microbiota regulates neurodevelopment and behavior." Neuropsychopharmacology : official publication of the American College of Neuropsychopharmacology vol. 40,1 (2015): 241-2. doi:10.1038/npp.2014.224.
Cummings, M., Breitling, R., and Takano, E. (2014). Steps towards the synthetic biology of polyketide biosynthesis. Fems Microbiology Letters 351(2), 116-125. doi: 10.1111/1574-6968.12365.
Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.

(56) References Cited

OTHER PUBLICATIONS

Daniel Garrido et al., "Utilization of galactooligosaccharides by *Bifidobacterium longum* subsp. *infantis* isolates", Food Microbiology, 33 (2013) 262-270.

Daniele, Stefano G et al. "Activation of MyD88-dependent TLR1/2 signaling by misfolded α-synuclein, a protein linked to neurodegenerative disorders." Science signaling vol. 8,376 ra45. May 12, 2015, doi:10.1126/scisignal.2005965.

Darfeuille-Michaud et al. High prevalence of adherent-invasive *Escherichia coli* associated with ileal mucosa in Crohn's disease . . . 2004. Gastroenterology 127(2):412-21.

Darlington, G.J., Liver Cell Lines. (1987) Meth Enzymol. 151:19-38.

Database UniProt [Online] Jun. 1, 2003 (Jun. 1, 2003), "subname:Full= possible pirin family protein {ECO:0000313|EMBL:AAO75294. 1};", XP00275366,retrieved from EBI accession No. UniProt:Q8ABC3 Database accession No. Q8ABC3.

Database WPI, Week 201801, Thomson Scientific, London, GB; AN 2017-834299, XP002787097, & WO 2017/209156 A1 (Morinaga Milk Ind Co. Ltd) Dec. 7, 2017 (Dec. 7, 2017) * abstract * of WO2017/2019156, Kobayashi, Youdai et al.

Database WPI,Week 201801, Thomson Scientific, London, GB; AN 2017-834299, XP002787097,& WO 2017/209156 A1 (Morinaga Milk Ind Co Ltd) Dec. 7, 2017 (Dec. 7, 2017) * abstract *.

Davis et al. (1971) "Genetic and Microbiological Research Technqiues," Methods Enzymol. 17A:79-143.

Davis et al., Genetic and Microbiological Research Techniques, Methods Enzymol. 1970; 17A:79-143.

Day, John G., McLellan, Mark R.," Cryopreservation and Freeze-Drying Protocols" Methods in Molecular Biology, 2007.

De Paepe et al. 'Trade-off between bile resistance and nutritional competence drives *Escherichia coli* diversification in the mouse gut.' PLoS Genetics. 2011, vol. 7, No. 6, e1002107.

De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.

Deangelis, M., et al., Selection of potential probiotic lactobacilli from pig feces to be used as additives in pelleted feeding (2006). Research in Microbiology, 157 (8), pp. 792-801.

Delgado, S., Ruiz, L., Hevia, A., Ruas-Madiedo, P., Margolles, A., and Sánchez, B. (2018). "Evidence ofthe In Vitro and In Vivo Immunological Relevance of Bifidobacteria," in The Bifidobacteria and Related Organisms.), 295-305.

Demarche, et al., Detailed analysis of sputum and systemic inflammation in asthma phenotypes: are paucigranulocytic asthmatics really non-inflammatory?, BMC Pulmonary Medicine, 2016; (16)46:1-13.

Dennis et al. 'DAVID: database for annotation, visualization, and integrated discovery.' Genome Bioi. 2003, vol. 4, No. 5, pp. 3.

Desbonnet L et al., "Gut microbiota depletion from early adolescence in mice: Implications for brain and behaviour", Brain Behav Immun. Aug. 2015;48:165-73. doi: 10.1016/j.bbi.2015.04.004. Epub Apr. 10, 2015.

Dheeraj Mohania et al., "Modulation of expression of Programmed Death-1 by administration of probiotic Dahi in DMH-induced colorectal carcinogenesis in rats", ACTA Biomed 2013; 84:102-109.

Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458.

Distrutti, et al., Gut Microbiota role in irritable bowel syndrome: New therapeutic strategies. World Journal of Gastroenterology. Feb. 21, 2016; 22(7): p. 2219-2241, XP002769875.

Distrutti, et al., Hydrogen sulphide induces u opioid receptor-dependent analgesia in a rodent model of visceral pain. Molecular Pain, 2010; 6(36):1-16.

Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.

DMSZ: Opening of Ampoules and Rehydration of Dried Cultures; (http://web.archive.org/web/20000 52411541 O/www.dsmz.de/open. htm); updated of website on Mar. 2000.

Dong, H., Rowland I Fau-Yaqoob, P., and Yaqoob, P. (2012). Comparative effects of six probiotic strains on immune function in vitro. Br J Nutr 108(3), 459-470. doi: 10.1017/S0007114511005824.

Dong-Hyun Kim and Young-Ho Jin, "Intestinal Bacterial B-Glucuronidase Activity of Patients with Colon Cancer", Arch Pharm Res vol. 24, No. 6, 564-567, 2001.

Drago, Lorenzo et al., Immunodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413.

Duck et al. 'Isolation of flagellated bacteria implicated in Crohn's disease.' Inflammatory Bowel Diseases. 2007, vol. 13, No. 10, pp. 1191-1201.

Duncan et al. (2002) "*Roseburia intestinalis* sp. nov., a novel saccharolytic, butyrate-producing bacterium from human faeces," International Journal Systematic Evolutionary Microbiology. 52:1615-1620.

Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.

Duncan et al. "Lactate-utilizing bacteria, isolated from human feces, that produce butyrate as a major fermentation product" Applied and environmental microbiology. 2004, vol. 70, No. 10, pp. 5810-5817.

Duncan, et al. *Roseburia intestinalis* sp. nov., a novel saccharolytic, butyrate-producing bacterium from human faeces. Int J Syst Evol Microbiol. Sep. 2002;52(Pt 5):1615-20.

Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.

Ebadi, M. et al, "Ubiquinone (Coenzyme O10) and Mitochondrai in Oxidative Stress of Parkinson's Disease", 2001, Biological Signals Recept. 10(3-4):224-253.

Eckburg, PB. et al., Diversity of the human intestinal microbial flora.Science. Jun. 10, 2005;308(5728):1635-8. Epub Apr. 14, 2005.

Eldrup, E. et al., "CSF and plasma concentrations of free norepinephrine, dopamine, 3,4-dihydroxyphenylacetic acid (DOPAC), 3,4-dihydroxyphenylalanine (DOPA), and epinephrine in Parkinson's disease", Acta Neurol Scand ,1995, 92(2): 116-21.

Elhenawy et al., Preferential packing of acidic glycosidases and proteases into bacteroides Outer membrane vesicles. mBio 5:e00909-14, pp. 1-12, 2014.

Elkins et al. 'Genes encoding bile salt hydrolases and conjugated bile salt transporters in Lactobacillus johnsonii 100-100 and other *Lactobacillus* species.' Microbiology. 2001, vol. 147, No. 12, pp. 3403-3412.

Elmadfa, 1., Klein, P., Meyer, AL. Immune-stimulating effects oflactic acid bacteria in vivo and in vitro (2010). Proceedings ofthe Nutrition Society, 69 (3), pp. 416-420.

Elsden, Sidney R. et al., "Amino Acid Utilization Patterns in Clostridial Taxonomy", 1979, Arch Microbiol, 123(2), 137-41.

Elsden, Sidney R. et al. "The End Products of the Metabolism of Aromatic Amino Acids by Clostridia", 1976, Arch Microbiol 107(3), 283-288.

Ely et al. (2000) "A family of six flagellin genes contributes to the Caulobacter crescentus flagellar filament," Journal of Bacteriology. 182(17):5001-5004.

Embl sequence AAO75294.1 (2003)—provided within the Office Action dated Feb. 16, 2018 in U.S. Appl. No. 15/631,952. 2 Pages.

Eren, A. Murat et al., "A single genus in the gut microbiome reflects host preference and specificity," The ISME Journal (2015) 9, 9-100 (2015).

ESR Dated Dec. 17, 2018, Appl. 18189521.0.

(56) References Cited

OTHER PUBLICATIONS

Estelle Devillard et al., Metabolism of Linoleic Acid by Human Gut Bacteria: Different Routes for Biosynthesis of Conjugated Linoleic Acid, Journal Of Bacteriology, Mar. 2007, vol. 189, No. 4, pp. 2566-2570.
European Communication dated Jun. 14, 2017 for EP Application No. 15817513.3.
Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1, 2018, accessed on Feb. 4, 2019.
Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons=evelo&rank=2, 2018, accessed on Feb. 4, 2019.
Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons=evelo&rank=3, 2018, accessed Feb. 4, 2019.
Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4, 2018, accessed Feb. 4, 2019.
Evelo Biosciences, Inc. Portfolio: https://evelobio.com/portfolio/, accessed Feb. 4, 2019.
Evelo Biosciences, Inc. website: https://evelobio.com/science/, accessed Feb. 4, 2019.
Extended European search report and opinion dated Aug. 23, 2016 for EP Application No. 16166001.4.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Faith et al. Identifying gut microbe-host phenotype relationships using combinatorial communities in gnotobiotic mice. Sci Transl Med 6(220):220ra11 (2014).
Faith et al. The long-term stability ofthe human gut microbiota. 2013. Science, 341(6141): 1237439.
Falony, et al., Coculture Fermentations of *Bifidobacterium* species and bacteroides thetaiotaomicron Reveal a mechanistic insight into the prebiotic effect of inulin-type Fructans. Applied and environmental microbiology, Apr. 2009;75(8):2312-2319.
Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892.
Fanning, S., Hall, L.J., Cronin, M., Zomer, A., MacSharry, J., Goulding, D., et al. (2012). Bifidobacterial surface-exopolysaccharide facilitates commensal-host interaction through immune modulation and pathogen protection. Proc Natl Acad Sci U S A 109(6), 2108-2113. doi:10.1073/pnas.1115621109.
Farmer, et al., Gut pain & visceral hypersensitivity. British journal of pain, 2013;7(1):39-47.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.

Federico E. Rey et al., "Dissecting the in Vivo Metabolic Potential of Two Human Gut Acetogens", The Journal of Biological Chemistry, vol. 285, No. 29, pp. 22082-22090, Jul. 16, 2010.
Felice C. et al. "Review article: selective histone deacetylase isoforms as potential therapeutic targets in inflammatory bowel diseases", 2015, Ailmentary Pharmacology and Therapeutics, 41:26-38.
Fenner, et al., *Bacteroides massiliensis* sp. nov., isolated from blood culture of a newborn. International Journal of systematic and evolutionary microbiology, 2005. 55:1335-1337.
Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056.
Ferro, Austin et al , "Short-term succinic acid treatment mitigates cerebellar mitochondrial OXPHOS dysfunction, neurodegeneration and ataxia in a Purkinje-specific spinocerebellar ataxia type 1 (SCA1) mouse model", 2017, Plos One. 12(12):e0188425.
Fischer A et al., "Recovery of learning and memory is associated with chromatin remodelling", Nature. May 10, 2007;447(7141):178-82. Epub Apr. 29, 2007.
Flores-Langarica et al. (2012) "Systemic flagellin immunization stimulates mucosal CD1 03+ dendritic cells and drives Foxp3+ regulatory T Cell and IgA responses in the mesenteric lymph node," Journal of Immunology. 189 (12):57 45-5754.
Foguem & Manckoundia, "Lewy Body Disease: Clinical and Pathological "Overlap Syndrome" Between Synucleinopathies (Parkinson Disease) and Tauopathies (Alzheimer Disease)", 2018, Current Neurology and Neuroscience Reports, 18:24.
Fraley et al. (1986) "Genetic Transformation in Higher Plants," Critical Reviews Plant Science. 4:1-46.
Frame et al., Production of fertile transgenic maize plants by silicon carbide whisker-mediated transformation, The Plant Journal. 1994; 6:941-948.
Frank, D. et al., Molecular-phylogenetic characterization of microbial community imbalances in human inflammatory bowel diseases. 2007. PNAS. 104(34):13780-5.
Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497.
Gaboriau-Routhiau et al. 'The key role of segmented filamentous bacteria in the coordinated maturation of gut helper T cell responses.' Immunity. 2009, vol. 31, No. 4, pp. 677-689.
Gagnon, melanie et al "Comparison ofthe Caco-2, HT-29 and the mucus-secreting HT29-MTX intestinal cell models to investigate *Salmonella* adhesion and invasion", 2013, Journal of Microbiological Methods. 94: 274-279.
Gait, M.J., (1984) Oligonucleotide Synthesis: A Practical Approach. Irl Press, pp. vii-xiii.
Galpern & Lang, "Interface between tauopathies and synucleinopathies: A tale of two proteins" 2006, Neurological Progress 59, 3, 449-458.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
GB1612190.7 International Search Report dated Apr. 12, 2017.
GB1809729.5 Examination Report dated Oct. 15, 2018.

(56) References Cited

OTHER PUBLICATIONS

G.E. Lewis Eds, Physiological Characterization of Clostridium Botulinum and Development of Practical Isolation and Identification Procedures, 1981, Biomedical Aspects of Botulism, p. 205-215.
GenBank Accession No. ABI48297.1 (Jul. 20, 2007) "Fia1 flagellin [Roseburia hominis]".
GenBank Accession No. ABY J02000000 (Nov. 8, 2013) Version 2. "Roseburia intestinal is L 1-82, whole genome shotgun sequencing project".
GenBank Accession No.'s ABY J02000001—ABY J02000409 search results page (Last Updated Apr. 24, 2015).
GenBank accession No. AJ312385 (Oct. 9, 2002) "Roseburia intestinalis 16S rRNA gene, strain L1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia horn in is Fla2 flagellin gene".
GenBank Accession No. M20983. (Apr. 26, 1993) "R.cecicola ftagellin gene".
Gennaro, A.R. "Quality Assurance and Control," from Remington: The Science and Practice of Pharmacy, 2000, Lippincott Williams & Wilkins, 20th ed., pp. 980-983.
Geraedts et al. 'Release of satiety hormones in response to specific dietary proteins is different between human and murine small intestinal mucosa.' Annals of Nutrition and Metabolism. 2010, vol. 56, No. 4, pp. 3018-3313.
Geuking et al. 'Intestinal bacterial colonization induces mutualistic regulatory T cell responses.' Immunity. 2011, vol. 34, No. 5, pp. 794-806.
Gewirtz et al. (2001) Cutting edge: bacterial flagellin activates basolaterally expressed TLR5 to induce epithelial proinflammatory gene expression. The Journal of Immunology. 167:(4)1882-1885.
Ghadimi, D. et al., Epigenetic imprinting by commensal probiotics inhibits the IL-23/IL-17 axis in an in vitro model of the intestinal mucosal immune system. JLB. 2012;92(4):895-911.
Giraud et al. 'Dissecting the genetic components of adaptation of *Escherichia coli* to the mouse gut.' PLoS Genetics.2008, vol. 4, No. 1, pp. e2.
Glauben, Rainer et al., "Histone Hyperacetylation Is Associated with Amelioration of Experimental Colitis in Mice", Journal of Immunology, 2006, 176: 5015-5022.
Goldin, B.R et al., Clinical indications for probiotics: an overview. Clin Infect Dis. Feb. 1, 2008;46 Suppl 2:S96-100; discussion S144-51. doi: 10.1086/523333.
Gonneaud Alexis, et al., "The histone deacetylase Hdac1 regulates inflammatory signalling in intestinal epithelial cells", 2014, Journal of Inflammation, 11: 43.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM. 08024-11.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (200 1 ). International Dairy Journal, 11 (1-2), pp. 19-25.
Gousia, P., et al., Antimicrobial resistance of major foodborne pathogens from major meat products (20II). Foodborne Pathogens and Disease, 8 (1), pp. 27-38.
Gray SG. and Dangond F. "Rationale for the use of histone deacetylase inhibitors as a dual therapeutic modality in multiple sclerosis.", Epigenetics. Apr.-Jun. 2006;1(2):67-75. Epub Mar. 5, 2006.
Greenspan et al., Defining epitopes: It's not as easy as it seems. Nature Biotechnology 7: 936-937, 1999.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487.
GT Biologies obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Guerrant, Gordon O. et al., "Analysis of Short-Chain Acids from Anaerobic Bacteria by High-Performance Liquid Chromatography", 1982, Journal of Clinical Microbiology, 16(2) 355-360.
Haabeth et al. A model for cancer-suppressive inflammation. (2012) OncoImmunology 1(1):1146-1152.
Hai-long Zhang et al., "Study on the Correlation of the Imbalance of TH17 Cells, Th1 Cell, Regulatory T Cells with ankylosing spondylitis Disease Activity Score", Medical Recapitulate, Dec. 2014, vol. 20, No. 24, pp. 4545-4555.
Halnes, Isabel et al., "Soluble Fibre Meal Challenge Reduces Airway Inflammation and Expression of GPR43 and GPR41 in Asthma", Nutrients, 2017, 9, 57, pp. 1-11.
Hammerich, L. et al., Interleukins in chronic liver disease: lessons learned from experimental mouse models. (2014) Clin Exp Gastroenterol. 7:297-306.
Hansen, et al., The role of mucosal immunity and host genetics in defining intestinal commensal bacteria. 2010. Curr. Opin. Gastroenterol., 26(6): 564-571.
Hapfelmeier et al. 'Reversible microbial colonization of germ-free mice reveals the dynamics of IgA immune responses.' Science. 2010, vol. 328, No. 5986, pp. 1705-1709.
Harrison Ian F, et al., "Neurorestoration induced by the HDAC inhibitor sodium valproate in the lactacystin model of Parkinson's is associated with histone acetylation and up-regulation of neurotrophic factors",2015, British Journal of Pharmacology, 172:4200-4215.
Hasegawa, Satoru et al. "Intestinal Dysbiosis and Lowered Serum Lipopolysaccharide-Binding Protein in Parkinson's Disease." PloS one vol. 10,11 e0142164. Nov. 5, 2015, doi:10.1371/journal.pone. 0142164.
Hayashi et al. The innate immune response to bacterial ftagellin is mediated by Toll-like receptor 5. Nature. 2001, vol. 410, No. 6832, pp. 1099-1103.
Heberle, H., Meirelles, G.V., da Silva, F.R., Telles, G.P., and Minghim, R. (2015). InteractiVenn: a web-based tool forthe analysis of sets through Venn diagrams. BMC Bioinformatics 16(1), 169. doi: 10.1186/s12859-015-0611-3.
Hedayat et al. (Mar. 1, 2012) "Prophylactic and therapeutic implications of toll-like receptor ligands," Medicinal Research Reviews. 32(2):294-325.
Hely Mariese A. et al., "Sydney Multicenter Study of Parkinson's Disease: Non-L-Dopa-Responsive Problems Dominate at 15 Years", 2005, Movement Disorders, 20(2): 190-9.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. PLOS ONE 4(4), e5184. doi: 10.1371/journal.pone.0005184.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of *Bifidobacterium animalis* subsp. lactis confers surface and functional characteristics. Appl Environ Microbiol 81(23), 7960-7968. doi: 10.1128/AEM. 02095-15.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in *Bifidobacterium* spp. Appl Environ Microbiol 80(1), 9-18. doi: 10.1128/AEM.02977-13.
Higgins, et al. CLUSTAL: A Package for Performing Multiple Sequence Alignment on a Microcomputer. Gene. 73 (1988): 237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.

(56) References Cited

OTHER PUBLICATIONS

Hinnen et al., Transformation of yeast, Proc. Natl. Acad. Sci. USA. Apr. 1978; 75:1929-1933.

Hoarau, Cyrille et al., Supernatant from Bifidobacterium Differentially Modulates Transduction Signaling Pathways for Biological Functions of Human Dendritic Cells, PLOS ONE, Public Library of Science, US, vol. 3, No. 7, Jul. 1, 2008 (Jul. 1, 2008), pp. e2753-1, XP009139666,ISSN: 1932-6203 *cf. abstract and conclusion, furthermore discussion part at p. 3, col. at the right side*.

Hoarau et al: "TLR2 Activation By Supernatant From Bifidobacterium Breve Modulates Maturation And Survival Of Human DCs Via Differential Effects On PI3Kinase, p38 And ERK Pathways",Journal of Allergy and Clinical Immuno, Elsevier, Amsterdam, NL, vol. 119, No. 1, Jan. 1, 2007 (Jan. 1, 2007), p. S258,XP005756921, ISSN: 0091-6749, DOI: 10.1016/J.JACI.2006.12.377 *cf. abs.No. 1008 at p. S258*.

Hoekema (1985) The Binary Plant Vector System Offset-drukkerij Kanters BB, Alblasserdam. Chapter V. pp. 63-71.

Hold et al. 'Oligonucleotide probes that detect quantitatively significant groups of butyrate-producing bacteria in human feces.' Applied and environmental microbiology. 2003, vol. 69, No. 7, pp. 4320-4324.

Holdeman, et al., Eubacterium contortum (Prevot) comb, nov.: Emendation of description and designation ofthe type strain. International journal of systematic bacteriology. Oct. 1971;21(4): 304-306.

Holland et al. (1990) "Secretion of Heterologous Proteins in *Escherichia coli*," Methods Enzymology. 182:132-143.

Hollenberg et al. (1997) "Production of recombinant proteins by methulotrophic yeasts," Current Opinion Biotechnology. 8(5):554-560.

Hong, Seung-Hye et al., "Alernative Biotransformation of Retinal to Retinoic Acid or Retinol by an Aldehyde Dehydrogenase from Bacillus cereus", 2016, Applied and Environmental Microbiology, 82(13) 3940-3946.

Hooper at al. 'Molecular analysis of commensal host-microbial relationships in the intestine.' Science. 2001; vol. 291, No. 5505, pp. 881-884.

Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.

Horwell, et al., The 'peptoid' approach to the design of non-peptide, small molecule agonists and antagonists of neuropeptides. 1995. Trends Biotechnol. 13(4):132-134.

Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.

Hougee, et al., Oral treatment with probiotics reduces allergic symptoms in ovalbumin-sensitized mice:a bacterial strain comparative study. Int Arch Allergy Immunol. 2010; 151:107-117.

Hoyles L. et al. Gastrointestinal Tract, Chapter 56. Handbook of Hydrocarbon and Lipid Microbiology Springer Verlag Berlin 2010, 3120-32.

Hsiao, Elaine Y et al. "Microbiota modulate behavioral and physiological abnormalities associated with neurodevelopmental disorders." Cell vol. 155,7 (2013): 1451-63. doi:10.1016/j.cell.2013.11.024.

Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob.160155.

Humira 20 mg/ 0.2 ml Solution for Injection in Pre-Filled Syringe—Summary of Product Characteristics, https://www.medicines.org.uk/emc/product/9080/smpc/print, accessed on Oct. 25, 2019, 30 pages.

Huot Philippe, "The pons and human affective processing—Implications for Parkinson's disease", 2015, EBioMedicine 2, 1592-1593.

Huycke, M M et al. "Multiple-drug resistant enterococci: the nature of the problem and an agenda for the future." Emerging infectious diseases vol. 4,2 (1998): 239-49. doi: 10.3201/eid0402.980211.

Hyland and Cox, "The regulation of veratridine-stimulated electrogenic ion transport in mouse colon by neuropeptide Y (NPY), Y1 and Y2 receptors", 2005, British Journal of Pharmacology,146(5), 712-722.

Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.

Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18.

Ibrahim et al., "Method for the isolation of highly purified *Salmonella flagellins*," Journal of Clinical Microbiology. Dec. 1985; 22(6):1040-1044.

Inaba et al., "Generation of large numbers of dendritic cells from mouse bone marrow cultures supplemented with granulocyte/macrophage colony-stimulating factor," J. Exp. Med. Dec. 1992; 176(6):1693-1702.

Interational Search Report for International Application No. PCT/GB2012/052495, dated Mar. 25, 2013.

International Preliminary Report dated Mar. 1, 2017 for International Application No. PCT/GB2015/054113.

International Preliminary Report on Patentability corresponding to International Patent Application No. PCT/GB2014/051123, dated Oct. 13, 2015.

International Preliminary Report on Patentability dated Sep. 17, 2019 for International Application Serial No. PCT/EP2018/065809, (13 pages).

International Preliminary Report on Patentability for International Application No. PCT/GB2012/051686 dated Jan. 14, 2014.

International Search Report dated Jan. 27, 2017 for International Application No. PCT/GB2016/053622.

International Search Report dated Feb. 10, 2016 for International Application No. PCT/GB2015/054113.

International Search Report dated Feb. 17, 2017 for International Application No. PCT/GB2016/053676.

International Search Report dated Mar. 7, 2016 for International Application No. PCT/GB2015/054112.

International Search report dated Mar. 15, 2003 for International Application No. PCT/GB2002/05255.

International Search Report dated Aug. 21, 2014 for International Application No. PCT/GB2014/051123.

International Search Report dated Aug. 26, 2016 for International application No. PCT/GB2016/051774.

International Search Report dated Aug. 26, 2016 for International application No. PCT/GB2016/051776.

International Search Report dated Sep. 6, 2016 for International application No. PCT/GB2016/051768.

International Search Report dated Sep. 6, 2016 for International application No. PCT/GB2016/051773.

International Search Report dated Sep. 6, 2016for International application No. PCT/GB2016/051770.

International Search Report dated Feb. 2, 2017 for International application No. PCT/GB2016/053620.

International Search Report dated Mar. 6, 2017 for International Application No. PCT/GB2016/053677.

International Search Report dated Aug. 24, 2018 for International Application Serial No. PCT/EP2018/065809, (6 pages).

International Search Report for International Application No. PCT/GB2012/051686 dated Jan. 31, 2013.

International search report with written opinion dated Feb. 26, 2018 for PCT/GB2017/053722.

International search report with written opinion dated Jun. 8, 2017 for GB Application No. 1616016.

International search report with written opinion dated Sep. 29, 2017 for GB Application No. 1621123.

International search report with written opinion dated Oct. 16, 2017 for PCT/GB2017/052076.

(56) References Cited

OTHER PUBLICATIONS

Inturri, R., Molinaro, A., Di Lorenzo, F., Blandino, G., Tomasello, B., Hidalgo-Cantabrana, C., et al. (2017). Chemical and biological properties ofthe novel exopolysaccharide produced by a probiotic strain of Bifidobacterium longum. Carbohydr Polym 174, 1172-1180. doi: 10.1016/j.carbpol.2017.07.039.

Ishikawa, et al., Effect of bifidobacteria to suppress Th17, Food Science and technology institute, 2008, 5 Pages.

Ispirli, H. et al., Characterization of functional properties of Enterococcus faecium strains isolated from human gut.Can. J. Microbiol. 61: 861-870 (2015) dx.doi.org/10.1139/cjm-2015-0446.

Israel, E. et al., Supplementary Appendix, Severe and difficult-to-treat asthma in adults. N. Engl J Med 2017;p. 377:965-76. DOI: 10.1056/NEJMra1608969.

Israel, et al., Severe and difficult-to-treat asthma in adults, The New England Journal of Medicine, Sep. 2017; 377(10):965-976.

Issue Notification dated Feb. 20, 2019 for Co-Pending U.S. Appl. No. 15/631,945.

Ito et al. (1983) "Transformation of Intact Yeast Cells Treated with Alkali Cations," J. Bacteriology. 153:163-168.

Ivanov, D., Emonet, C., Foata, F., Affolter, M., Delley, M., Fisseha, M., et al. (2006). A serpin from the gut bacterium Bifidobacterium longum inhibits eukaryotic elastase-like serine proteases. J Biol Chem 281(25), 17246-17252. doi: 10.1074/jbc.M601678200.

Ivanov et al. 'Induction of intestinal Th17 cells by segmented filamentous bacteria.' Cell. 2009, vol. 139, No. 3, pp. 485-498.

Jackson MS, Bird AR, McOrist AL. Comparison of two selective media forthe detection and enumeration of Lactobacilli in human faeces (2002). J Microbial Methods. 51 (3), pp. 313-321.

Jacobs, S. A., Huang, F., Tsien, J. Z. and Wei, W. (2016). Social Recognition Memory Test in Rodents. Bio-protocol 6(9): e1804. DOI:10.21769/BioProtoc.1804.

Jagveer Singh et al., "Bifidobacterium longum, a lactic acid-producing intestinal bacterium inhibits colon cancer and modulates the intermediate biomarkers of colon carcinogenesis", Carcinogenesis vol. 18 No. 4 pp. 833-841, 1997.

Jarchum et al., "Toll-Like Receptor 5 Stimulation Protects Mice from Acute Clostridium difficile Colitis," Infection and Immunity. Apr. 2011; 79(4):1498-1503.

Jawad, S. et al., Elevated serum levels of interleukin-17A in uveitis patients.Ocul Immunol Inflamm. Dec. 2013;21(6):434-9. doi: 10.3109/09273948.2013.815786. Epub Aug. 19, 2013.

Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.

Jeon, Byoung Seung, "Production of hexanoic acid from D-galactitol by a newly isolated *Clostridium* sp. BS-1", 2010, Appl Microbiol Biotechnol, 88 (5) 1161-1167.

Jeon, Byoung Seung et al., "*Megasphaera hexanoica* sp. nov., a medium-chain carboxylic acid-producing bacterium isolated from a cow rumen", 2017, International Journal of Systematic and Evolutionary Microbilogy, 67, 2114-2120.

Jeon, Byoung Seung et al., "Production of medium-chain carboxylic acids by *Megasphaera* sp. MH with supplemental electron acceptors", Biotechnology for Biofuels, 2016, 9, 129.

Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714.

Jiao et al., Blockade of Notch Signaling Ameliorates Murine Collagen-Induced Arthritis via Suppressing Th1 and Th17 Cell Responses. 2014; Pathology, 184(4):1085-1093.

Joblin K N., "Ruminal Acetogens and Their Potential to Lower Remnant Methane Emissions." Australian Journal of Agricultural Research, vol. 50. No. 8. 1999, pp. 1307-1313. XP001010439.

Johnsen, Lea G. et al., "Gas chromatography—mass spectrometry data processing made easy", Journal of Chromatography A. 2017, 1503: 57-64.

Kadi Linda et al. "Differential effects of chemokines on oligodendrocyte precursor proliferation and myelin formation in vitro", Journal of Neuroimmunology, 2006, 174:133-146.

Kailasapathy, K. Microencapsulation of Probiotic Bacteria:Technology and Potential Applications. Curr. Issues Intest. Microbiol. (2002) 3: 39-48.

Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.

Kanauchi, et al., Eubacterium limosum (probiotic) and its metabolites showed anti-inflammatory effects and increased mucosal barrier function in colitis. Gastroenterology, 2005;128: p. A281, XP009193489.

Kang and Kim, 2015, "Suppression of NMDA receptor function in mice prenatally exposed to valproic acid improves social deficits and repetitive behaviors", Frontiers in Molecular Neuroscience, 2015, 8:(17), 1-9.

Kang et al. (2010) "Dysbiosis of fecal microbiota in Crohn's disease patients as revealed by a custom phylogenetic microarray," Inflammatory Bowel Diseases. 16(12):2034-2042.

Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.

Kantak PA et al., "Obsessive-compulsive-like behaviors in house mice are attenuated by a probiotic (*Lactobacillus rhamnosus* GG)", Behav Pharmacol. Feb. 2014;25(1):71-9. doi: 10.1097/FBP.0000000000000013.

Karaffova, et al., Interaction of TGF-B4 and IL-17 with IgA secretion in the intestine of chickens fed with E. faecium AL41 and challenged with S. Enteritidis. Research in Veterinary science. 2015:75-79.

Kari Shoaf et al., "Prebiotic Galactooligosaccharides Reduce Adherence of Enteropathogenic *Escherichia coli* to Tissue Culture Cells", Infection and Immunity, Dec. 2006, vol. 74. No. 12, p. 6920-6928.

Karin, M. Nuclear factor-kappaB in cancer development and progression. Nature. May 25, 2006;441(7092):431-6.

Kehr J., "Monitoring chemistry of brain microenvironment: biosensors, microdialysis and related techniques", 1999, Chapter 41. In: Modern techniques in neuroscience research. (Eds. U. Windhorst and H. Johansson) Springer-Verlag GmbH., Heidelberg, Germany. 1149-1198.

Keller et al.. "DNA Probes", 1994. Stockton Press. New York. XP002158943 108660 pp. 594-596.

Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.

Kelly, et al., Commensal gut bacteria: mechanisms of immune modulation. TRENDS in immunology, 2005;26(6):326-333.

Kenealy and Weimer, "Production of caproic acid by cocultures of ruminal cellulolytic bacteria and Clostridium Kluyveri grown on cellulose and ethanol", 1995, Appl Microbial Cell Physiol, 44, 507-513.

Kingsley M. A Personalized Approach to Managing 18D. Gastroenterology and Hepatology 12(5)308-315, May 2016.

Kinnebrew et al., Interleukin 23 production by intestinal CD1 03(+)CD11 b(+) dendritic cells in response to Interleukin 23 production by intestinal CD1 03(+ )CD11 b(+) dendritic cells in response to bacterial flagellin enhances mucosal innate immune defense, Immunity. 2012; 36(2): 276-287.

Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x.

Kirsty Minton: Mucosal immunology: The ins and outs of gut inflammation, The journal of immunology, 4(2), Feb. 1, 2004: pp. 81-81, XP055252701.

Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001.

(56) References Cited

OTHER PUBLICATIONS

Kitahara et al., *Bacteroides plebeius* sp. nov. and *Bacteroides coprocola* sp. nov., isolated from human faeces, 2005; Int J Syst Ev Microbiol 55: 2143-47.

Kitahara, M. et al., *Bacteroides plebeius* sp. nov. and *Bacteroides coprocola* sp. nov., isolated from human faeces. International journal of systematic and evolutionary microbiology. 2005; 55: 2143-2147.

Kitahara, Maki et al., *Bateroides plebeius* sp. nov. and *Bacteroides coprocola* sp. nov., isolated from human faeces, International Jounal of systematic and Evolutionary Microbiology, (2005), vol. 55, 2143-2147, DOI 10.1099/ijs.063788.0.

Koenders, M.I. et al., Interleukin-17 Acts Independently of TNF-a under Arthritic Conditions. (2006) J. Immunol. 176:6262-6269.

Kogyo, S. Lactic Acid Bacteria, Intestinal Flora ad Health II; Physiological effects of heat-treated lactococcus "EF-2001" and application to food. Mar. 30, 2001, vol. 44, No. 6, pp. 35-39.

Kondziella, W, "A New Method for the Measurement of Muscle Relaxation in White Mice" Arch Int Pharmacodyn Ther. Dec. 1, 1964;152:277-84.

Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.

Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.

Kverka, M. et al., Oral administration of Parabacteroides distasonis antigens attenuates experimental murine colitis through modulation of immunity and microbiota composition. Clinical & Experimental Immunology. 2010; 163:250-259.

Laetitia Rodes et al., "Microencapsulated *Bifidobacterium longum* subsp. infantis ATCC 15697 Favorably Modulates Gut Microbiota and Reduces Circulating Endotoxins in F344 Rats", BioMed Research International, vol. 2014, Article ID 602832,11 pages.

Lahteinen, T., et al., A Pro biotic properties of Lactobacillus isolates originating from porcine intestine and feces (20 10) Anaerobe, 16 (3), pp. 293-300.

Lakhdari, et al. Identification of NF-KB Modulation Capabilities within Human Intestinal Commensal Bacteria. J Biomed Biotechnol. 2011; 2011: 282356.

Lapadula, G. et al., "Adalimumab in the Treatment of Immune-Mediated Diseases", International Journal of Immunopathology and Pharmacology, 2014, vol. 27, No. 1(s), 33-48.

Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.

Laureen Crouzet et al., "The altered gut microbiota of IBS patients plays a key role in visceral hypersensitivity: specific role of sulphate-reducing bacteria", INRA Symposium, 2012.

Lavallie et al. (1995) "Gene fusion expression systems in *Escherichia coli*," Current Opinion Biotechnology. 6 (5):501-506.

Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.

Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x.

Lebeer, S., Verhoeven, T.L., Francius, G., Schoofs, G., Lambrichts, I., Dufrene, Y., et al. (2009). Identification of a Gene Cluster for the Biosynthesis of a Long, Galactose-Rich Exopolysaccharide in Lactobacillus rhamnosus GG and Functional Analysis of the Priming Glycosyltransferase. Appl Environ Microbiol 75(11), 3554-3563. doi: 10.1128/AEM.02919-08.

Lee Do Yeon et al., "Kynurenic acid attenuates MPP-induced dopaminergic neuronal cell death via a Bax-mediated mitochondrial pathway",2008, European Journal of Cell Biology 87:389-397.

Lee, et al. Intestinal microbiota in pathophysiology and management of irritable bowel syndrome . 2014. World J Gastroenterol. 20(27): 8886-8897.

Lejeune et al. Efficiency of Recombinant Human TNF in Human Cancer Therapy. Cancer Immun. 6:6 (2006).

Leser et al. 'Culture-independent analysis of gut bacteria: the pig gastrointestinal tract microbiota revisited'. Applied and Environmental Microbiology. 2002, vol. 68, No. 2, pp. 673-690.

Leslie, et al., Trehalose and sucrose protect both membranes and proteins in intact bacteria during drying. (1995) Appl. Environ. Microbiol. 61, 3592-3597.

Letran et al. 'TLR5-deficient mice lack basal inflammatory and metabolic defects but exhibit impaired CD4 T cell responses to a flagellated pathogen.' The Journal of Immunology. 2011, vol. 186, No. 9, pp. 5406-5412.

Li, C.Y., Lin He Fau-Lai, C.-H., Lai Ch Fau-Lu, J.J.-Y., Lu Jj Fau-Wu, S.-F., Wu Sf Fau-Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.

Li, et al,. Screening and Identification of Lactobacillus animalis strain and characteristics of its bacteriostatic protein, Weishengwuxue Tongbao 2009; 36(7): 1001-1007.

Li Q et al., "The microbiota-gut-brain axis and its potential therapeutic role in autism spectrum disorder", Neuroscience. Jun. 2, 2016;324:131-9. doi: 10.1016/j.neuroscience.2016.03.013. Epub Mar. 8, 2016.

Lilley et al., Methods in Enzymology; DNA Structure Part A: Synthesis and Physical Analysis of DNA. 1992; vol. 2011. pp. v-vii.

Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.

Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., Blautia hansenii comb. nov., Blautia hydrogenotrophica comb. nov., Blautia luti comb. nov., Blautia producta comb. nov., Blautia schinkii comb. nov. and description of *Blautia wexlerae* sp. nov., isolated from human faeces. 2008. Int J Syst Evol Microbiol 58,1896-1902.

Liu, Y., et al., Human-derived probiotic Lactobacillus reuteri strains differentially reduce intestinal inflannuation (20 10). American Journal of Physiology—Gastrointestinal and Liver Physiology, 299 (5), pp. G1087-G1096.

Ljungh, A, Wadstrorn, T. Lactic acid bacteria as probiotics (2006). Current Issues in Intestinal Microbiology, 7 (2), pp. 73-90.

Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.

Lopetuso et al. Commensal Clostridia: leading players in the maintenance of gut homeostasis. 2013. Gut Pathogens, 5: 23.

Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11.

Lopez-Boado, Y. S. et al., Bacterial Exposure Induces and Activates Matrilysin in Mucosal Epithelial Cells. J Cell Biol148, 1305-1315 (2000).

Louis et al. 'Diversity, metabolism and microbial ecology of butyrate-producing bacteria from the human large Intestine.' FEMS Microbiology Letters. 2009, vol. 294, No. 1, pp. 1-8.

Louis et al. 'Diversity of human colonic butyrate-producing bacteria revealed by analysis of the butyryl-GoA: acetate GoA-transferase gene.' Environmental Microbiology. 2010, vol. 12, No. 2, pp. 304-314.

(56) References Cited

OTHER PUBLICATIONS

Louis et al. 'Organization of butyrate synthetic genes in human colonic bacteria: phylogenetic conservation and horizontal gene transfer.' FEMS Microbiology Letters. 2007, vol. 269, No. 2, pp. 240-247.

Lozupone. Diversity, stability and resilience of the human gut microbiota. 2012. Nature. Sep. 13, 2012; 489 (7415): 220-230.

López, P., González-Rodríguez, I., Gueimonde, M., Margolles, A., and Suarez, A. (2011). Immune Response to Bifidobacterium bifidum Strains Support Treg/Th17 Plasticity. PLOS ONE 6(9), e24776. doi: 10.1371/journal.pone.0024776.

López, P., Gueimonde, M., Margolles, A., and Suárez, A. (2010). Distinct Bifidobacterium strains drive different immune responses in vitro. International Journal of Food Microbiology 138(1), 157-165. doi: https://doi.org/10.1016/j.ijfoodmicro.2009.12.023.

Ludolph, A C et al. "Tauopathies with parkinsonism: clinical spectrum, neuropathologic basis, biological markers, and treatment options." European journal of neurology vol. 16,3 (2009): 297-309. doi:10.1111/j.1468-1331.2008.02513.x.

Luger, D. and Caspi, R.R., New perspectives on effector mechanisms in uveitis. (2008) Semin. Immunopathol. 30(2): 134-143.

Álvarez-Martin, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/s00253-007-1115-5.

Lyons, et al., Bacterial strain-specific induction of Foxp3 T regulatory cells is protective in murine allergy models. Clinical & Experimental Allergy. 2010; 40:811-819.

Machiels, et al., Predominant dysbiosis in patients with ulcerative colitis is different from Crohn's disease patients, Inflammatory Bowel Diseases, Microbiology 2012. 8th Congress of ECCO. (This Abstract is in 7th Congress 2012).

Machiels, K. A decrease of the butyrate-producing species Roseburia hominis and Faecalibacterium prausnitzii defines dysbiosis in patients with ulcerative colitis.Gut. Aug. 2014;63(8):1275-83. doi: 10.1136/gutjnl-2013-304833. Epub Sep. 10, 2013.

Macpherson, AJ. et al., IgA responses in the intestinal mucosa against pathogenic and non-pathogenic microorganisms. Oct. 2001. 3(12). 1021-1035.

Macpherson, AJ., et al., The functions of mucosal T cells in containing the indigenous commensal flora of the intestine.Cell Mol Life Sci. Dec. 2002;59(12):2088-96.

Macpherson et al. 'IgA adaptation to the presence of commensal bacteria in the intestine.' Gut-Associated Lymphoid Tissues. Springer Berlin Heidelberg, 2006. 117-136.

Macsharry et al., Immunomodulatory effects of feeding with bifidobacterium longum on allergen-induced lung inflammation in the mouse. Pulmonary pharmacology & Therapeutics. 2012;25:325-334.

Mahowald et al. 'Characterizing a model human gut microbiota composed of members of its two dominant bacterial phyla.' Proceedings of the National Academy of Sciences. 2009, vol. 106, No. 14, pp. 5859-5864.

Maintaining Cultures for Biotechnology and Industry (1996) Jennie C. Hunter-Cevera, Academic Press.

Mallya et al. 'Characterization of the five novel Ly-6 superfamily members encoded in the MHC, and detection of cells expressing their potential ligands.' Protein Science. 2006, vol. 15, No. 10, pp. 2244-2256.

Manczak, Maria et al., "Differential Expression of Oxidative Phosphorylation Genes in Patients with Alzheimer's Disease",2004, NeuroMolecular Medicine, vol. 5, 147-162.

Manni et al., A tale of two cytokines: IL-17 and IL-22 in asthma and infection. Expert Rev Respir Med. Feb. 2014 ; 8(1): 25-42. doi:10.1586/17476348.2014.854167.

Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.

Martin et al., Cloning, Nucleotide Sequence, and Taxonomic Implications of the Flagellin Gene of Roseburia cecicola, Journal of Bacteriology. Jun. 1988; 170(6):2612-2617.

Martin R. et al., Isolation of lactobacilli from sow milk and evaluation of their probiotic potential. J of dairy research 76(4)418-425. Nov. 2009.

Masco, L., et al., Identification of Bifidobacterium Species Using rep-PCR Fingerprinting. Systematic and Applied Microbiology 26(4):557-63 • Dec. 2003.

Matsuda F et al: Evaluation of a probiotics,BBG-01, for enhancement of immunogenicity of an oral inactivated cholera vaccine and safety: A randomized, double-blind, placebo-controlled trial in Bangladeshi children under 5 years of age,Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.

Matthes, et al., Simultaneous rapid chemical synthesis of over one hundred oligonucleotides on a microscale. Apr. 1984. EMBO Journal, 3(4): p. 801-805.

Maya, J.R. et al., Emerging Therapies for Noninfectious Uveitis: What May Be Coming to the Clinics. (2014) J. Ophthalmology. 310329.

Mayer, Emeran A. et al., "Gut Microbes and the Brain: Paradigm Shift in Neuroscience", Journal of Neuroscience Nov. 12, 2014, 34 (46) 15490-15496; DOI: https://doi.org/10.1523/JNEUROSCI.3299-14.2014.

Mazmanian et al. 'An immunomodulatory molecule of symbiotic bacteria directs maturation of the host immune system.' Cell. 2005, vol. 122, No. 1, pp. 107-118.

Mazmanian, SK., An immunomodulatory molecule of symbiotic bacteria directs maturation of the host immune system.Cell. Jul. 15, 2005;122(1):107-18.

McCarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17.

McClymont, S.A., Putnam Al Fau-Lee, M.R., Lee Mr Fau-Esensten, J.H., Esensten Jh Fau-Liu, W., Liu W Fau-Hulme, M.A., Hulme Ma Fau-Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.

Mcintosh et al. 'Mechanism of conjugated linoleic acid and vaccenic acid formation in human faecal suspensions and pure cultures of intestinal bacteria.' Microbiology. 2009, vol. 155, No. 1, pp. 285-294.

Mclaughlin., "Mclaughlin et al. Fatty acid chain length determines cholecystokinin secretion and effect on human gastric motility. Gastroenterology. 1999, vol. 116, No. 1, pp. 46-53".

Menard, S., Laharie D Fau-Asensio, C., Asensio C Fau-Vidal-Martinez, T., Vidal-Martinez T Fau-Candalh, C., Candalh C Fau-Rullier, A., Rullier A Fau-Zerbib, F., et al. (2005). Bifidobacterium breve and Streptococcus thermophilus secretion products enhance T helper 1 immune response and intestinal barrier in mice. Experimental Biology and Medicine (Maywood) 230(10), 749-756.

Meyer et al. (1992) "The use of cassava mosaic virus as a vector system for plants," Gene. 110:213-217.

Meyza, et al. The BTBR mouse model of idiopathic autism—Current view on mechanisms. 2017. Neurosci Biobehav Rev.;76(Pt A):99-110.

Michel and Prat, "One more role for the gut:microbiota and blood brain barrier", 2016, Ann Transl Med. 4(1): 15.

Mikayama, et al., Molecular cloning and functional expression of a cDNA encoding glycosylation-inhibiting factor. Proc.Nati.Acad. Sci. USA, Nov. 1993; vol. 90: 10056-1 0060.

Milani, C., Mangifesta, M., Mancabelli, L., Lugli, G.A., Mancino, W., Viappiani, A., et al. (2017). The Sortase-Dependent Fimbriome of the Genus Bifidobacterium: Extracellular Structures with Potential To Modulate Microbe-Host Dialogue. Appl Environ Microbiol 83(19). doi: 10.1128/AEM.01295-17.

(56) References Cited

OTHER PUBLICATIONS

Mincheol Kim et al., "Towards a taxonomic coherence between average nucleotide identity and 16S rRNA gene sequence similarity for species demarcation of prokaryotes", International Journal of Systematic and Evolutionary Microbiology (2014), 64, 346-351.
Miossec et al., Targeting IL-17 and TH17 cells in chronic inflammation, 2012; Nature Drug Discovery 11, 763-776.
Miossec, P. et al. Targeting IL-17 and TH17 cells in chronic inflammation. Nat Rev Drug Discov. Oct. 2012;11(10):763-76. doi: 10.1038/nrd3794.
Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.
Mitropoulou, G. et al. Immobilization Technologies in Probiotic Food Production. (2013) Journal Nutr Metab. (2013) 716861.
Miyake, et al., Phylogenetic analysis of the genus bifidobacterium and related genera based on 16S rDNA sequences. Microbiol. Immunol. 1998; 42(10): 661-667.
Miyake, T. et al., Phylogenetic Analysis of the Genus *Bifidobacterium* and Related Genera Based on 16S rDNA Sequences. Microbiol. Immunol. 1998; 42(10):661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques, 1st edition. An intensive laboratory course. 1998.
Monteleone et al., IL-10-dependent partial refractoriness to Toll-like receptor stimulation modulates gut mucosal dendritic cell function, European Journal of Immunology. 2008; 38(6):1533-1547.
Monteleone, I. et al., Th17-related cytokines: new players in the control of chronic intestinal inflammation. (2011) BMC Medicine. 2011, 9:122.
Mortaz, E. et, al., Anti-Inflammatory Effects of Lactobacillus Rahmosus and Bifidobacterium Breve on Cigarette Smoke Activated Human Mcrophiages, PLoS ONE, Apr. 21,20i15, 10(8):e0136455.DOI:10.1371, Journal.pone.0136455.
Moss and Nunez-Montiel, "Analysis of Short-Chain Acids from Bacteria by Gas-Liquid Chromatography with a Fused-Silica Capillary Column",1982, Journal of Clinical Microbiology, 15(2) 308-311.
Moss, C. Wayne, "Production of Phenylacetic and Hydroxyphenylacetic Acids by Clostridium botulinum Type G", 1980, J Clin Microbiol, 11(6), 743-745.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS ONE 9(8): 6105518.
Mulder et al. 'Environmentally-acquired bacteria influence microbial diversity and natural innate immune responses at gut surfaces'. Bmc Biology. 2009, vol. 7, No. 1, pp. 79.
Murofushi, Y., Villena, J., Morie, K., Kanmani, P., Tohno, M., Shimazu, T., et al. (2015). The toll-like receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027.
Narushima, et al., Characterization of the 17 strains of regulatory T cell-inducing human-derived Clostridia. Gut Microbes Mar. 18, 2014; 5:3, 333-339.
Naughton PJ; Grant G. (2005) Modelling of salmonellosis In: Microbial Ecology of the Growing Animal Holzapfel WH, Naughton PJ. (Eds). London, Elsevier, pp. 235-257.
NCBI Reference Sequence: NR_026314.1, Blautia hydrogenotrophica strain S5a36 16S ribosomal RNA gene, partial sequence (Feb. 3, 2015), 3 pages.
NCBI Reference Sequence: NR_041278.1, Bacteroids coprocola strain M16165 ribosomal RNA gene, partial sequence. Aug. 8, 2011 National Center for Biotechnology Information, NIH.
Neeser, J.R., et al., Lactobacillus johnsonii Lal shares carbohydrate-binding specificities with several enteropathogenic bacteria (2000). Glycobiology, 10 (II), pp. II93-II99.
Neilson and Allard, "Aliphatic Compounds",Organic Chemicals in The Environment, Mechanisms of Degradation and Transformation 2nd Ed 2013, p. 655.
Neilson and Allard, "Halogenated Arenes and Carboxylates with Chlorine, Bromine, or Iodine Substituents", 2013, Organic Chemicals in The Environment, Mechanisms of Degredation and Transformation 2nd Ed, p. 851.
Neish, A. S. et al., Prokaryotic Regulation of Epithelial Responses by Inhibition of IκB-α Ubiquitination. Science 289, 1560 (2000).
Neish et al., TLRS in the Gut. II. Flagellin-induced inflammation and antiapoptosis, American Journal of Physiology—Gastrointestinal and Liver Physiology. 2007;292:G462-466.
Nelson, Robert S. et al., "Mixed Carboxylic Acid Production by Megasphaera elsdenni from Glucose and Lignocellulosic Hydrolysate", 2017 Fermentation, 3, 10.
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274.
Neville, B.A., Functional genomics of motile commensal intestinal bacteria. PhD Thesis. University College Cork. 2013. 281 Pages.
Neville, et al., Characterization of pro-inflammatory flagellin proteins produced by Lactobacillus ruminis and related motile Lactobacilli. PloS one. Jul. 2012;7(7):e40592.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.
Ng et al., Archaeal flagella, bacterial flagella and type IV pili: a comparison of genes and posttranslation modification, Journal of Molecular Microbiology and Biotechnology. 2006;11:167-191.
Nicolau, D.P. Current challenges in the management of the infected patient (20II). Current Opinion in Infectious Diseases, 24 (Suppll), pp. SI-S10.
Non-Final Office Action dated Oct. 8, 2019 for U.S. Appl. No. 16/265,238.
Non-Final Office Action dated Oct. 9, 2019 for U.S. Appl. No. 15/969,543.
Notice of Allowance dated Feb. 3, 2016 for U.S. Appl. No. 14/349,907.
Notice of Allowance dated Mar. 6, 2017 for U.S. Appl. No. 14/249,710.
Notice of Allowance dated Mar. 30, 2011 for U.S. Appl. No. 10/285,224.
Notice of Allowance dated Apr. 25, 2016 for U.S. Appl. No. 14/232,475.
Notice of allowance dated Jun. 16, 2017 for U.S. Appl. No. 14/249,710.
Notice of Allowance dated Aug. 23, 2016 for U.S. Appl. No. 14/232,475.
Notice of allowance dated Sep. 1, 2017 for U.S. Appl. No. 15/357,850.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 22, 2017 for U.S. Appl. No. 15/359,988.
Notice of Allowance dated Nov. 24, 2017 for U.S. Appl. No. 15/070,605.
Notice of Publication dated Dec. 27, 18 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in

(56) References Cited

OTHER PUBLICATIONS

SCID Mice through Promoting CXCR-2-Dependent Angiogenesis. (2005) J. Immunol. 175: 6177-6189.

Numasaki, M. et al., Interleukin-17 promotes angiogenesis and tumor growth. Blood. Apr. 1, 2003;101(7):2620-7. Epub Oct. 31, 2002.

Nutsch et al., T cell tolerance and immunity to commensal bacteria. Current Opinion in Immunology. Aug. 2012; 24 (4):385-391.

O'Connell Motherway, M., Kinsella, M., Fitzgerald, G.F., and Sinderen, D. (2013). Transcriptional and functional characterization of genetic elements involved in galactooligosaccharide utilization by Bifidobacterium breve UCC2003. Microbial biotechnology 6(1), 67-79. doi: 10.1111/1751-7915.12011.

O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x.

O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci U S A 108(27), 11217-11222. doi: 10.1073/pnas.1105380108.

Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5.

Odile Menard et al, "Gnotobiotic Mouse Immune Response Induced by *Bifidobacterium* sp. Strains Isolated from Infants", Applied and Environmental Microbiology, Feb. 2008, p. 660-666.

Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Office Action dated Mar. 19, 2019 for U.S. Appl. No. 16/031,024.

Ohashi, Y., Ushida, K. Health-beneficial effects of probiotics: Its mode of action (2009). Animal Science Journal, 80 (4), pp. 361-371.

Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.

Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609.

Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325.

O'Sullivan et al., "Bacterial Supplementation in the Irritable Bowel Syndrome. A Randomised Double-Blind Placebo-Controlled Crossover Study", Digest Liver Dis. 2000. pp. 294-301.

Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.

Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-696.

Pace et al. Macrophage activiation: Priming activity from a T-cell hybridoma is attributable to interferon. (1983) PNAS. 80:3782-6.

Package leaflet: Information forthe patient; Humira 20 mg solution for injection in pre-filled sringe, adalimumab, last revised Mar. 2019, 18 pages.

Package leaflet: Information for the user, Remicade 100 mg powder for concentrate for solution for infusion, infliximab, last revised in Mar. 2019, 12 pages.

Package Leaflet: Information for the user, Simponi 100 mg solution for injection in pre-filled pen, golimumab, last revised in Apr. 2019,17 pages.

Padmanabhan, Roshan et al., "Non-contiguous finished genome sequence and description of *Megasphaera massiliensis* sp.nov.", 2013, Standards in Genomic Sciences 8:525-538.

Pakkenberg, B et al. "The absolute number of nerve cells in substantia nigra in normal subjects and in patients with Parkinson's disease estimated with an unbiased stereological method." Journal of neurology, neurosurgery, and psychiatry vol. 54,1 (1991): 30-3. doi:10.1136/jnnp.54.1.30.

Pal Rishi et al., "Role of neuroinflammation and latent transcription factors in pathogenesis of Parkinson's disease", Neurological Research, 2016, 38(12), 1111-1122.

Pang, et al., Crystal structure of human pirin: an iron-binding nuclear protein and transcription cofactor. Journal of Biological Chemistry, 279(2); Jan. 9, 2004:1491-1498.

Parabacteroides distasonis (Eggerth and Gagnon) Sakamoto and Benno (ATCC 8503). Sep. 19, 2017. 2 Pages.

Parfenov A.I., "Pain syndrome in the practice of a gastroenterologist", RMJ Breast Cancer, 2008; 0: 32.

Park, Jieun et al., Neuroprotective effect of Ruminococcus albus on oxidatively stressed SH-SY5Y cells and animals, 2017, Scientific Reports, 7:14520:DOI 10.1038/s41598-017-15163-57.

Park, S.K. et al., *Blautia stercoris* sp. nov., isolated from human faeces. International journal of systematic and evolutionary microbiology. 2012; 62(4): 776-779.

Patel., R. et al., Determination of 16S rRNA sequences of enterococci and application to species identification of nonmotile enterococcus gallinarum isolates. Journal of clinical microbiology, 1998; 36(11):3399-3407.

Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804.

PCR (Introduction to Biotechniques Series), 2nd ed. (Newton & Graham eds., 1997, Springer Verlag).

PCT/EP2017/025038 International Preliminary Report on Patentability dated Jun. 6, 2018, 8 Pages. .

PCT/EP2017/025038 International Search Report and Written Report dated Jun. 12, 2017.

PCT/EP2017/025038 Written Opinion of the International Preliminary Examining Authority dated Jan. 1, 2018.

(56) References Cited

OTHER PUBLICATIONS

PCT/EP2017/025038 Written Opinion of the International Preliminary Examining Authority dated Jan. 25, 2018.
PCT/GB2017/052076 Written Opinion ofthe International Preliminary Examining Authority dated Jun. 21, 2018, 11 Pages.
PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Pearson, WR. An introduction to sequence similarity ("Homology") searching. Current protocols in bioinformatics/editoral board, Andreas D Baxevanis. [et al], 2013; 0 3:10. 1002/0471250953.bi0301s42. doi:10.1002/0471250953.bi0301s42.
Pedro Berraondo et al., "Cytokines in clinical cancer immunotherapy", British Journal of Cancer, 2019, 120:6-15.
Petersen et al. Intestinal colonization with phylogenetic group B2 *Escherichia coli* related to inflammatory bowel disease: a systematic review and meta-analysis. 2015. Scand J Gastroenterol.;50(10): 1199-207.
Peterson et al. 'Catecholamines increase conjugative gene transfer between enteric bacteria.' Microbial Pathogensis. 2011, vol. 51, No. 1, pp. 1-8.
Petsuriyawong et al. 'Screening of probiotic lactic acid bacteria from piglet feces'. Nature Science. 2011, vol. 45, pp. 245-253.
Ping Dong et al., "The role of intestinal bifidobacteria on immune system development in young rats", Early Human Development 86 (2010) 51-58.
Pinto-Sánchez, M.I., Smecuol, E.C., Temprano, M.P., Sugai, E., González, A., Moreno, M.L., et al. (2017). Bifidobacterium infantis NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Pirooznia, Sheila K, and Felice Elefant. "Targeting specific HATs for neurodegenerative disease treatment: translating basic biology to therapeutic possibilities." Frontiers in cellular neuroscience vol. 7 30. Mar. 28, 2013, doi: 10.3389/fncel.2013.00030.
Polak J.M. and McGee J.O., In Situ Hybridization: Principles and Practice, Oxford University Press. 1990; pp. vii-viii.
Potrykus (1991) "Gene Transfer to Plants: Assessment of Published Approaches and Results," Annu. Rev. Plant Physiol. Plant Mol. Biol. 42:205-225.
Prakash, et al., Complete genome sequences of rat and mouse segmented filamentous bacteria, a potent inducer of th17 cell differentiation. Cell Host & Microbe. Sep. 2011;10(3):273-284.
Prospective Studies Collaboration, "Cholesterol, diastolic blood pressure, and stroke: 13,000 strokes in 450,000 people in 45 prospective cohorts. Prospective studies collaboration", Lancet. Dec. 23-30, 1995;346(8991-8992):1647-53.
Pryde et al. 'The microbiology of butyrate formation in the human colon.' FEMS Microbiology Letters. 2002. vol. 217,No. 2, pp. 133-139.
Przedborski, Serge et al., "The parkinsonian toxin MPTP: action and mechanism", Restorative Neurology and Neuroscience, 2000, 16(2):135-142.
Psaty BM et al, "Health outcomes associated with various antihypertensive therapies used as first-line agents: a network meta-analysis.",JAMA. May 21, 2003;289(19):2534-44.
Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Rajilic-Stojanovic, et al. The first 1000 cultures species of the human gastrointestinal micriobiota. FEMS Mlcriobiol Rev, vol. 38, 2014. pp. 996-1047.
Reddy, K.B.P.K., et al., Role of cryoprotectants on the viability and functional properties of probiotic lactic acid bacteria during freeze drying (2009). Food Biotechnology, 23 (3), pp. 243-265.

Reiff,C. and Kelly,D.,Inflammatory bowel disease, gut bacteria and probiotic therapy. International journal of medical microbiology, 2010;300:25-33.
Remicade 100mg powder for concentrate for solution for infusion— Summary of Product Characteristics, accessed Oct. 25, 2019, 28 pages.
Reuter, G. (2001). The Lactobacillus and Bifidobacterium microflora of the human intestine: composition and succession. Current Issues in Intestinal Microbiology 2(2), 43-53.
Rhee et al.,Toll-Like Receptor 5 Engagement Modulates Tumor Development and Growth in a Mouse Xenograft Model of Human Colon Cancer. Gastroenterology. Aug. 2008;135(2):518-528.
Rhee, Young-Kyung et al.., Antihumor Activity of *Bifidobacterium* Spp. isolated from a healthy Korean, Arch Pharm Res vol. 23, No. t, 482-487 2000.
Riedel, Thomas et al., "High metabolic versatility of different toxigenic and non-toxigenic Clostridioides Difficile isolates", 2017, International Journal of Medicine Microbiology, 307(6), 311-320.
Riquelme. Will 4D Pharma be UK's next Microbiome leader? Feb. 2, 2015, LABIOTECH.eu [online].
Robertson, J.M.C., et al., Lack of flagella disadvantages *Salmonella enterica* serovar Enteritidis during the early stages of infection in the rat (2003). Journal of Medical Microbiology, 52 (1), pp. 91-99.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Roddick and Britz, "Production of Hexanoic Acid by Free and Immobilised Cells of Megasphaera elsdenii: Influence of in-situ Product Removal Using Ion Exchange Resin", 1999, Chem Technol and Biotech, 69 (3), 383-391.
Roe, et al., DNA Isolation and Sequencing: Essential Techniques. John Wiley & Sons, New York, New York. 1996; pp. v-vii.
Rong, Y., Dong, Z., Hong, Z., Jin, Y., Zhang, W., Zhang, B., et al. (2017). Reactivity toward Bifidobacterium longum and Enterococcus hirae demonstrate robust CD8(+) T cell response and better prognosis in HBV-related hepatocellular carcinoma. Experimental Cell Research 358(2), 352-359. doi: 10.1016/j.yexcr.2017.07.009.
Roseburia. Ubiome, 2018. Accessed on Jun. 25, 2018; Available at: https://shop.ubiome.com/pages/roseburia-1.
Round et al. 'The Toll-like receptor 2 pathway establishes colonization by a commensal of the human microbiota.' Science. 2011, vol. 332, No. 6032, pp. 974-977.
Rudinger J, "Characteristics of the amino acids as components of a peptide hormone sequence," Peptide Hormones, JA Parsons Edition, University Park Press, Jun. 1976, pp. 1-7.
Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb. 2016.01193.
Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.
Russell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.
Russell, Wendy R. et al., "Major phenylpropanoid-derived metabolites in the human gut can arise from microbial fermentation of protein", 2013, Mol Nutr Food Res, 57(3), 523-535.
Sagar, et al., Bifidobacterium breve and lactobacillus rhamnosus treatment is as effective as budesonide at reducing inflammation in a murine model for chronic asthma. Respiratory Research. 2014; 15(46):1-17.
Saiki, et al., Primer-directed enzymatic amplification of DNA with a thermostable DNA polymerase. 1988. Science, 239. pp. 487-491.
Sakamato, et al., *Parabacteroides faecis* sp. nov., isolated from human faeces. International Journal of Systematic and Evolutionary Microbiology (2015), 65, 1342-1346.

(56) References Cited

OTHER PUBLICATIONS

Sakamoto, et al., *Parabacteroides gordonii* sp. nov., isolated from human blood cultures. International Journal of Systematic and Evolutionary Microbiology (2009), 59, 2843-2847.

Sakamoto, et al., *Parabacteroides johnsonii* sp. nov., isolated from human faeces. International Journal of Systematic and Evolutionary Microbiology (2007), 57, 293-296.

Sakamoto, M. et al., Reclassification of Bacteroides distasonis, Bacteroides goldsteinii and Bacteroides merdae as *Parabacteroides distasonis* gen. nov., comb. nov., Parabacteroides goldsteinii comb. nov. and Parabacteroides merdae comb. nov. International journal of systematic and evolutionary microbiology. 2006; 56:1599-1605.

Sakamoto Mitsuo et al., Reclassfication of Baceroides distasonis, Bacteroides goldsteinii and Bacteroides merdae as *Parabacteroides distasonis* gen. nov., comb. nov., Parabacteroides goldsteinii comb. nov. and Parabacteroides merdae comb. nov., International Journal of Systematic and Evolutionary Microbiology (2006) 56, 15-99-1605. DOI 10.1099/ijs.0.0641920.

Sakamoto, Mitsuo et al. "Reclassification of Bacteroides distasonis, Bacteroides goldsteinii and Bacteroides merdae as *Parabacteroides distasonis* gen. nov., comb. nov., Parabacteroides goldsteinii comb. nov. and Parabacteroides merdae comb. nov. ",Journal of Systematic and Evolutionary Microbiology, 2006, vol. 56, No. 7, 1599-1605.

Salix Pharmaceuticals, Inc. FDA Highlights of Prescribing Information—XIFAXAN (rifaximin tablet). Revised Nov. 2015.

Salminen et al. 'Probiotics: how should they be defined?.' Trends in Food Science & Technology. 1999, vol. 10, No. 3, pp. 107-110.

Salonen et al., Gastrointestinal microbia in irritable bowel syndrome: present state and perspectives. Microbiology. 2010; 156: 3205-3215.

Savignac HM et al., "Bifidobacteria exert strain-specific effects on stress-related behavior and physiology in BALB/c mice.", Neurogastroenterol Motil. Nov. 2014;26(11):1615-27. doi: 10.1111/nmo.12427. Epub Sep. 24, 2014.

Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.

Scatton Bernard et al., "Reduction of Cortical Dopamine, Noradrenaline, Serotonin and Their Metabolites in Parkinson's Disease", (1983) Brain Research, 275(2): 321-8.

Scher et al., Expansion of intestinal Prevotella copri correlates with enhanced susceptibility to arthritis. 2013; eLIFE 2, e01202, 20 Pages.

Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.

Schiavi, E., Plattner, S., Rodriguez-Perez, N., Barcik, W., Frei, R., Ferstl, R., et al. (2018). Exopolysaccharide from *Bifidobacterium longum* subsp. longum 35624 modulates murine allergic airway responses. Benef Microbes, 1-14. doi: 10.3920/BM2017.0180.

Schieck, M. et al., Genetic variation in TH17 pathway genes, childhood asthma, and total serum IgE levels.(2014) J Allergy Clin Immunol. 133(3):888-91.

Schleifer, K.H. et al., Transfer of *Streptococcus faecalis* and *Streptococcus faecium* to the Genus *Enterococcus* nom. rev. as Enterococcus faecalis comb. nov. and Enterococcus faecium comb. nov. Int J Syst Evol Microbiol, Jan. 1984 34: 31-34, doi:10.1099/00207713-34-1-31.

Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.

Schouten, et al., Cow milk allergy symptoms are reduced in mice fed dietary synbiotics during oral sensitization with whey. Nutritional Immunology. 2015; 139(7):1390-403.

Schreiber, O, et al., Lactobacillus reuteri prevents colitis by reducing P-selectin-associated leukocyte- and plateletendothelial cell interactions (2009). American Journal of Physiology-Gastrointestinal and Liver Physiology, 296 (3), pp. G534-G542.

Schulke et al. (Aug. 26, 2011) "A fusion protein of ftagellin and ovalbumin suppresses the 25 TH2 response and prevents murine intestinal allergy," The Journal of Allergy and Clinical Immunology. 128(6):1340-1348.

Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.

Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 672-4679.

Scuotto, Angelo et al., In silico mining and characterization of bifidobacterial lipoprotein with CHHP domain secreted in an aggregated form, International J. of Biol. Macromolecutes 82(2016), 653-662.

Sczesnak, et al., The genome of th17 cell-inducing segmented filamentous bacteria reveals extensive auxolrophy and adaptations to the intestinal environment. Cell Host Microbe. Sep. 2011;10 (3):260-272.

Severijnen, A. J. et al., Chronic Arthritis Induced in Rats by Cell Wall Fragments of *Eubacterium* Species from the Human Intestinal Flora. Infection and Immunity, 1990, vol. 58, No. 2, 523-528.

Severijnen, et al., Chronic Arthritis Induced in Rats by Cell Wall Fragments of *Eubacterium* Species from the Human Intestinal Flora. Infection and Immunity, Feb. 1990; 58(2): p. 523-528.

Sgadari, C. et al., Interferon-inducible protein-10 identified as a mediator of tumor necrosis in vivo. (1996) PNAS. 93:13791-6.

Sgadari et al. Mig, the Monokine Induced By Interferon-g, Promotes Tumor Necrosis In Vivo. (1997) Blood. 89:2635-43.

Shabgah, A.G. et al., Interleukin-17 in human inflammatory diseases. Postepy Dermatol Alergol. Aug. 2014; 31 (4): 256-261.

Shaw, William, "Increased urinary excretion of a 3-(3-hydroxphenyl)-3-hydroxpropionic acid (HPHPA), an abnormal phenylalanine metabolite of *Clostridia* spp. in the gastrointestinal tract, in urine sample from patients with autism and schizophrenia", 2010, Nutritional Neuroscience 13(3), 135-143.

Shevach et al., Current Protocols in Immunology. John Wiley & Sons. New York, New York. 1992. Table of Contents only, as accessed online at URL: http://www.4ulr.com/products/curentprotocols/immunology_toc.html. [Last Accessed Jun. 18, 2015].

Shortt, Colette et al., "Systematic review of the effects of the intestinal microbiota on selected nutrients and non-nutrients",2017, Eur J Nutr, 57:25-49, DOI 10.1007/00394-017-1546-4.

Simon, et al., Peptoids: A modular approach to drug discover, Oct. 1992. PNAS, 89(20):9367-9371.

Simponi 100 mg solution for injection in pre-filled pen—Summary of Product Characteristics, https://www.medicines.org.uk/emc/products/5133/smpc/print, accessed Oct. 25, 2019, 21 pages.

Simpson-Herren, L. et al., Kinetic parameters and growth curves for experimental tumor systems. Cancer Chemother Rep. Jun. 1970;54(3):143-74.

Sisson, G. et al., Randomised clinical trial: a liquid multi-strain probiotic vs. placebo in the irritable bowel syndrome—a 12 week double-blind study. Aliment Pharmacol Ther. 2014; 40: 51-62.

Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255.

Sivieri, K. et al., Probiotic enterococcus faecium CRL 183 inhibit chemically induced colon cancer in male wistar rats. Eur Food Res Technol. 2008; 228:231-237.

Skolnick, et al. From genes to protein structure and function: novel applications of computational approaches in the genomic era. Trends Biotechnol. Jan. 2000;18(1):34-9. Review.

(56) References Cited

OTHER PUBLICATIONS

Skountzou, et al., *Salmonella flagellins* are potent adjuvants for inlranasally administered whole inactivated influenza vaccine. Vaccine. May 2010; 28(24):4103-4112.
Smart, Kathleen F. et al., "Analytical platform for metabolome analysis of microbial cells using methyl chloroformate derivatization followed by gas chromatography-mass spectrometry", 2010, Nature Protocols. 10:1709-29.
Smith and Waterman, "Comparison of biosequences", Advances in Applied Mathematics, vol. 2, Issue 4, Dec. 1981, pp. 482-489.
Smith, C.L., et al., Lactobacillus fermentum BRII and fmcto-oligosaccharide partially reduce jejunal inflammation in a model of intestinal mucositis in rats (2008). Nutrition and Cancer, 60 (6), pp. 757-767.
Smith et al. Comparison of Biosequences. Advances in Applied Mathematics. 2:482-489 (1981).
Sokol et al. 'Faecalibacterium prausnitzii is an anti-inftammatory commensal bacterium identified by gut microbiota analysis of Crohn disease patients.' Proceedings ofthe National Academy of Sciences. 2008, vol. 105, No. 43, pp. 6731-16736.
Sokol et al. 'Low counts of Faecalibacterium prausnitzii in colitis microbiota.' Inflammatory bowel diseases. 2009, vol. 15, No. 8, pp. 1183-1189.
Song et al., Impact of Schistosoma Japonicum Infection on Collagen-Induced Arthritis in DBA/1 Mice: A Murine Model of Human Rheumatoid Arthritis. 2011; PLoS ONE 6, e23453, 10 pAGES.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Spor, A. et al., Unravelling the effects ofthe environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.
Strasser, S. et al., Influence of lyophilization, fluidized bed drying, addition of protectants, and storage on the viability oflactic acid bacteria (2009). Journal of Applied Microbiology, 107 (1), pp. 167-177.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Strus et al. Distinct effects of Lactobacillus plantarum KL30B and *Escherichia coli* 3A1 on the induction and development of acute and chronic inflammation. 2015. Cent Eur J Immunol.40(4):420-30.
Sudha B. Singh and Henry C. Lin, "Hydrogen Sulfide in Physiology and Diseases of the Digestive Tract", Microorganisms 2015, 3, 866-889; doi:10.3390/microorganisms3040866.
Sun, D. et al., The role of Th17-associated cytokines in the pathogenesis of experimental autoimmune uveitis (EAU). (2015) Cytokine. 74(1):76-80.
Sun, et al., Exploring gut microbes in human health and disease: Pushing the envelope. Genes Dis. Dec. 2014; 1(2):132-139.doi:10.1016/j.gendis.2014.08.001.
Sun, S. et al., "Proton pump inhibitor monotherapy and the risk of cardiovascular events in patients with gastro-esophageal reflux disease: a meta-analysis",2017, Neurogastroenterology and Motiliy., 29:e12926, 1-10, DOI: 10.1111/nmo.13260Ol.
Supplement to: Israel, et al., Severe and difficult-to-treat asthma in adults. N Engl J Med 2017; 377:965-76.
Suzanne L. Topalian et al., "Survival, Durable Tumor Remission, and Long-Term Safety in Patients With Advanced Melanoma Receiving Nivolumab", Journal of Clinical Oncology, vol. 32, No. 10, Apr. 1, 2014, pp. 1-12.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.
Takahama, Umeo et al., "Nitrogen Oxides Toxicology ofthe Aerodigestive Tract", 2013, Adv Mol Toxicology, 7, 129-177, Section 4.3.3.
Takashi Nakamura et al., "Evaluation ofthe Effects of Dietary Organic Germanium, Ge-132, and Raffinose Supplementation on Caecal Flora in Rats", Bioscience of Microbiota, Food and Health vol. 31 (2), 37-45, 2012.
Tamanai-Shacoori, et al., *Roseburia* spp.: a marker of health?. Future Microbiology Review 12(2), 157-170 (2017).
Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tang, Ying et al, "Inhibiting Histone Deacetylase 2 (HDAC2) Promotes Functional Recovery From Stroke" 2017, Journal of the American Heart Association, 6(10), 1-28.
Tang,PhD, Jiaqi et al, "Prenatal Hypoxia Induced Dysfunction in Cerebral Arteries of Offspring Rats" 2017, Journal of the American Heart Association, 6(10), 1-12.
Tankou Stephanie et al, "Investigation of probiotics in multiple sclerosis", 2018, Multiple Sclerosis Journal 24(1), 58-63.
Tap et al. Towards the human intestinal microbiota phylogenetic core. 2009. Environ Microbiol, 11(10):2574-84.
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Tatusova et al. (1999) "BLAST 2 Sequences, a new tool for comparing protein and nucleotide sequences," FEMS Microbial. Lett. 174(2):247-250.
Tatusova et al., BLAST 2 Sequences, a new tool for comparing protein and nucleotidesequences, FEMS Microbiology Letters 174 (1999) 247-250.
Tatusova et al., Erratum to BLAST 2 Sequences, a new tool for comparing protein and nucleotide sequences, FEMS Microbiology Letters 177 (1999) 187-188.
Teng, L. J et al., PCR Assay for Species-Specific Identification ofBacteroides thetaiotaomicron. J Clin Microbiol38, 1672-1675 (2000).
Terciz, Janos et al., Inflammation and Colon Cancer, Gastroenterology, 2010: 138: 2101-2114.
Tesmer, LA. et al., Th17 cells in human disease. Immunol Rev. 2008;223:87-113.
Tilg, et al., Roseburia hominis: a novel guilty player in ulcerative colitis pathogenesis? Gut, Oct. 14, 2013;63(8)1204-1205.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLOS ONE 8(3), e59259. doi: 10.1371/journal.pone.0059259.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.

(56) References Cited

OTHER PUBLICATIONS

Travis, et al. Complete genome sequence of the human gut symbiont Roseburia hominis. Genome announcements. 2015; 3(6):e01286-15.
Tremaroli, et al., A role for the gut microbiota in energy harvesting? Gut. Dec. 2010; 59(12):1589-1590.
Trueman (1995) "Heterologous Expression in Yeast," Methods Molecular Biology. 49:341-354.
Tsukinowa, et al., Fecal microbiota of a dugong (*Dugong dugong*) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484.
Turnbaugh, et al., An obesity-associated gut microbiome with increased capacity for energy harvest. Nature. Dec. 2006;444(7122):1027-1031.
Turnbaugh et al., Diet-induced obesity is linked to marked but reversible alterations in the mouse distal gut microbiome. Cell Host & Microbe. Apr. 2008;3(4):213-223.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amserdam, The Netherlands, pp. 641-666.
Turroni, F., Taverniti V Fau-Ruas-Madiedo, P., Ruas-Madiedo P Fau-Duranti, S., Duranti S Fau-Guglielmetti, S., Guglielmetti S Fau-Lugli, G.A., Lugli Ga Fau-Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Ukena, et al., Probiotic *Escherichia coli* Nissle 1917 inhibits leaky gut by enhancing mucosal integrity, PloS one. Dec. 2007;2(12):e1308.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306.
Untergasser, et al., Primer3Plus, an enhanced web interface to Primer3, Nucleic Acids Res. 2007;35(Web Server issue):W71-W74.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.
U.S. Appl. No. 15/915,889 Notice of Allowance dated Jun. 4, 2018.
U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/359,144 Office Action dated Apr. 10, 2018.
U.S. Appl. No. 15/359,972 Office Action dated Apr. 4, 2018.
U.S. Appl. No. 15/431,393 Office Action dated Jul. 30, 2018.
U.S. Appl. No. 15/631,945 Office Action dated Jul. 5, 2018.
U.S. Appl. No. 15/631,945 Office Action dated May 15, 2018.
U.S. Appl. No. 15/631,952 Office Action dated Feb. 16, 2018.
U.S. Appl. No. 15/631,952 Office Action dated Jul. 19, 2018.
U.S. Appl. No. 15/673,270 Office Action dated Apr. 10, 2018.
U.S. Appl. No. 15/679,857 Office Action dated Aug. 6, 2018.
U.S. Appl. No. 15/679,857 Office Action dated Feb. 14, 2018.
U.S. Appl. No. 15/700,007 Non-Final Office Action dated Jun. 10, 2019.
U.S. Appl. No. 15/700,007 Office Action dated Jun. 1, 2018.
U.S. Appl. No. 15/704,245 Non-Final Office Action dated Jul. 3, 2019.
U.S. Appl. No. 15/704,245 Non-Office Action dated Dec. 16, 2019.
U.S. Appl. No. 15/704,245 Office Action dated Sep. 17, 2018.
U.S. Appl. No. 15/803,723 Notice of Allowance dated Feb. 13, 2018.
U.S. Appl. No. 15/842,635 Office Action dated Aug. 27, 2018.
U.S. Appl. No. 16/100,349 Final Office Action dated May 1, 2019.
U.S. Appl. No. 15/842,635 Non-Final Office Action dated May 29, 2019.
U.S. Appl. No. 16/022,577 Non-Final Office Action dated Jul. 9, 2019.
Utkin, Ilya et al, "Isolation and Characterization of *Desulfitobacterium dehalogenans* gen. nov., sp. nov., an Anaerobic Bacterium which Reductively Dechlorinates Chlorophenolic Compounds", 1994, Int J Sys Bacteriol 44(4) 612-9.
Van den Tweel, W.J.J. et al., "Catabolism of DL-x-phenylhydracrylic, phenylacetic and 3-and 4-hydroxyphenylacetic acid via homogentisic acid in a *Flavobacterium* sp.", 1988, Arch Microbiol, 149(3)207-213.
Van De Bogert, et al., Immunomodulatory properties of streptococcus and veillonella isolates from the human small intestine microbiota, PLOS One, Dec. 2014: 1-20, DOI:10.1371/journal.pone.0114277.
Van de Pol, M.A. et al., Sybiotics reduce allergen-induced T-helper 2 respond and improve peak expiatory flow in allergic asthmatics, Allergy 2011 ;66:39-47.
Van De Veerdonk, et al., The Anti-CD20 antibody rituximab reduces the Th17 cell response. Arthritis & Rheumatism. Jun. 2011; 63(6):1507-1516.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.
Van Nevel et al., "Conrol of Rumen Methanogenesis." Environmental Monitoring and Assessment, vol. 42, 1996, pp. 73097, XP000979267.
Van Tilburg, M. Can we treat visceral hypersensitivity in functional abdominal pain? Lancet Gastroenterolhepatol, 2017; 2 Pages.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8.
Vetrovsky, T. and Baldrian, P., The variability of the 16S rRNA gene in bacterial genomes and its consequences for bacterial community analyses. Plos One. Feb. 2013;8(2): e57923.
Viaud, Sophie et al. "The intestinal microbiota modulates the anticancer immune effects of cyclophosphamide." Science (New York, N.Y.) vol. 342,6161 (2013): 971-6. doi:10.1126/science.1240537.
Vijay-Kumar, et al., Deletion of TLR5 results in 10 spontaneous colitis in mice. The Journal of Clinical Investigation. Dec. 2007;117(12):3909-3921.
Vijay-Kumar et al., Flagellin Treatment Protects against Chemicals, Bacteria, Viruses, and Radiation. The Journal of Immunology. 2008;180(12):8280-8285.
Vorstman, Jacob A S et al. "Proline affects brain function in 22q11DS children with the low activity COMT 158 allele." Neuropsychopharmacology : official publication of the American College of Neuropsychopharmacology vol. 34,3 (2009): 739-46. doi:10.1038/npp.2008.132.

(56) References Cited

OTHER PUBLICATIONS

Waisman, Ari et al., "The role of IL-17 in CNS diseases", Acta Neuropathologica, Springer Verlag, Berlin, DE, 2015, vol. 129, No. 5, 625-637.
Walker et al. 'Dominant and diet-responsive groups of bacteria within the human colonic microbiota.' The ISME Journal. 2010, vol. 5, No. 2, pp. 220-230.
Wallace, R. John et al., "Metabolic properties of Eubacterium pyruvativorans, a ruminal "hyper-ammonia-producing" anaerobe with metabolic properties analogous to those of Clostridium kluyveri", 2004, Microbiology 150, 2921-2930.
Wang, Chun-Sai-Er, et al., VSL#3 can prevent ulcerative colitis-associated carcinogenesis in mice, Oct. 7, 2018, vol. 24, Issue 37, pp. 4254-4262.
Wang et al. 16S rRNA gene-based analysis of fecal microbiota from preterm infants with and without necrotizing enterocolitis. 2009. ISME J. 3(8): 944-954.
Wang, Feng, Bifidobacterium can mitigate intestinal immunopathology in the context of CTLA-4 blockade, PNA, Jan. 2, 2018 Vol. 115, No. 1, pp. 157-161.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22.
Wang, Huiying et al. "Effect of Probiotics on Central Nervous System Functions in Animals and Humans: A Systematic Review." Journal of neurogastroenterology and motility vol. 22,4 (2016): 589-605. doi:10.5056/jnm16018.
Wang, R.F., and Kushner, S.R. (1991). Construction of versatile low-copy-number vectors for cloning, sequencing and gene expression in Escherichia coli. Gene 100, 195-199. doi: https://doi.org/10.1016/0378-1119(91)90366-J.
Wang W., Lyophilization and development of solid protein pharmaceuticals. International J. Pharmaceutics 203: 1-60, 2000.
Wang, Yan, and Lloyd H Kasper. "The role of microbiome in central nervous system disorders." Brain, behavior, and immunity vol. 38 (2014): 1-12. doi:10.1016/j.bbi.2013.12.015.
Watson, et al., Signal transduction in Campylobacter jejuni-induced cytokine production. Cellular Microbiology. 2005;7(5):655-665.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038.
Weigel, et al., Comparative analysis of murine marrow-derived dendritic cells generated by Flt3L or GMCSF/IL-4 and matured with immune stimulatory agents on the in vivo induction of antileukemia responses. Blood. Dec. 2002;100(12):4169-4176.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Weon et al., "TIO2 Nanotubes with Open Channels as Deactivation-Resistant Photocatalyst for the Degradation of Volatile Organic Compounds", 2016, Environmental Science & Technology, 50, 2556-2563.
Werth, et al., The transcription factor grainyhead-like 2 regulates the molecular composition of the epithelial apical junctional complex. Development. 2010;37(22):3835-3845.
West and Johnstone, "New and emerging HDAC inhibitors for cancer treatment", The Journal of Clinical Investigation, 2014, 124, 30-39.
Westermann, C., Gleinser, M., Corr, S.C., and Riedel, C.U. (2016). A Critical Evaluation of Bifidobacterial Adhesion to the Host Tissue. Front Microbiol 7, 1220. doi: 10.3389/fmicb.2016.01220.
Williams, N.T. Probiotics (2010). American Journal of Health-System Pharmacy, 67 (6), pp. 449-458.
Wilson, et al., The TLR5 ligand flagellin promotes asthma by priming allergic responses to indoor allergens. Nature Medicine. Nov. 2012;18(11):1705-1710.
Workman et al. Guidelines for the welfare and use of animals in cancer research (2010) Br. J. Cancer. 102:1555-77.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11 (61):1-13.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921.
Xiong, Xiyue et al., "Urinary 3-(3-Hydroxphenyl)-3-3hydroxypropionic Acid, 3-Hydroxyphenylacetic Acid, and 3-Hydroxyhippuric Acid Are Elevated in Children with Autism Spectrum Disorders", 2016, BioMed Research International, Article ID 9485412, 8 pages.
Xu, et al., A genomic view of the human-Bacteroides thetaiotaomicron symbiosis. Science. Mar. 28, 2003; 299(5615):2074-6.
Xu, et al., Differential development of murine dendritic cells by GM-CSF versus Flt3 ligand has implications for inflammation and trafficking. J. Immunology. 2007;179(11):7577-7584.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Xu, J. et al., "Message from a human gut symbiont: sensitivity is a prerequisite for sharing", Trends in microbiology, 12(1), Jan. 1, 2004: pp. 21-28, XP055253932.
Xue, Zheng-kai, "Isolation and identification of a caproic acid-producing K-1 strain from Luzhou-flavor Liquor Pit Mud", 2014, Journal of Chemical and Pharmaceutical Research, 6(7), 2021-2025.
Yang, Changa et al., Non-invasive imaging of toll-like receptor 5 expressing using 131 labelled mAb in the mice bearing H22 tumors, Oncol. Lett. 2014., 7(6). 1919-1924., Published online Apr. 2014. il2. DOI: 10.3892/ol.2014.2025.
Yang, Changya et al., Non-invasive imaging of Toll-like receptor 5 expression using 131I-labeled mAb in the mice bearing H22 tumors, Oncology Letters, 7:1919-1924, 2014, DOI: 10.3892/00.2014.2025.
Yang, Fang, "The clinical significance of the imbalance of TH17 and Treg cells and their related cytokines in peripheral blood of Parkinson's disease patients", International Journal of clinical and experimental medicine, 2016, vol. 9, No. 9, 17946-17951.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Yao, W., et al., Cultivation-Independent Analysis of the Development of the Lactobacillus spp. Community in the Intestinal Tract of Newborn Piglets (2011) Agricultural Sciences in China, 10 (3), pp. 438-447.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Yoon, et al., Structural basis of TLR5-flagellin recognition and signaling. Science. Feb. 2012; 335(6070):859-864.
Yoshinori Kohwi et al., "Antitumor Effect of Bifidobacterium Infant's in Mice", Gann, 69, 613-618; Oct. 1978.
Yq et al. Therapeutic Modulation of the Gut Microbiota in IBD—More Questions to Be Answered. (2016). J. Dig. Dis., Oct. 15, 1751-2980, 12422, Epub ahead of print.
Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.

(56) References Cited

OTHER PUBLICATIONS

Yu, et al., Utilization of major fucosylated and sialylated human milk oligosaccharides by isolated human gut microbes. Glycobiology, 2013; 23(11):1281-1292.
Yu, N.Y., Wagner, J.R., Laird, M.R., Meili, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249.
Yuliana and Garcia, Influence of Pediococcus acidilactici as a starter on the flavour of tempoyak (fermented durian), 2009, Indian J Biotechnol 8 304-310.
Yun, J.H., et al., Isolation and characterization of potential pro biotic lactobacilli from pig feces (2009). Journal of Basic Microbiology, 49 (2), pp. 220-226.
Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).
Yurdusev, N. et al., InfectInunun 57,724-731 (1989).
Yutin, N. and Galperin, M.Y., A genomic update on clostridial phylogeny:Gram-negative spore formers and other misplaced Clostridia. Environmental microbiology. Oct. 2013; 15(10): 2631-2641.
Zadori, Denes et al., "Kynurenines in Parkinson's disease: therapeutic perspectives", 2012, Journal of Neural Transmission, 119, 2, 275-283.
Zhang, B. et al., Oral administration of enterococcus faecalis FK-23 suppresses Th17 cell development and attenuates allergic airway responses in mice. International journal of molecular medicine. 2012; 30:248-254.
Zhang, B. et al., The Prevalence of Th17 Cells in Patients With Gastric Cancer. 2008. Biochem Biophys Res Commun 374 (3), 533-537.
Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.
Zheng, B. et al., Bifidobacteriu breve attenuates murine dextran sodium sulfate-induced colitis and increases regulatory T cell responses. PLOS one. May 2014; 9(5).
Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441.
Zheng, Bin et al., Bifodobacterium breve Attenuates Murine Dexran Doium Sulfate-Induced Colitis and Increases Regulatory T Cell Responses, PLOS ONE, vol. 9, Isue 5, e95441, May 2014.
Zheng, Zhen et al. "Peripheral brain-derived neurotrophic factor in autism spectrum disorder: a systematic review and meta-analysis", 2016, Scientific Reports, 6(31241) 1-8.
Zhongyuan, T. et al., The inflammation regulation effects of enterococcus faecium HDRsEf1 on human enterocyte-like HT-29 cells. Animal cells and systems. Mar. 2016;20(2):70-76.
Zhou et al. Central and peripheral hypersensitivity in the irritable bowel syndrome. 2010. Pain. 148(3): 454-461.
Zhou, Linghong, and Jane A Foster. "Psychobiotics and the gut-brain axis: in the pursuit of happiness." Neuropsychiatric disease and treatment vol. 11 715-23. Mar. 16, 2015, doi:10.2147/NDT.S61997.
Zhu, S. and Qian, Y., IL-17/IL-17 receptor system in autoimmune disease: mechanisms and therapeutic potential. Clinical Science (2012) 122, 487-511.
Zhu, Xiaoyu et al., "Production of high-concentration n-caproic acid from lactate through fermentation using a newly isolated Ruminococcaceae bacterium CPB6", 2017, Biotechnology Biofuels 10:102, 1-12.
Zitomersky, N. et al., Characterization of Adherent Bacteroidales from Intestinal Biopsies of Children and Young Adults with Inflammatory Bowel Disease. PLOS one. 2013; 8(6).
Zitvogel, et al., Type I interferons in anticancer immunity. Nature Reviews. Jul. 2015:405-414.
Aklujkar, Muktak et al., "Anaerobic degradation of aromatic amino acids by the hyperthrmophilic archaeon Ferroglobus placidus", Microbiology, 2014, 160, 2694-2709.
Angelova, Plamena R. et al., "Role of mitochondrial ROS in the brain: from physiology to neurodegeneration", FEBS Letters, 592, 2018, 692-702.
Dolpady, Jayashree et al., "Oral Probiotic VSL#3 Prevents Autoimmune Diabetes by Modulating Microbiota and Promoting Indoleamine 2,3-Dioxygenase-Enriched Tolerogenic Intestinal Environment" Journal of Diabetes Research, 2016, 12 pages.
Dufek, Michal et al., "Interleukin-6 May Contribute to Mortality in Parkinson's Disease Patients: A 4-Year Prospective Study", Parkinson's Disease, 2015, 5 pages.
Kim, Geon Ha et al., "The Role of Oxidative Stress in Neurodegenerative Diseases", Experimental Neurobiology, Dec. 24, 2015 (4):325-340.
Koma, Daisuke et al., "Production of Aromatic Compounds by Metabolically Engineered Escherichia coli with an Expanded Shikimate Pathway", Applied and Environmental Microbilogy, 2012, vol. 78, No. 17, 6203-6216.
Kong, Liang et al., "Retinoic acid ameliorates blood-brain barrier disruption following ischemic stroke in rats", Pharmacological Research,99, 2015, 125-136.
Liu, Zewen et al., "Oxidative Stress in Neurodegenerative Diseases; From Molecular Mechanisms to CLinical Applications", Oxidative Medicine and Cellular Longevity, 2017, 11 pages.
Mallikarjuna, Nimgampalle et al., Role of Lactobacillus plantarum MTCC1325 in membrane-bound transport ATPases system in Alzheimer's disease-induced rat brain, BioImpacts, 2016, 6(4), 203-209.
M.C. Muya et al., "Effect of Megasphaera elsdenii NCIMB 41125 dosing on rumen development, volatile fatty acid production and blood B-hydroxybutyrate in neonatal dairy calves", Journal of Animal Physiology and Animal Nutrition 99, 2015, 913-918.
McLarmon, James G., "Chemokine lnterleukin-8 (IL-8) in Alzheimer's and Other Neurodegenerative Diseases", Journal of Alzheimer's Disease & Parkinsonism, vol. 6, issue 5, 2016, 4 pages.
Mukaida Naofumi, "Interleukin-8: An Expanding Universe Beyond Neutrophil Chemotaxis and Activation", Int. J. Hematol., 2000, 72:391-398 https://www.ncbi.nlm.nih.gov/pubmed/11197203.
Pereira, Jessica Ramos et al, "IL-6 serum levels are elevated in Parkinson's disease patients with fatigue compared to patients without fatigue", J. Neurol Sci., 2016:370:153-156 https://doi.org/10.1016/j.jns.2016.09.030.
Scalzo Paula et al., "Serum levels of interleukin-6 are elevated in patients with Parkinson's disease and correlate with physical performance", Neuroscience Letters, vol. 468, Issue 1, Jan. 1, 2010, pp. 56-58.
Tsukahara, Takamitsu et al., "Stimulation of butyrate production through the metabolic interaction among lactic acid bacteria, Lactobacillus acidophilus, and lactic acid-utilizing bacteria, Megasphaera elsdenii, in porcine cecal digesta", Animal Science Journal, 2006, 77, 454-461.
Wang, Yang et al., "Antioxidant Properties of Probiotic Bacteria", Nutrients, 2017, 9, 521, 15 pages.
Yin, Lian-Hu et al., "Early post-treatment with 9-cis retinoic acid reduces neurodegeneration of dopaminergic meurons in a rat model of Parkinson's disease", BMC Neuroscience, 2012, 13:120.
Zhang, Xiu-Zhen et al., "Valproic acid as a promising agent to combat Alzheimer's disease", Brain Research Bulletin 81, 2010, 3-6.
Nallabelli, Nayudu et al., "Biochemical and genome sequence analyses of Megasphaera sp. strain DISK18 from dental plaque of a healthy individual reveals commensal lifestyle", Scientific Reports, 2016, 6:33665, 14 pages.
Abbas, Ata, and Sanjay Gupta. "The role of histone deacetylases in prostate cancer." Epigenetics vol. 3,6 (2008): 300-9. doi:10.4161/epi.3.6.7273.
Allen, Irving C. et al., The NLRP3 inflammasome functions as a negative regulator of tumorigenesis during colitis-associated cancer, 2010, J Exp Aled.;207(5):1045-56.

(56) References Cited

OTHER PUBLICATIONS

Andreeff MD, PhD, Michael et al., Cell Proliferation and Differentiation, 2003, Holland-Frei Cancer Medicine. 6th edition, Chapter 3, 21 pages.

Arvigo, M et al., Somatostatin and dopamine receptor interaction in prostate and lung cancer cell lines, 2010, J Endocrinol. ;207(3):309-17.

Ascierto, Paolo A et al., The role of BRAF V600 mutation in melanoma, 2012, Journal of Translational Medicine, 10,85, 9 pages.

Bae S, et al., α-Enolase expressed on the surfaces of monocytes and macrophages induces robust synovial inflammation in rheumatoid arthritis. J Immunol. Jul. 1, 2012;189(1):365-72. doi:10.4049/jimmunol.1102073. Epub May 23, 2012. PMID: 22623332.

Barnes, P.J. et al., Histone acetylation and deacetylation: importance in inflammatory lung diseases, Eur Resp, 2005, 25:552-563.

Bektas, Arsun et al. "Human T cell immunosenescence and inflammation in aging." Journal of leukocyte biology vol. 102,4 (2017): 977-988. doi:10.1189/jlb.3RI0716-335R.

Bell, Ryan A V, and Lynn A Megeney. "Evolution of caspase-mediated cell death and differentiation: twins separated at birth." Cell death and differentiation vol. 24,8 (2017): 1359-1368. doi:10.1038/cdd.2017.37.

Berthoud et al., "MIG (CXCL9) is a more sensitive measure than IFN-γ of vaccine induced T-cell responses in volunteers receiving investigated malaria vaccines"(2009) J Immunol Methods 340(1)33-41.

Bettelli E, Carrier Y, Gao W, Korn T, Strom TB, Oukka M, Weiner HL, Kuchroo VK. Reciprocal developmental pathways for the generation of pathogenic effector TH17 and regulatory T cells. Nature. May 11, 2006;441(7090):235-8. doi: 10.1038/nature04753. Epub Apr. 30, 2006. PMID: 16648838.

Bhat, Kumar M. R. et al., Transcriptional regulation of human MAP2 gene in melanoma: role of neuronal bHLH factors and Notch1signaling, 2006, Nucleic Acids Res.;34(13):3819-32.

Bloch F, et al., "Production ofTNF-alpha ex vivo is predictive of an immune response to flu vaccination in a frail elderly population", Eur Cytokine Netw. Sep. 1, 2016;27(3):63-67. English. doi: 10.1684/ecn.2016.0378. PMID: 27910810.

Bonner et al., Significance ofNeuron-specific Enolase Levels before and during Therapy for Small Cell LungCancer1 (2000) Clinical Cancer Research 6:597-601.

Bovenschen, H. Jorn et al., Foxp3 +Regulatory T Cells of Psoriasis Patients Easily Differentiate intoIL-17A-Producing Cells and Are Found in Lesional Skin, J Invest Dermatol, vol. 131, 2011, pp. 1853-1860.

Butler, Lisa M. et al., Suberoylanilide Hydroxamic Acid, an Inhibitor of Histone Deacetylase, Suppresses the Growth of Prostate Cancer Cells in Vitro and in Vivo, 2000,Cancer Res. 60:5165-5170.

Chai,Yuan-yuan et al. (2012), Antioxidant Activities of Stilbenoids from Rheum emodi Wall, Evidence-Based Complementary and Alternative Medicine, Article ID 603678, 7 pages, doi:10.1155/2012/603678.

Chan, Jason R et al. "IL-23 stimulates epidermal hyperplasia via TNF and IL-20R2-dependent mechanisms with implications for psoriasis pathogenesis." The Journal of experimental medicine vol. 203,12 (2006): 2577-87. doi:10.1084/jem.20060244.

Chen, Ming-Huang et al., Gene Expression-Based Chemical Genomics Identifies Potential Therapeutic Drugs in Hepatocellular Carcinoma, 2011,PLoS One.;6(11):e27186.

Cheng,H-W et al., Identification of thioridazine, an antipsychotic drug, as an antiglioblastoma and anticancer stem cell agent using public gene expression data, 2015, Cell Death Dis.;6:e1753.

Christensen, Dan P et al., Histone Deacetylase (HDAC) Inhibition as a Novel Treatment for Diabetes Mellitus (2011), Mol Med, 17 (5-6), 370-390.

Chuang, De-Maw et al., Multiple roles of HDAC inhibition in neurodegenerative conditions, Trends in Neurosciences, 2009, vol. 32, No. 11, pp. 591-601.

Chun, Pusoon, Histone deacetylase inhibitors in hematological malignancies and solid tumors, 2015, Arch Pharm Res. 38(6):933-49.

Coffman, Robert L et al. "Vaccine adjuvants: putting innate immunity to work." Immunity vol. 33,4 (2010): 492-503. doi:10.1016/j.immuni.2010.10.002.

Corsini, Emanuela et al., High interleukin-10 production is associated with low antibody response to influenza vaccination in the elderly, J Leukocyte Biol 2006 80, 376-382.

Darrah, Patricia A. et al., IL-10 production differentially influences the magnitude, quality, and protective capacity of Th1 responses depending on the vaccine platform, J Exp Med, 2010 207(7), 1421-1433.

De Baere, Siegrid et al., Development of a HPLC-UV method forthe quantitative determination of four short-chain fatty acids and lactic acid produced by intestinal bacteria during in vitro fermentation, (2013) J Pharm Biomed Anal, 80: 107-115.

Devarajan,Eswaran et al, Down-regulation of caspase 3 in breast cancer: a possible mechanism for chemoresistance, 2002, Oncogene. 12;21(57):8843-51.

Didierlaurent AM, et al., Enhancement of adaptive immunity by the human vaccine adjuvant AS01 depends on activated dendritic cells. J Immunol. Aug. 15, 2014;193(4):1920-30. doi: 10.4049/jimmunol.1400948. Epub Jul. 14, 2014. PMID: 25024381.

Fernández-Ruiz M, et al. "Baseline serum interleukin-6 to interleukin-2 ratio is associated with the response to seasonal trivalent influenza vaccine in solid organ transplant recipients", Vaccine.Dec. 16, 2015;33(51):7176-7182. doi: 10.1016/j.vaccine.2015.10.134. Epub Nov. 10, 2015. PMID: 26555352.

Fülöp T, Dupuis G, Witkowski JM, Larbi A. The Role of Immunosenescence in the Development of Age-Related Diseases. Rev Invest Clin. Mar.-Apr. 2016;68(2):84-91. PMID: 27103044.

Fraietta, Joseph A et al. "Determinants of response and resistance to CD19 chimeric antigen receptor (CAR) T cell therapy of chronic lymphocytic leukemia." Nature medicine vol. 24,5 (2018): 563-571. doi:10.1038/s41591-018-0010-1.

Fulop, Tamas et al., "Immunosenescence and Cancer "(2013) Critical Reviews in Oncogenesis 2013;18(6):489-513.

Fulop, Tamas et al. "Immunosenescence and Inflamm-Aging As Two Sides of the Same Coin: Friends or Foes?." Frontiers in immunology vol. 8 1960. Jan. 10, 2018, doi:10.3389/fimmu.2017.01960.

Gasche, Christoph et al. (2000) A Simple Classification of Crohn's Disease: Report of the Working Party for the World Congresses of Gastroenterology, Vienna 1998, Inflammatory Bowel Diseases 6: 8-15.

Gaur and Aggarwal, Regulation of proliferation, survival and apoptosis by members of the TNF superfamily* (2003).Biochem Pharmacol. ;66(8):1403-8.

Genbank NCBI Reference Sequence:NR_133027.1, Megasphaera massiliensis strain NP3 16S ribosomal RNA, partial sequence, accessed Nov. 25, 2020.

Genbank NCBIReference Sequence: JX424772.1, Megasphaera massiliensis strain NP3 16Sribosomal RN Agene, partial sequence., retrieved from EBI accession No. EMSTD:JX424772, accessed Dec. 2, 2020.

Genbank NCBIReference Sequence: LN998020.1, *Megasphaera* sp. MTCC 12521 partial 16S rRNAgene, strain MTCC 12521, isolate DISK18, relrieved from EBI accession No. EMSTD:LN998020, accessed Dec. 2, 2020.

Gerland Vaux, Apoptosis in the development and treatment of cancer, 2005, Carcinogenesis.Feb. 2005;26(2):263-70.

Glenn, Justin D and Whartenby, Katharine, Mesenchymal stem cells: Emerging mechanisms of immunomodulation and therapy, World J Stem Cells Nov. 26, 2014; 6(5): 526-539, ISSN 1948-0210.

Goldin, B. R. and Gorbach, S. L., Clinical Indications for Probiotics: An Overview, Clin Infect Dis., 2008, vol. 46, No. 2, pp. 96-100.

Grabiec, Aleksander M et al., Targeting histone deacetylase activity in rheumatoid arthritis and asthma as prototypes of inflammatory disease: should we keep our HATs on?, 2008, Arthritis Res Ther. 10:226.

(56) References Cited

OTHER PUBLICATIONS

Haumaitre, Cécile et al. "Histone deacetylase inhibitors modify pancreatic cell fate determination and amplify endocrine progenitors." Molecular and cellular biology vol. 28,20 (2008): 6373-83. doi:10.1128/MCB.00413-08.
Heng, Boon Chin et al., Strategies for directing the differentiation of stem cells into the cardiomyogenic lineage in vitro (2004) Cardiovasc Res. Apr. 1, 2004;62(1):34-42.
Hommes, D W et al., Mitogen activated protein (MAP) kinase signal transduction pathways and novel anti-inflammatory targets, Gut Jan. 2003;52(1):144-51. doi: 10.1136/gut.52.1.144.
Hoover, David M. et al., The Structure of Human Macrophage Inflammatory Protein-3x/CCL20,2002, J Biol Chem. 277(40):37647-54.
Huang, Yunda et al., Cell-Mediated Immune Predictors of Vaccine Effect on Viral Load and CD4 Count in a Phase 2Therapeutic HIV-1 Vaccine Clinical Trial, EBio Medicine (Cell) 2017, 24,195-204.
Jandaghi, Pouria et al., Expression of DRD2 Is Increased in Human Pancreatic Ductal Adenocarcinoma and Inhibitors Slow Tumor Growth in Mice, 2016, Gastroenterology;151 (6):1218-1231.
Johnsen, LG et al,, Gas chromatography—mass spectrometry data processing made easy., 2017, J Chromatogr A, 1503, 57-64.
Jones, Jeremy C. et al., Non-V600BRAF Mutations Define a Clinically Distinct Molecular Subtype of Metastatic Colorectal Cancer, 2017, J Clin Oncol. Aug. 10, 2017;35(23): 2624-2630.
Jung et al ,HDAC2 overexpression confers oncogenic potential to human lung cancer cells by deregulating expression of apoptosis and cell cycle proteins (2012) J Cell Biochem113: 2167-2177.
Kaser,Arthur et al., Increased Expression of CCL20 in Human Inflammatory Bowel Disease, 2004,J ClinImmunol.;24(1):74-85.
Knudsen, Niels Peter H et al. "Different human vaccine adjuvants promote distinct antigen-independent immunological signatures tailored to different pathogens." Scientific reports vol. 6 19570. Jan. 21, 2016, doi:10.1038/srep19570.
Kondelkova, Kateřina et al., Regulatory T Cells (Treg) And Their Roles In Immune System With Respect To Immunopathological Disorders, 2010,ActaMedica (Hradec Kralove).;53(2):73-7.
Leal, I S et al. "Interleukin-6 regulates the phenotype of the immune response to a tuberculosis subunit vaccine." Immunology vol. 103,3 (2001): 375-81. doi:10.1046/j.1365-2567.2001.01244.x.
Lee, Sang Hoon et al, "Characterization of microbiome in bronchoalveolar lavage fluid of patients with lung cancer comparing with benign mass like lesions", Lung Cancer, Elsevier, Amsterdam, NL, vol. 102, Oct. 31, 2016 (Oct. 31, 2016), pp. 89-95, XP029848342, ISSN: 0169-5002, DOI:10.1016/J.LUNGCAN.2016.10.016.
Leng, Corinna etal., Reduction of graft-versus-host disease by histone deacetylase inhibitor suberonylanilide hydroxamic acid is associated with modulation of inflammatory cytokine milieu and involves inhibition of STAT1 (2006), Experimental Hematology 34 (2006) 776-787.
Leoni, Flavio et al. "The histone deacetylase inhibitor ITF2357 reduces production of pro-inflammatory cytokines in vitro and systemic inflammation in vivo." Molecular medicine (Cambridge, Mass.) vol. 11,1-12 (2005): 1-15. doi:10.2119/2006-00005. Dinarello.
Li et al, "Aluminum Hydroxide Adjuvants Activate Caspase-1 and Induce IL-113 andIL-18 Release" (2007) J Immunol, 178(8),5271-5276.
Li, Hanfen et al., Aluminum Hydroxide Adjuvants Activate Caspase-1 and Induce IL-1β and IL-18 Release, JImmunol Apr. 15, 2007, 178 (8) 5271-5276; DOI:https://doi.org/10.4049/jimmunol.178.8.5271.
Li, Jie et al., Genome-wide shRNA screen revealed integrated mitogenic signaling between dopamine receptor D2 (DRD2) and epidermal growth factor receptor (EGFR) in glioblastoma, 2014,Oncotarget.;5(4):882-93.
Li, Wei et al., "Structural changes of gut microbiota in Parkinson's disease and its correlation with clinical features", Science China Life Sciences, 2017, vol. 60, No. 11:1223-1233.
Lim, Jae Sung et al., Flagellin-dependentTLR5/caveolin-1 as a promising immune activator in immunosenescence, Aging Cell, 2015, 14, pp. 907-915.
Liu, Feifei et al., Targeting ERK, an Achilles' Heel of the MAPK pathway, in cancer therapy, 2018, Acta Pharmaceutica Sinica B; 8, 4; 552-562.
Livak KJ, Schmittgen TD., Analysis of relative gene expression data using real-time quantitative PCR and the 2(-Delta Delta C(T)) Method. Methods. Dec. 2001;25(4):402-8. doi: 10.1006/meth.2001.1262. PMID: 11846609.
Luo, Jie et al., Vascular endothelial growth factor promotes the activation of hepatic stellate cells in chronic schistosomiasis, Immunology and Cell Biology, 2016, pp. 1-9.
Maddodi, Nityanand et al., OncogenicBRAFV600E Induces Expression of Neuronal Differentiation Marker MAP2 in Melanoma Cells by Promoter Demethylation and Downregulation of Transcription Repressor HES1, Jan. 1, 2010, The Journal Of Biological Chemistry vol. 285,No. 1, pp. 242-254.
Mao, Min etal., Dopamine D2 receptor blocker thioridazine induces cell death in human uterine cervical carcinoma cell line SiHa, 2015,J Obstet Gynaecol Res.;41(8):1240-5.
Martinon, Fabio et al., The Inflammasome: A Molecular Platform Triggering Activation of Inflammatory Caspases and Processing of proIL-β, (2002) Mol Cell .;10(2):417-26.
Menezes, Joao R. L. and Luskin, Marla B., Expression of Neuron-Specific Tubulin Defines a Novel Population in the Proliferative Layers of the Developing Telencephalon,1994, Journal of Neuroscience, 14 (9) 5399-5416.
Minamiya Y, et al., Expression of histone deacetylase 1 correlates with a poor prognosisin patients with adenocarcinoma of the lung. Lung Cancer. Nov. 2011;74(2):300-4.doi: 10.1016/j.lungcan.2011.02.019. Epub Apr. 5, 2011. PMID: 21466904.
Mohanty, Subhasis et al. "Prolonged proinflammatory cytokine production in monocytes modulated by interleukin 10 after influenza vaccination in older adults." The Journal of infectious diseases vol. 211,7 (2015): 1174-84. doi:10.1093/infdis/jiu573.
Molsey, Amber et al., Glucose Regulates Insulin Gene Transcription by Hyperacetylation of Histone H4*, 2003, The Journal OfBiological Chemistry, 278, 19660-6.
Monneret C., Histone deacetylase inhibitors for epigenetic therapy of cancer. Anticancer Drugs. Apr. 2007;18(4):363-70. doi: 10.1097/CAD.0b013e328012a5db. Erratum in: Anticancer Drugs. Jun. 2007;18(5):219. PMID: 17351388.
Morel S, et al. "Adjuvant System AS03 containing α-tocopherol modulates innate immune response and leads to improved adaptive immunity", Vaccine. Mar. 16, 2011;29(13):2461-73. doi: 10.1016/j.vaccine.2011.01.011. Epub Jan. 20, 2011. PMID:21256188.
Mu, Jiasheng et al., Thioridazine, an antipsychotic drug, elicits potent antitumor effects in gastric cancer, ONCOLREP., vol. 31, No. 5, 2014, pp. 2107-2114.
Murphy, Craig A et al. "Divergent pro- and antiinflammatory roles for IL-23 and IL-12 in joint autoimmune inflammation." The Journal of experimental medicine vol. 198,12 (2003): 1951-7. doi:10.1084/jem.20030896.
Mwakwari, Sandra et al., Macrocyclic Histone Deacetylase Inhibitors, 2010, Curr Top Med Chem. 10 (14): 1423-40.
Nocito, Antonio et al, Serotonin Regulates Macrophage-Mediated Angiogenesis in a Mouse Model of Colon Cancer Allografts, 2008, Cancer Res., 68(13):5152-8.
Nowak, Elizabeth C. et al, Tryptophanhydroxylase-1 regulates immune tolerance and inflammation, 2012, JEM,209(11):2127.
Park, Matthew K et al., The CXC ChemokineMurine Monokine Induced by IFN-γ (CXC Chemokine Ligand 9) Is Made by APCs,Targets Lymphocytes Including Activated B Cells, and Supports AntibodyResponses to a Bacterial Pathogen In Vivo, J Immunol Aug. 1, 2002, 169 (3)1433-1443; DOI: https://doi.org/10.4049/jimmunol.169.3.1433.
Park, Mi Sun et al., Thioridazine inhibits angiogenesis and tumor growth by targeting the VEGFR-2/PI3K/mTOR pathway in ovarian cancer xenografts,2014, Oncotarget.;5(13):4929-34.

(56) References Cited

OTHER PUBLICATIONS

Pornour, Majid et al. New Perspective Therapy of Breast Cancer Based on Selective Dopamine Receptor D2 Agonist and Antagonist Effects on MCF-7 Cell Line, 2015, Recent Pat Anticancer Drug Discov.;10(2):214-23.
Prabhu, Varun Vijay et al., DDIS-08.The Small Molecule Imipridone ONC201 Is Active In Glioblastoma With Drd2pathwayDysregulation, Nov. 1, 2017,Neuro-Oncology, vol. 19, issue suppl 6, p. vi60, abstract.
Quint, Karl et al., Clinical significance of histone deacetylases 1, 2, 3, and 7: HDAC2 is an independent predictor of survival in HCC (2011), Virchows Arch 459:129-139, DOI10.1007/S00428-011-1103-0.
Reddy, Pavan et al., Histone deacetylase inhibition modulates indoleamine 2,3-dioxygenase-dependent DC functions and regulates experimental graft-versus-host disease in mice, J Clin Invest, vol. 118, 2008, pp. 2562-2573.
Reilly, Christopher M et al. "HDAC inhibition inlupus models." Molecular medicine (Cambridge, Mass.) vol. 17,5-6 (2011 ):417-25. doi:10.2119/molmed.2011.00055.
Ren, Ke and Torres, Richard, Role ofinterleukin-1 during pain and inflammation, 2009, Brain Res Rev.;60(1):57-64.
Ren, Yuan et al., Therapeutic effects of histone deacetylase inhibitors in a murine asthma model, Inflamm. Res., 2016, 65:995-1008, DOI 10.1007/s00011-016-0984-4.
Ruan, Y. et al., Interleukin 8 enhances the immune response of ducks to avian influenza vaccine, 2014, Acta Virol. 58(4):356-8.
Sachlos,Eleftherios et al., Identification of Drugs Including a Dopamine Receptor Antagonist that Selectively Target Cancer Stem Cells, 2012, Cell.;149(6):1284-97.
Saito, Akiko et al., A synthetic inhibitor of histone deacetylase, MS-27-275, with marked in vivo antitumor activity against human tumors, 1999,ProcNatl Acad Sci USA. 96:4592-4597.
Sasaki-Imamura, Takako et al. "Production of indole from L-tryptophan and effects of these compounds on biofilm formation by Fusobacterium nucleatum ATCC 25586." Applied and environmental microbiology vol. 76,13 (2010): 4260-8. doi:10.1128/AEM.00166-10.
Selvan, Senthamil et al., Expression of neuron specific enolase (NSE) in metastatic melanoma: Implications for progression of disease (2008), Cancer Research, AACR Annual Meeting Apr. 12-16, 2008.
Shin, Ji Hyun et al., Sertindole, a Potent Antagonist at Dopamine D2 Receptors, Induces Autophagy by Increasing Reactive Oxygen Species in SH-SY5Y Neuroblastoma Cells, 2012, Biol Pharm Bull. ;35(7):1069-75.
Singh, Nagendra et al. "Activation of Gpr109a, receptor for niacin and the commensal metabolite butyrate, suppresses colonic inflammation and carcinogenesis." Immunity vol. 40,1 (2014): 128-39. doi:10.1016/j.immuni.2013.12.007.
Soltani, Mohammad H et al, Microtubule-Associated Protein 2, a Marker of Neuronal Differentiation, Induces Mitotic Defects, Inhibits Growth of Melanoma Cells, and Predicts Metastatic Potential of Cutaneous Melanoma, 2005, Am J Pathol;166:1841-50.
Song CK, et al., Chemotherapy enhances CD8(+) T cell-mediated antitumor immunity induced by vaccination with vaccinia virus. Mol Ther. Aug. 2007;15(8):1558-63. doi: 10.1038/sj.mt.6300221. Epub Jun. 5, 2007. PMID: 17551502.
Song, Jaehwi et al, Increased expression of histone deacetylase 2 is found in human gastric cancer, 2005, APMIS 113: 264-268.
Spengler, Gabriella et al., ThioridazineInduces Apoptosis of Multidrug-resistant Mouse Lymphoma Cells Transfected with the Human ABCB1 and Inhibits the Expression ofP-Glycoprotein, 2011 ,AnticancerRes. ;31(12):4201-5.
Su, Baowei et al., The effects of IL-6 and TNF-alpha as molecular adjuvants on immune responses to FMDV and maturation of dendritic cells by DNA vaccination. (2008)Vaccine. 26. 5111-22. 10.1016/j.vaccine.2008.03.089.
Tanaka and Sakaguchi, Regulatory T cells in cancer immunotherapy, 2017,Cell Res.;27(1):109-118.

Tanaka, Toshio et al. "IL-6 in inflammation, immunity, and disease." Cold Spring Harbor perspectives in biology vol. 6,10 a016295. Sep. 4, 2014, doi:10.1101/cshperspect.a016295.
Tao, R., de Zoeten, E.,Özkaynak, E. et al., Deacetylase inhibition promotes the generation and function of regulatory T cells. (2007) Nat Med 13, 1299-1307, https://doi.org/10.1038/nm1652.
Terry, Natalie, and Kara Gross Margolis. "Serotonergic Mechanisms Regulating the GI Tract: Experimental Evidence and Therapeutic Relevance." Handbook of experimental pharmacology vol. 239 (2017): 319-342. doi:10.1007/164_2016_103.
Thangaraju, Muthusamy et al., GPR109A Is a G-protein-Coupled Receptor for the Bacterial Fermentation Product Butyrate and Functions as a Tumor Suppressor in Colon (2009). Cancer Res. 67, 9: 2826-2832, Published Online First Mar. 10, 2009; DOI:10.1158/0008-5472.CAN-08-4466.
Toshkov, Ilia A et al. "Mitigation of Radiation-Induced Epithelial Damage by the TLR5 Agonist Entolimod in a Mouse Model of Fractionated Head and Neck Irradiation." Radiation research vol. 187,5 (2017): 570-580. doi:10.1667/RR14514.1.
Tovar-Castillo, LE, et al., Under-expression of VHL and over-expression of HDAC-1, HIF-1alpha, LL-37, and IAP-2 in affected skin biopsies of patients with psoriasis. Int J Dermatol. Mar. 2007;46(3):239-46.doi: 10.1111/j.1365-4632.2006.02962.x. PMID: 17343577.
UniProtKB—P15056 (BRAF_HUMAN), https://www.uniprot.org/uniprot/P15056,accessed Dec. 18, 2020.
Visnyei, Koppany et al., A Molecular Screening Approach to Identity and Characterize Inhibitors of Glioblastoma Stem Cells, 2011,Mol Cancer Ther.;10(10):1818-28.
Vizin, Tjasa, and Janko Kos. "Gamma-enolase: a well-known tumour marker, with a less-known role in cancer." Radiology and oncology vol. 49,3 217-26. Aug. 21, 2015, doi:10.1515/raon-2015-0035.
Walmsley, R S et al. "A simple clinical colitis activity index." Gut vol. 43,1 (1998): 29-32. doi:10.1136/gut.43.1.29.
Wang, Xia, and Yong Lin. "Tumor necrosis factor and cancer, buddies or foes?." Acta pharmacologica Sinica vol. 29,11 (2008): 1275-88. doi:10.1111/j.1745-7254.2008.00889.x.
Weinberger, Birgit, Adjuvant strategies to improve vaccination of the elderly population, Current Opinion in Pharmacology 2018, 41:34-41.
Xie, Songbo et al., Microtubule-Binding Proteins as Promising Biomarkers of Paclitaxel Sensitivity in Cancer Chemotherapy, 2016; Med Res Rev; 36,2: 300-312.
Zhang, Mingming et al., Butyrate inhibits interleukin-17 and generates Tregs to ameliorate colorectal colitis in rats, 2016, BMC Gastroenterol.; 16: 84.
Zhang, Zhenhuan et al., Quantitation of HDAC1 mRNA expression in invasive carcinoma of the breast,(2005), Breast Cancer Research and Treatment, 94: 11-16, DOI10.1007/s10549-005-6001-1.
Zhi, Qiongjie et al. "Predictive and prognostic value of preoperative serum tumor markers in resectable adenosqamous lung carcinoma." Oncotarget vol. 7,40 (2016): 64798-64809. doi:10.18632/oncotarget.11703.
Zhou, Qing et al. "Program death-1 signaling and regulatory T cells collaborate to resist the function of adoptively transferred cytotoxic T lymphocytes in advanced acute myeloid leukemia." Blood vol. 116,14 (2010): 2484-93. doi:10.1182/blood-2010-03-275446.
Zimmerman Stephan et al, Reduced Body Size and Decreased Intestinal Tumor Rates in HDAC2-Mutant Mice, 2007, Cancer Res 67: 9047-54.
Ahmed, Suaad, "In vitro Characterization of Gut Microbiota-Derived Bacterial Strains With Neurorotective Properties", Frontiers in Cellular Neuroscience, 2019, vol. 13, article 402, pp. 1-17.
Mori, Andres et al., "The vaccine adjuvant alum inhibits IL-12 by promoting PI3 kinase signaling while chitosan does not inhibit IL-12 and enhances Th1 and Th17 responses" (2012), Eur J Immunol 42, 2709-2719.
Park, Jun H et al. "Development of type 2 diabetes following intrauterine growth retardation in rats is associated with progressive epigenetic silencing of Pdx1." The Journal of clinical investigation vol. 118,6 (2008): 2316-24. doi:10.1172/JCI33655.

(56) References Cited

OTHER PUBLICATIONS

Qin, Meng-Bin et al, Inhibition of SPHK1 Suppresses Phorbol 12-Myristate 13-Acetate-Induced Metastatic Phenotype in Colorectal Cancer HT-29 Cells, Oncology Research Featuring Preclinical and Clinical Cancer Therapeutics, 2011, vol. 19, No. 12, pp. 573-582(10).

Yuille Samantha et al, "Human gut bacteria as potent class I histone deacetylase inhibitors in vitro through production of butyric acid and valeric acid", PLOS ONE, vol. 13, No. 7, Jul. 27, 2018(Jul. 27, 2018), XP009508155.

Keshavarzian MD., Ali et al., "Colonic Bacterial Composition in Parkinson's Disease", Movement Disorders, 2015, vol. 30, No. 10, 1351-1360.

Wang, Guohua et al., HDAC inhibition prevents white matter injury by modulating microglia/macrophage polarization through the GSK3β/PTEN/AKt axis, (2015) PNAS 112(9):2583-2858.

Yoshikawa, Shota et al., "Valerate productions by Megasphaera elsdenii isolated from pig feces", Journal of Bioscience and Bioengineering, 2018, vol. 125. No. 5, pp. 519-524.

Oct. 16, 2020 Pre-interview First Office Action U.S. Appl. No. 16/714,092.

Hong, Seung-Hye et al "Alternative Biotransformation of Retinal to Retinoic Acid or Retinol by an Aldehyde Dehydrogenase from Bacillus cereus ." Applied and Environmental Microbiology 82.13 (2016): 3940-3946. Web. Mar. 18, 2020.

International Preliminary Report on Patentability dated Sep. 23, 2019 for International Application No. PCT/EP2018/065903.

International Search Report and Written Opinion dated Feb. 6, 2019 for International Application No. PCT/EP2018/065903.

McDonald, Julie A. K. et al., "Inhibiting Growth of Clostridioides difficile by Restoring Valerate, Produced by the Intestinal Microbiota", Gastroenterology, 2018, 155:1495-1507.

Mar. 2, 2022 Non-Final Office Action U.S. Appl. No. 17/221,011.

Michel, Laure, and Alexandre Prat. "One more role for the gut: microbiota and blood brain barrier." Annals of translational medicine vol. 4,1 (2016): 15. doi:10.3978/j.issn.2305-5839.2015.10.16.

Sampson, T. et al., "Gut Microbiota Regulate Motor Deficits and Neuroinflammation in a Model of Parkinson's Disease", Cell, 2016, vol. 167, pp. 1469-1480.

Uenishi, H. et al., "Physiological function of lactic acid bacteria and factors thereof", Journal of Cookery Science of Japan, 2013, vol. 46, No. 2, pp. 129-133.

Van Kessel, S. et al, "Gut bacterial tyrosine decarboxylases restrict levels of levodopa in the treatment of Parkinson's disease", Nature Communications, 2019, 10:310, pp. 1-11.

Ohnishi, A., "Biomedia: What is the big walnut-like sphere" lurking within the body? Bioengineering, 2016, vol. 94, No. 8, p. 500.

GenBank Accession No. NR_044054.1 (Feb. 3, 2015) Blautia wexlerae strain SSM 19850 16S ribsomal RNA gene, partial sequence.

GenBank Accession No. NR_117867.1 (Feb. 3, 2015) Blautia stercoris strain GAM6-1 16S ribsomal RNA gene, partial sequence.

Genbank NCBI Reference Sequence: NR_026314 (Feb. 3, 2015), Blautia hydrongentrophica strain S5a36 16S ribosomal RNA gene, partial sequence, accessed Feb. 5, 2019.

Giustini, A. et al., Chapter 34: Traumatic and nontraumatic brain injury, Handbook of Clinical Neurology, Neurological Rehabilitation, 2013, vol. 110 (3rd series), pp. 401-409.

Koh, Gar Yee et al., Parabacteroides distasonis attenuate toll-like receptor 4 signaling and Akt activation and blocks colon tumor formulation in high-fat-diet-fed azoxymethane-treated mice, International Journal of Cancer, 2018, 143, 1797-1805. Accepted Article, doi: 10.1002/ijc.31559, Apr. 26, 2018.

Lefeber, Dirk J. et al., Th1-DirectingAdjuvants Increase the Immunogenicity of Oligosaccharide-Protein Conjugate Vaccines Related to *Streptococcus pneumoniae* Type 3, Infect Immun, Dec. 2003, 71(12)6915-6920.

Olafsdottir, Thorunn et al., "Molecular signatures of vaccine adjuvants", Vaccine, 2015, 33(40)5302-5307.

Sonnenburg, et al., Genomic and Metabolic Studies of the Impact of Probiotics on a Model Gut Symbiont and Host. PLoS Biol, 2006,4(12): e413, pp. 1-17, https://doi.org/10.1371/journal.pbio.0040413. ,Published online Nov. 28, 2006.

Written Opinion for PCT/US2017/066709 dated Jun. 4, 2018 (Published as W02018112363) owned by Evelo Biosciences, Inc.

Written Opinion for PCT/US2017/066713 dated Aug. 13, 2018 (Published as WO2018/112365) owned by Evelo Biosciences, Inc.

\* cited by examiner

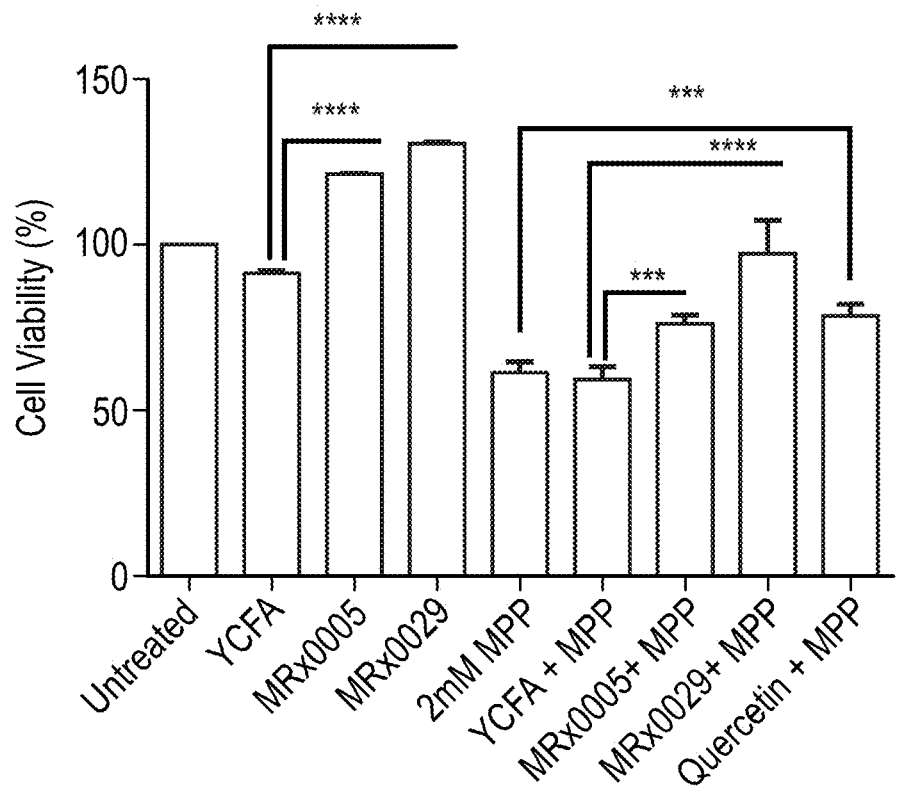
FIG. 1 Protection against neurotoxicity
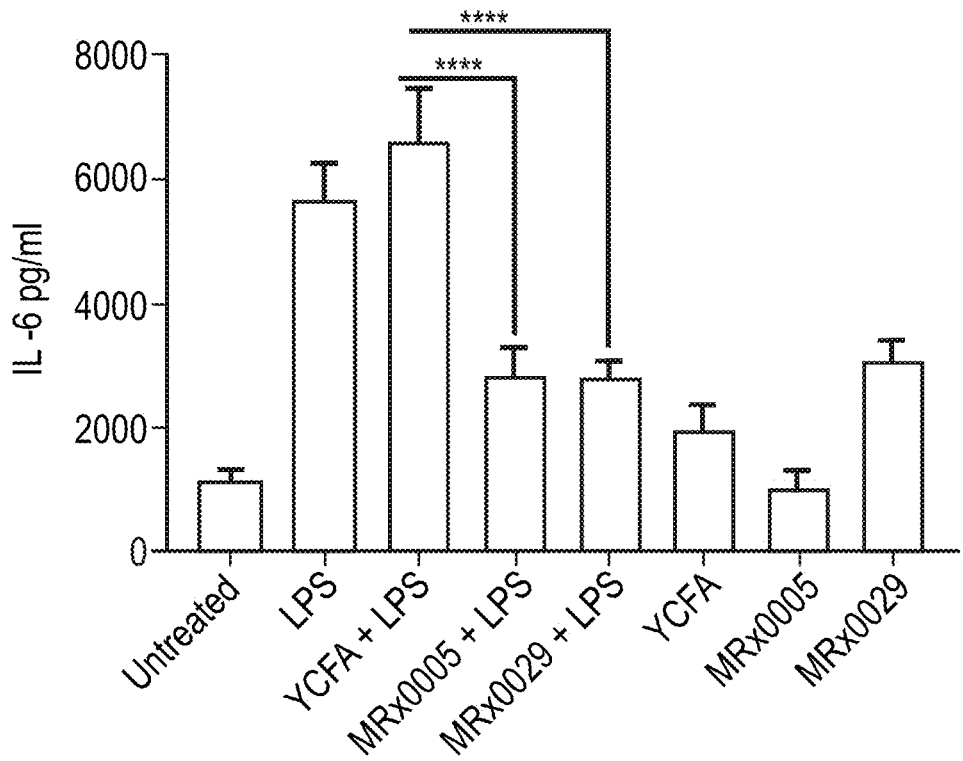
FIG. 2 Secretion of IL-6 from U373

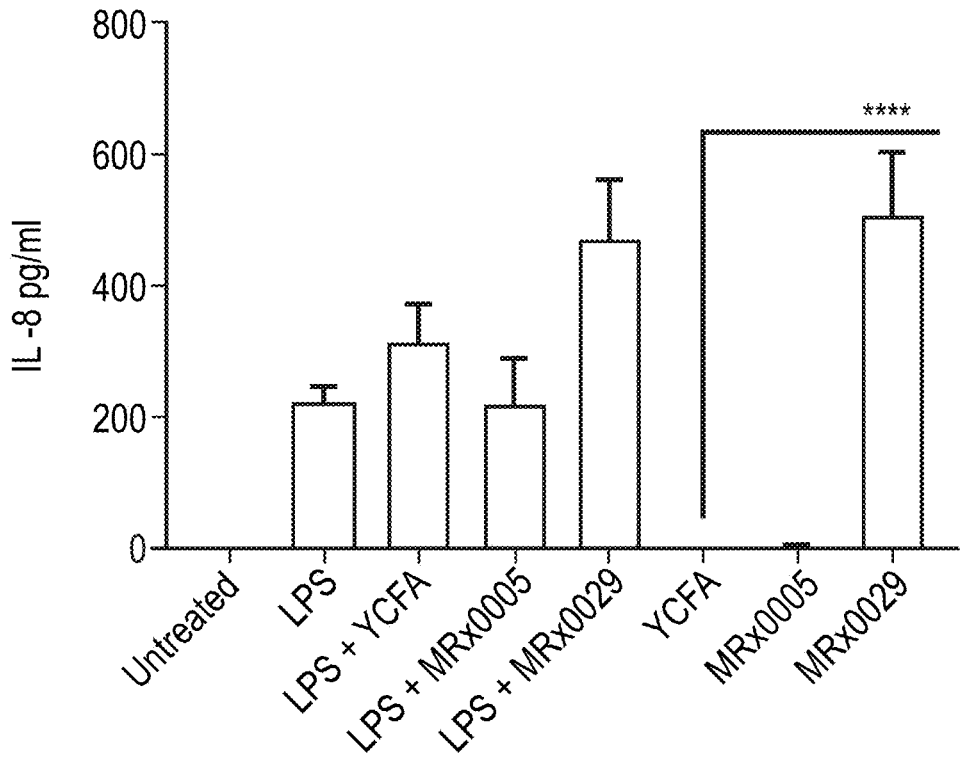
FIG. 3 Secretion of IL-8 from U373
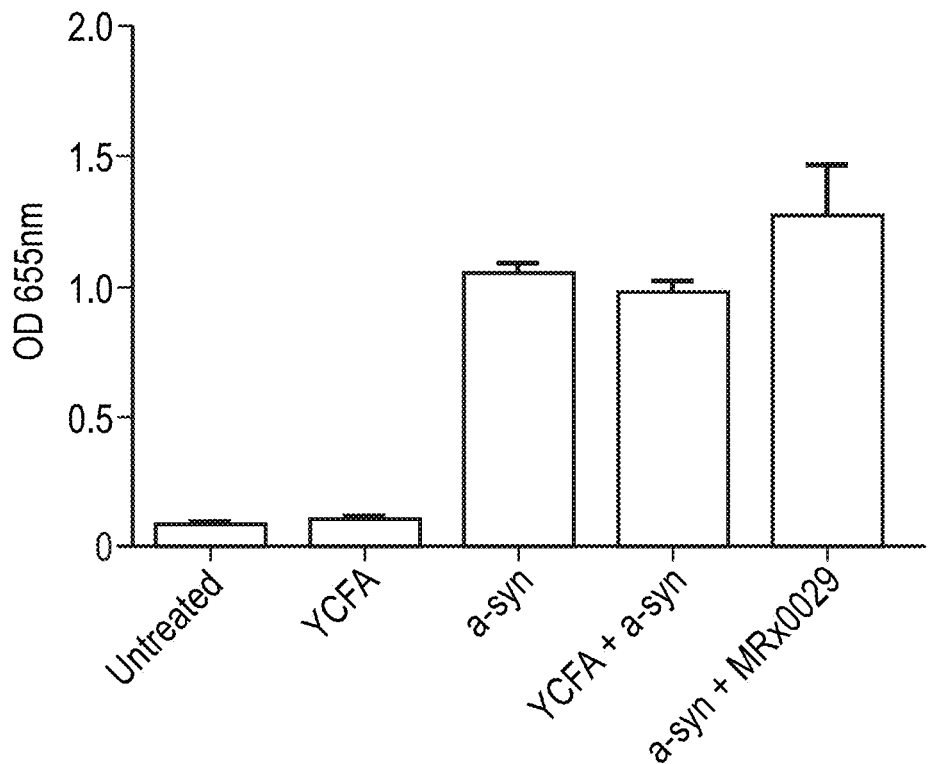
FIG. 5 Inhibition of a-synuclein-induced NFkB-AP1 activation in HEK-TLR4

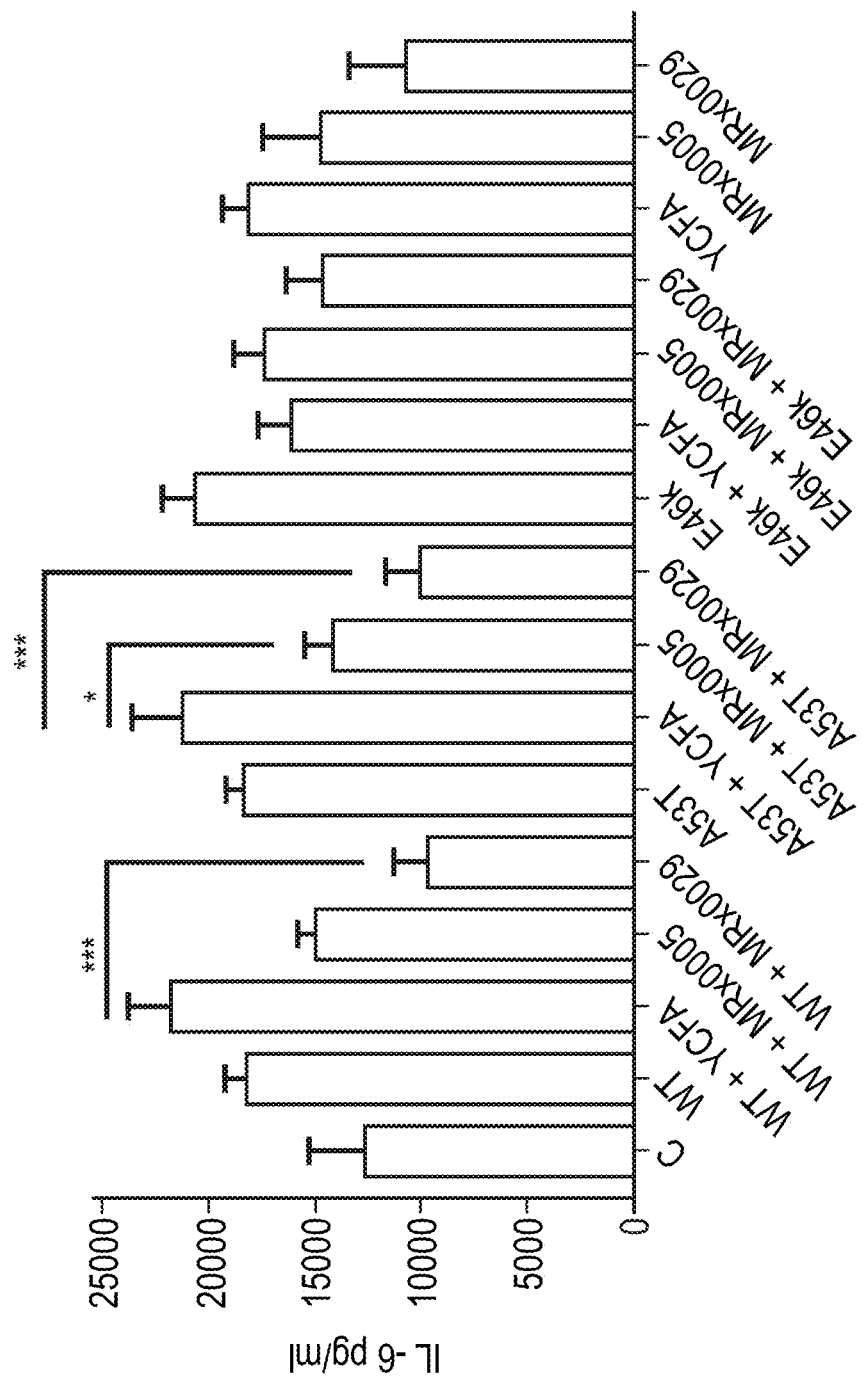

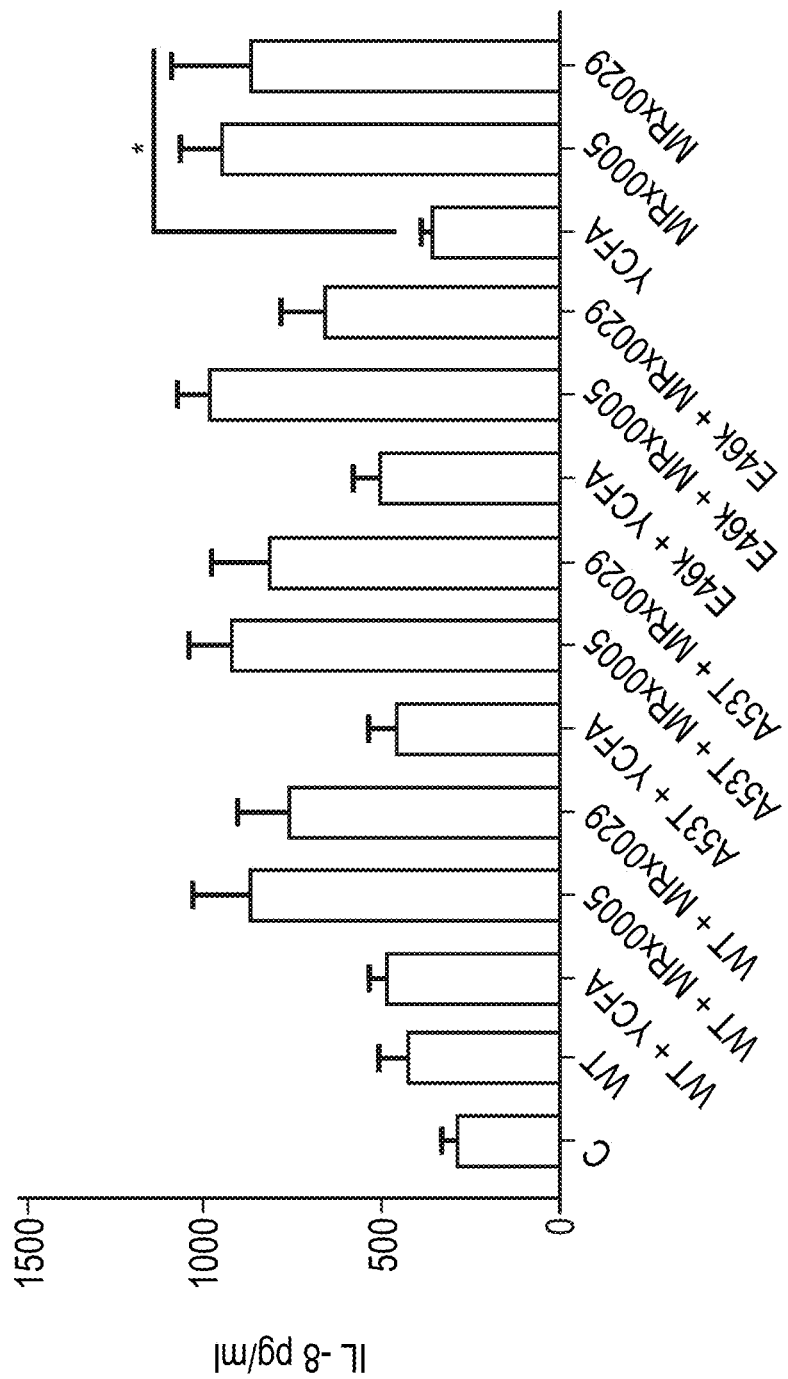

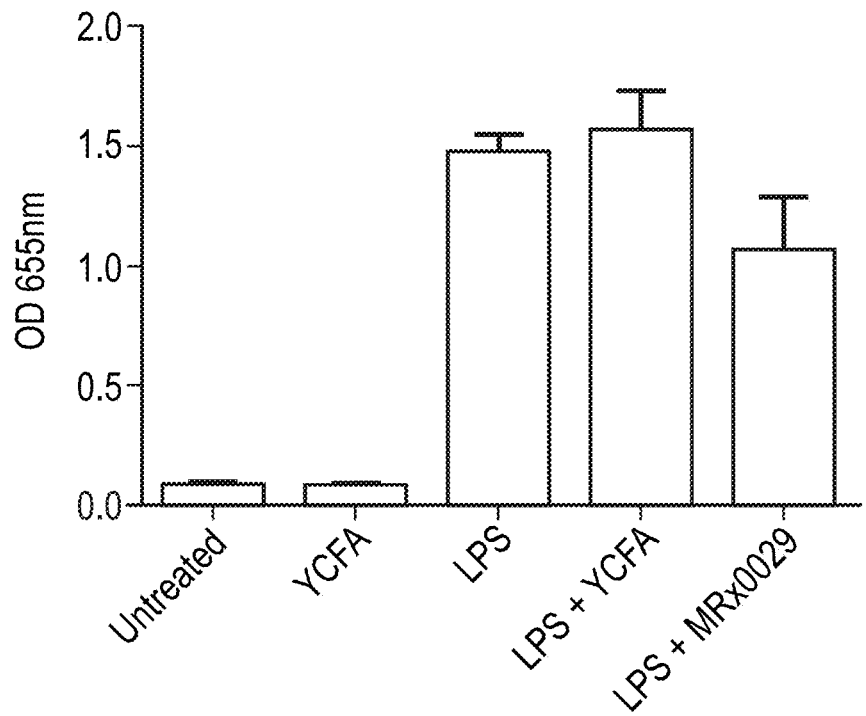
FIG. 6 Inhibition of LPS-induced NFkB-AP1 activation in HEK-TLR4
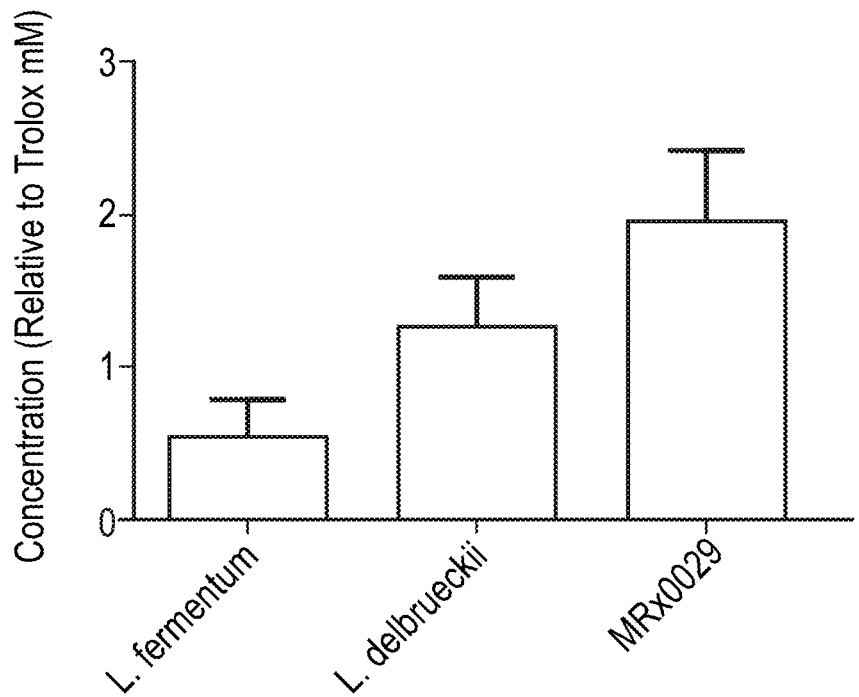
FIG. 8 Antioxidant Capacity Assay

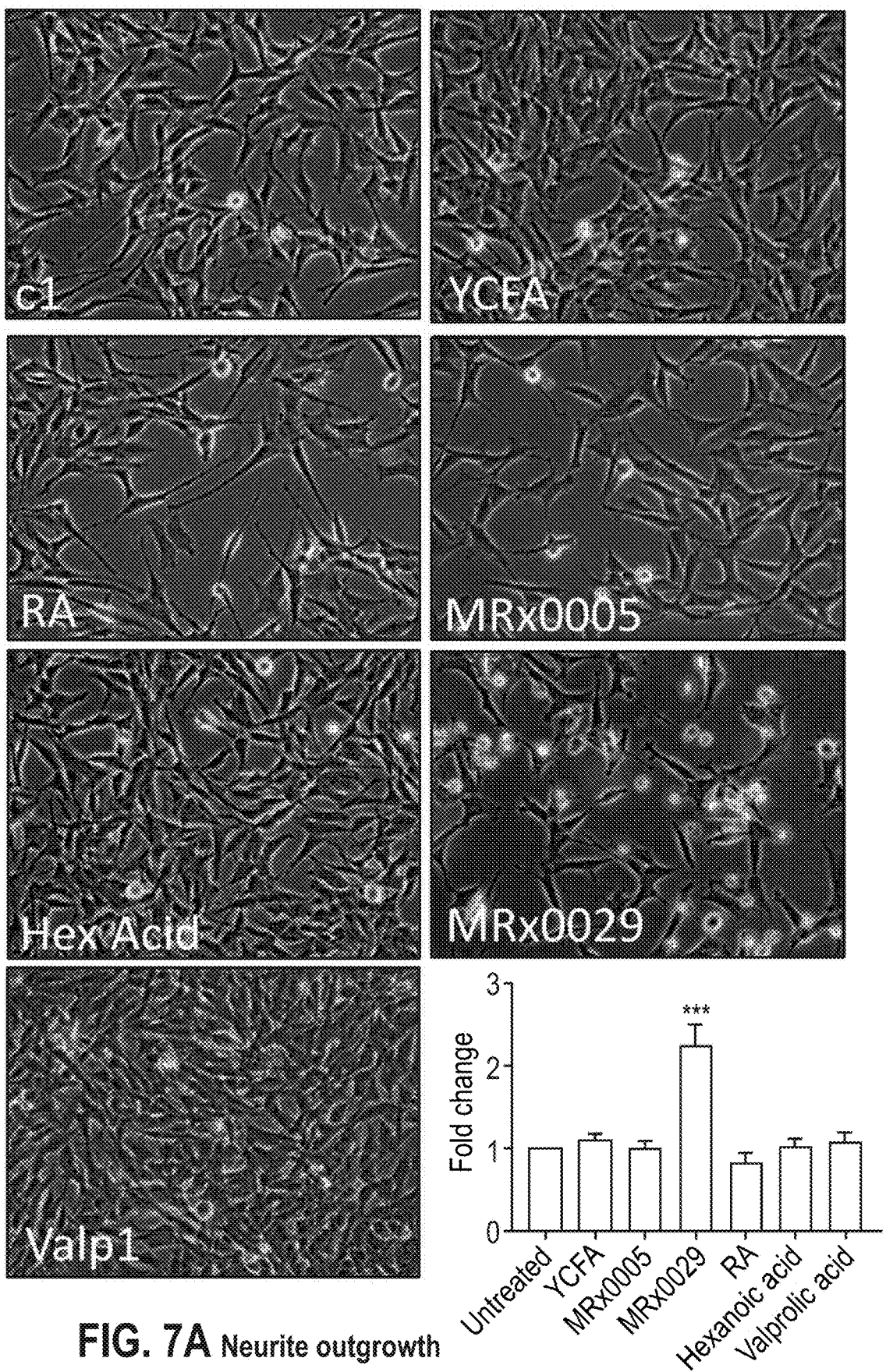
FIG. 7A Neurite outgrowth

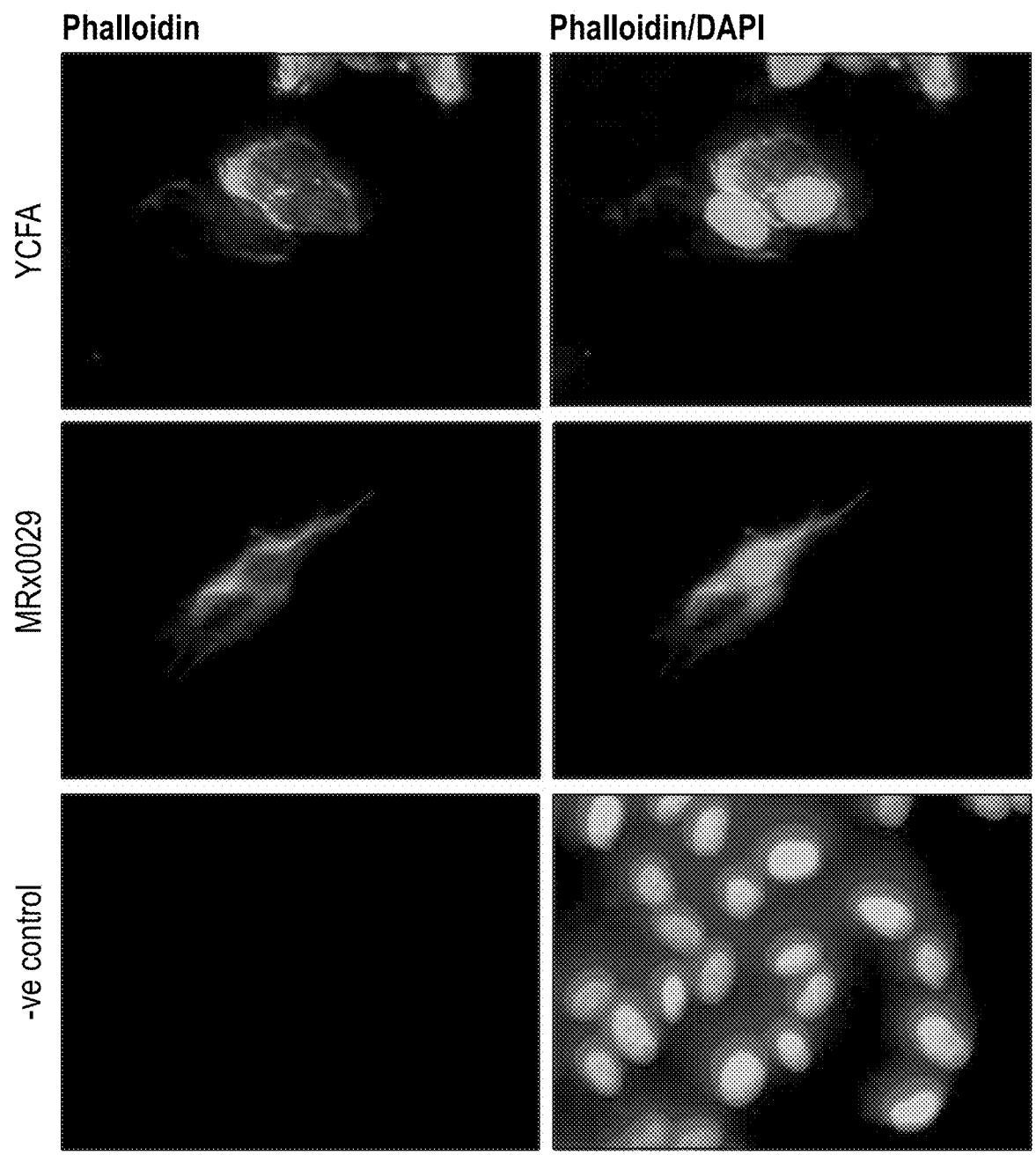
FIG. 7B (contd.)

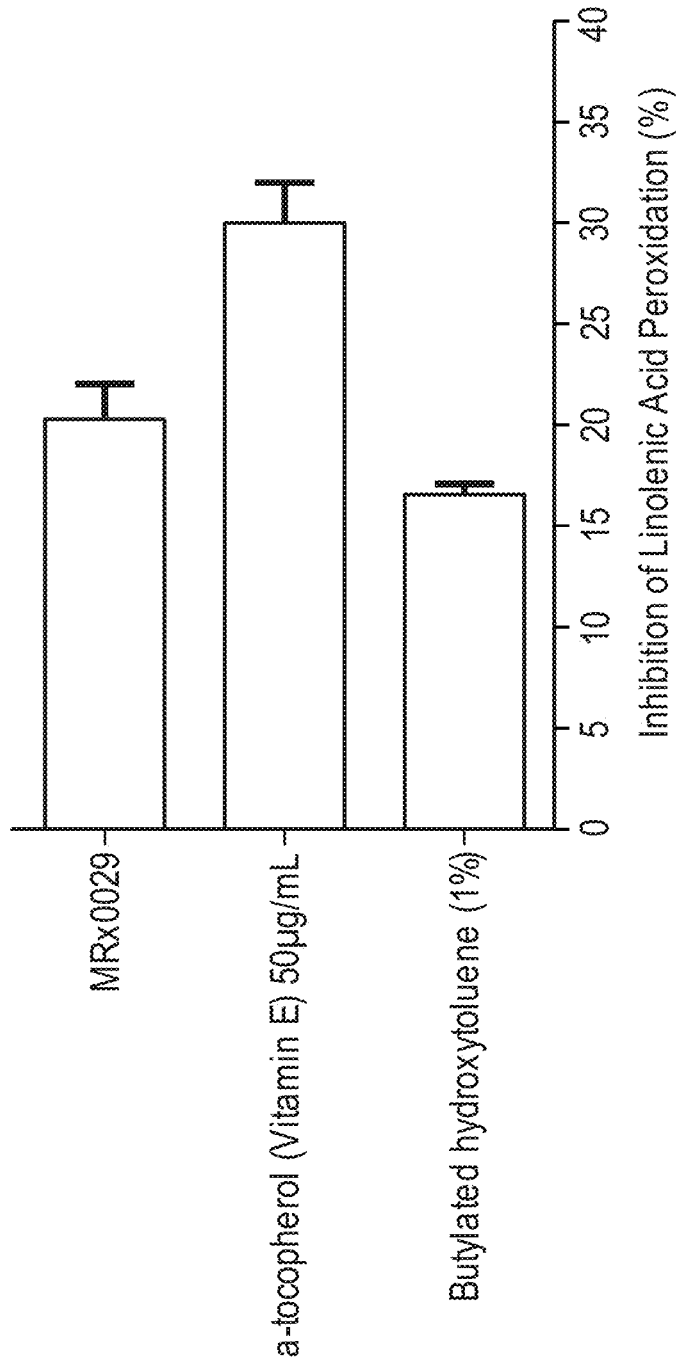

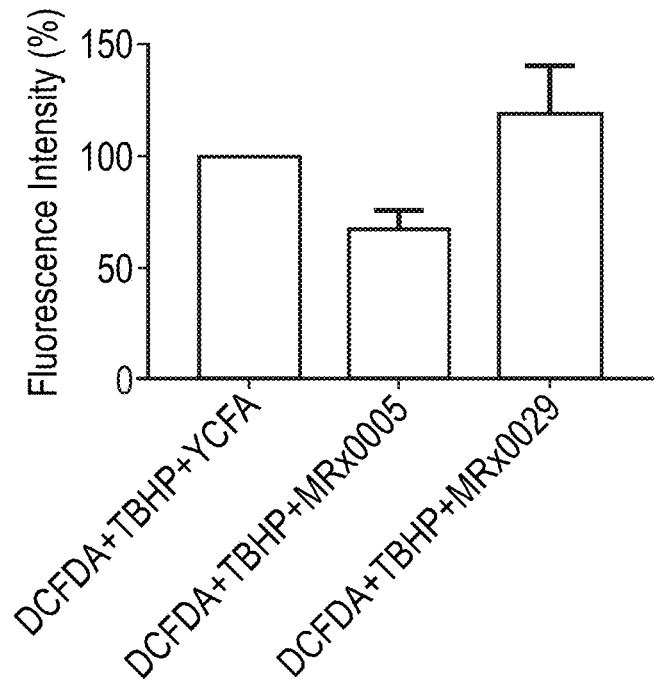
FIG. 10A Total ROS production
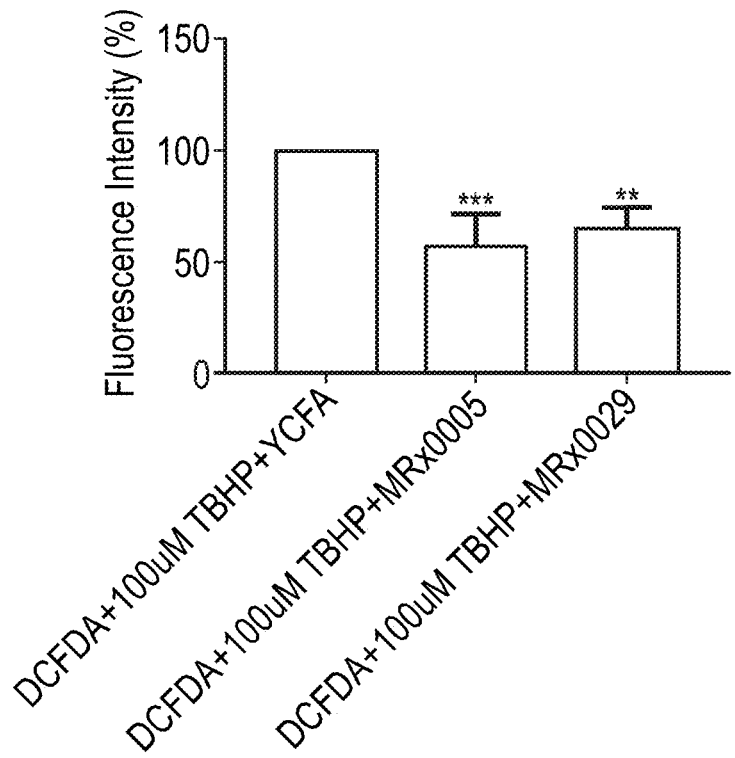
FIG. 10B Total ROS production

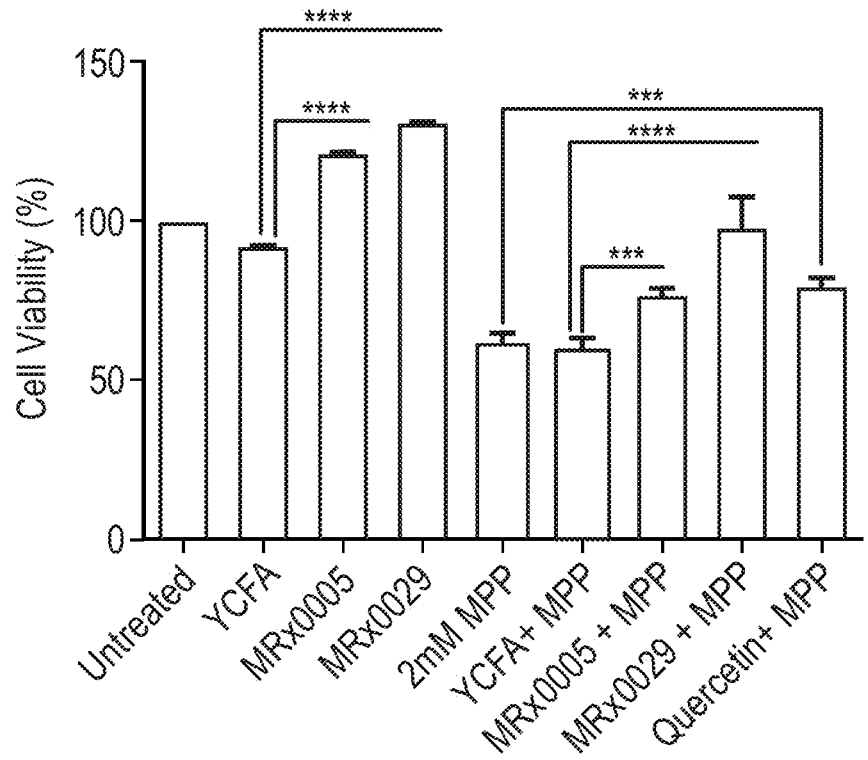
FIG. 11 Neuroprotection – cell viability
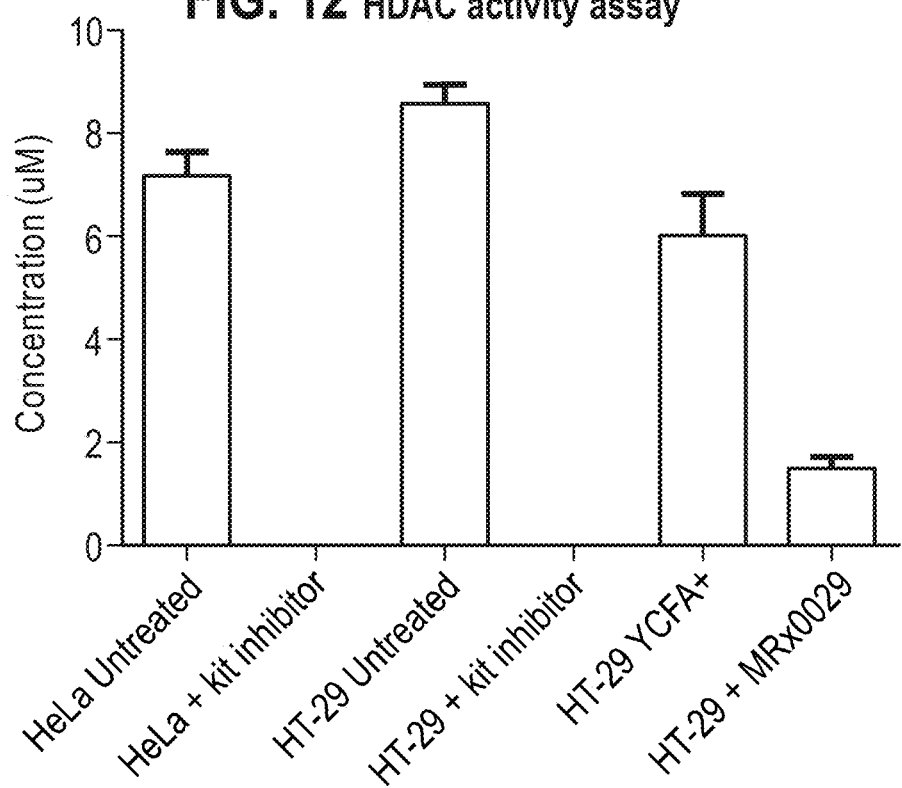
FIG. 12 HDAC activity assay

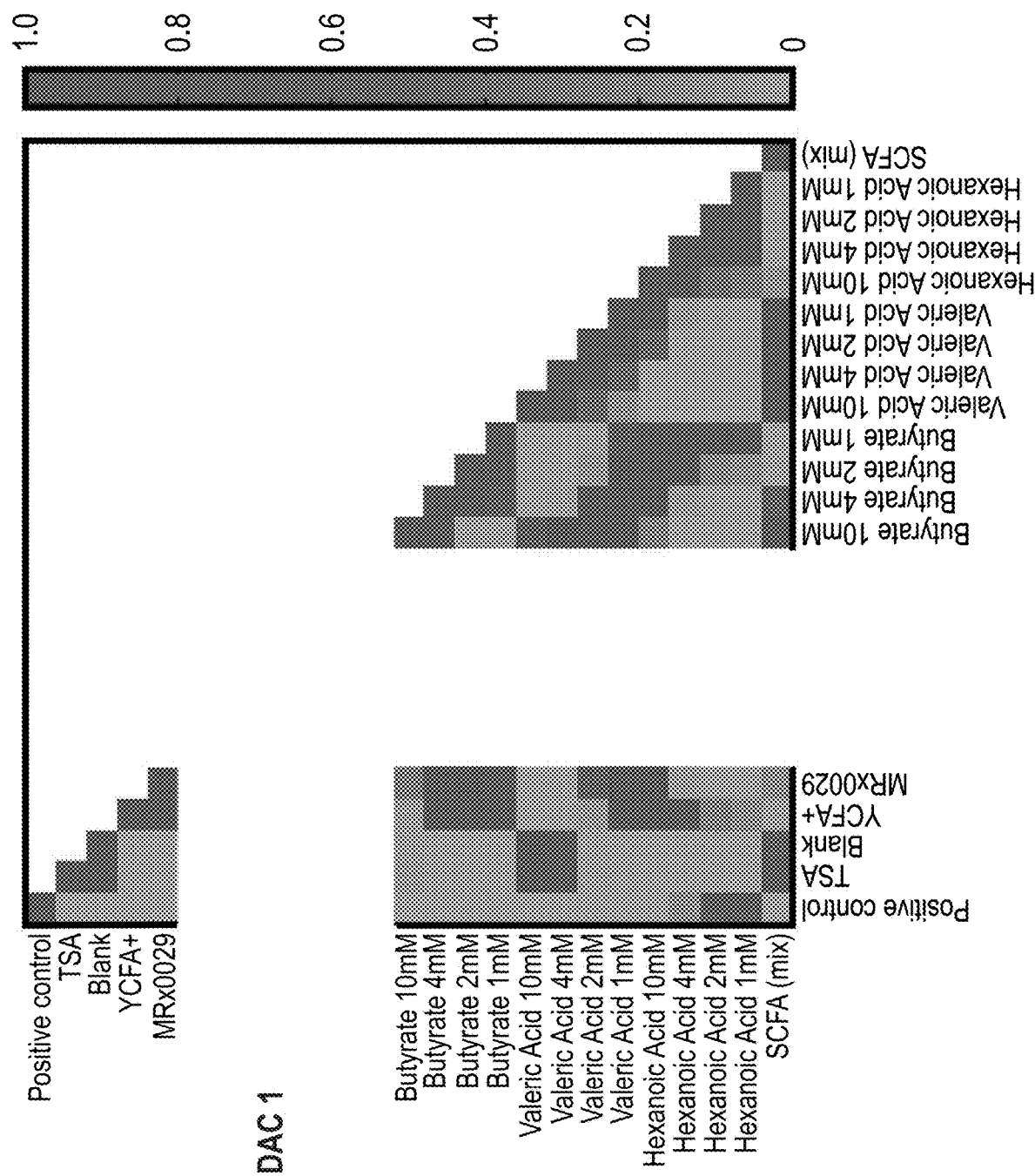
FIG. 14A HDAC 1

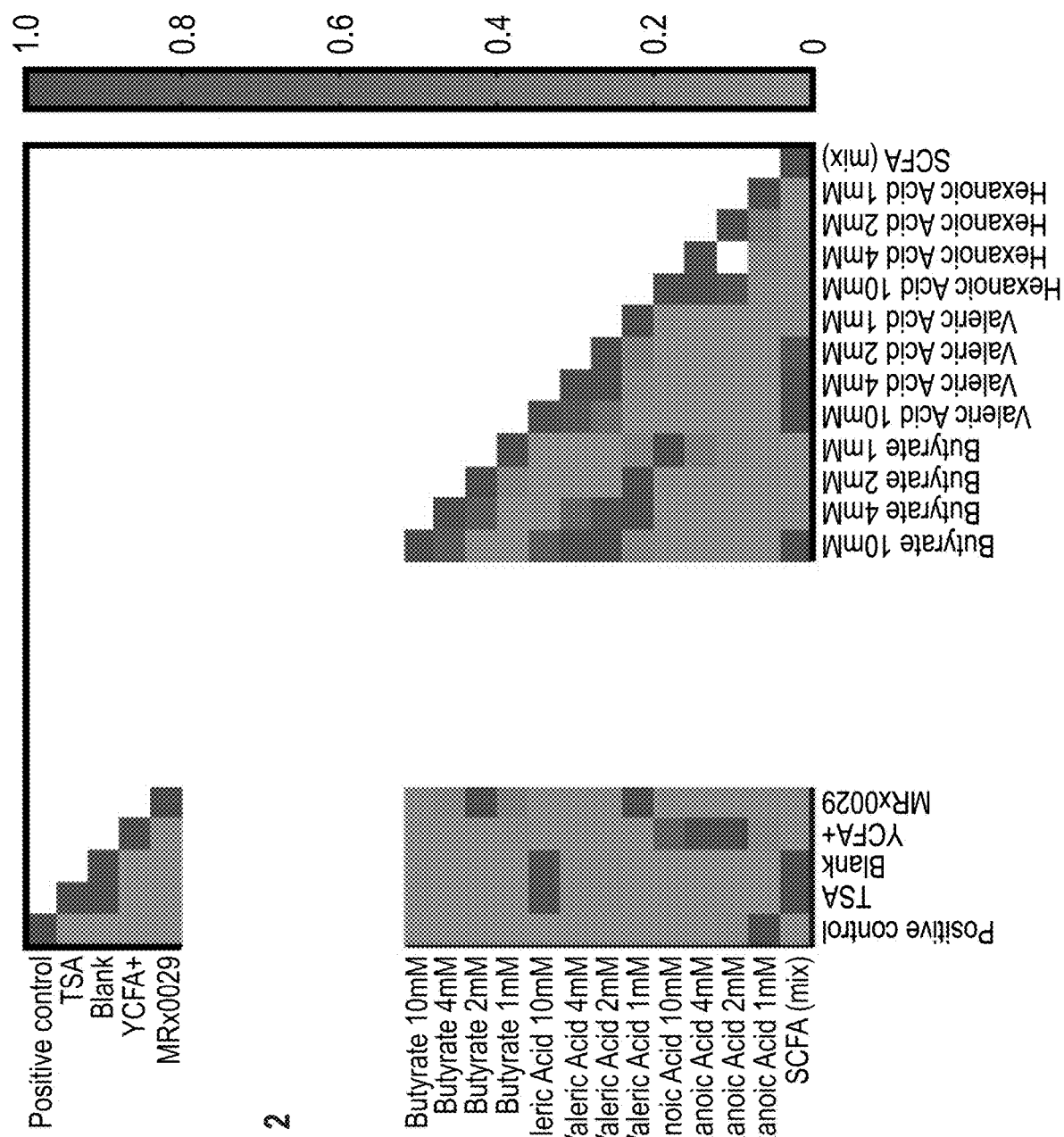
FIG. 14B HDAC 2

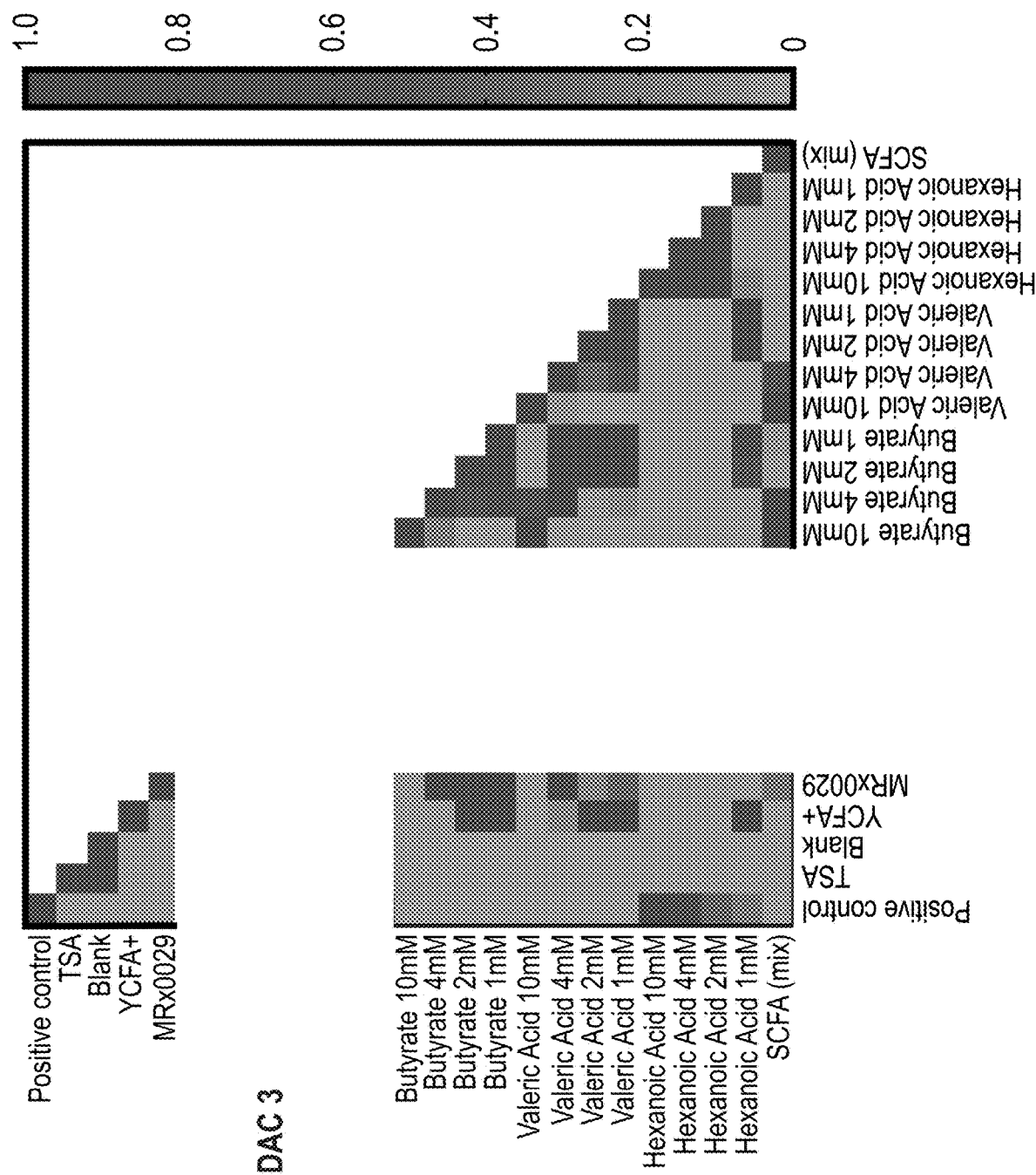
FIG. 14C HDAC 3

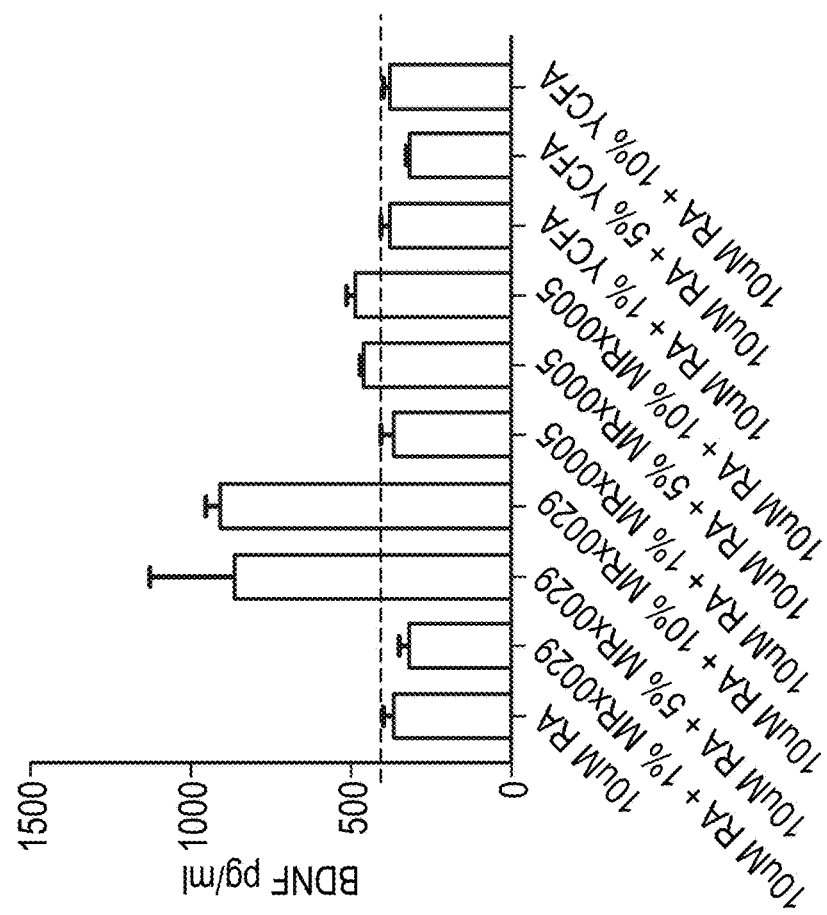
FIG. 18 BDNF secretion from SH-SY-5Y
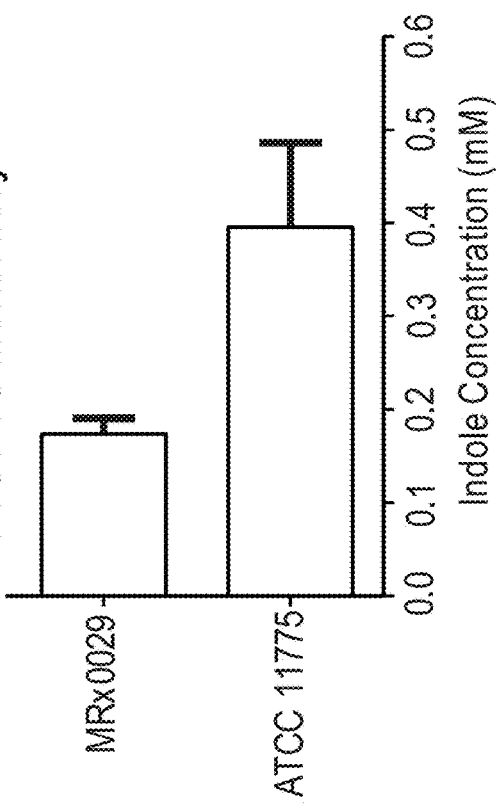
FIG. 16 Indole Assay
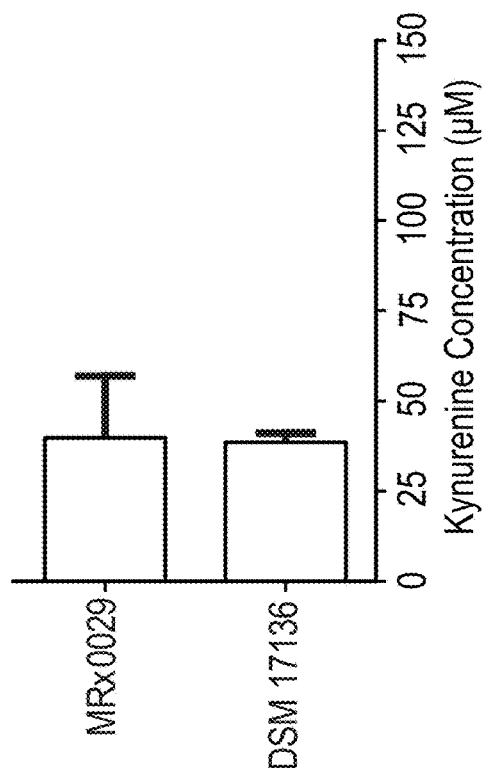
FIG. 17 Kynurenine Assay

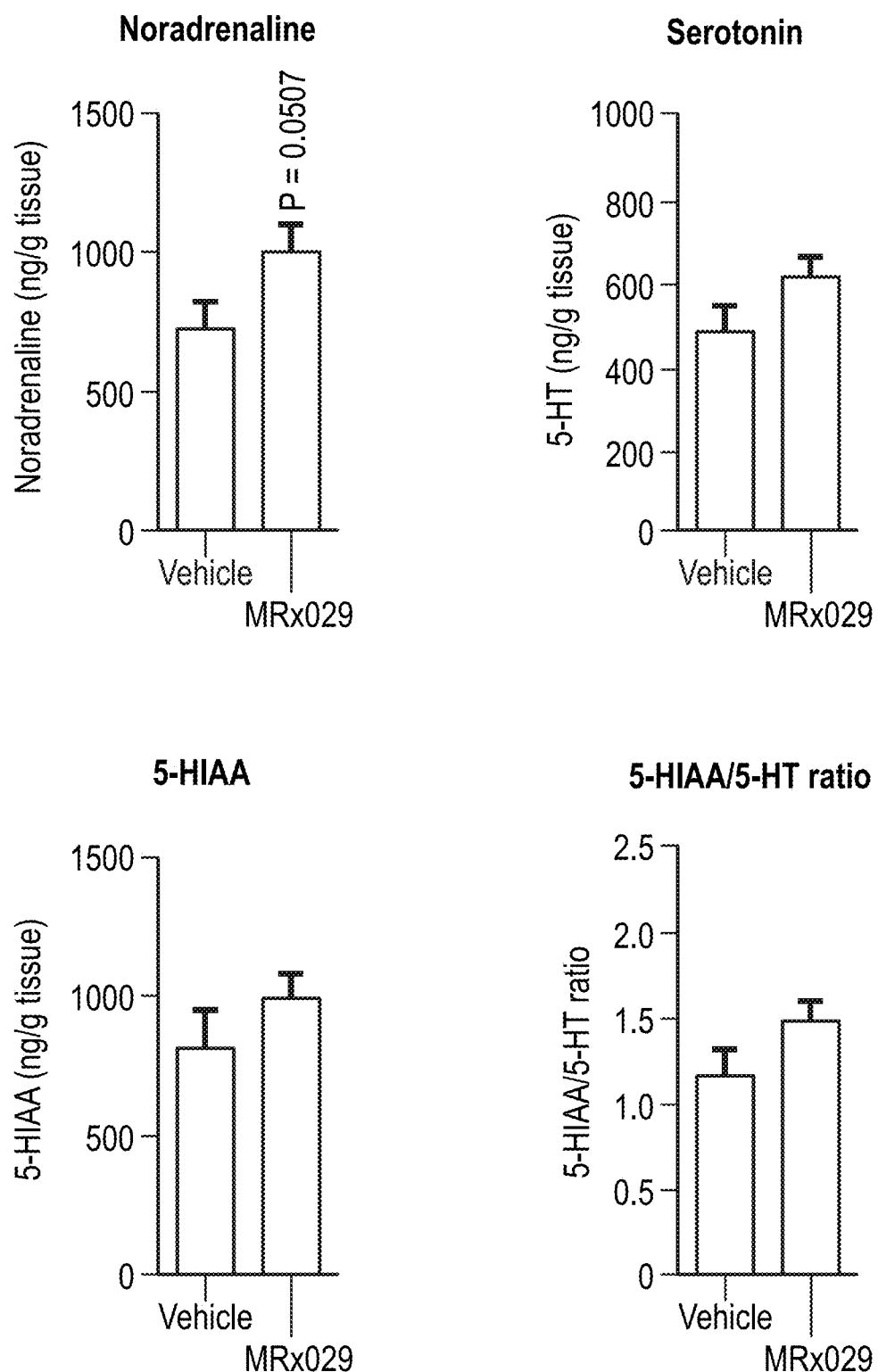
FIG. 19 Production of neurotransmitters in the brain

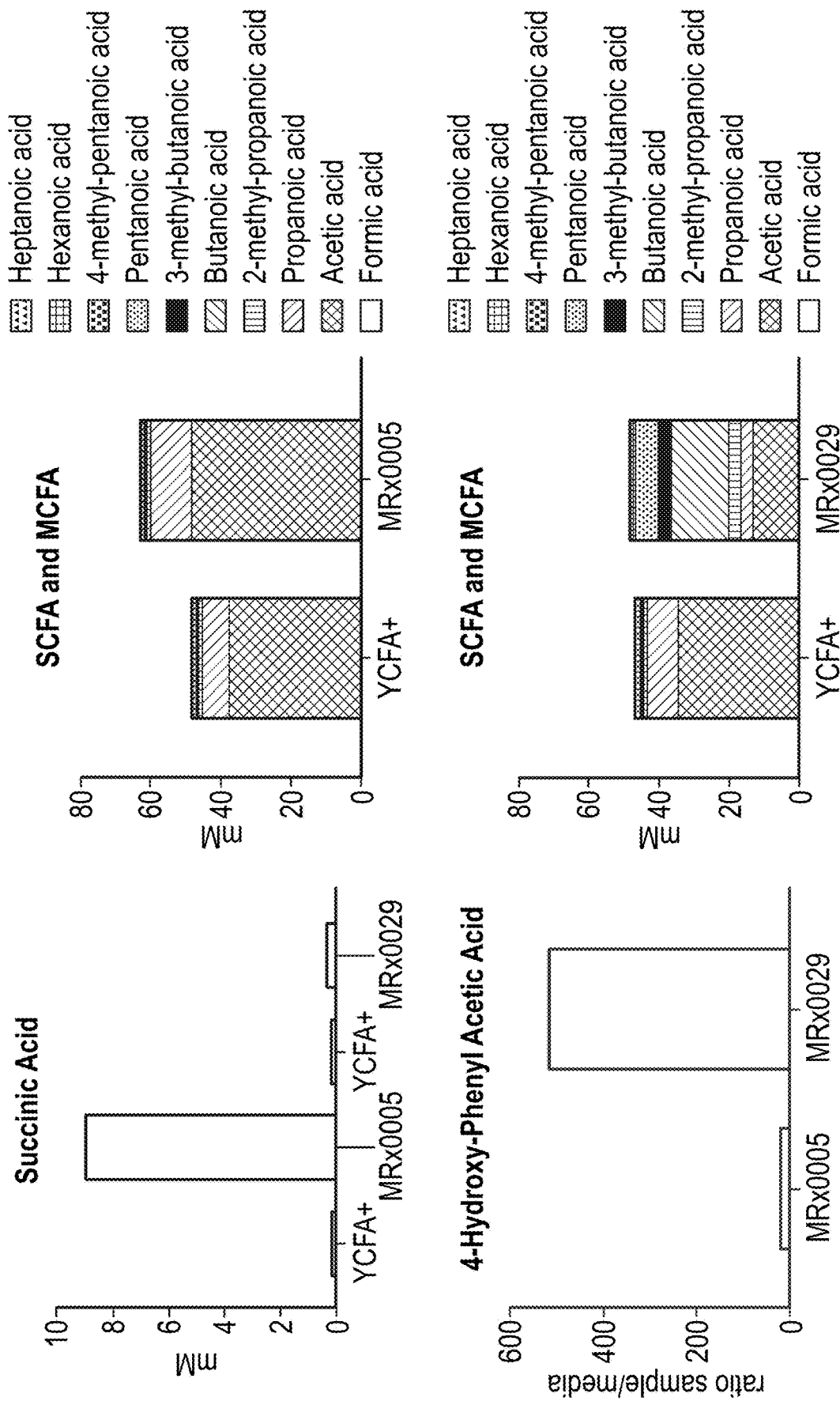
FIG. 20 Bacterial metabolites in the supernatant

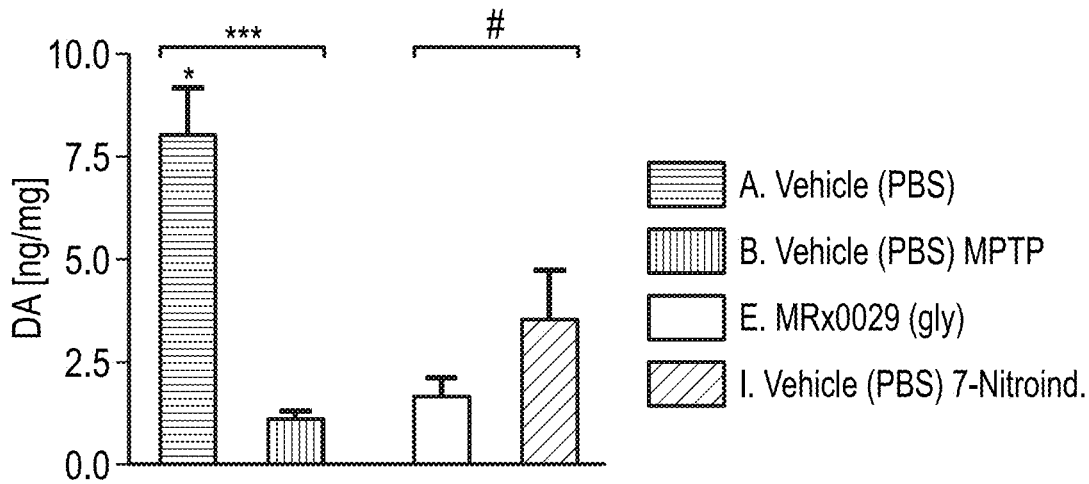
FIG. 21A DA
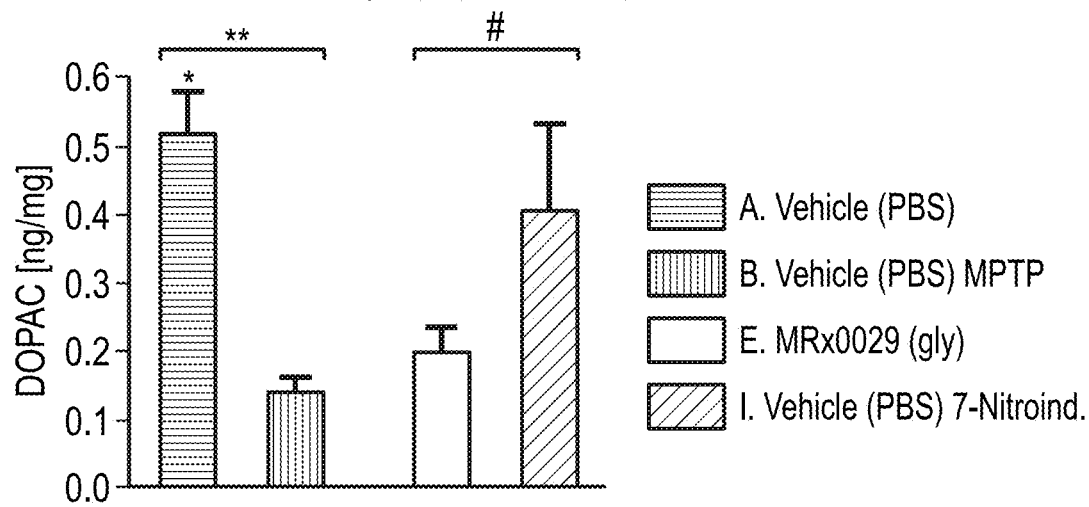
FIG. 21B DOPAC
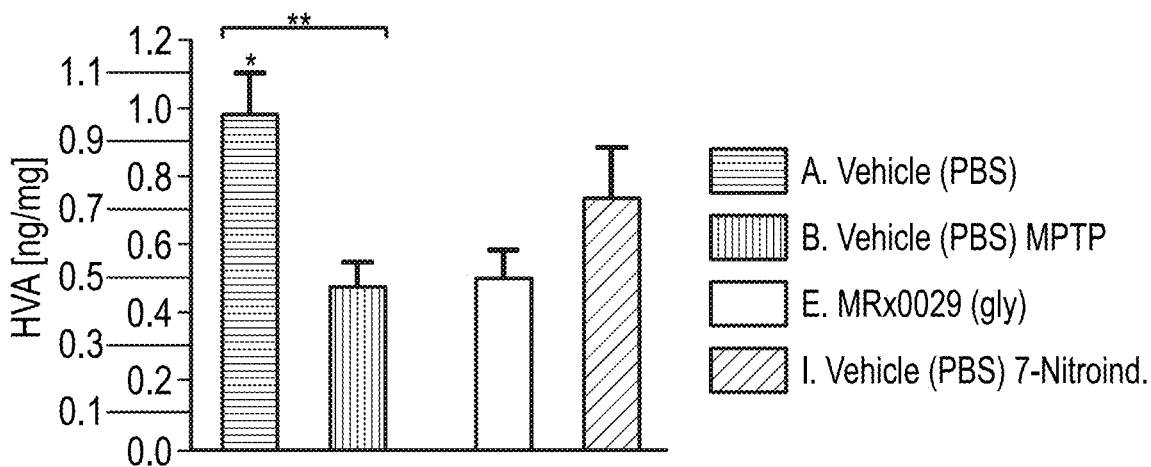
FIG. 21C HVA

FIG. 22C
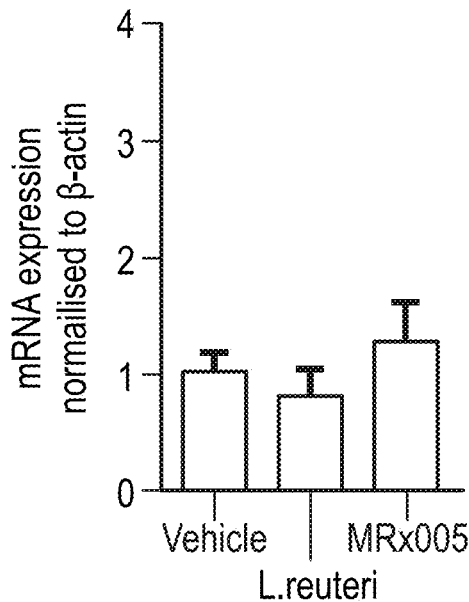
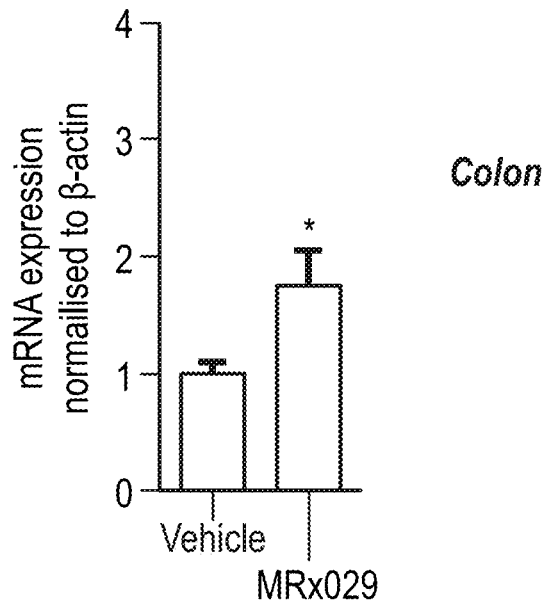
Colon
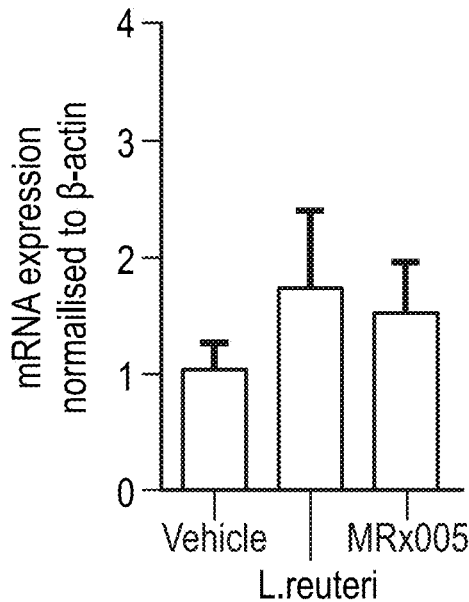
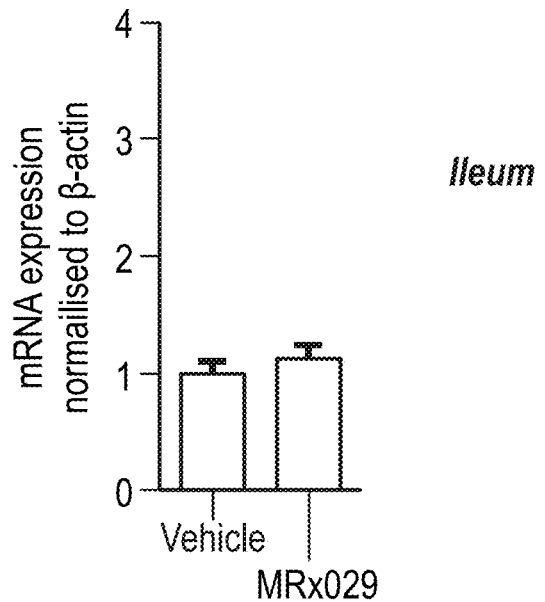
Ileum

FIG. 22E Permeability in the Ileum
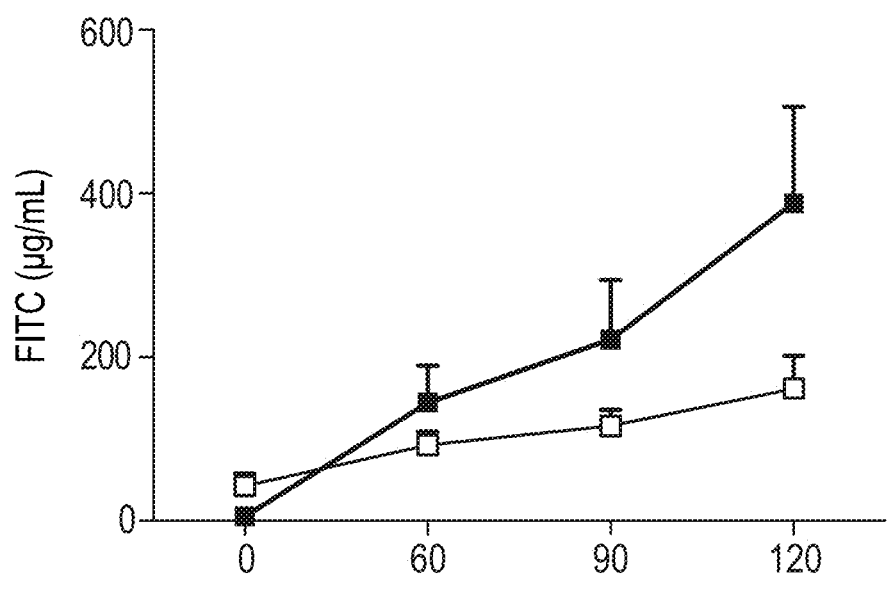
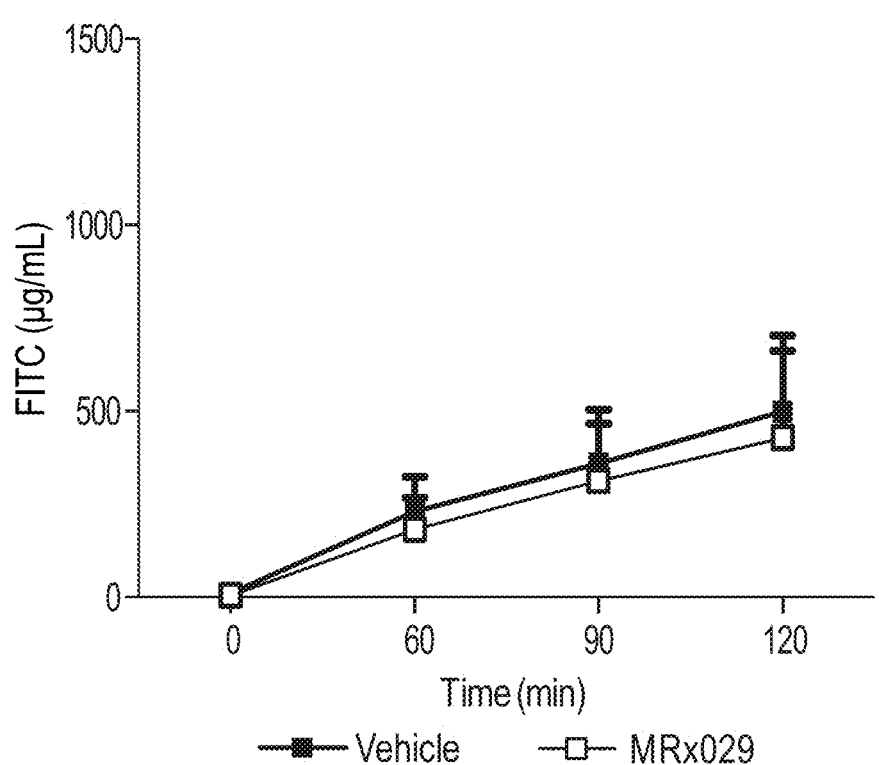

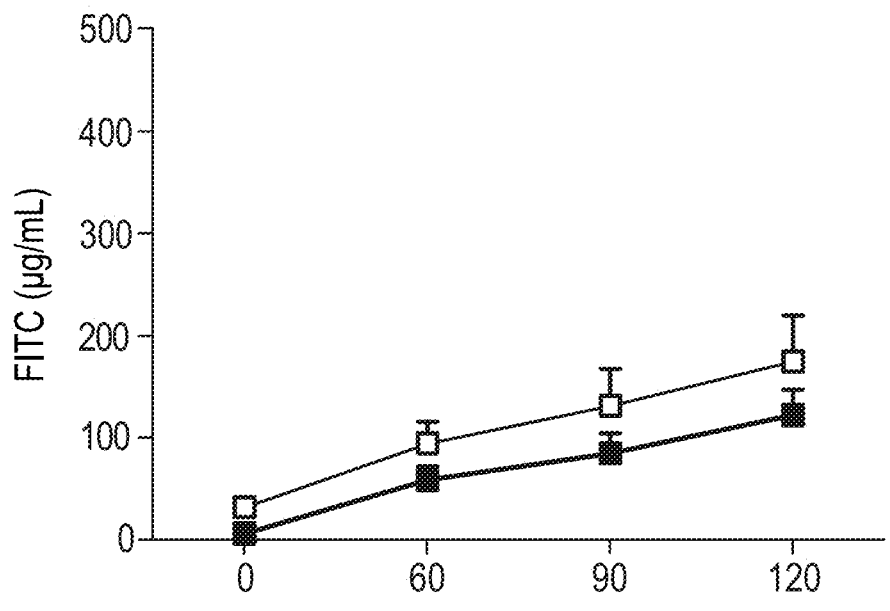
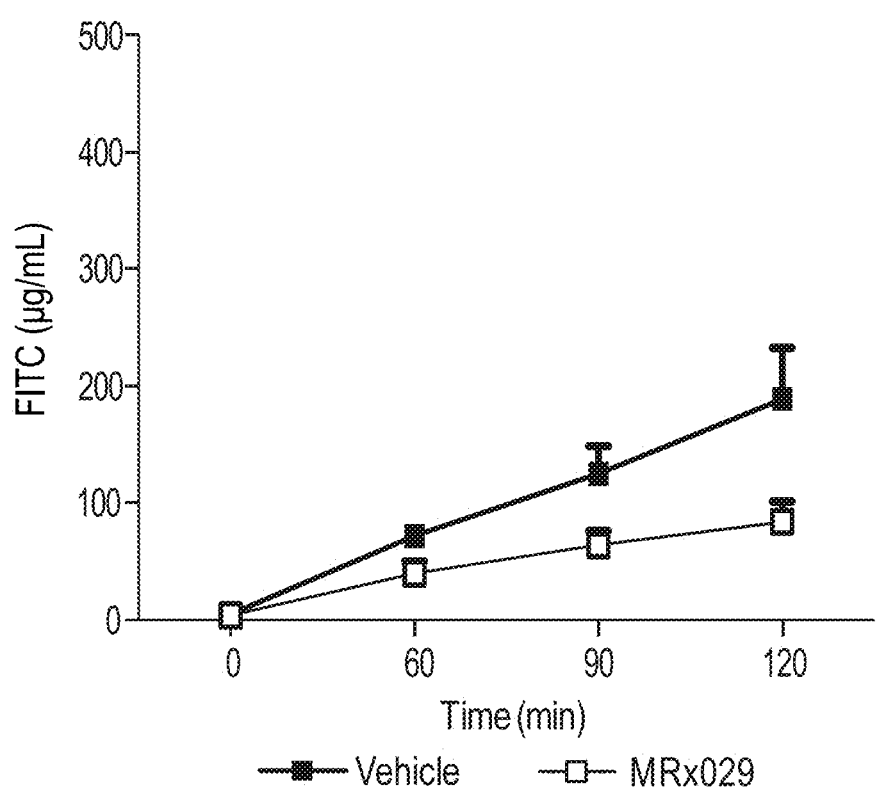
FIG. 22F Permeability in the colon

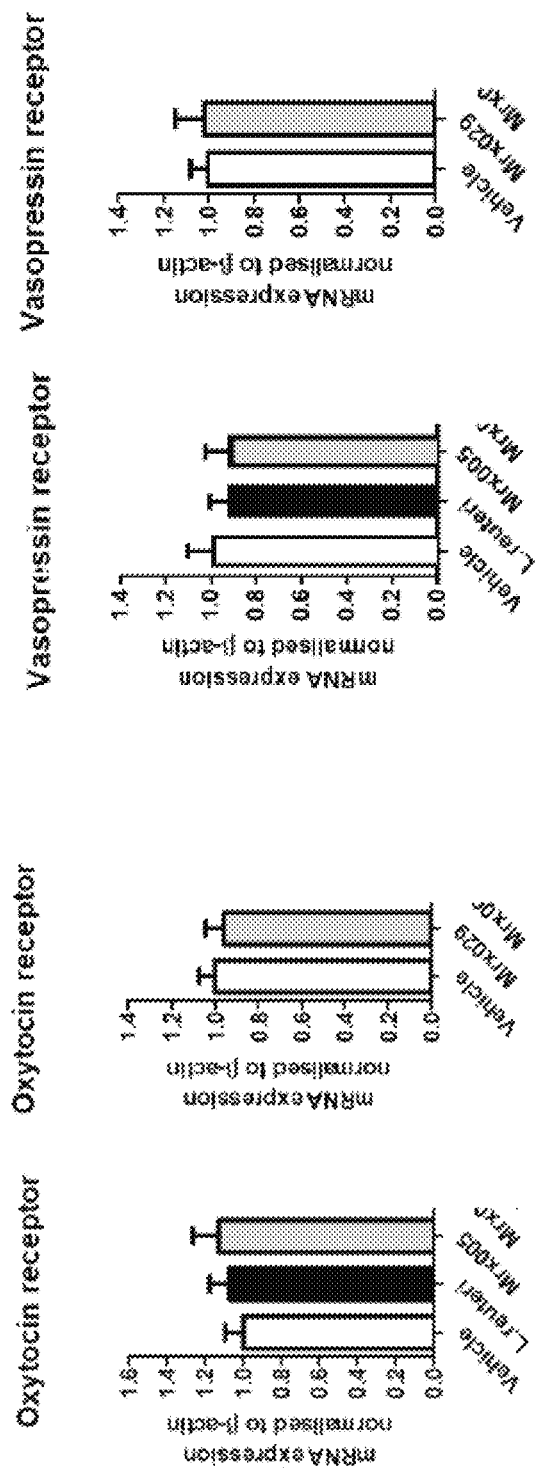
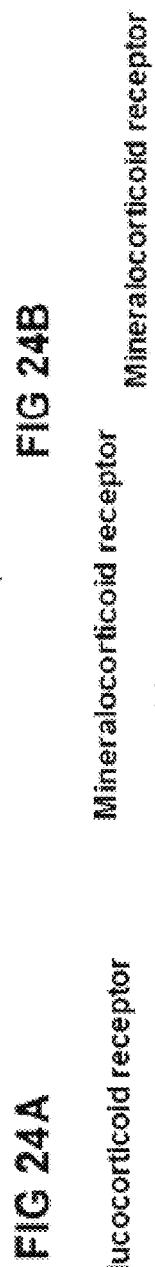
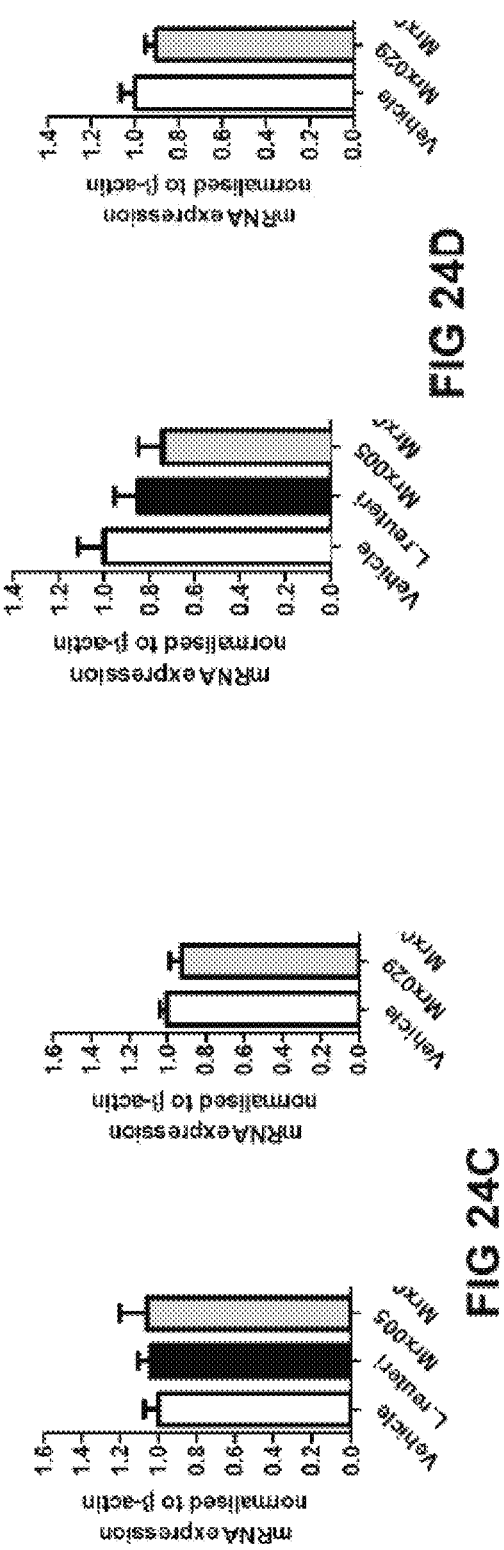
FIG 24A, FIG 24B, FIG 24C, FIG 24D

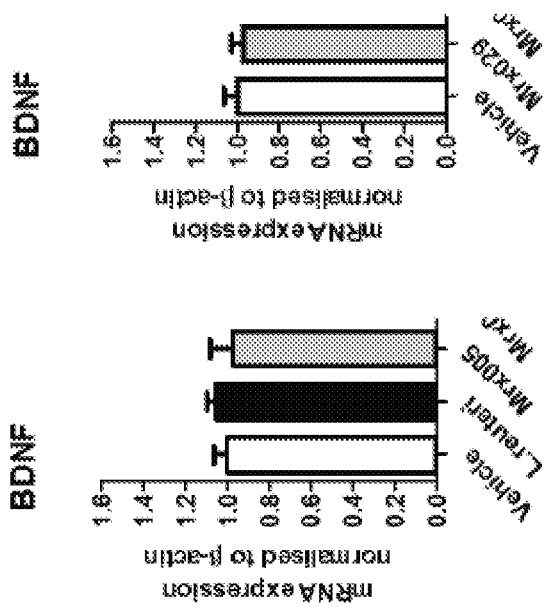
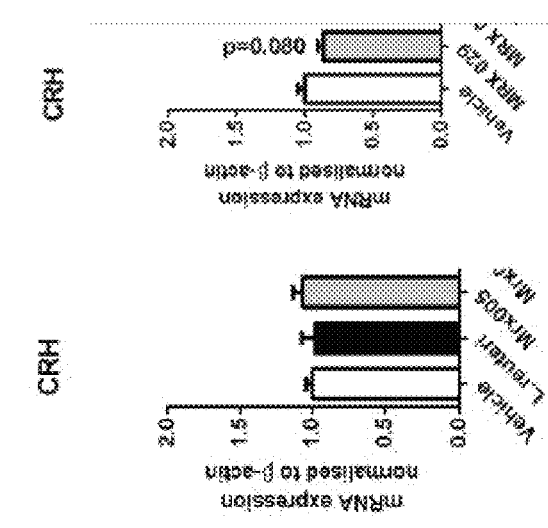
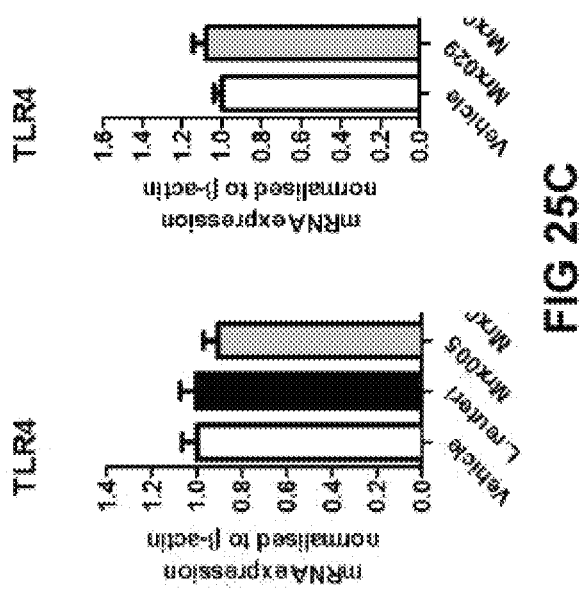
FIG 25A
FIG 25B
FIG 25C

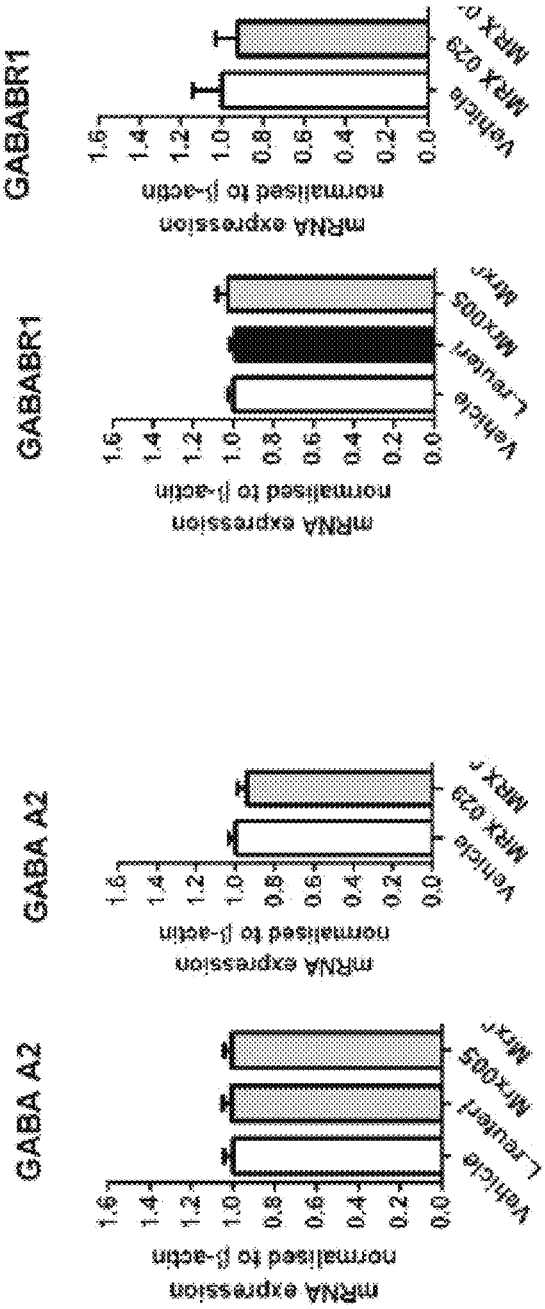

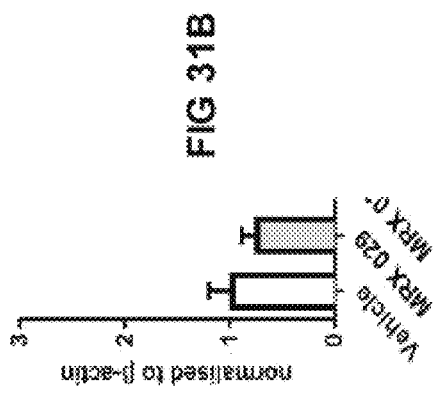
FIG 31A
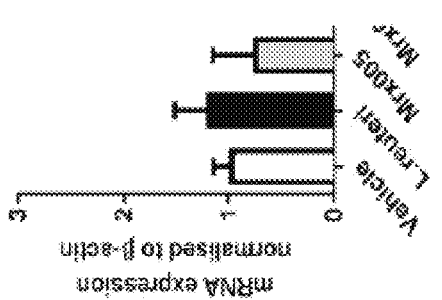
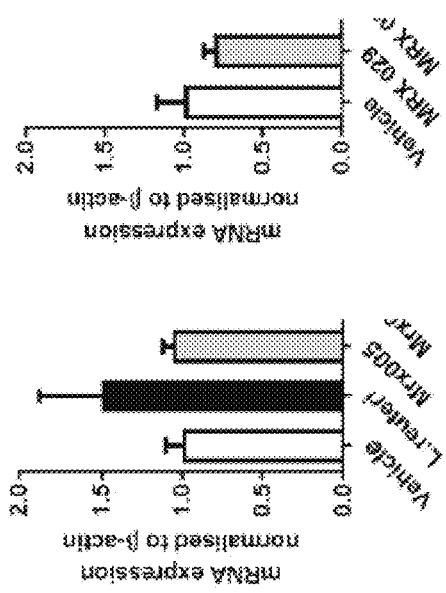
FIG 31C
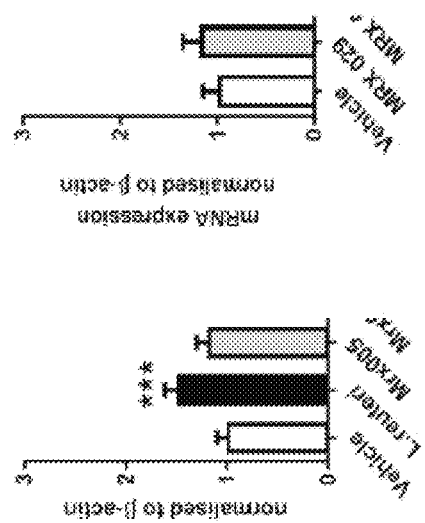
FIG 31B
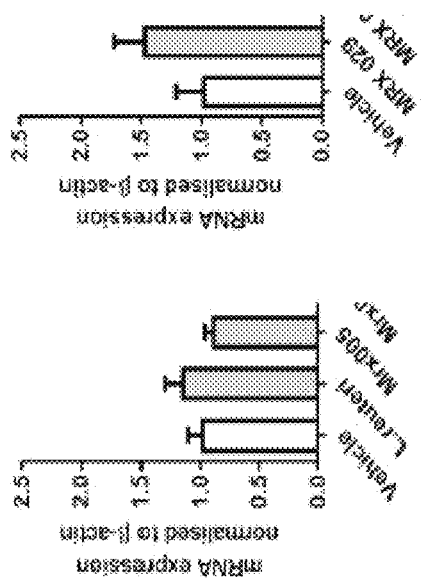
FIG 31D

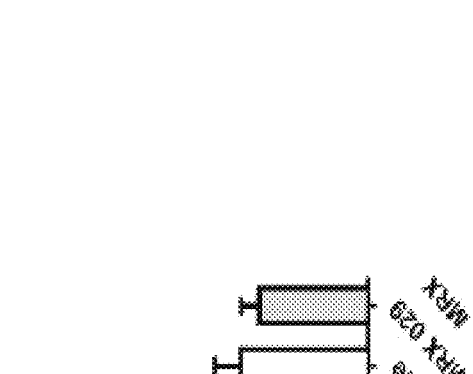
FIG 33B
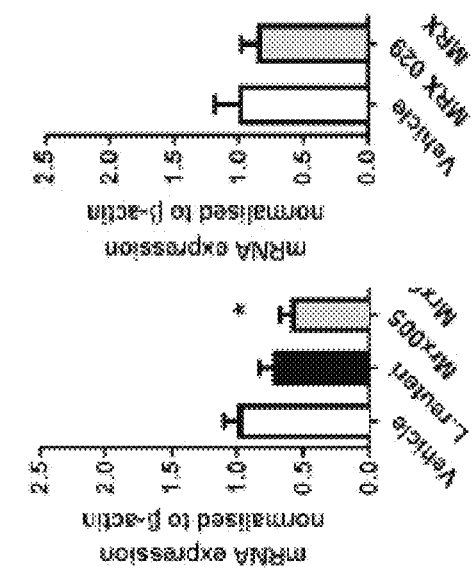
FIG 33D
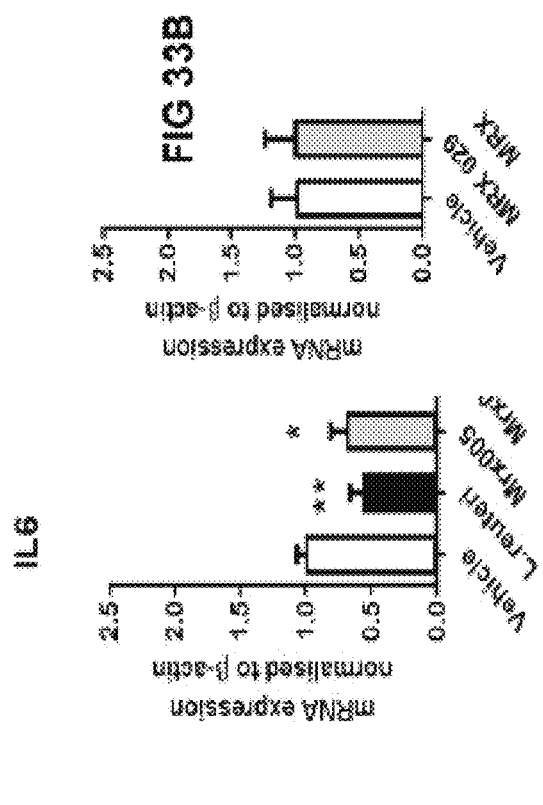
FIG 33A
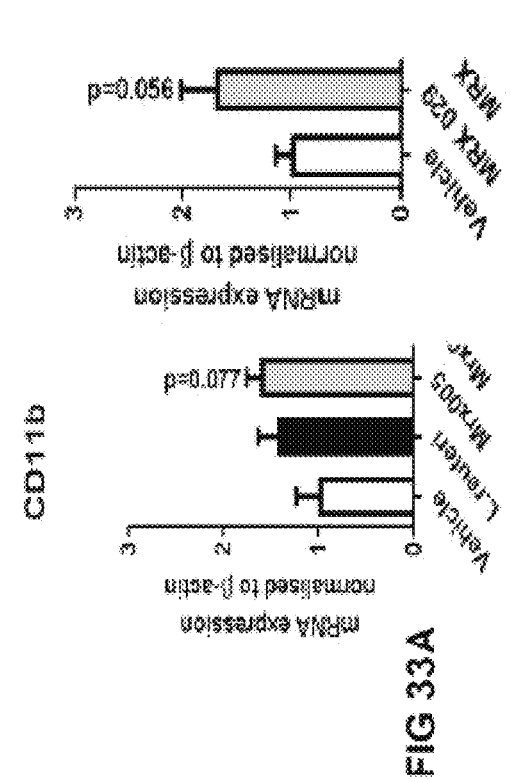
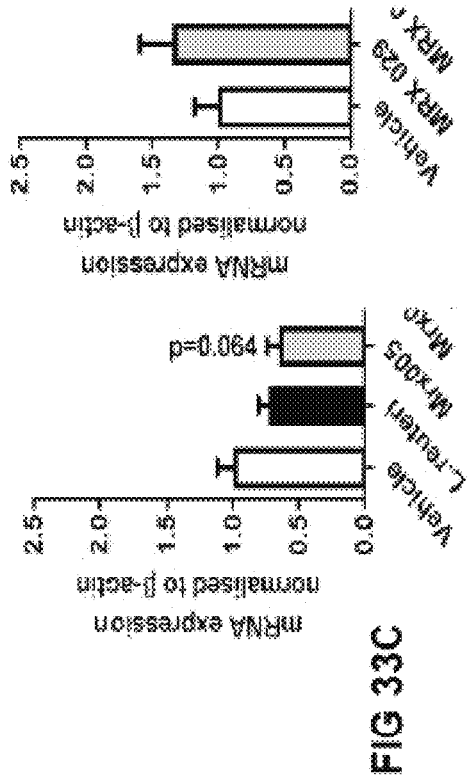
FIG 33C

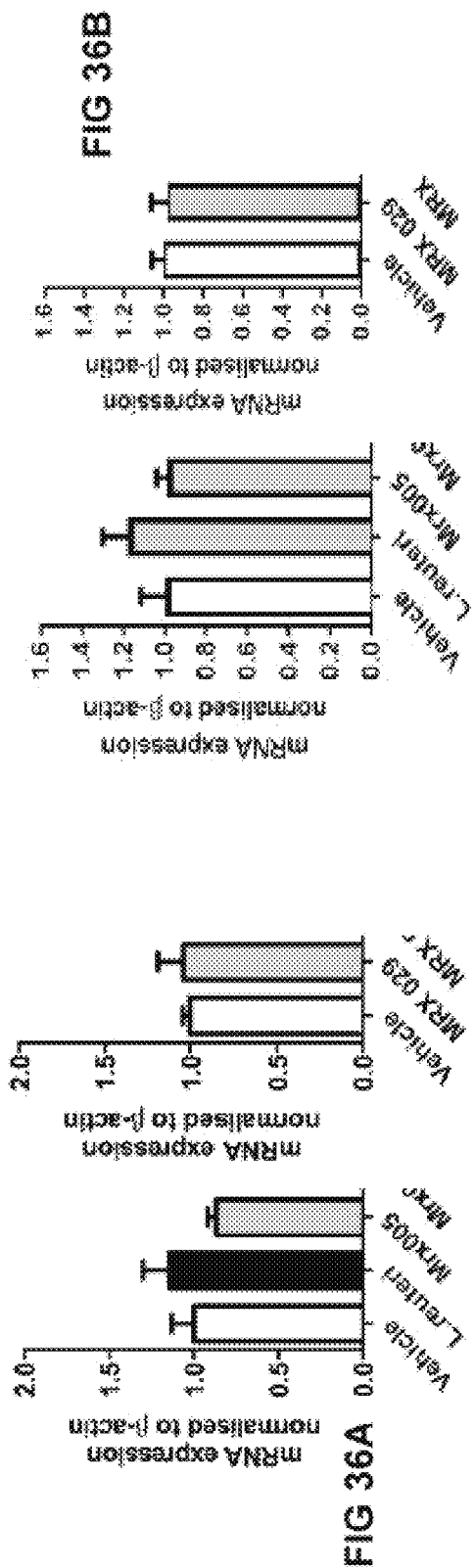
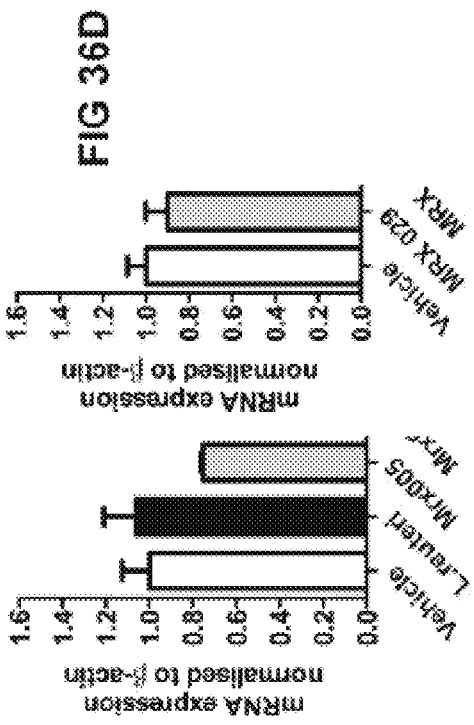
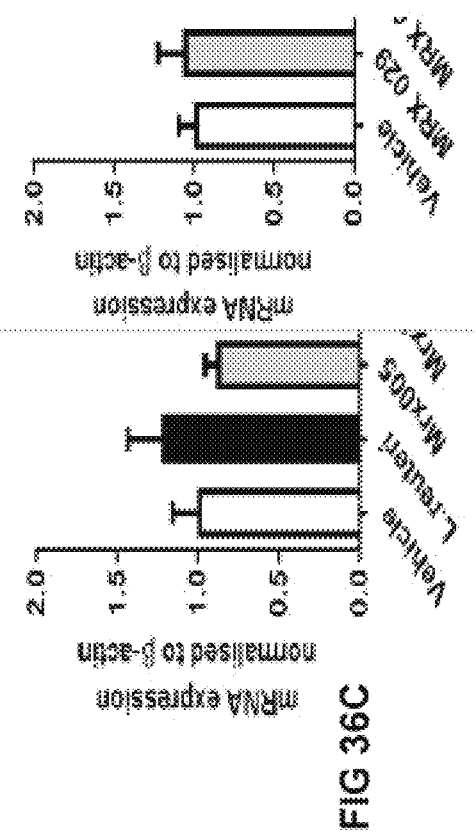
FIG 36A, FIG 36B, FIG 36C, FIG 36D

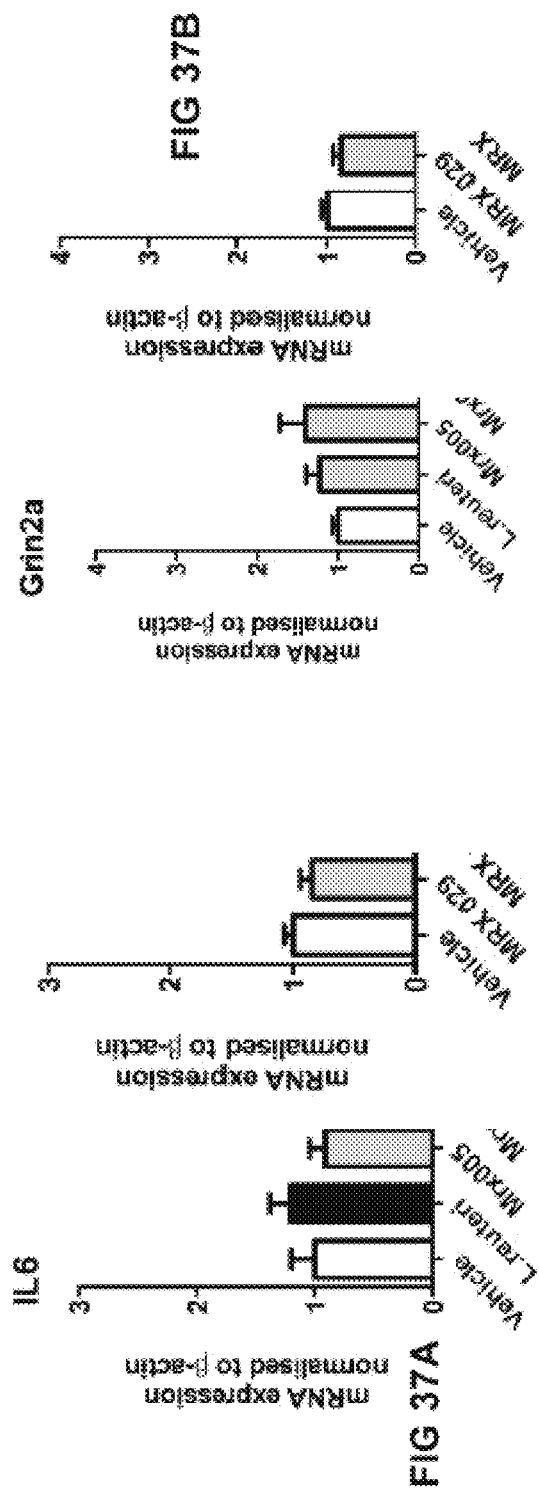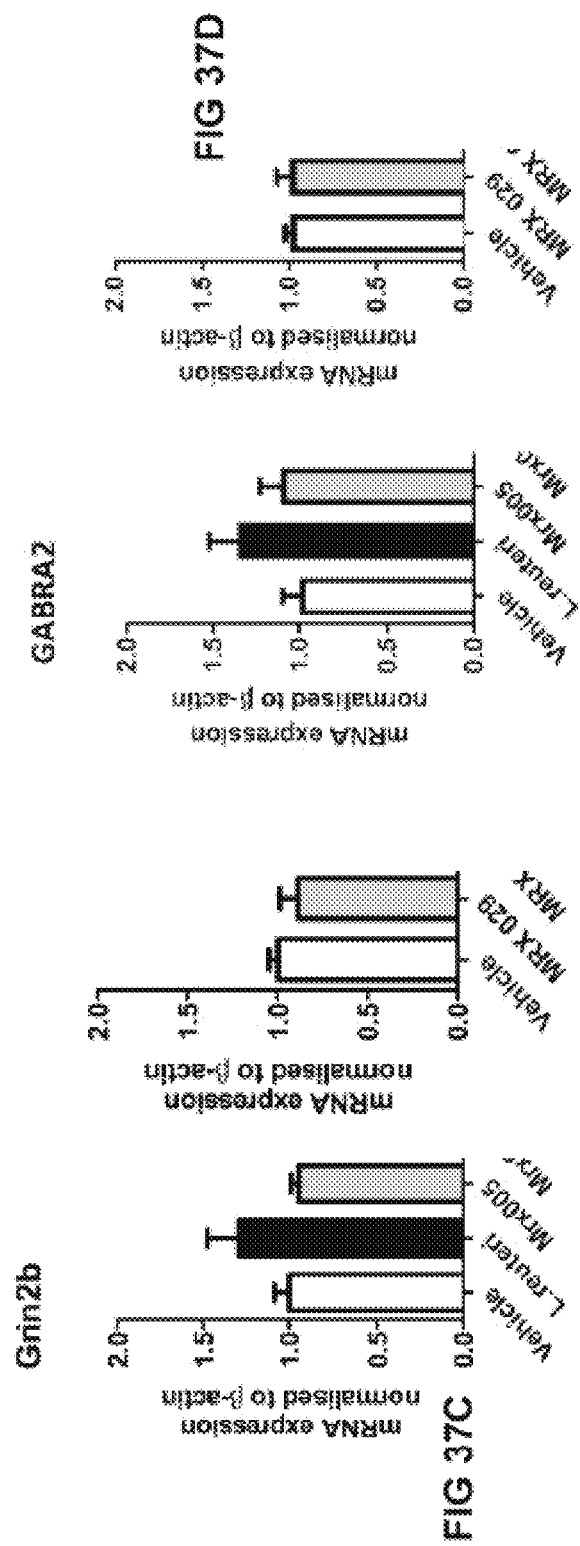

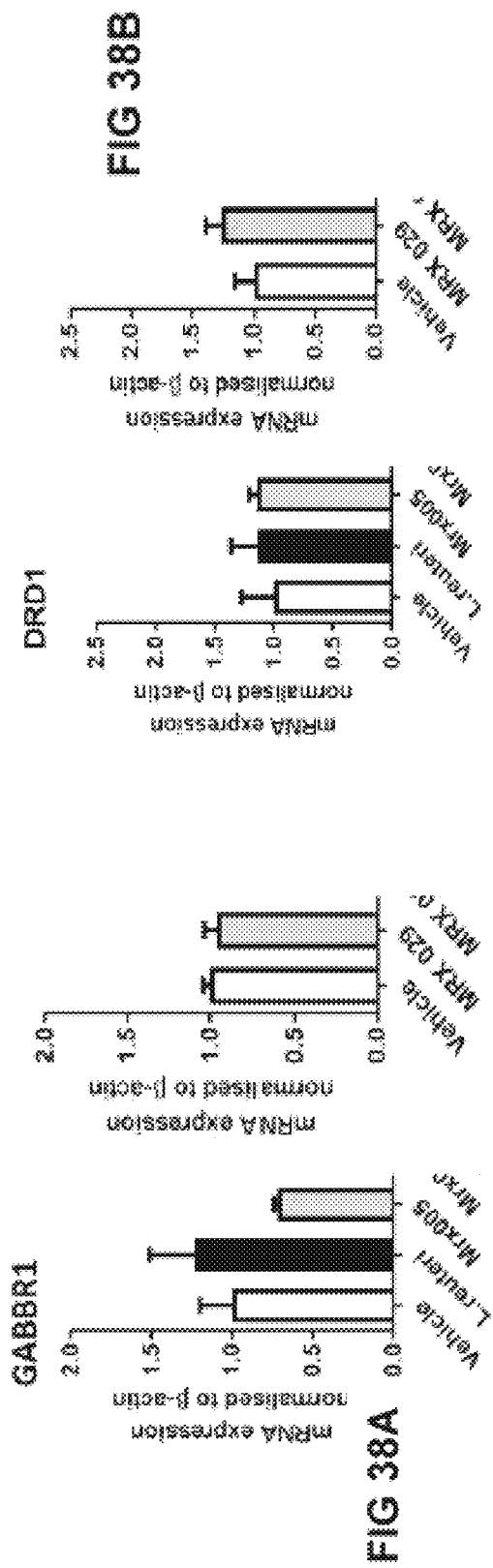
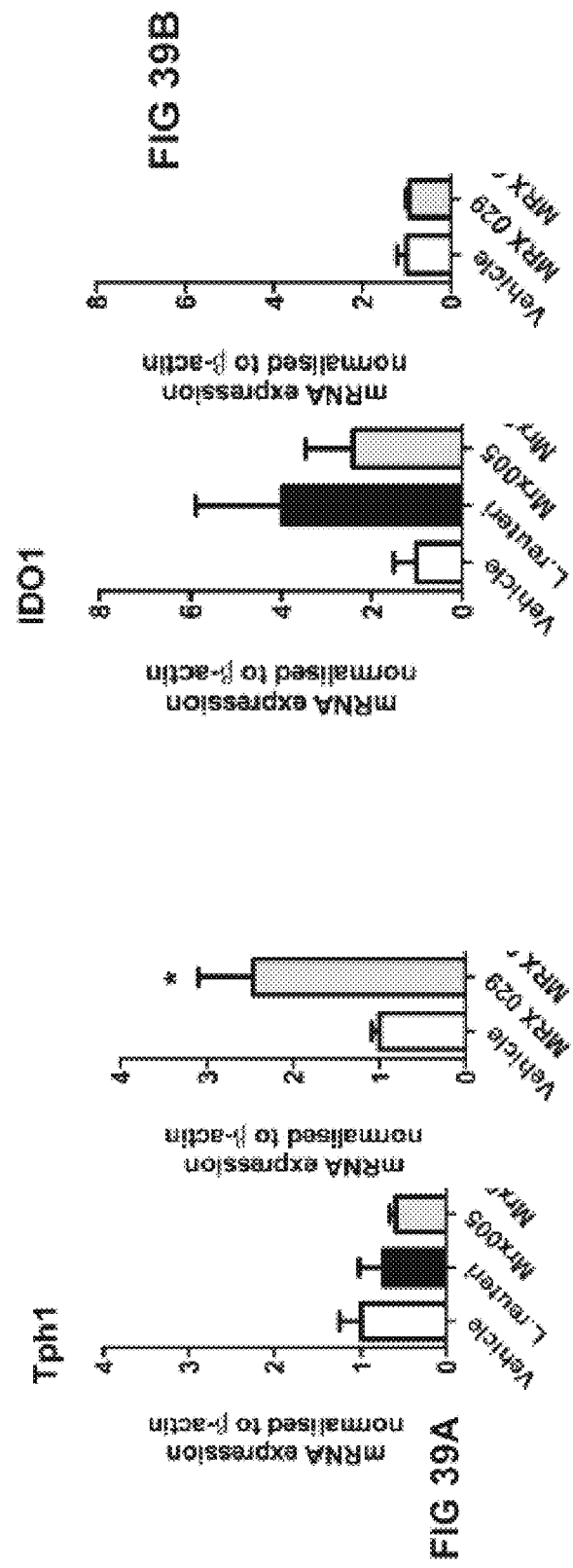

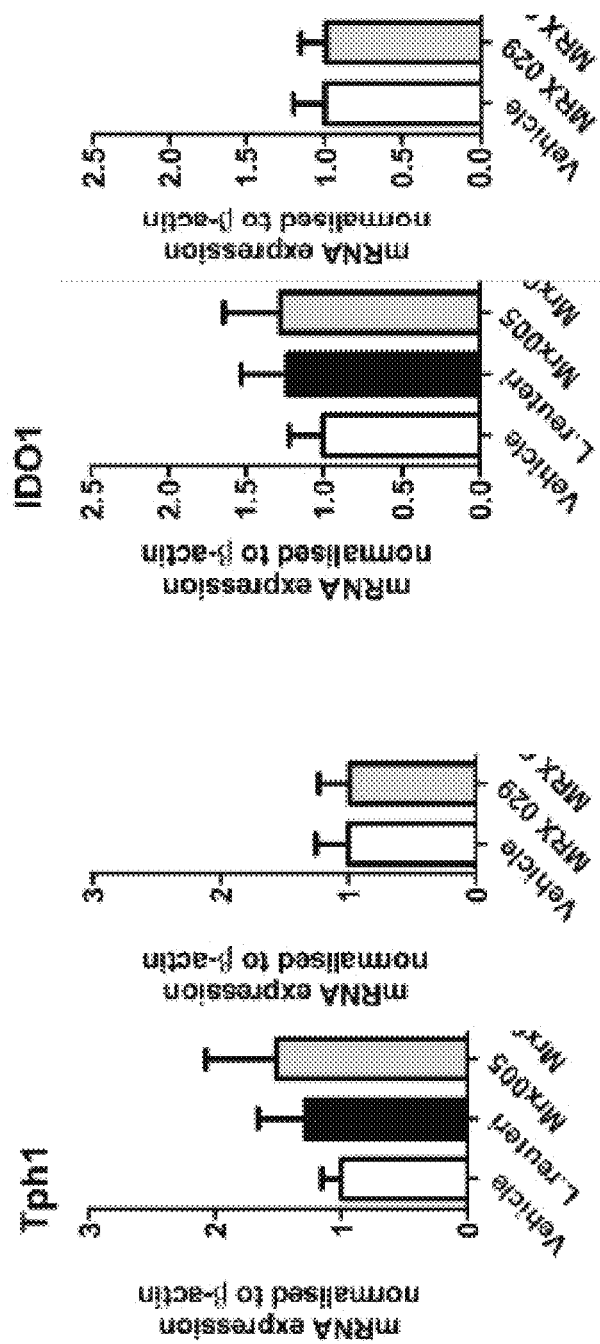

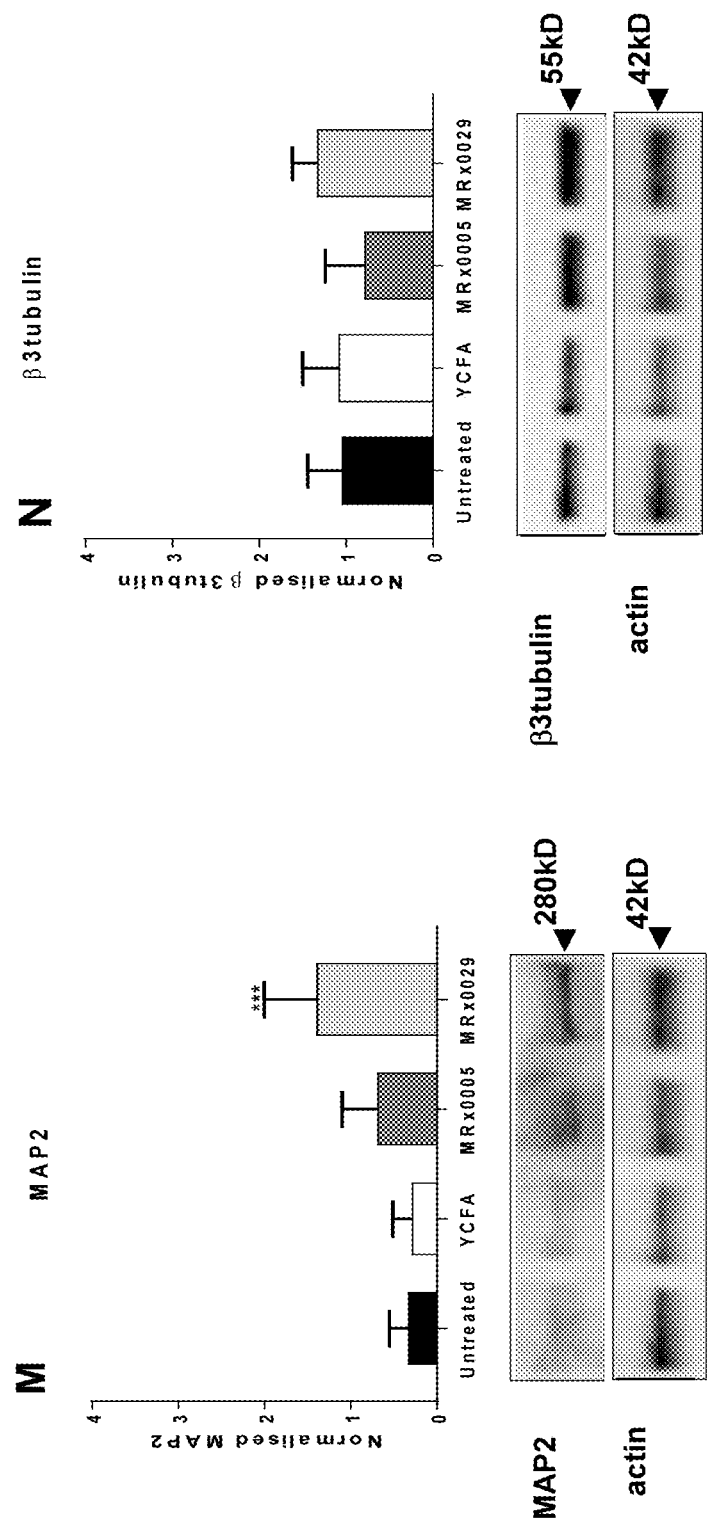

SEQUENCE LISTING

```
<160> NUMBER OF SEQ ID NOS: 38

<210> SEQ ID NO 1
<211> LENGTH: 1519
<212> TYPE: DNA
<213> ORGANISM: Megasphaera massiliensis
<220> FEATURE:
<223> OTHER INFORMATION: Megasphaera massiliensis strain NP3

<400> SEQUENCE: 1
agagtttgat cctggctcag gacgaacgct ggcggcgtgc ttaacacatg caagtcgaac      60
gagaagagat gagaagcttg cttcttatca attcgagtgg caaacgggtg agtaacgcgt     120
aagcaacctg cccttcagat ggggacaaca gctggaaacg gctgctaata ccgaatacgt     180
tctttccgcc gcatgacggg aagaagaaag ggaggccttc gggctttcgc tggaggaggg     240
gcttgcgtct gattagctag ttggaggggt aacggcccac caaggcgacg atcagtagcc     300
ggtctgagag gatgaacggc cacattggga ctgagacacg gcccagactc ctacgggagg     360
cagcagtggg gaatcttccg caatggacga aagtctgacg gagcaacgcc gcgtgaacga     420
tgacggcctt cgggttgtaa agttctgtta tatgggacga acagggcatc ggttaatacc     480
cggtgtcttt gacggtaccg taagagaaag ccacggctaa ctacgtgcca gcagccgcgg     540
taatacgtag gtggcaagcg ttgtccggaa ttattgggcg taaagggcgc gcaggcggca     600
tcgcaagtcg gtcttaaaag tgcggggctt aaccccgtga ggggaccgaa actgtgaagc     660
tcgagtgtcg gagaggaaag cggaattcct agtgtagcgg tgaaatgcgt agatattagg     720
aggaacacca gtggcgaaag cggctttctg gacgacaact gacgctgagg cgcgaaagcc     780
```

```
aggggagcaa acgggattag atacccoggt agtcctggcc gtaaacgatg gatactaggt      840
gtaggaggta tcgactcctt ctgtgccgga gttaacgcaa taagtatccc gcctggggag      900
tacggccgca aggctgaaac tcaaaggaat tgacggggc  ccgcacaagc ggtggagtat      960
gtggtttaat tcgacgcaac gcgaagaacc ttaccaagcc ttgacattga ttgctacgga     1020
aagagatttc cggttcttct tcggaagaca agaaaacagg tggtgcacgg ctgtcgtcag     1080
ctcgtgtcgt gagatgttgg gttaagtccc gcaacgagcg caaccccctat cttctgttgc    1140
cagcacctcg ggtggggact cagaagagac tgccgcagac aatgcggagg aaggcgggga    1200
tgacgtcaag tcatcatgcc ccttatggct tgggctacac acgtactaca atggctctta    1260
atagagggac gcgaaggagc gatccggagc aaaccccaaa aacagagtcc cagttcggat    1320
tgcaggctgc aactcgcctg catgaagcag gaatcgctag taatcgcagg tcagcatact    1380
gcggtgaata cgttcccggg ccttgtacac accgcccgtc acaccacgaa agtcattcac    1440
acccgaagcc ggtgaggcaa ccgcaaggaa ccagccgtcg aaggtgggg  cgatgattgg    1500
ggtgaagtcg taacaaggt                                                  1519
```

<210> SEQ ID NO 2
<211> LENGTH: 1398
<212> TYPE: DNA
<213> ORGANISM: Megasphaera massiliensis
<220> FEATURE:
<223> OTHER INFORMATION: Megasphaera massiliensis strain MRX0029

<400> SEQUENCE: 2

```
tgagaagctt gcttcttatc gattctagtg gcaaacgggt gagtaacgcg taagcaacct      60
gcccttcaga tggggacaac agctggaaac ggctgctaat accgaatacg ttctttccgc     120
cgcatgacgg gaagaagaaa gggaggcctt cgggctttcg ctggaggagg ggcttgcgtc     180
tgattagcta gttggagggg taacggccca ccaaggcgac gatcagtagc cggtctgaga     240
ggatgaacgc ccacattggg actgagacac ggcccagact cctacgggag gcagcagtgg     300
ggaatcttcc gcaatggacg aaagtctgac ggagcaacgc cgcgtgaacg atgacggcct     360
tcgggttgta aagttctgtt atatgggacg aacaggacat cggttaatac ccggtgtctt     420
tgacggtacc gtaagagaaa gccacggcta actacgtgcc agcagccgcg gtaatacgta     480
ggtggcaagc gttgtccgga attattgggc gtaaagggcg cgcaggcggc atcgcaagtc     540
ggtcttaaaa gtgcggggct taaccccgtg aggggaccga aactgtgaag ctcgagtgtc     600
ggagaggaaa gcggaattcc tagtgtagcg gtgaaatgcg tagatattag gaggaacacc     660
agtggcgaaa gcggctttct ggacgacaac tgacgctgag gcgcgaaagc caggggagca     720
aacgggatta gataccccgg tagtcctggc cgtaaacgat ggatactagg tgtaggaggt     780
atcgactcct tctgtgccgg agttaacgca ataagtatcc gcctggggga gtacggccgc     840
aaggctgaaa ctcaaaggaa ttgacggggg cccgcacaag cggtggagta tgtggtttaa     900
ttcgacgcaa cgcgaagaac cttaccaagc cttgacattg attgctacgg aaagagattt     960
ccggttcttc ttcggaagac aagaaaacag gtggtgcacg gctgtcgtca gctcgtgtcg    1020
tgagatgttg ggttaagtcc cgcaacgagc gcaacccccta tcttctgttg ccagcacctc    1080
gggtggggac tcagaagaga ctgccgcaga caatgcggag gaaggcgggg atgacgtcaa    1140
gtcatcatgc cccttatggc ttgggctaca cacgtactac aatggctctt aatagaggga    1200
agcgaaggag cgatccggag caaaccccaa aacagagtc  ccagttcgga ttgcaggctg    1260
caactcgcct gcatgaagca ggaatcgcta gtaatcgcag gtcagcatac tgcggtgaat    1320
```
acgttcccgg gccttgtaca caccgcccgt cacaccacga aagtcattca cacccgaagc    1380
cggtgaggca accgcaag                                                 1398

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatcaagatc attgctcctc                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgtcaagaa agggtgtaac                                               20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtatcgtgg aaggactcat g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atgccagtga gcttcccgtt c                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcagcaccg ctaacagagg                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
cattggcgct tctctcctc                                                 19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagaggaatt ttgacactgg                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccatgtact cttcactttc                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagtcacact ggtgaaatcc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcttgctgc caaactatct                                                20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctcccctg gatcaggat                                                 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
gccatcaaac tcgtccatca                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cattacctgc tctacgtttg                                              20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agatggacat aagatgaggt g                                            21

<210> SEQ ID NO 17
<211> LENGTH: 1403
<212> TYPE: DNA
<213> ORGANISM: Parabacteroides distasonis
<220> FEATURE:
<223> OTHER INFORMATION: Parabacteroides distasonis strain MRX0005

<400> SEQUENCE: 17
amccgggtgg cgaccggcgc acgggtgagt aacgcgtatg caacttgcct atcagagggg     60
gataacccgg cgaaagtcgg actaataccg catgaagcag ggatcccgca tgggaatatt    120
tgctaaagat tcatcgctga tagataggca tgcgttccat taggcagttg gcggggtaac    180
ggcccaccaa accgacgatg gatagggtt ctgagaggaa ggtcccccac attggtactg     240
agacacggac caaactccta cgggaggcag cagtgaggaa tattggtcaa tgggcgtgag    300
cctgaaccag ccaagtcgcg tgagggatga aggttctatg gatcgtaaac ctcttttata    360
agggaataaa gtgcgggacg tgtcccgttt tgtatgtacc ttatgaataa ggatcggcta    420
actccgtgcc agcagccgcg gtaatacgga ggatccgagc gttatccgga tttattgggt    480
ttaaagggtg cgtaggcggc cttttaagtc agcggtgaaa gtctgtggct caaccataga    540
attgccgttg aaactgggag gcttgagtat gtttgaggca ggcggaatgc gtggtgtagc    600
ggtgaaatgc atagatatca cgcagaaccc cgattgcgaa ggcagcctgc caagccatta    660
ctgacgctga tgcacgaaag cgtggggatc aaacaggatt agataccctg gtagtccacg    720
cagtaaacga tgatcactag ctgtttgcga tacactgtaa gcggcacagc gaaagcgtta    780
agtgatccac ctggggagta cgccggcaac ggtgaaactc aaaggaattg acggggccc     840
gcacaagcgg aggaacatgt ggtttaattc gatgatacgc gaggaacctt acccgggttt    900
gaacgcattc ggacmgakgt ggaaacacat tttctagcaa tagccatttg cgaggtgctg    960
catggttgtc gtcagctcgt gccgtgaggt gtcggcttaa gtgccataac gagcgcaacc   1020
cttgccacta gttactaaca ggtaaagctg aggactctgg tgggactgcc agcgtaagct   1080
gcgaggaagg cggggatgac gtcaaatcag cacggcccct acatccgggg cgacacacgt   1140
gttacaatgg cgtggacaaa gggaagccac ctggcgacag gagcgaatc cccaaaccac    1200

```
gtctcagttc ggatcggagt ctgcaacccg actccgtgaa gctggattcg ctagtaatcg    1260
cgcatcagcc atggcgcggt gaatacgttc ccgggccttg tacacaccgc ccgtcaagcc    1320
atgggagccg ggggtacctg aagtccgtaa ccgcgaggat cggcctaggg taaaactggt    1380
gactggggct aagtcgtacg ggg                                            1403
```

```
<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gattactgct ctggctccta g                                               21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gactcatcgt actcctgctt g                                               21

<210> SEQ ID NO 20
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ctgtccacct tcc                                                        13

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aatggtgaag gtcggtgtg                                                  19

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtggagtcat actggaacat gtag                                            24

<210> SEQ ID NO 23
<211> LENGTH: 11
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 23
cagccctggt g                                                            11

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gctgccttga tgtttacttt gac                                               23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcaaccgaag tatgaaataa cca                                               23

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gaagagtgat gaccatcc                                                     18

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agccagagtc cttcagaga                                                    19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccttagcca ctccttctgt                                                   20

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 29
atttccaatg ctctcct                                                   17

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccctgtatcg taagaacggt                                                20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gccaccattg atcacgttga                                                20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cccaagcaac tagcccctc                                                 19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggcagcacat cagggtagtc                                                20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtagccgtga tgtggtcatt t                                              21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 35
ctgtgcgccc agattacct                                                  19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctcggctttg tgaaggtgct                                                 20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggcttcatgg catcaacttc a                                               21

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtggtggtgg tggtg                                                      15
```

COMPOSITIONS COMPRISING BACTERIAL STRAINS

CROSS-REFERENCE

This application is a continuation of International Application No. PCT/EP2018/065903, filed Jun. 14, 2018, which claims the benefit of Great Britain Application No. 1709468.1, filed Jun. 14, 2017, Great Britain Application No. 1709534.0, filed Jun. 15, 2017, Great Britain Application No. 1712851.3, filed Aug. 10, 2017, Great Britain Application No. 1803826.5, filed Mar. 9, 2018, Great Britain Application No. 1805989.9, filed Apr. 11, 2018, Great Britain Application No. 1805990.7, filed Apr. 11, 2018, Great Britain Application No. 1805991.5, filed Apr. 11, 2018, Great Britain Application No. 1806779.3, filed Apr. 25, 2018, and Great Britain Application No. 1806780.1, filed Apr. 25, 2018, all of which are hereby incorporated by reference in their entirety.

SEQUENCE LISTING

The instant application contains a Sequence Listing which has been submitted electronically in ANSI format and is hereby incorporated by reference in its entirety. Said ANSI copy, created on Jan. 17, 2020, is named 56708-727_301_SL.txt and is 14,725 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germfree animals which have an impaired immune system that is functionally reconstituted following the introduction of commensal bacteria [3-5].

Dramatic changes in microbiota composition have been documented in gastrointestinal disorders such as inflammatory bowel disease (IBD). For example, the levels of *Clostridium* cluster XIVa bacteria are reduced in IBD patients whilst numbers of *E. coli* are increased, suggesting a shift in the balance of symbionts and pathobionts within the gut [6-9].

In recognition of the potential positive effect that certain bacterial strains may have on the animal gut, various strains have been proposed for use in the treatment of various diseases (see, for example, [10-13]). Also, certain strains, including mostly *Lactobacillus* and *Bifidobacterium* strains, have been proposed for use in treating various inflammatory and autoimmune diseases that are not directly linked to the intestines (see [14] and [15] for reviews). However, the relationship between different diseases and different bacterial strains, and the precise effects of particular bacterial strains on the gut and at a systemic level and on any particular types of diseases are poorly characterised, particularly for neurodegenerative disorders.

Recently, there has been increased interest in the art regarding alterations in the gut microbiome that may play a pathophysiological role in human brain diseases [16]. Preclinical and clinical evidence are strongly suggesting a link between brain development and microbiota [17]. A growing body of preclinical literature has demonstrated bidirectional signalling between the brain and the gut microbiome, involving multiple neurocrine and endocrine signalling systems. Indeed, increased levels of *Clostridium* species in the microbiome have been linked to brain disorders [18], and an imbalance of the *Bacteroidetes* and *Firmicutes* phyla has also been implicated in brain development disorders [19]. Suggestions that altered levels of gut commensals, including those of *Bifidobacterium, Lactobacillus, Sutterella, Prevotella* and *Ruminococcus* genera and of the Alcaligenaceae family are involved in immune-mediated central nervous system (CNS) disorders, are questioned by studies suggesting a lack of alteration in the microbiota between patients and healthy subjects [19]. There have also been suggestions that the administration of probiotics may be beneficial in the treatment of neurological disorders. However, these studies failed to conclude that probiotic compositions per se can achieve therapeutic benefits with respect to the treatment of neurodegeneration and did not show any useful effects for any particular bacteria [20, 21]. This indicates that, at present, the practical effect of the link between the microbiome and human brain diseases is poorly characterised. Accordingly, more direct analytical studies are required to identify the therapeutic impact of altering the microbiome on neurodegenerative disorders.

There is a requirement in the art for new methods of treating neurodegenerative disorders. There is also a requirement for the potential effects of gut bacteria to be characterised so that new therapies using gut bacteria can be developed.

SUMMARY OF THE INVENTION

The inventors have developed new therapies for treating and preventing neurodegenerative disorders. In particular, the inventors have identified that commensal bacteria that produce certain organic acids have neuroprotective activities and may be effective for treating neurodegenerative disease. Related to this, the inventors have also identified that adding organic acids to compositions comprising commensal bacteria, or using organic acids in combination with commensal bacteria, may provide enhanced therapeutic effects, in particular in the treatment of neurodegenerative disorders.

The inventors have identified that commensal bacterial strains that produce one or more organic acids with the formula $R^x$—COOH, wherein $R^x$ comprises an alkyl group comprising in the range of 4 to 11 carbons, or wherein $R^x$ comprises a phenyl group with a substituent hydroxyl group, wherein optionally the hydroxyl group is at position 4, may be effective for treating neurodegenerative diseases. In another aspect of the invention, the inventors have found that a combination of a commensal bacterial strain and an organic acid may be effective for treating or preventing neurodegenerative diseases. As used herein, the terms "the combination of the invention", "the therapeutic combination of the invention" and "the therapeutic combination" may be used interchangeably and refer to a therapeutic combination of: (a) a composition comprising a commensal bacterial strain; and (b) a composition comprising an organic acid. It is to be understood that the term "combination" in the context of the therapeutic combination does not refer to components (a) and (b) of the combination necessarily being in the same composition and/or administered at the same time.

As described in the examples, administration of compositions comprising *Megasphaera massiliensis* can protect against reactive oxygen species and prevent inflammation, thus acting as a neuroprotectant. The inventors have identified that *Megasphaera massiliensis* produces certain organic acids including hexanoic acid, valeric acid and 4-hydroxyphenylacetic acid. The inventors have also identified that treatment with *Megasphaera massiliensis* can reduce the activation of proinflammatory molecules, such as NFκB and IL-6, by LPS and mutant α-synuclein. The inventors have also found that *Megasphaera massiliensis* can increase the activation of the pro-inflammatory cytokine IL-8, which can help to promote neuron myelination. The inventors have also identified that treatment with a combination of *Megasphaera massiliensis* and retinoic acid can increase the secretion of brain-derived neurotrophic factor (BDNF), which can help promote neurogenesis and neuritogenesis and/or prevent cell death. The inventors have identified that treatment with *Megasphaera massiliensis* can attenuate oxidative stress, reduce histone deacetylation activity and lipid peroxidation in vitro, which can help to reduce cell death and apoptosis. In particular, the inventors have identified that treatment with *Megasphaera massiliensis*, which can produce valeric acid, can reduce histone deacetylation, which can help to reduce cell death and apoptosis. The inventors have also identified that *Megasphaera massiliensis* can produce indole that can attenuate inflammation and oxidative stress. The inventors have also demonstrated that treatment with *Megasphaera massiliensis* can increase kynurenine levels. Furthermore, the inventors have also found that *Megasphaera massiliensis* can produce hexanoic acid, which can be neuroprotective or neurorestorative, for example by promoting neurite outgrowth. The inventors have found that *Megasphaera massiliensis* that can produce hexanoic acid increase the expression of MAP2 (Microtubule-associated protein 2), which is thought to be essential for microtubule formation in neuritogenesis. Therefore, the inventors have found that *Megasphaera massiliensis* that can produce hexanoic acid can be used to promote neurite outgrowth. *Megasphaera massiliensis* and other bacteria that produce organic acids like hexanoic acid, valeric acid and 4-hydroxyphenylacetic acid may therefore be useful for treating neurodegenerative disorders.

Thus, in a first aspect, the invention describes a composition comprising a commensal bacterial strain for use in a method of treating or preventing a neurodegenerative disorder, wherein the strain produces one or more organic acids each having the following formula: $R^x$—COOH, wherein $R^x$ comprises an alkyl group comprising at least 4 carbons, or wherein $R^x$ comprises a phenyl group with a substituent hydroxyl group, wherein optionally the hydroxyl group is at position 4.

In a second aspect, the invention provides a composition comprising a commensal bacterial strain and one or more organic acids having the formula $R^n$—COOH or pharmaceutically acceptable salts or esters thereof. In preferred embodiments, the composition comprises one or more of the organic acids valproic acid, valeric acid, hexanoic acid, retinoic acid, and 4-hydroxyphenylacetic acid or pharmaceutically acceptable salts or esters thereof. The examples demonstrate that such combinations have therapeutic benefits.

In some embodiments, the invention describes a composition comprising a commensal bacterial strain for use in a method of treating or preventing a disease in a subject, wherein the composition is to be administered in combination with one or more organic acids or pharmaceutically acceptable salts or esters thereof. The examples demonstrate that such combinations may be particularly effective.

In some embodiments, the invention describes a composition comprising one or more organic acids or pharmaceutically acceptable salts or esters thereof for use in a method of treating or preventing a disease in a subject, wherein the composition is to be administered in combination with a commensal bacterial strain. The examples demonstrate that such combinations may be particularly effective.

Preferred embodiments of both aspects of the invention are discussed below and throughout the application.

In some embodiments, the commensal bacterial strain produces a short chain fatty acid. Preferably, the short chain fatty acid is butyric acid. Butyrate may contribute to reducing impermeability of the blood brain barrier, which has a neuroprotective effect.

In some embodiments, the composition is for use in a method of treating or preventing disease.

In some embodiments, the compositions are for use in a method of treating or preventing a neurodegenerative disorder.

In particular embodiments, the compositions are for use in a method of treating or preventing a disease or condition selected from the group consisting of: Parkinson's disease, including progressive supranuclear palsy, progressive supranuclear palsy, Steele-Richardson-Olszewski syndrome, normal pressure hydrocephalus, vascular or arteriosclerotic parkinsonism and drug-induced parkinsonism; Alzheimer's disease, including Benson's syndrome; multiple sclerosis; Huntington's disease; amyotrophic lateral sclerosis; Lou Gehrig's disease; motor neurone disease; prion disease; spinocerebellar ataxia; spinal muscular atrophy; dementia, including Lewy body, vascular and frontotemporal dementia; primary progressive aphasia; mild cognitive impairment; HIV-related cognitive impairment, progressive inflammatory neuropathy, and corticobasal degeneration.

In preferred embodiments, the compositions of the invention are for use in a method of treating or preventing Parkinson's disease, such as environmental, familial or Parkinson's associated with general inflammatory status. The inventors have identified that treatment with the compositions of the invention can reduce the activation of proinflammatory molecules, such as NFκB and IL-6, by LPS and mutant α-synuclein in in vitro models of environmental and familial Parkinson's.

In some embodiments, the compositions of the invention are for use in a method of treating or preventing early-onset neurodegenerative disease. In some embodiments, the compositions of the invention are for use in a method of preventing or delaying onset or progression of a neurodegenerative disorder.

In preferred embodiments, the invention provides a combination comprising a bacterial strain of the species *Megasphaera massiliensis*, and an organic acid selected from the list consisting of hexanoic acid, valeric acid, valproic acid, retinoic acid or 4-hydroxyphenylacetic acid for use in the treatment of Parkinson's disease. Combinations using *Megasphaera massiliensis* and hexanoic acid may be particularly effective for use in a method of treating neurodegenerative diseases, in particular Parkinson's. Preferred compositions of the invention comprise a commensal bacteria and retinoic acid. Further preferred compositions of the invention comprise a commensal bacteria and hexanoic acid. Further preferred compositions of the invention comprise a commensal bacteria and valeric acid In some embodiments of the invention, the commensal bacterial strain is from the genus selected from the list consisting of *Bacteroides, Enterococcus, Escherichia, Klebsiella, Bifidobacterium, Staphylococcus, Lactobacillus, Megasphaera, Clostridium, Proteus, Pseudomonas, Salmonella, Faecalibacterium, Peptostreptococcus* or *Peptococcus*, or a combination thereof. In some embodiments, the commensal bacterial strain is from the genus *Megasphaera*. In some preferred embodiments the strain is of the species *Megasphaera massiliensis*. Closely related strains may also be used, such as bacterial strains that have a 16S rRNA sequence that is at least 95%, 96%, 97%, 98%, 99%, 99.5% or 99.9% identical to the 16S rRNA sequence of a bacterial strain of *Megasphaera massiliensis*. Preferably, the bacterial strain has a 16S rRNA sequence that is at least 95%, 96%, 97%, 98%, 99%, 99.5% or 99.9% identical to SEQ ID NO: 2. Preferably, the bacterial strain for use in the invention has the 16S rRNA sequence represented by SEQ ID NO:2.

In preferred embodiments, the strain for use in the invention produces one or more organic acids each having the following formula: $R^x$—COOH, wherein $R^x$ comprises an alkyl group comprising at least 4 carbons, or wherein $R^x$ comprises a phenyl group with a substituent hydroxyl group, wherein optionally the hydroxyl group is at position 4, wherein the organic acid is effective in the treatment or prevention of a neurodegenerative disorder. In some embodiments, the strain for use in the invention produces an organic acid selected from the list consisting of hexanoic acid, valeric acid, valproic acid, retinoic acid or 4-hydroxyphenylacetic acid. Preferably, strains of the invention are capable of increasing the activation of IL-8 and reducing the activation of IL-6.

In some embodiments of the invention, the commensal bacterial strain of the composition is engineered to produce the organic acid of the invention.

In some embodiments, the compositions of the invention are for oral administration. Oral administration of the strains of the invention and where applicable the organic acid of the invention can be effective for neurodegenerative disorders. Also, oral administration is convenient for patients and practitioners and allows delivery to and/or partial or total colonisation of the intestine.

In certain embodiments, the composition of the invention comprises one or more pharmaceutically acceptable excipients or carriers.

In certain embodiments, the composition of the invention comprises a commensal bacterial strain that has been lyophilised. Lyophilisation is an effective and convenient technique for preparing stable compositions that allow delivery of bacteria.

In certain embodiments, the invention provides a food product comprising any of the compositions as described above.

In certain embodiments, the invention provides a vaccine composition comprising the composition as described above.

Additionally, the invention provides a method of treating or preventing neurodegenerative diseases, comprising administering a composition comprising a commensal bacterial strain that produces one or more organic acids each having the following formula: $R^x$—COOH, wherein $R^x$ comprises an alkyl group comprising at least 4 carbons, or wherein $R^x$ comprises a phenyl group with a substituent hydroxyl group, wherein optionally the hydroxyl group is at position 4.

The invention also provides a method of treating or prevention neurodegenerative diseases comprising administering a combination of a commensal bacterial strain and an organic acid or a pharmaceutically acceptable salt or ester thereof.

In developing the above invention, the inventors have identified and characterised a bacterial strain that is particularly useful for therapy. The *Megasphaera massiliensis* strain of the invention is shown to be effective for treating the diseases described herein, such as neurodegenerative diseases. Therefore, in another aspect, the invention provides a cell of the *Megasphaera massiliensis* strain deposited under accession number NCIMB 42787, or a derivative thereof. The invention also provides compositions comprising such cells, or biologically pure cultures of such cells. The invention also provides a cell of the *Megasphaera massiliensis* strain deposited under accession number NCIMB 42787, or a derivative thereof, for use in therapy, in particular for the diseases described herein.

In certain embodiments of either aspect of the invention, the composition is for use in treating brain injury. The neuroprotective activity of the compositions of the invention and their ability to reduce levels of histone deacetylase activity (HDAC) may make them useful for treating brain injury. In preferred embodiments, the compositions of the invention are for use in treating stroke, such as treating brain injury resulting from a stroke.

BRIEF DESCRIPTION OF DRAWINGS

FIG. 1: Cell viability of neuroblastoma cells
FIG. 2: Downregulation of IL-6 secretion
FIG. 3: Secretion of IL-8
FIGS. 4A-4B: Inhibition of α-synuclein IL-6 and IL-8 secretion: Secretion of IL-6 from U373 (FIG. 4A); Secretion of IL-8 from U373 (FIG. 4B)
FIG. 5: Inhibition of α-synuclein induced NFκB promoter activation
FIG. 6: Inhibition of LPS induced NFκB promoter activation
FIGS. 7A-7B: Promoting neurite outgrowth: light microscopy and MAP2 gene expression (FIG. 7A), Phalloidin immunofluorescence microscopy (FIG. 7B)
FIG. 8: Change in antioxidant capacity
FIG. 9: Change in total anti-oxidant capacity (lipid oxidation)
FIGS. 10A-10B: Change in ROS levels in (FIG. 10A) U373 cells and (FIG. 10B) SHSY-5Y cells
FIG. 11: Neuroprotection-cell viability.
FIG. 11 shows the same data as FIG. 1.
FIG. 12: Change in histone deacetylase (HDAC) activity

FIGS. 14A-14C: HDAC1 inhibition (FIG. 14A), HDAC2 inhibition (FIG. 14B), HDAC3 inhibition (FIG. 14C)

FIG. 16: Level of Indole production

FIG. 17: Level of Kyrunenine production

FIG. 18: Level of BDNF production

FIG. 19: Levels of metabolite production—neurotransmitters in the brain

FIG. 20: Levels of metabolite production—organic acids in the supernatant

FIGS. 21A-21C: Mean Dopamine (DA) levels (FIG. 21A), DOPAC levels (FIG. 21B) and HVA levels (FIG. 21C) in striatum. Data is displayed as Mean+SEM.

FIGS. 22A-22F: Effect on intestinal barrier function. IL-8 (FIG. 22A), TJP1, TJP2, Occludin and Villin (FIG. 22B), TJP1, Colon and Ileum (FIG. 22C), Occludin, Colon and Ileum (FIG. 22D), Permeability in the Ileum (FIG. 22E), Permeability in the colon (FIG. 22F)

FIGS. 24A-24D: Changes in Hippocampal Receptor Expression—FIG. 24A) Oxytocin Receptor, FIG. 24B) Vasopressin Receptor, FIG. 24C) Glucocorticoid Receptor and FIG. 24D) Mineralocorticoid Receptor FIGS. 25A-25C: Changes in Hippocampal Expression of FIG. 25A) Corticotropin-Releasing Hormone (CRH), FIG. 25B) BDNF Expression and FIG. 25C) TLR4

FIG. 26A) Changes in Hippocampal Corticotropin Releasing Hormone Receptor 1 (CRFR1) Expression and FIG. 26B) Corticotropin Releasing Hormone Receptor 2 (CRFR2) Expression

FIG. 28A) Changes in Hippocampal Integrin Alpha M (CD11b) Expression and FIG. 28B) Changes in Hippocampal Serotonin 1A Receptor (5-HT1A receptor) Expression FIG. 29A) Changes in Hippocampal Glutamate Ionotropic Receptor NMDA Type Subunit 2A (Grin2A) and FIG. 29B) Glutamate Ionotropic Receptor NMDA Type Subunit 2B (Grin2B) expression FIGS. 30A-30C: Changes in Hippocampal Expression of FIG. 30A) Gamma-Aminobutyric Acid A Receptor 2 (GABA A2), FIG. 30B) Gamma-Aminobutyric Acid B Receptor 1 (GABA BR1) and FIG. 30C) Dopamine Receptor 1 (DRD1)

FIGS. 31A-31D: Changes in Amygdala Receptor Expression—FIG. 31A) Oxytocin Receptor, FIG. 31B) Vasopressin Receptor, FIG. 31C) Glucocorticoid Receptor and FIG. 31D) Mineralocorticoid Receptor

FIGS. 33A-33D: Changes in Amygdala Expression of FIG. 33A) Integrin Alpha M (CD11b), FIG. 33B) Interleukin-6 (IL-6), FIG. 33C) Glutamate Ionotropic Receptor NMDA Type Subunit 2A (Grin2A) and FIG. 33D) Glutamate Ionotropic Receptor NMDA Type Subunit 2B (Grin2B)

FIGS. 36A-36D: Changes in Prefrontal Cortex Expression of FIG. 36A) Toll-like Receptor 4 (TLR-4), FIG. 36B) Corticotropin Releasing Hormone Receptor 1 (CRFR1), FIG. 36C) Corticotropin Releasing Hormone Receptor 2 (CRFR2) and FIG. 36D) Integrin Alpha M (CD11b)

FIGS. 37A-37D: Changes in Prefrontal Cortex Expression of FIG. 37A) Interleukin-6 (IL-6), FIG. 37B) Glutamate Ionotropic Receptor NMDA Type Subunit 2A (Grin2A), FIG. 37C) Glutamate Ionotropic Receptor NMDA Type Subunit 2B (Grin2B) and FIG. 37D) GABA-A Receptor Alpha 2 Subunit (GABRA2)

FIGS. 38A-38B: Changes in Prefrontal Cortex Expression of FIG. 38A) GABA-A Receptor Type B Receptor Subunit 1 (GABBR1) and FIG. 38B) Dopamine Receptor 1 (DRD1)

FIGS. 39A-39B: Changes in Colon Expression of FIG. 39A) Tryptophan Hydroxylase-1 (Tph1) and FIG. 39B) Indoleamine2,3-Dioxygenase-1 (IDO1)

FIGS. 40A-40B: Changes in Ileum Expression of FIG. 40A) Tryptophan Hydroxylase-1 (Tph1) and FIG. 40B) Indoleamine2,3-Dioxygenase-1 (IDO1)

DISCLOSURE OF THE INVENTION

Bacterial Strains

Figure 7B:
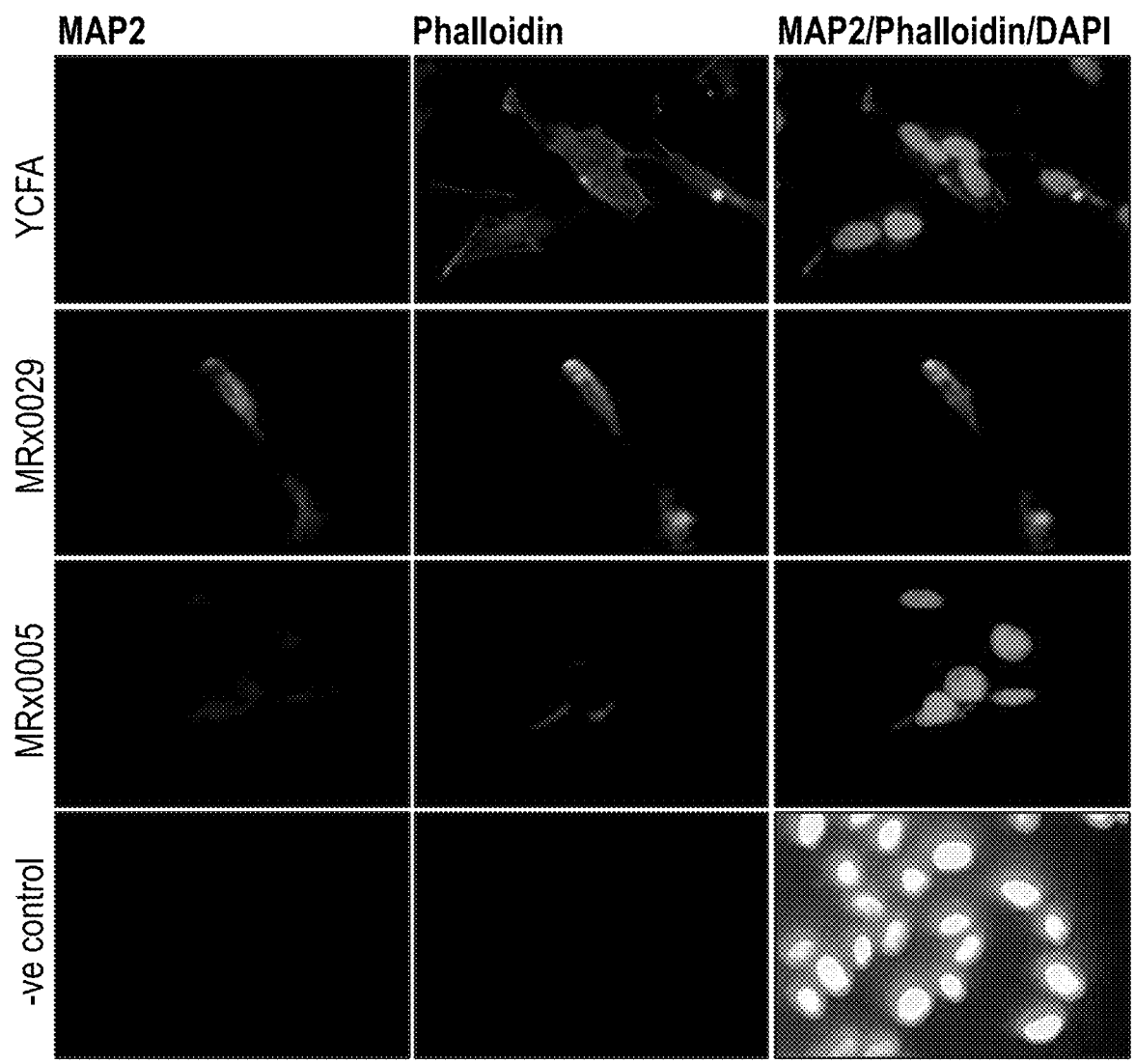

The compositions of the invention comprise a commensal bacterial strain useful for treating or preventing diseases. In a first aspect, the commensal bacterial strains of the invention produce one or more organic acids each having the following formula: R$^x$—COOH, wherein R$^x$ comprises an alkyl group comprising at least 4 carbons, or wherein R$^x$ comprises a phenyl group with a substituent hydroxyl group, wherein optionally the hydroxyl group is at position 4. In a second aspect, the invention provides compositions comprising a commensal bacterial strain and one or more organic acids having the formula R—COOH, or pharmaceutically acceptable salts or esters thereof. The commensal bacterial strain of the second aspect may or may not produce an organic acid according to the invention.

The inventors have found that certain commensal bacterial strains reduce the activation of inflammatory cytokines such as IL-6 and increase the activation of the inflammatory cytokine IL-8. IL-8 has been implicated in myelin sheath formation. Chronic inflammation induced by IL-6 can ultimately lead to cell death. Therefore, the commensal bacterial strains of the invention are particularly useful in the treatment or prevention of neurodegenerative disorders. In some embodiments, the commensal bacterial species are useful in the treatment of conditions characterised by the enhanced activation of IL-6. In some embodiments, the compositions of the invention are for use in the treatment or prevention of neurodegenerative diseases characterised by demyelination. Many neurodegenerative diseases are characterised by demyelination. Demyelination impedes the propagation of action potentials within neurons, impairing effective communication within the nervous system. IL-8 has been shown to contribute positively to myelin sheath formation and repair [22]. Therefore, the compositions of the invention are particularly beneficial in the treatment or prevention of neurodegenerative disorders characterised by demyelination, such as Multiple Sclerosis.

The inventors have found that the commensal bacteria of the invention alleviate symptoms of neurodegenerative diseases in models of the disease. For example, the inventors have found that the particular commensal bacteria strains promote neurite outgrowth in vitro, and may therefore be used in promoting neuron restoration for the treatment or prevention of neurodegenerative diseases. Thus, commensal bacterial strains of the invention are for use in the treatment or prevention of neurodegenerative diseases.

The commensal bacterial strain of the first aspect of the invention may produce one or more of the organic acids of the invention and be administered in combination with one or more of the organic acids of the invention.

Commensal bacterial strains of the second aspect that are beneficial for the treatment or prevention of neurodegenerative diseases may be administered in combination with an organic acid that has the neurorestorative or neuroprotective properties described herein.

The commensal bacterial strains of the first and second aspect of the invention comprise those that exhibit the beneficial effects across the IL-6/IL-8 axis, whether or not the commensal bacterial strain produces one or more of the organic acids according to the invention.

The inventors have also found that the commensal bacterial strains of invention increase the activation of BDNF. BDNF is a neurotrophic growth factor that has been shown to enhance neuron differentiation and survival. The effect is most prominently observed when a commensal bacterial strain is administered in combination with the organic acid of the invention. Thus, the compositions of the invention can be used in a method of enhancing nerve cell survival in the treatment or prevention of neurodegenerative diseases.

As used herein, "increasing" or "decreasing" "activation" refers to enhancing or reducing the concentration of bioactive biomolecules available for performing physiological functions, preferably following administration to the gastrointestinal tract. In other words, "increasing" or "decreasing" refers to the modulating the level of a biomolecule such that a physiological response is appropriately modified. This may be achieved, for example, by modulating the expression or secretion of the biomolecule.

The compositions of the invention comprise a commensal bacterial strain. A commensal bacterial strain is a symbiont derived from the gastrointestinal tract of a mammal, such as a human. Examples of genera from which the commensal bacterial strain may be derived include *Bacteroides, Enterococcus, Escherichia, Klebsiella, Bifidobacterium, Staphylococcus, Lactobacillus, Megasphaera, Clostridium, Proteus, Pseudomonas, Salmonella, Faecalibacterium, Peptostreptococcus* or *Peptococcus*. In some embodiments, the commensal bacterial strain is of the genus *Megasphaera*. Preferably, *Megasphaera* species for use in the invention include *Megasphaera elsdenii, Megasphaera cerevisiae, Megasphaera massiliensis, Megasphaera indica, Megasphaera paucivorans, Megasphaera sueciensis* and *Megasphaera micronuciformis*. A further example of a *Megasphaera* species for use in the invention is *Megasphaera hexanoica*. The *Megasphaera* are obligately anaerobic, lactate-fermenting, gastrointestinal microbe of ruminant and non-ruminant mammals, including humans. Preferably, the bacterial strain is derived from the species to which the composition is intended to be administered.

The type strain of *M. massiliensis* is NP3 (=CSUR P245=DSM 26228) [23]. The GenBank accession number for the 16S rRNA gene sequences of *M. massiliensis* strain NP3 is JX424772.1 (disclosed herein as SEQ ID NO:1).

The *Megasphaera massiliensis* bacterium tested in the Examples is referred to herein as strain MRx0029. MRX0029 and MRx0029 are used herein interchangeably. A 16S rRNA sequence for the MRx0029 strain that was tested is provided in SEQ ID NO:2. Preferably, the bacteria for use in the invention is of the species *Megasphaera massiliensis*, in particular the strain MRx0029.

Strain MRx0029 was deposited with the international depositary authority NCIMB, Ltd. (Ferguson Building, Aberdeen, AB21 9YA, Scotland) by 4D Pharma Research Ltd. (Life Sciences Innovation Building, Cornhill Road, Aberdeen, AB25 2Z S, Scotland) on 13 Jul. 2017 as "*Megasphaera massiliensis* MRx0029" and was assigned accession number NCIMB 42787. All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

Commensal bacterial strains closely related to the strain tested in the examples are also expected to be effective for treating or preventing neurodegenerative diseases. In certain embodiments, the bacterial strain for use in the invention has a 16S rRNA sequence that is at least 95%, 96%, 97%, 98%, 99%, 99.5% or 99.9% identical to the 16S rRNA sequence of a bacterial strain of *Megasphaera massiliensis*. Preferably, the bacterial strain for use in the invention has a 16S rRNA sequence that is at least 95%, 96%, 97%, 98%, 99%, 99.5% or 99.9% identical to SEQ ID NO: 2. Preferably, the bacterial strain for use in the invention has the 16S rRNA sequence represented by SEQ ID NO:2.

Commensal bacterial strains that are biotypes of strains MRx0029 are also expected to be effective for treating or preventing neurodegenerative disorders. A biotype is a closely related strain that has the same or very similar physiological and biochemical characteristics.

Strains that are biotypes of MRx0029 and that are suitable for use in the invention may be identified by sequencing other nucleotide sequences for strains MRx0029. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). Other suitable sequences for use in identifying biotype strains may include hsp60 or repetitive sequences such as BOX, ERIC, $(GTG)_5$ (SEQ ID NO:38), or REP [24]. Biotype strains may have sequences with at least 95%, 96%, 97%, 98%, 99%, 99.5% or 99.9% sequence identity to the corresponding sequence of the strain MRx0029. In some embodiments, a commensal bacterial strain useful in the invention is one that produces organic acids of the invention. Such biotypes may be identified by profiling the production of metabolites of a bacterial strain. Metabolite profiling can be used to identity candidate bacterial strains that produce the neurostimulatory organic acids of the invention. Metabolite profiling can be performed by mass spectrometry. Candidate strains that produce the organic acid and that are suitable for the uses described herein can then be identified by performing the methods and assays as set out in the examples.

Alternatively, suitable biotypes capable of producing an organic acid of the invention are those that contain metabolic pathways that produce the organic acids. Such strains can be identified by genomic analysis, for example by determining whether the bacterial strain encodes for enzymes required for the biosynthesis of the desired organic acids. For example, hexanoic acid production is a multistep catalytic process requiring the presence of multiple enzymes. A crucial step in the production of hexanoic acid is the condensation of acetyl-CoA and butyric-CoA to form a C6 acyl-CoA intermediate, such as 3-ketohexanoyl-CoA. Enzymes required for the production of C4 and C2-CoA precursors are well known to a person skilled in the art. An example of a suitable enzyme for the condensation of C2 and C4 precursors is Beta-ketothiolase. Enzymatic pathways for the formation of C4 CoA are known to have activity with C6 substrates. Therefore, once the C6 intermediate has been formed, enzymes that catalyse the production C4 butyrl-CoA are also suitable for the generation of hexanoic acid. As such, suitable biotypes are those that encode C4-CoA and C2-CoA production-enzymes and an enzyme with beta-ketothiolase activity. Suitable strains may be identified using homology sequence searching databases such as BLASTP or UNIPROT KB by using query sequences of well known enzymes involved in the production of hexanoic acid.

Listed below are bacteria that are known to produce organic acids of use according to the invention, together with supporting references. Using these lists and referenced documents, further strains and species useful for treating neurodegenerative disorders may be identified.

The following species and strains are known to produce hexanoic acid and so may be useful in the compositions of the invention. Preferably, the compositions of the invention comprise a bacterial strain of a species selected from: *Megasphaera hexanoica* [25], in particular strain *Megasphaera hexanoica* KFCC11466P (KR101745084B1); *Megasphaera* sp. MH [26]; *Megasphaera elsdenii* [27] and [28], in particular strain *Megasphaera elsdenii* NCIMB 702410 [29]; *Clostridium kluyveri* [30]; *Clostridium* sp. BS-1 [31], CPB6 (*Ruminococcaceae* bacterium, Clostridium cluster IV) [32]; *Lactobacillus sanfranciscensis* CB 1 [33]; *Pediococcus acidilactici* [34]; *Lysinibacillus* spp. Y20 [35] or *Eubacterium pyruvativorans* (1-6) [36].

*Bacillus cereus* is known to produce retinoic acid and so may be useful in the compositions of the invention [37]. In certain embodiments, the composition of the invention comprises a strain of the species *Bacillus cereus*.

The following genera, species and strains are known to produce (4)-hydroxyphenylacetic acid and so may be useful in the compositions of the invention. Preferably, the compositions of the invention comprise a bacterial strain of the genus *Clostridia* [38] and [39], preferably a bacterial strain of the species *C. difficile* [40] and [41], in particular strains *C. difficile* CDC A567 [42], *C. difficile* DSM 101085 [43], *C. difficile* DSM 102978 [43], *C. difficile* DSM 102860 [43], and *C. difficile* DSM 28666 [43]; *C. putrefaciens* [44]); *C. stricklandii* [44] and Great Plains Lab, Organic Acid Test, Nutritional and Metabolic Profile, Clostridia Bacterial Markers); *C. lituseburense* [44] and Great Plains Lab, Organic Acid Test, Nutritional and Metabolic Profile, Clostridia Bacterial Markers; *C. subterminale* [45], [46] and [44]; *C. propionicum* [44] [46]; *C. clostridiiforme* [46]; *C. cochlearium* [46]; *C. glycolicum* [46]; *C. hastiforme* [46]; *C. irregularis* [46]; *C. perfringens* [47]; or *C. botulinum* Type G [48] and [49]. Preferably, the compositions of the invention comprise a bacterial strain of a species selected from: *Bacteroides fragilis* [50] and [51]); *Bacteroides thetaiotaomicron* [51]; *Bacteroides eggerthii* [51]; *Bacteroides ovatus* [51]; *Parabacteroides distasonis* [51]; *Eubacterium hallii* [51]; *Clostridium bartlettii* [51]; *Porphyromonas gingivalis* [52]; *Flavobacterium* sp. [53]; *Desulfitobacterium dehalogenans* [54] and [55]; *Desulfitobacterium hafniense* DCB-2 [54]; or *Streptomyces sentonii* [56].

Commensal bacteria that have neuroprotective properties but do not produce organic acids in accordance with the first aspect of the invention may be useful in the second aspect of the invention, in compositions in combination with an organic acid. Bacteria which may be employed in the compositions of the second aspect of the present invention include those belonging to the genera *Roseburia* (e.g. *Roseburia hominis*), *Bacteroides, Parabacteroides* (e.g. *Parabacteroides distasonis*), *Blautia* (e.g. *Blautia hydrogenotrophica, Blautia stercoris, Blautia wexlerae*), *Ruminococcus* (e.g. *Ruminococcus albus* [57]), *Clostridium* (e.g. *Clostridium butyricum* [58]), *Lactococcus* (e.g. *Lactococcus lactis, Lactococcus rhamnosus*), *Bifidobacterium* (e.g. *Bifidobacterium breve, Bifidobacterium longum, Bifidobacterium adolescentis, Bifidobacterium lactis, Bifidobacterium infantis*), *Lactobacillus* (e.g. *Lactobacillus paracasei, Lactobacillus delbrueckii, Lactobacillus brevis, Lactobacillus plantarum, Lactobacillus acidophilus*) or *Streptococcus* (e.g. *Streptococcus thermophilus*) ([59], [60]), Alternatively, strains that are biotypes of strains MRX0029 and that are suitable for use in the invention may be identified by using strains MRX0029 and restriction fragment analysis and/or PCR analysis, for example by using fluorescent amplified fragment length polymorphism (FAFLP) and repetitive DNA element (rep)-PCR fingerprinting, or protein profiling, or partial 16S or 23S rDNA sequencing. In preferred embodiments, such techniques may be used to identify other *Megasphaera massiliensis* strains.

In certain embodiments, strains that are biotypes of strains MRX0029 and that are suitable for use in the invention are strains that provide the same pattern as strains MRX0029 when analysed by amplified ribosomal DNA restriction analysis (ARDRA), for example when using Sau3AI restriction enzyme (for exemplary methods and guidance see, for example, [61]). Alternatively, biotype strains are identified as strains that have the same carbohydrate fermentation patterns as strains MRX0029.

Other commensal bacterial strains that are useful in the compositions and methods of the invention, such as biotypes of MRX0029, may be identified using any appropriate method or strategy, including the assays described in the examples. For instance, strains for use in the invention may be identified by culturing with neuroblastoma cells and then assessing cytokine levels and levels of neuroprotection or neuroproliferation. In particular, bacterial strains that have similar growth patterns, metabolic type and/or surface antigens to MRX0029 may be useful in the invention. A useful strain will have comparable immune modulatory activity to MRX0029. In particular, a biotype strain will elicit comparable effects on the neurodegenerative disease models and comparable effects on cytokine levels to the effects shown in the Examples, which may be identified by using the culturing and administration protocols described in the Examples.

A particularly preferred strain of the invention is the *Megasphaera massiliensis* MRX0029 strain. This is the exemplary strain tested in the examples and shown to be effective for treating disease. Therefore, the invention provides a cell, such as an isolated cell, of the *Megasphaera massiliensis* strain MRX0029, or a derivative thereof. The invention also provides a composition comprising a cell of the *Megasphaera massiliensis* strain MRX0029, or a derivative thereof. The invention also provides a biologically pure culture of the *Megasphaera massiliensis* strain MRX0029. The invention also provides a cell of the *Megasphaera massiliensis* strain MRX0029, or a derivative thereof, for use in therapy, in particular for the diseases described herein.

A particularly preferred strain of the invention is the *Megasphaera massiliensis* strain deposited under accession number NCIMB 42787. This is the exemplary MRx0029 strain tested in the examples and shown to be effective for treating disease. Therefore, the invention provides a cell, such as an isolated cell, of the *Megasphaera massiliensis* strain deposited under accession number NCIMB 42787, or a derivative thereof. The invention also provides a composition comprising a cell of the *Megasphaera massiliensis* strain deposited under accession number NCIMB 42787, or a derivative thereof. The invention also provides a biologically pure culture of the *Megasphaera massiliensis* strain deposited under accession number NCIMB 42787. The invention also provides a cell of the *Megasphaera massiliensis* strain deposited under accession number NCIMB 42787, or a derivative thereof, for use in therapy, in particular for the diseases described herein.

A derivative of the strain of the invention may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable therapeutic activity to the MRX0029 strain. In particular, a derivative strain will elicit comparable effects on the neurodegenerative disease models and comparable effects on cytokine levels to the effects shown in the Examples, which may be identified by using the culturing and administration protocols described in the Examples. A derivative of the MRX0029 strain will generally be a biotype of the MRX0029 strain.

References to cells of the *Megasphaera massiliensis* MRX0029 strain encompass any cells that have the same safety and therapeutic efficacy characteristics as the strain MRX0029, and such cells are encompassed by the invention.

In preferred embodiments, the bacterial strains in the compositions of the invention are viable and capable of partially or totally colonising the intestine.

A further commensal bacteria that may be used in the compositions of the invention is the species *Parabacteroides distasonis*. The examples demonstrate that *Parabacteroides distasonis* and *Megasphaera massiliensis* both have neuroprotective activities, but produce different metabolites and may have different mechanisms of action and specific neuroprotective activities. Therefore, these species may be particularly effective when used in combination. In preferred embodiments, the composition comprises a strain of the species *Parabacteroides distasonis* and a strain of the species *Megasphaera massiliensis*. The composition may also include an organic acid, as defined herein.

The *Parabacteroides distasonis* bacterium deposited under accession number NCIMB 42382 was tested in the Examples and is also referred to herein as strain MRx0005. MRX0005, MRX005, MRx005 and MRx0005 are used herein interchangeably. A 16S rRNA sequence for the MRx0005 strain that was tested is provided in SEQ ID NO:17. Strain MRx0005 was deposited with the international depositary authority NCIMB, Ltd. (Ferguson Building, Aberdeen, AB21 9YA, Scotland) by GT Biologics Ltd. (Life Sciences Innovation Building, Aberdeen, AB25 2ZS, Scotland) on 12 Mar. 2015 as "*Parabacteroides* sp 755" and was assigned accession number NCIMB 42382. GT Biologics Ltd. Subsequently changed its name to 4D Pharma Research Limited.

In preferred embodiments, the invention provides a composition comprising the strain deposited at NCIMB under accession number NCIMB 42787, or a derivative or biotype thereof, and the strain deposited at NCIMB under accession number NCIMB 42382, or a derivative or biotype thereof, preferably for use in therapy, preferably for use in treating a neurodegenerative disease such as Parkinson's disease.

In certain embodiments, the composition of the invention does not comprise a bacterial strain of the genus *Megasphaera*. In certain embodiments, the composition of the invention does not comprise a bacterial strain of the species *Megasphaera massiliensis*. In certain embodiments, the composition of the invention does not comprise the *Megasphaera massiliensis* strain deposited under accession number NCIMB 42787.

Organic Acids

As demonstrated in the Examples, one or more organic acids described herein have neuroprotective and/or neurorestorative properties. For example, the organic acids of the invention may promote neurite outgrowth. Neurite outgrowth is the process of neuritogenesis, which refers to the formation of axonal or dendritic projections from the cell body of a neuron. Axons and dendrites are responsible for receiving and transmitting action potentials. Thus, increasing neurite outgrowth can restore or preserve effective communication within neural networks within the nervous system. Therefore, in some embodiments, organic acids suitable for use in the invention are those capable of promoting neurite outgrowth. Such organic acids may be for use in a method of preventing disease. In some embodiments, the organic acids are for use in a method of treating or preventing a neurodegenerative disease.

The one or more organic acids comprise the following formula: R—COOH.

In some embodiments, R comprises an alkyl group. As referred to herein, an alkyl group is a linear, branched, or cyclic saturated hydrocarbon chain or any substituent derived therefrom. In some embodiments, R comprises an alkenyl group. As referred to herein, an alkenyl group is a linear, branched, or cyclic unsaturated hydrocarbon comprising at least one carbon-to-carbon double bond, or any substituent derived therefrom. In some embodiments, R comprises an alkynyl group. As referred to herein, an alkynyl group is a linear, branched, or cyclic unsaturated hydrocarbon comprising at least one carbon-carbon triple bond, or any substituent derived therefrom. In some embodiments, R comprises an aryl group. As referred to herein, an aryl group is a linear, branched or cyclic aromatic hydrocarbon, or any substituent derived therefrom.

As referred to herein, a substituent is an atom or group of atoms that replaces one or more hydrogens of the parent hydrocarbon chain. In some embodiments, R comprises one or more substituents. In some embodiments, the one or more substituents are selected from the list consisting of hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, carboxamide, amine, imine, nitrate, nitrile, nitrite, pyridyl, sulfhydryl, sulphide, disulphide, sulfinyl, sulfonyl, sulfino, sulfo, carbonothioyl, catechol or a combination thereof.

In some embodiments, R comprises at least 4 carbon atoms. In some embodiments, R comprises at least 5, 6, 7, 8, 9, 10, 11, 12, 13, 14, 15, 16, 17, 18 or 19 carbon atoms. In some embodiments, R comprises in the range of 4 to 19 carbon atoms.

In some embodiments, R comprises in the range of 4 to 11 carbons. In some embodiments, R comprises an alkyl group consisting of 5 carbon atoms. In some embodiments, the one or more organic acids comprise hexanoic acid. The inventors have found that hexanoic acid and bacterial strains described herein that produce hexanoic acid enhance neurite outgrowth. As such, these organic acids can be used to promote neurite outgrowth. In some embodiments, these organic acids can be used to promote neurite outgrowth in the treatment or prevention of a neurodegenerative disease. Exemplary bacterial strains of the invention that produce hexanoic acid comprise those from the genus *Megasphaera*.

In some embodiments, R comprises an alkyl group consisting of 4 carbon atoms. In some embodiments, the one or more organic acids comprise valeric acid. Valeric acid and pentanoic acid are herein used interchangeably. The inventors have found that valeric acid and commensal bacterial strains described herein that produce valeric acid can reduce histone deacetylation. In particular the inventors have found that valeric acid histone deacetylase inhibitor. Histone deacetylases (HDACs) regulate gene expression by modulating chromatin acetylation. The overexpression of different isoforms of HDACs has been found in several types of cancer cells as well as in neurological and inflammatory pathologies. In humans, there are a total of 13 HDACs, which are categorised into four main classes—Class I (HDACs 1, 2, 3 and 8), Class IIa (HDACs 4, 5, 7 and 9) and Class IIb (HDACs 6 and 10), Class III (sirt1-sirt7) and class IV (HDAC 11). The inventors have found that valeric acid is a class 1 HDAC inhibitor.

In some embodiments, R comprises a branched alkyl group. In some embodiments, R comprises at least 5 carbon atoms. In some embodiments, R comprises in the range of 5 to 9 carbon atoms. In some embodiments, R comprises a butyric group. In some embodiments, R consists of a butyl group and a propyl group. In some embodiments, the one or more organic acids comprise valproic acid. The inventors have shown increases neurite outgrowth and thus can be for use in a method of neurorestoration. Valproic acid has also been shown to aid neurorestoration in a rat model of PD [62], although not in combination with a bacterial therapy. Valproic acid has been shown to increase MAP2 expression.

In some embodiments, R comprises an aryl group. In some embodiments, the aryl group is a phenyl group. In some embodiments, the phenyl group comprises a hydroxyl group. In some embodiments, the hydroxyl group is at ring position 2, 3, 4, 5 or 6. In some embodiments, the hydroxyl group is at ring position 4. In some embodiments, R consists of a 4-hydroxyphenylacetyl group. In some embodiments, the one or more organic acids comprise 4-hydroxyphenylacetic acid. The inventors have shown that this organic acid or bacterial strains described herein that produce this organic acid can be used to promote neurite outgrowth. 4-hydroxyphenylacetic acid is also an antioxidant. In some embodiments, the one or more organic acids comprising 4-hydroxyphenylacetic acid can be used in the treatment or prevention of neurodegenerative disorders to reduce oxidative stress. 4-hydroxyphenylacetic acid is an intermediate of dopamine and norepinephrine. Dopamine and norepinephrine (also known as noradrenaline) are neurotransmitters acting in the sympathetic nervous system. Levels of dopamine and norepinephrine are reduced in subjects suffering from neurodegenerative diseases, for example Parkinson's disease. The inventors have found that commensal bacterial strains described herein that produce 4-hydroxyphenylacetic acid increase the levels of noradrenaline, serotonin or 5-hydroxytryptamine (5-HT) in the brain. Therefore, 4-hydroxyphenylacetic acid may be useful in the treatment or prevention of neurodegenerative diseases characterised by lower levels of norepheniphrine, dopamine, serotonin or 5-hydroxytryptamine. In some embodiments, 4-hydroxyphenylacetic acid may be useful in the treatment or prevention of neurodegenerative diseases.

In some embodiments, R comprises an alkenyl group. In some embodiments, the alkenyl group is at least partially cyclical. As referred to herein, a "partially cyclical" group is a hydrocarbon chain comprising a linear chain portion and a cyclical chain portion. In some embodiments, the partially cyclical alkenyl group comprises 19 carbon atoms. In some embodiments, R comprises in the range of 1 to 8 methyl substituent groups. In some embodiments, R comprises in the range of 1 to 8 carbon-to-carbon double bonds. In some embodiments, the organic acid is retinoic acid or a derivative thereof. The inventors have found that these organic acids when administered in combination with the bacterial strains of the invention increase the activation of BDNF. As such, in some embodiments, these organic acids may be used to increase the activation of BDNF. In some embodiments, these organic acids can be used to increase the activation of BDNF in the treatment or prevention of neurodegenerative diseases.

The organic acids for use in the invention may be identified by using the culturing and administration protocols described in the Examples. For instance. organic acids for use in the invention can be identified by culturing with neuroblastoma cells and then assessing cytokine levels and levels of neuroprotection or neuroproliferation and neuritogenesis. A useful organic acid may enhance neurite outgrowth activity at least comparable to valproic acid, hexanoic acid or retinoic acid, as shown in the Examples. In particular, a useful organic acid may elicit comparable effects on the neurodegenerative disease models and comparable effects on cytokine and growth factor levels, to the effects shown in the Examples, when the organic acid is administered in combination with a commensal bacterial strain of the invention. For example, suitable organic acids will increase the activation of BDNF comparable with retinoic acid when administered in combination with a bacterial strain of the invention. In the first aspect, the organic acid is produced by the commensal bacterial strain of the invention.

In some embodiments, suitable organic acids of the invention as those that act together with the commensal bacterial strain of the invention to enhance a therapeutic response. For instance, the Examples show that administration of valproic acid together with MRX0029 increases the secretion of BDNF. BDNF can help support the survival of existing neurons and helps the growth and development of new neurons and synapses. Therefore, certain organic acids of the invention may be for use in methods of neuropreservation, or in other words, to prevent neuron death.

The compositions of the invention may further comprise short chain fatty acids (SCFAs). SCFAs are organic acids comprising a carboxylic acid group bonded to a linear or branched hydrocarbon alkyl group consisting of 0 to 4 carbon atoms. SCFAs have been shown to regulate the permeability of the blood brain barrier. In particular, SCFAs have been shown to redress defective BBB permeability, thus restoring permeability to physiologically appropriate levels. In some embodiments, the SCFA is selected from the list consisting of formic acid, ethanoic acid, propanoic acid, butyric acid, 2-methylpropanoic acid isovaleric acid, or a salts or esters thereof. In some embodiments, the SCFA is part of the therapeutic combination. In some embodiments, the SCFA is produced by the commensal bacterial strain of the invention.

In some embodiments, the SCFA for use in the invention is butyric acid or a salt thereof. In some embodiments, the commensal bacterial strain produces butyric acid or a salt thereof. In some embodiments, the commensal bacterial strain that produces butyric acid or a salt thereof is the *M. massiliensis* strain referred to herein as strain MRX0029. Suitable biotypes of the bacterial strain that produce the SCFA can be identified using any of the other methods described in the previous section, for example, metabolite profiling, genome analysis, or amplified ribosomal DNA restriction analysis.

In some embodiments, the compositions of the invention may further comprise succinic acid or a salt thereof. In some embodiments, the commensal bacterial strain produce succinic acid or a salt thereof. In some embodiments, the commensal bacterial strain that produces succinic acid is the strain referred to herein as strain MRX0005. Succinic acid is a Krebs cycle metabolite involved in oxidative phosphorylation. Dysfunction of oxidative phosphorylation has been reported in neurodegenerative disorders including Alzheimer's disease, Parkinson's disease and Spinocerebellar ataxia type 1 [63,64]). Therefore increasing the availability of succinic acid may reverse defects in oxidative phosphorylation and increase mitochondrial activity to improve the health of neurons subject to neurodegenerative disease, such as PD [65].

Therapeutic Uses

As demonstrated in the examples, the bacterial compositions of the invention are effective for treating neurodegenerative disorders. In particular, treatment with compositions of the invention increase neuroproliferation or neuritogenesis or act as a neuroprotectant against agents that destroy neurons, such as dopaminergic neurons. Therefore, the compositions of the invention may be useful for treating or preventing neurodegenerative diseases that are the result of neuron death.

Compositions of the invention can decrease the activation of the NFκB promoter, which activates cytokine production, for example IL-1β, IL-1α, IL-18, TNFα and IL-6. Treating cells with mutant α-synuclein is a model for familial Parkinson's. A point mutation at position 53 from adenine to threonine leads to α-synuclein mis-folding. The incorrectly folded α-synuclein subsequently aggregates into insoluble fibrils which form Lewy bodies. Therefore, the compositions of the invention may be useful for treating or preventing neurodegenerative disorders that are the result of neuroinflammation, protein misfolding and/or environmental exposure. Compositions of the invention can be used for treatment of familial Parkinson's. Activation of the NFκB promoter is mediated through the TLR4 ligand. TLR4 is known to mediate cell death in the mouse model MPTP, which simulates of Parkinson's disease. Compositions of the invention can be used to inhibit the ability of TLR4 to activate the NFκB promoter. Of particular relevance for PD, both TLR2 and TLR4 were found to be upregulated in brains of PD patients [66]. Moreover α-syn has been described as a ligand for TLR2 [67] and we have demonstrated that α-syn is also a ligand for TLR4 using HEK-TLR4 cells [68].

Compositions of the invention decrease the secretion of pro-inflammatory cytokines such as IL-6, which can be induced by lipopolysaccharide (LPS). Treatment of cells with LPS simulates Parkinson's caused by environmental factors. Compositions of the invention can be used to decrease IL-6 secretion. Compositions of the invention can be used for treatment of environmental Parkinson's.

Compositions of the invention can increase the secretion of IL-8. IL-8 has been shown to play a role in neuron myelination. In some embodiments, compositions of the invention can be used to increase IL-8 secretion.

The therapeutic compositions of the invention can increase the activation of BDNF. BDNF acts on certain neurons of the central nervous system to support the survival of existing neurons and help the growth and development of new neurons and synapses. BDNF is active in the hippocampus, cortex and basal forebrain, and is important for long-term memory. The compositions of the invention can therefore be used to increase the secretion of BDNF. The compositions may therefore be used in the treatment of neurodegenerative diseases associated with the impairment of long-term memory. The compositions of the invention may be used for improving long-term memory, in particular for improving long-term memory that is impaired by a neurodegenerative disease.

In certain embodiments, the compositions of the invention increase the mitochondria metabolic activity in neuronal cells.

Examples of neurodegenerative diseases to be treated by compositions of the invention include: Parkinson's disease, including progressive supranuclear palsy, progressive supranuclear palsy, Steele-Richardson-Olszewski syndrome, normal pressure hydrocephalus, vascular or arteriosclerotic parkinsonism and drug-induced parkinsonism; Alzheimer's disease, including Benson's syndrome; multiple sclerosis; Huntington's disease; amyotrophic lateral sclerosis; Lou Gehrig's disease; motor neurone disease; prion disease; spinocerebellar ataxia; spinal muscular atrophy; dementia, including Lewy body, vascular and frontotemporal dementia; primary progressive aphasia; mild cognitive impairment; HIV-related cognitive impairment, progressive inflammatory neuropathy, and corticobasal degeneration.

In certain embodiments, the compositions of the invention are for use in reducing neuron death, in particular, in the treatment of neurodegenerative disorders. In certain embodiments, the compositions of the invention are for use in protecting neurons, in particular in the treatment of neurodegenerative disorders.

In certain embodiments, the compositions of the invention are for use in reducing or preventing loss of dopaminergic cells in the substantia nigra. In certain embodiments, the compositions of the invention are for use in reducing or preventing the degeneration of dopaminergic neurons in the substantia nigra pars compacta. In certain embodiments, the compositions of the invention are for use in reducing or preventing the degeneration of dopaminergic neurons in the substantia nigra pars compacta and the consequent loss of their projecting nerve fibers in the striatum. In certain embodiments, the compositions of the invention are for use in reducing or preventing loss of nigrostriatal dopaminergic neurons.

In certain embodiments, the compositions of the invention are for use in increasing dopamine levels. In certain embodiments, the compositions of the invention are for use in increasing DOPAC (3,4-Dihydroxyphenylacetic acid) levels. In certain embodiments, the compositions of the invention are for use in increasing dopamine and DOPAC levels. In certain embodiments, the dopamine and/or DOPAC levels are increased in the striatum. Dopamine and DOPAC levels may be measured using any appropriate method known in the art, such as a radioenzymatic method, for example in plasma or CSF (for example as described in [69]), or a reverse-phase HPLC method, perhaps with electrochemical detection, for example in plasma or CSF (for example as described in [70]).

The neuroprotective properties of the compositions of the invention, as shown in the Examples, mean that the compositions may be particularly effective for preventing or delaying onset or progression of neurodegenerative disorders. In certain embodiments, the compositions of the invention are for use in delaying onset or progression of neurodegenerative disorders.

Modulation of the Microbiota-Gut-Brain Axis

Communication between the gut and the brain (the microbiota-gut-brain axis) occurs via a bidirectional neurohumoral communication system. Recent evidence shows that the microbiota that resides in the gut can modulate brain development and produce behavioural phenotypes via the microbiota-gut-brain axis. Indeed, a number of reviews suggest a role of the microbiota-gut-brain axis in maintaining central nervous system functionality and implicate dysfunction of the microbiota-gut-brain axis in the development of central nervous system disorders and conditions [16], [19], [71].

The bidirectional communication between the brain and the gut (i.e. the-gut-brain axis) includes the central nervous system, neuroendocrine and neuroimmune systems, including the hypothalamus-pituitary-adrenal (HPA) axis, sympathetic and parasympathetic arms of the autonomic nervous system (ANS), including the enteric nervous system (ENS) and the vagus nerve, and the gut microbiota.

As demonstrated in the examples, the compositions of the present invention can modulate the microbiota-gut-brain axis and reduce cell death associated with neurodegenerative disorders. Accordingly, the compositions of the invention may be useful for treating or preventing neurodegenerative disorders, in particular those disorders and conditions associated with dysfunction of the microbiota-gut-brain axis.

In particular embodiments, the compositions of the invention may be useful for treating or preventing a disease or condition selected from the group consisting of: Parkinson's disease, including progressive supranuclear palsy, progressive supranuclear palsy, Steele-Richardson-Olszewski syndrome, normal pressure hydrocephalus, vascular or arteriosclerotic parkinsonism and drug-induced parkinsonism; Alzheimer's disease, including Benson's syndrome; multiple sclerosis; Huntington's disease; amyotrophic lateral sclerosis; Lou Gehrig's disease; motor neurone disease; prion disease; spinocerebellar ataxia; spinal muscular atrophy; dementia; including Lewy body; vascular and frontotemporal dementia; primary progressive aphasia; mild cognitive impairment; HIV-related cognitive impairment, progressive inflammatory neuropathy, and corticobasal degeneration.

The compositions of the invention may be particularly useful for treating or preventing chronic disease, treating or preventing disease in patients that have not responded to other therapies (such as treatment with Levodopa, dopamine agonists, MAO-B inhibitors, COMT inhibitors, Glutamate antagonists, and/or anticholinergics), and/or treating or preventing the tissue damage and symptoms associated with dysfunction of the microbiota-gut-brain axis.

In certain embodiments, the compositions of the invention modulate the CNS. In some embodiments, the compositions of the invention modulate the autonomic nervous system (ANS). In some embodiments, the compositions of the invention modulate the enteric nervous system (ENS). In some embodiments, the compositions of the invention modulate the hypothalamic, pituitary, adrenal (HPA) axis. In some embodiments, the compositions of the invention modulate the neuroendocrine pathway. In some embodiments, the compositions of the invention modulate the neuroimmune pathway. In some embodiments, the compositions of the invention modulate the CNS, the ANS, the ENS, the HPA axis and/or the neuroendocrine and neuroimmune pathways. In certain embodiments, the compositions of the invention module the levels of commensal metabolites and/or the gastrointestinal permeability of a subject.

The signalling of the microbiota-gut-brain axis is modulated by neural systems. Accordingly, in some embodiments, the compositions of the invention modulate signalling in neural systems. In certain embodiments, the compositions of the invention modulate the signalling of the central nervous system. In some embodiments, the compositions of the invention modulate signalling in sensory neurons. In other embodiments, the compositions of the invention modulate signalling in motor neurons. In some embodiments, the compositions of the invention modulate the signalling in the ANS. In some embodiments, the ANS is the parasympathetic nervous system. In preferred embodiments, the compositions of the invention modulate the signalling of the vagus nerve. In other embodiments, the ANS is the sympathetic nervous system. In other embodiments, the compositions of the invention modulate the signalling in the enteric nervous system. In certain embodiments, the signalling of ANS and ENS neurons responds directly to luminal contents of the gastrointestinal tract. In other embodiments, the signalling of ANS and ENS neurons responds indirectly to neurochemicals produced by luminal bacteria. In other embodiments, the signalling of ANS and ENS neurons responds to neurochemicals produced by luminal bacteria or enteroendocrine cells. In certain preferred embodiments, the neurons of the ENS activate vagal afferents that influence the functions of the CNS. In some embodiments, the compositions of the invention regulate the activity of enterochromaffin cells.

Neurodegenerative Diseases

Parkinson's Disease

Parkinson's disease is a common neurodegenerative disease neuropathologically characterised by degeneration of heterogeneous populations of neural cells (dopamine-producing cells). The clinical diagnosis of Parkinson's disease requires bradykinesia and at least one of the following core symptoms: resting tremor; muscle rigidity and postural reflex impairment. Other signs and symptoms that may be present or develop during the progression of the disease are autonomic disturbances (sialorrhoea, seborrhoea, constipation, micturition disturbances, sexual functioning, orthostatic hypotension, hyperhydrosis), sleep disturbances and disturbances in the sense of smell or sense of temperature. Parkinson's disease is a neurodegenerative diseases that may develop or persist due to dysfunction of the microbiota-gut-brain axis. Therefore, in preferred embodiments, the compositions of the invention are for use in treating or preventing Parkinson's disease in a subject.

In further preferred embodiments, compositions of the invention are for use in a method of treating or preventing Parkinson's disease. Compositions of the invention may improve motor and cognitive functions in models of Parkinson's disease. Treatment with the compositions may modulate signalling in the central, autonomic and enteric nervous systems; may modulate the activity of the HPA axis pathway; may modulate neuroendocrine and/or neuroimmune pathways; and may modulate the levels of commensal metabolites, inflammatory markers and/or gastrointestinal permeability of a subject, all of which are implicated in the neuropathology of Parkinson's disease. In preferred embodiments, the invention provides a composition comprising a bacterial strain of the species *Megasphaera massiliensis* for use in a method of treating or preventing Parkinson's disease. Compositions using *Megasphaera massiliensis* may be particularly effective for treating Parkinson's disease. The composition may further comprise an organic acid.

In preferred embodiments, the compositions of the invention prevent, reduce or alleviate one or more of the symptoms of Parkinson's disease in a subject. In preferred embodiments, the compositions of the invention prevent, reduce or alleviate one or more core symptoms of Parkinson's disease in a subject. In certain embodiments, the compositions of the invention prevent, reduce or alleviate bradykinesia in a subject. In certain embodiments, the compositions of the invention prevent, reduce or alleviate resting tremor; muscle rigidity and/or postural reflex impairment in a subject. In certain embodiments, the compositions of the invention prevent, reduce or alleviate one or more symptoms associated with Parkinson's disease progression selected from autonomic disturbances (sialorrhoea, seborrhoea, constipation, micturition disturbances, sexual functioning, orthostatic hypotension, hyperhydrosis), sleep disturbances and disturbances in the sense of smell or sense of temperature.

In preferred embodiments, the compositions of the invention prevent, reduce or alleviate depressive symptoms comorbid with Parkinson's disease. In certain embodiments, the compositions of the invention improve verbal memory and/or executive functions. In certain embodiments, the compositions of the invention improve attention, working memory, verbal fluency and/or anxiety.

In other preferred embodiments, the compositions of the invention prevent, reduce or alleviate cognitive dysfunctions comorbid with Parkinson's disease.

In certain embodiments, the compositions of the invention prevent, reduce or alleviate Parkinson's disease progression. In certain embodiments, the compositions of the invention prevent, reduce or alleviate later motor complications. In certain embodiments, the compositions of the invention prevent, reduce or alleviate late motor fluctuations. In certain embodiments, the compositions of the invention prevent, reduce or alleviate neuronal loss. In certain embodiments, the compositions of the invention improve symptoms of Parkinson's disease dementia (PDD). In certain embodiments, the compositions of the invention prevent, reduce or alleviate impairment of executive function, attention and/or working memory. In certain embodiments, the compositions of the invention improve dopaminergic neurotransmission. In certain embodiments, the compositions of the invention prevent, reduce or alleviate impaired dopaminergic neurotransmission.

In some embodiments, the compositions of the invention improve the symptoms of Parkinson's disease according to a symptomatic or diagnostic scale. In certain embodiments, the tests for assessing symptomatic improvement of motor function in Parkinson's disease is the Unified Parkinson's Disease Rating Scale. In particular, UPDRS II considers the activity of daily life and UPDRS III considers motor-examination.

In some embodiments, the compositions of the invention improve the symptoms associated with PDD according to a symptomatic or diagnostic test and/or scale. In certain embodiments, the test or scale is selected from the Hopkins Verbal Learning Test—Revised (HVLT-R); the Delis-Kaplan Executive Function System (D-KEFS) Color-Word Interference Test; the Hamilton Depression Rating Scale (HAM-D 17; depression); the Hamilton Anxiety Rating Scale (HAM-A; anxiety) and the Unified Parkinson's Disease Rating Scale (UPDRS; PD symptom severity).

In some embodiments, the compositions of the invention improve the Clinical Global Impression-Global Improvement (CGI-I) scale for assessing psychiatric and neurological disorders. In some embodiments, the compositions of the invention display a positive effect on global social and occupational impairment of the subject with Parkinson's disease.

In certain embodiments, the compositions of the invention are for use in treating or preventing neurological disorders such as Parkinson's disease in a subject wherein said use involves reducing or preventing loss of dopaminergic cells in the substantia nigra. In certain embodiments, the compositions of the invention are for use in treating or preventing neurological disorders such as Parkinson's disease in a subject wherein said use involves reducing or preventing the degeneration of dopaminergic neurons in the substantia nigra pars compacta. In certain embodiments, the compositions of the invention are for use in treating or preventing neurological disorders such as Parkinson's disease in a subject wherein said use involves reducing or preventing the degeneration of dopaminergic neurons in the substantia nigra pars compacta and the consequent loss of their projecting nerve fibers in the striatum. In certain embodiments, the compositions of the invention are for use in treating or preventing neurological disorders such as Parkinson's disease in a subject wherein said use involves reducing or preventing loss of nigrostriatal dopaminergic neurons.

In certain embodiments, the compositions of the invention are for use in treating or preventing neurological disorders such as Parkinson's disease in a subject wherein said use involves increasing dopamine levels. In certain embodiments, the compositions of the invention are for use in treating or preventing neurological disorders such as Parkinson's disease in a subject wherein said use involves increasing DOPAC levels. In certain embodiments, the compositions of the invention are for use in treating or preventing neurological disorders such as Parkinson's disease in a subject wherein said use involves increasing dopamine and DOPAC levels. In certain embodiments, the dopamine and/or DOPAC levels are increased in the striatum.

Alzheimer's Disease and Dementia

In DSM-5, the term dementia was replaced with the terms major neurocognitive disorder and mild neurocognitive disorder. Neurocognitive disorder is a heterogeneous class of psychiatric diseases. The most common neurocognitive disorder is Alzheimer's disease, followed by vascular dementias or mixed forms of the two. Other forms of neurodegenerative disorders (e.g. Lewy body disease, frontotemporal dementia, Parkinson's dementia, Creutzfeldt-Jakob disease, Huntington's disease, and Wernicke-Korsakoff syndrome) are accompanied by dementia.

Alzheimer's disease and dementia are also characterised by neuronal loss, so the neuroprotective and neuroproliferative effects shown in the examples for the compositions of the invention indicate that they may be useful for treating or preventing these conditions.

The symptomatic criteria for dementia under DSM-5 are evidence of significant cognitive decline from a previous level of performance in one or more cognitive domains selected from: learning and memory; language; executive function; complex attention; perceptual-motor and social cognition. The cognitive deficits must interfere with independence in everyday activities. In addition, the cognitive deficits do not occur exclusively in the context of a delirium and are not better explained by another mental disorder (for example MDD or schizophrenia).

In addition to the primary symptom, subjects with neurodegenerative disorders display behavioural and psychiatric symptoms including agitation, aggression, depression, anxiety, apathy, psychosis and sleep-wake cycle disturbances.

Neurodegenerative disorders may develop or persist due to dysfunction of the microbiota-gut-brain axis. Therefore, in preferred embodiments, the compositions of the invention are for use in treating or preventing neurodegenerative disorders in a subject. In preferred embodiments, the neurodegenerative disorder is Alzheimer's disease. In other embodiments, the neurodegenerative disorder is selected from vascular dementias; mixed form Alzheimer's disease and vascular dementia; Lewy body disease; frontotemporal dementia; Parkinson's dementia; Creutzfeldt-Jakob disease; Huntington's disease; and Wernicke-Korsakoff syndrome.

In preferred embodiments, the compositions of the invention prevent, reduce or alleviate one or more of the symptoms of neurodegenerative disorders in a subject. In certain embodiments, the compositions of the invention prevent, reduce or alleviate the occurrence of cognitive decline in a subject. In certain embodiments, the compositions of the invention improve the level of performance of a subject with neurodegenerative disorders in one or more cognitive domains selected from: learning and memory; language; executive function; complex attention; perceptual-motor and social cognition. In some embodiments, the compositions of the invention prevent, reduce or alleviate the occurrence of one or more behavioural and psychiatric symptoms associated with neurodegenerative disorders selected from agitation, aggression, depression, anxiety, apathy, psychosis and sleep-wake cycle disturbances.

In certain embodiments, the compositions of the invention prevent, reduce or alleviate symptomatic disease by intervention in suspected pathogenic mechanisms at a preclinical stage. In certain embodiments, the compositions of the invention improve disease modification, with slowing or arrest of symptom progression. In some embodiments, the slowing or arrest of symptom progression correlates with evidence in delaying the underlying neuropathological process. In preferred embodiments, the compositions of the invention improve symptoms of neurodegenerative disorders comprising enhanced cognitive and functional improvement. In preferred embodiments, the compositions of the invention improve the behavioural and psychiatric symptoms of dementia (BPSD). In preferred embodiments, the compositions of the invention improve the ability of a subject with neurodegenerative disorder to undertake everyday activities.

In preferred embodiments, the compositions of the invention improve both cognition and functioning in a subject with Alzheimer's disease. In some embodiments, the composition of the invention improves the cognitive endpoint in a subject with Alzheimer's disease. In some embodiments, the compositions of the invention improve the functional endpoint in a subject with Alzheimer's disease. In preferred embodiments, the compositions of the invention improve the cognitive and functional endpoint in a subject with Alzheimer's disease. In yet further preferred embodiments, the compositions of the invention improve the overall clinical response (the global endpoint) in a subject with Alzheimer's disease.

In some embodiments, the compositions of the invention improve the symptoms of neurodegenerative disorders according to a symptomatic or diagnostic test. In certain embodiments, the tests for assessing symptomatic improvement of Alzheimer's disease (and other neurodegenerative disorders) are selected from objective cognitive, activities of daily living, global assessment of change, health related quality of life tests and tests assessing behavioural and psychiatric symptoms of neurodegenerative disorders.

In certain embodiments, the objective cognitive tests for assessment of symptomatic improvement use the Alzheimer's disease Assessment Scale cognitive subscale (ADAS-cog) and the classic ADAS scale. In certain embodiments, symptomatic improvement of cognition is assessed using the Neurophysiological Test Battery for Use in Alzheimer's Disease (NTB).

In some embodiments, the global assessment of change test uses the Clinical Global Impression-Global Improvement (CGI-I) scale for assessing psychiatric and neurological disorders. In some embodiments, the global scale is the Clinician's Interview Based Impression of Change plus (CIBIC-plus). In some embodiments, the global scale is the Alzheimer's Disease Cooperative Study Unit Clinician's Global Impression of Change (ADCS-CGIC).

In certain embodiments, the health related quality of life measures are the Alzheimer's Disease-Related QOL (ADRQL) and the QOL-Alzheimer's Disease (QOL-AD).

In certain embodiments, the tests assessing behavioural and psychiatric symptoms of neurodegenerative disorders are selected from the Behavioural pathology in Alzheimer's Disease Rating Scale (BEHAVE-AD); the Behavioural Rating Scale for Dementia (BRSD); the Neuropsychiatric Inventory (NPI); and the Cohen-Mansfield Agitation Inventory (CMAI).

In some embodiments, the compositions of the invention are particularly effective at preventing, reducing or alleviating neurodegenerative disorders when used in combination with another therapy for treating neurodegenerative disorders. In certain embodiments, such therapies include acetylcholinesterase inhibitors including donepezil (Aricept®), galantamine (Razadyne®) and rivastigmine (Exelon®), and memantine.

Multiple Sclerosis

Multiple sclerosis (MS) is a demyelinating disease in which the myelin sheath surrounding neurons in the brain and spinal cord are damaged. The exact underlying causes of MS are unknown, but are thought to vary between individuals. Certain forms of MS are hereditary. Environmental factors are also thought to contribute to MS. In some individuals, a combination of both genetic and environmental factors may trigger the onset of MS.

There are a wide variety of symptoms associated with MS. Subjects may exhibit almost any neurological symptom associated with the impairment of autonomic, visual, motor or sensory control. The exact symptoms will vary depending on the site of neuronal damage/demyelination.

IL-8 has been implicated in the formation of myelin sheaths. The compositions of the invention may therefore be for use in the remyelination of neurons in subjects with MS. The compositions of the invention may also be used to protect neurons from demyelination. In other words, the compositions of the invention may be for use in a method of treating or preventing multiple sclerosis by restoring or preventing loss of neuron myelin sheaths.

In some embodiments, the compositions of the invention prevent, reduce or alleviate one or more symptoms of MS in a subject. In some embodiments, the compositions of the invention prevent, reduce or alleviate fatigue in a subject. In certain embodiments, the compositions of the invention prevent, reduce or alleviate resting tremor, muscle weakness, muscle spasms, muscle stiffness, paraesthesia and/or ataxia in a subject. In certain embodiments, the compositions of the invention prevent, reduce or alleviate one or more symptoms associated with MS progression selected from the list consisting of autonomic disturbances: constipation, micturition disturbances, sexual functioning, dysphagia, dysarthria, syncope, vertigo and/or dizziness; sleep disturbances; and disturbances in the sense of smell or sense of temperature. In some embodiments, the compositions of the invention prevent, reduce or alleviate one or more ocular symptoms associated with MS. In some embodiments, the ocular symptom is selected from the list consisting of loss of vision, eye pain, colour blindness, double vision and/or involuntary eye movements in a subject.

In some embodiments, the compositions of the invention prevent, reduce or alleviate dizziness, vertigo, neuropathic pain, musculoskeletal pain, cognitive dysfunction, bowel incontinence, dysphagia, dysarthria, or any combination thereof.

In some embodiments, the compositions of the invention prevent, reduce or alleviate depressive symptoms or anxiety comorbid with MS.

In some embodiments, the compositions of the invention the improvement of symptoms are determined using the 2017 McDonald criteria for diagnosing MS.

In certain embodiments, treatment with the compositions of the invention results in a reduction in MS incidence or MS severity. In certain embodiments, the compositions of the invention are for use in reducing relapse incidence or relapse severity. In certain embodiments, treatment with the compositions of the invention prevents a decline in motor function or results in improved motor function associated with MS. In certain embodiments, the compositions of the invention are for use in preventing a decline in motor function or for use in improving motor function in the treatment of MS. In certain embodiments, treatment with the compositions of the invention prevents the development of paralysis in MS. In certain embodiments, the compositions of the invention are for use in preventing paralysis in the treatment of MS.

In certain embodiments the compositions of the invention are for use in preventing multiple sclerosis in a patient that has been identified as at risk of multiple sclerosis, or that has been diagnosed with early-stage multiple sclerosis or "relapsing-remitting" multiple sclerosis. The compositions of the invention may be useful for preventing the development of MS. The compositions of the invention may be useful for preventing the progression of MS. In certain embodiments, the compositions of the invention are for use in a patient identified as having a genetic predisposition to MS, such as major histocompatibility complex (MHC) class II phenotype, human leukocyte antigen (HLA)-DR2 or HLA-DR4.

The compositions of the invention may be useful for managing or alleviating multiple sclerosis. The compositions of the invention may be particularly useful for reducing symptoms associated with multiple sclerosis. Treatment or prevention of multiple sclerosis may refer to, for example, an alleviation of the severity of symptoms or a reduction in the frequency of exacerbations or the range of triggers that are a problem for the patient. In certain embodiments, the compositions of the invention slow or stop progression of the disease.

In certain embodiments, the compositions of the invention are for use in treating relapsing-remitting MS. In alternative embodiments, the compositions of the invention are for use in treating progressive MS, such as secondary progressive MS (SPMS), which develops over time following diagnosis of RRMS, primary progressive MS (PPMS) which exhibits gradual continuous neurologic deterioration and progressive relapsing MS (PRMS), which is similar to PPMS but with overlapping relapses.

In certain embodiments, the compositions of the invention are for use in treating one or more of symptoms of MS selected from the group consisting of: fatigue, vision problems, numbness, tingling, muscle spasms, muscle stiffness, muscle weakness, mobility problems, pain, problems with thinking, learning and planning, depression and anxiety, sexual problems, bladder problems, bowel problems, speech and swallowing difficulties.

Neurochemical Factors, Neuropeptides and Neurotransmitters and the Microbiota-Gut-Brain Axis As outlined above, the microbiota-gut-brain axis is modulated by a number of different physiological systems. The microbiota-gut-brain axis is modulated by a number of signalling molecules. Alterations in the levels of these signalling molecules results in neurodegenerative diseases. The experiments performed by the inventors indicate that administration of *Megasphaera* commensal bacterial strains, and in particular *Megasphaera massiliensis*, can modulate levels of indole and kynurenine. Dysregulation of these metabolites can lead to neurodegenerative diseases, such as Parkinson's disease.

In certain embodiments, the compositions of the invention modulate the levels of brain monoamines and metabolites thereof. In preferred embodiments the metabolite is kynurenine. In certain embodiments, the compositions of the invention modulate kynurenine, which is the main route of tryptophan metabolism, which serves as a route to nicotinamide adenine dinucleotide (NAD+) production. Kynurenine can be metabolized to neuroactive compounds such as kynurenic acid (KYNA) and 3-hydroxy-1-kynurenine (3-OH-1-KYN), and in further steps to quinolinic acid (QUIN). Dysregulation of the kynurenine pathway can lead to activation of the immune system and the accumulation of potentially neurotoxic compounds. Alterations in the kynurenine metabolism may be involved in the development of Parkinson's diseases. Kynurenine levels have been demonstrated to be decreased in the frontal cortex, putamen and substantia nigra pars compacta of patients with PD (Parkinson's disease) [72]. Therefore, in certain embodiments the compositions of the invention are for use in increasing the levels of kynurenine in the treatment of Parkinson's disease.

In certain embodiments of the invention the compositions of the invention can increase the levels kynurenin. Increased levels of kynurenine have been shown to attenuate MPP+-induced neuronal cell death in vitro in a human dopaminergic neuroblastoma cell line [73]. In certain embodiments kynurenine and kynurenic acid, can activate GI aryl hydrocarbon receptor (Ahr) and GPR35 receptors. Activation of Ahr receptor induces IL-22 production, which can inhibit local inflammation. Activation of GPR35 inducing the production of inositol triphosphate and Ca2+ mobilization.

In certain embodiments, the compositions of the invention modulate the levels of indole. In preferred embodiments the metabolite is kynurenine. In certain embodiments, the compositions of the invention modulate kynurenine, which it the main route of tryptophan metabolism.

The signalling of the microbiota-gut-brain axis is modulated by levels of neurochemical factors, neuropeptides and neurotransmitters. Accordingly, in certain embodiments, the compositions of the invention modulates levels of neurochemical factors, neuropeptides and neurotransmitters. Accordingly, in certain preferred embodiments, the compositions of the invention directly alter CNS biochemistry.

The signalling of the microbiota-gut-brain axis is modulated by levels of γ-aminobutyric acid (GABA). Accordingly, in preferred embodiments, the compositions of the invention modulate the levels of GABA. GABA is an inhibitory neurotransmitter that reduces neuronal excitability. In certain embodiments, the compositions of the invention increase the levels of GABA. In certain embodiments, the compositions of the invention decrease the levels of GABA. In certain embodiments, the compositions of the invention alter GABAergic neurotransmission. In certain embodiments, the compositions of the invention modulate the level of GABA transcription in different regions of the central nervous system. In certain embodiments, the commensal derived GABA crosses the blood-brain barrier and affects neurotransmission directly. In certain embodiments, the compositions of the invention lead to a reduction of GABA in the hippocampus, amygdala and/or locus coeruleus. In certain embodiments, the compositions of the invention lead to an increase of GABA in cortical regions.

Immune Response

The signalling of the microbiota-gut-brain axis is modulated by alterations in the immune response and inflammatory factors and markers. Accordingly, in certain embodiments, the compositions of the invention may modulate the immune response. In certain embodiments, the compositions of the invention modulate the systemic levels of circulating neuroimmune signalling molecules. In certain preferred embodiments, the compositions of the invention modulate pro-inflammatory cytokine production and inflammation. In certain embodiments, the compositions of the invention modulate the inflammatory state. In certain embodiments, the compositions of the invention decrease IL-6 production and secretion. In certain embodiments, the compositions of the invention decrease the activation of the NFκB promoter. In certain embodiments, the compositions of the invention are able to modulate the activation of IL-6 production by the potent pro-inflammatory endotoxin lipopolysaccharide (LPS). In certain embodiments, the compositions of the invention are able to modulate the activation of the NFκB promoter by LPS and α-synuclein mutant proteins such as A53T. Increased circulating levels of cytokines are closely associated with various neurodegenerative disorders, including Parkinson's, dementia and Alzheimer's. In certain embodiments, the compositions of the invention are for use in reducing IL-6 levels and/or NFκB levels in the treatment of a neurodegenerative disorder. In some embodiments, the compositions of the invention increase the secretion of IL-8. IL-8 has been shown to induce myelin sheath formation and restore or preserve effective neuronal communication. Thus, in some embodiments, the compositions of the invention are for use in inducing myelin sheath formation in the treatment of neurodegenerative diseases. In some embodiments, the compositions of the invention are for use in restoring neuronal communication. In some embodiments, the compositions of the invention are for use in preserving neuronal communication.

The signalling of the microbiota-gut-brain axis is modulated by levels of commensal metabolites. Accordingly, in certain embodiments, the compositions of the invention modulate the systemic levels of microbiota metabolites. In certain preferred embodiments, the compositions of the invention modulate the level of short chain fatty acids (SCFAs). In certain embodiments the level of SCFAs is increased or decreased. In some embodiments, the level of SCFAs is increased. In some embodiments, the SCFA is butyric acid (BA) (or butyrate). In some embodiments, the SCFA is propionic acid (PPA). In some embodiments, the SCFA is acetic acid. In certain embodiments, the compositions of the invention modulate the ability of SCFAs to cross the blood-brain barrier.

Histone acetylation and deacetylation are important epigenetic regulators of gene expression. An imbalance in histone acetylation and deacetylation can result in apoptosis. Dysregulation of such histone acetyltransferases has been implicated in the pathogenesis associated with age-associated neurodegenerative diseases, such as Parkinson's disease, Huntington's disease, Alzheimer's disease, amyotrophic lateral sclerosis and cognitive decline [74]. Accordingly, in certain embodiments, the compositions of the invention can modulate histone deacetylase activity. In certain embodiments, the compositions of the invention can reduce histone deacetylase activity. In certain embodiments, the compositions of the invention can reduce histone acetylase activity. In certain embodiments, the compositions of the invention can reduce class 1 histone deacetylase activity.

Patients with neurodegenerative diseases, including Parkinson's disease, Huntington's disease, Alzheimer's disease and amyotrophic lateral sclerosis, exhibit high levels of lipid peroxidation. Lipid are vulnerable to oxidation by reactive oxygen species, and the brain is rich in polyunsaturated fatty acids. Accordingly, in certain embodiments, the compositions of the invention can modulate lipid peroxidation. In certain embodiments, the compositions of the invention can reduce lipid peroxidation. Reducing the oxidative damage caused by reactive oxygen species can be used to target early the stages neurodegenerative diseases. Accordingly, in certain embodiments, the compositions of the invention are for use in treating early stage neurodegeneration. Also accordingly, in certain embodiments, the compositions of the invention are for use in preventing the development of a neurodegenerative disorder. In such embodiments, the compositions of the invention may be for use in a patient that has been identified as at risk of developing a neurodegenerative disorder.

The signalling of the microbiota-gut-brain axis is modulated by levels of gastrointestinal permeability. Accordingly, in some embodiments, the compositions of the invention alter the integrity of the gastrointestinal tract epithelium. In certain embodiments, the compositions of the invention modulate the permeability of the gastrointestinal tract. In certain embodiments, the compositions of the invention modulate the barrier function and integrity of the gastrointestinal tract. In certain embodiments, the compositions of the invention modulate gastrointestinal tract motility. In certain embodiments, the compositions of the invention modulate the translocation of commensal metabolites and inflammatory signalling molecules into the bloodstream from the gastrointestinal tract lumen.

The signalling of the microbiota-gut-brain axis is modulated by microbiome composition in the gastrointestinal tract. Accordingly, in certain embodiments, the compositions of the invention modulates the microbiome composition of the gastrointestinal tract. In certain embodiments, the compositions of the invention prevents microbiome dysbiosis and associated increases in toxic metabolites (e.g. LPS). In certain embodiments, the compositions of the invention modulate the levels of Clostridium in the gastrointestinal tract. In preferred embodiments, the compositions of the invention reduce the level of Clostridium in the gastrointestinal tract. In certain embodiments, the compositions of the invention reduce the levels of Campylobacter jejuni. In certain embodiments, the compositions of the invention modulate the proliferation of harmful anaerobic bacteria and the production of neurotoxins produced by these bacteria. In certain embodiments, the compositions of the invention modulate the microbiome levels of Lactobacillus and/or Bifidobacterium. In certain embodiments, the compositions of the invention modulate the microbiome levels of Sutterella, Prevotella, Rumincoccus genera and/or the Alcaligenaceae family. In certain embodiments, the compositions of the invention increase the level of *Lactobacillus plantarum* and/or *Saccharomyces boulardii*.

Brain Injury

The examples demonstrate that the compositions of the invention are neuroprotective and have HDAC inhibitory activity. HDAC2 is a crucial target for functional recovery from stroke [75] and HDAC inhibition can prevent white matter injury [76], so the compositions of the invention may be useful in the treatment of brain injury.

In certain embodiments, the compositions of the invention are for use in treating brain injury. In some embodiments, the brain injury is a traumatic brain injury. In some embodiments, the brain injury is an acquired brain injury. In some embodiments, the compositions of the invention are for use in treating brain injury resulting from trauma. In some embodiments, the compositions of the invention are for use in treating brain injury resulting from a tumour. In some embodiments, the compositions of the invention are for use in treating brain injury resulting from a stroke. In some embodiments, the compositions of the invention are for use in treating brain injury resulting from a brain haemorrhage. In some embodiments, the compositions of the invention are for use in treating brain injury resulting from encephalitis. In some embodiments, the compositions of the invention are for use in treating brain injury resulting from cerebral hypoxia. In some embodiments, the compositions of the invention are for use in treating brain injury resulting from cerebral anoxia.

In preferred embodiments, the compositions of the invention are for use in treating stroke. The effects shown in the examples are particularly relevant to the treatment of stroke. Stroke occurs when blood flow to at least a part of the brain is interrupted. Without an adequate supply of blood to provide oxygen and nutrients to the brain tissue and to remove waste products from the brain tissue, brain cells rapidly begin to die. The symptoms of stroke are dependent on the region of the brain which is affected by the inadequate blood flow. Symptoms include paralysis, numbness or weakness of the muscles, loss of balance, dizziness, sudden severe headaches, speech impairment, loss of memory, loss of reasoning ability, sudden confusion, vision impairment, coma or even death. A stroke is also referred to as a brain attack or a cerebrovascular accident (CVA). The symptoms of stroke may be brief if adequate blood flow is restored within a short period of time. However, if inadequate blood flow continues for a significant period of time, the symptoms can be permanent.

In some embodiments, the stroke is cerebral ischemia. Cerebral ischemia results when there is insufficient blood flow to the tissues of the brain to meet metabolic demand. In some embodiments, the cerebral ischemia is focal cerebral ischemia, i.e. confined to a specific region of the brain. In some embodiments the cerebral ischemia is global cerebral ischemia, i.e. encompassing a wide area of the brain tissue. Focal cerebral ischemia commonly occurs when a cerebral vessel has become blocked, either partially or completely, reducing the flow of blood to a specific region of the brain. In some embodiments the focal cerebral ischemia is ischemic stroke. In some embodiments, the ischemic stroke is thrombotic, i.e. caused by a thrombus or blood clot, which develops in a cerebral vessel and restricts or blocks blood flow. In some embodiments the ischemic stroke is a thrombotic stroke. In some embodiments, the ischemic stroke is embolic, i.e. caused by an embolus, or an unattached mass that travels through the bloodstream and restricts or blocks blood flow at a site distant from its point of origin. In some embodiments the ischemic stroke is an embolic stroke. Global cerebral ischemia commonly occurs when blood flow to the brain as a whole is blocked or reduced. In some embodiments the global cerebral ischemia is caused by hypoperfusion, i.e. due to shock. In some embodiments the global cerebral ischemia is a result of a cardiac arrest.

In some embodiments the subject diagnosed with brain injury has suffered cerebral ischemia. In some embodiments, the subject diagnosed with brain injury has suffered focal cerebral ischemia. In some embodiments, the subject diagnosed with brain injury has suffered an ischemic stroke. In some embodiments, the subject diagnosed with brain injury has suffered a thrombotic stroke. In some embodiments, the subject diagnosed with brain injury has suffered an embolic stroke. In some embodiments, the subject diagnosed with brain injury has suffered global cerebral ischemia. In some embodiments, the subject diagnosed with brain injury has suffered hypoperfusion. In some embodiments, the subject diagnosed with brain injury has suffered a cardiac arrest.

In some embodiments, the compositions of the invention are for use in treating cerebral ischemia. In some embodiments, the compositions of the invention are for use in treating focal cerebral ischemia. In some embodiments, the compositions of the invention are for use treating ischemic stroke. In some embodiments, the compositions of the invention are for use in treating thrombotic stroke. In some embodiments, the compositions of the invention are for use in treating embolic stroke. In some embodiments, the compositions of the invention are for use in treating global cerebral ischemia. In some embodiments, the compositions of the invention are for use in treating hypoperfusion.

In some embodiments, the stroke is hemorrhagic stroke. Hemorrhagic stroke is caused by bleeding into or around the brain resulting in swelling, pressure and damage to the cells and tissues of the brain. Hemorrhagic stroke is commonly a result of a weakened blood vessel that ruptures and bleeds into the surrounding brain. In some embodiments, the hemorrhagic stroke is an intracerebral hemorrhage, i.e. caused by bleeding within the brain tissue itself. In some embodiments the intracerebral hemorrhage is caused by an intraparenchymal hemorrhage. In some embodiments the intracerebral hemorrhage is caused by an intraventricular hemorrhage. In some embodiments the hemorrhagic stroke is a subarachnoid hemorrhage i.e. bleeding that occurs outside of the brain tissue but still within the skull. In some embodiments, the hemorrhagic stroke is a result of cerebral amyloid angiopathy. In some embodiments, the hemorrhagic stroke is a result of a brain aneurysm. In some embodiments, the hemorrhagic stroke is a result of cerebral arteriovenous malformation (AVM).

In some embodiments the subject diagnosed with brain injury has suffered hemorrhagic stroke. In some embodiments, the subject diagnosed with brain injury has suffered an intracerebral hemorrhage. In some embodiments, the subject diagnosed with brain injury has suffered an intraparenchymal hemorrhage. In some embodiments, the subject diagnosed with brain injury has suffered an intraventricular hemorrhage. In some embodiments, the subject diagnosed with brain injury has suffered a subarachnoid hemorrhage. In some embodiments, the subject diagnosed with brain injury has suffered cerebral amyloid angiopathy. In some embodiments, the subject diagnosed with brain injury has suffered a brain aneurysm. In some embodiments, the subject diagnosed with brain injury has suffered cerebral AVM.

In some embodiments, the compositions of the invention are for use in treating hemorrhagic stroke. In some embodiments, the compositions of the invention are for use in treating an intracerebral hemorrhage. In some embodiments, the compositions of the invention are for use in treating an intraparenchymal hemorrhage. In some embodiments, the compositions of the invention are for use in treating an intraventricular hemorrhage. In some embodiments, the compositions of the invention are for use in treating a subarachnoid hemorrhage. In some embodiments, the compositions of the invention are for use in treating a cerebral amyloid angiopathy. In some embodiments, the compositions of the invention are for use in treating a brain aneurysm. In some embodiments, the compositions of the invention are for use in treating cerebral AVM.

Restoration of adequate blood flow to the brain after a period of interruption, though effective in alleviating the symptoms associated with stroke, can paradoxically result in further damage to the brain tissue. During the period of interruption, the affected tissue suffers from a lack of oxygen and nutrients, and the sudden restoration of blood flow can result in inflammation and oxidative damage through the induction of oxidative stress. This is known as reperfusion injury, and is well documented not only following stroke, but also following a heart attack or other tissue damage when blood supply returns to the tissue after a period of ischemia or lack of oxygen. In some embodiments the subject diagnosed with brain injury has suffered from reperfusion injury as a result of stroke. In some embodiments, the compositions of the invention are for use in treating reperfusion injury as a result of stroke.

A transient ischemic attack (TIA), often referred to as a mini-stroke, is a recognised warning sign for a more serious stroke. Subjects who have suffered one or more TIAs are therefore at greater risk of stroke. In some embodiments the subject diagnosed with brain injury has suffered a TIA. In some embodiments, the compositions of the invention are for use in treating a TIA. In some embodiments, the compositions of the invention are for use in treating brain injury in a subject who has suffered a TIA.

High blood pressure, high blood cholesterol, a familial history of stroke, heart disease, diabetes, brain aneurysms, arteriovenous malformations, sickle cell disease, vasculitis, bleeding disorders, use of nonsteroidal anti-inflammatory drugs (NSAIDs), smoking tobacco, drinking large amounts of alcohol, illegal drug use, obesity, lack of physical activity and an unhealthy diet are all considered to be risk factors for stroke. In particular, lowering blood pressure has been conclusively shown to prevent both ischemic and hemorrhagic strokes [77], [78]. In some embodiments, the compositions of the invention are for use in treating brain injury in a subject who has at least one risk factor for stroke. In some embodiments the subject has two risk factors for stroke. In some embodiments the subject has three risk factors for stroke. In some embodiments the subject has four risk factors for stroke. In some embodiments the subject has more than four risk factors for stroke. In some embodiments the subject has high blood pressure. In some embodiments the subject has high blood cholesterol. In some embodiments the subject has a familial history of stroke. In some embodiments the subject has heart disease. In some embodiments the subject has diabetes. In some embodiments the subject has a brain aneurysm. In some embodiments the subject has arteriovenous malformations. In some embodiments the subject has vasculitis. In some embodiments the subject has sickle cell disease. In some embodiments the subject has a bleeding disorder. In some embodiments the subject has a history of use of nonsteroidal anti-inflammatory drugs (NSAIDs). In some embodiments the subject smokes tobacco. In some embodiments the subject drinks large amounts of alcohol. In some embodiments the subject uses illegal drugs. In some embodiments the subject is obese. In some embodiments the subject is overweight. In some embodiments the subject has a lack of physical activity. In some embodiments the subject has an unhealthy diet.

The examples indicate that the compositions of the invention may be useful for treating brain injury and aiding recovery when administered before the injury event occurs. Therefore, the compositions of the invention may be particularly useful for treating brain injury when administered to subjects at risk of brain injury, such as stroke.

In certain embodiments, the compositions of the invention are for use in reducing the damage caused by a potential brain injury, preferably a stroke. The compositions may reduce the damage caused when they are administered before the potential brain injury occurs, in particular when administered to a patient identified as at risk of a brain injury.

The examples indicate that the compositions of the invention may be useful for treating brain injury and aiding recovery when administered after the injury event occurs. Therefore, the compositions of the invention may be particularly useful for treating brain injury when administered to subjects following a brain injury, such as stroke.

In some embodiments, the compositions of the invention treat brain injury by reducing motoric damage. In some embodiments, the compositions of the invention treat brain injury by improving motor function. In some embodiments, the compositions of the invention treat brain injury by improving muscle strength. In some embodiments, the compositions of the invention treat brain injury by improving memory. In some embodiments, the compositions of the invention treat brain injury by improving social recognition. In some embodiments, the compositions of the invention treat brain injury by improving neurological function.

Treatment of brain injury may refer to, for example, an alleviation of the severity of symptoms. Treatment of brain injury may also refer to reducing the neurological impairments following stroke. Compositions of the invention for use in treating stroke may be provided to the subject in advance of the onset of stroke, for example in a patient identified as being at risk of stroke. Compositions of the invention for use in treating stroke may be provided after a stroke has occurred, for example, during recovery. Compositions of the invention for use in treating stroke may be provided during the acute phase of recovery (i.e. up to one week after stroke). Compositions of the invention for use in treating stroke may be provided during the subacute phase of recovery (i.e. from one week up to three months after stroke). Compositions of the invention for use in treating stroke may be provided during the chronic phase of recovery (from three months after stroke).

In certain embodiments, the compositions of the invention are for use in combination with a secondary active agent. In certain embodiments, the compositions of the invention are for use in combination with aspirin or tissue plasminogen activator (tPA). Other secondary agents include other antiplatelets (such as clopidogrel), anticoagulants (such as heparins, warfarin, apixaban, dabigatran, edoxaban or rivaroxaban), antihypertensives (such as diuretics, ACE inhibitors, calcium channel blockers, beta-blockers or alpha-blockers) or statins. The compositions of the invention may improve the patient's response to the secondary active agent.

In certain embodiments, the compositions of the invention reduce the effect of ischemia on tissues. In certain embodiments, the compositions of the invention reduce the amount of damage to tissues caused by ischemia. In certain embodiments, the tissues damaged by ischemia are the cerebral tissues. In certain embodiments, the compositions of the invention reduce necrosis or the number of necrotic cells. In certain embodiments, the compositions of the invention reduce apoptosis or the number of apoptotic cells. In certain embodiments, the compositions of the invention reduce the number of necrotic and apoptotic cells. In certain embodiments, the compositions of the invention prevent cell death by necrosis and/or apoptosis. In certain embodiments, the compositions of the invention prevent cell death by necrosis and/or apoptosis caused by ischemia. In certain embodiments, the compositions of the invention improve the recovery of the tissue damaged by ischemia. In certain embodiments, the compositions of the invention improve the speed of clearance of necrotic cells and/or apoptotic cells. In certain embodiments, the compositions of the invention improve the efficacy of the clearance of necrotic cells and/or apoptotic cells. In certain embodiments, the compositions of the invention improve the replacement and/or regeneration of cells within tissues. In certain embodiments, the compositions of the invention improve the replacement and/or regeneration of cells within tissues damaged by ischemia. In certain embodiments, the compositions of the invention improve the overall histology of the tissue (for example upon a biopsy).

Modes of Administration

Preferably, the compositions of the invention are to be administered to the gastrointestinal tract in order to enable delivery to and/or partial or total colonisation of the intestine with the commensal bacterial strain of the invention. Generally, the compositions of the invention are administered orally, but they may be administered rectally, intranasally, or via buccal or sublingual routes. In some embodiments, a composition comprises the strain and the organic acid of the invention. In some embodiments, separate compositions of the organic acid and the commensal bacterial strain are provided.

In certain embodiments, the compositions comprising the commensal bacterial strain of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to prevent an inflammatory or autoimmune disease developing in her child in utero and/or after it is born.

The compositions of the invention may be administered to a patient that has been diagnosed with a neurodegenerative disease, or that has been identified as being at risk of a neurodegenerative disease. The compositions may also be administered as a prophylactic measure to prevent the development of neurodegenerative disease in a healthy patient.

The compositions of the invention may be administered to a patient that has been identified as having an abnormal gut microbiota. For example, the patient may have reduced or absent colonisation by *Megasphaera*, and in particular *Megasphaera massiliensis*.

The compositions comprising the bacteria of the invention may be administered as a food product, such as a nutritional supplement.

In some embodiments, a composition comprising a pharmaceutically acceptable salt or ester of the organic acid may be administered intravenously. In some embodiments, the organic acid is lyophilised and administered orally.

In some embodiments, the composition comprising the commensal bacterial strain and the composition comprising the organic acid are to be administered simultaneously, separately or sequentially. Each of the different compositions may be administered by any combination of the modes of administration described herein. Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises bacteria. In some embodiments, the composition further comprises an organic acid or a pharmaceutically acceptable salt or ester thereof. In preferred embodiments of the invention, the composition is formulated in freeze-dried form. For example, the composition of the invention may comprise granules or gelatin capsules, for example hard gelatin capsules, comprising a bacterial strain of the invention and/or an organic acid of the invention. In some embodiments, the organic acid of the invention and the bacteria of the invention and formulated as separate compositions. In some embodiments, each of the separate compositions are formulated in a freeze-dried form. General guidance on the formulation of the compositions of the invention can be found for example, in *Aulton's Pharmaceutics: The Design and Manufacture of Medicines*.

Preferably, the composition of the invention comprises lyophilised bacteria. Lyophilisation of bacteria is a well-established procedure and relevant guidance is available in, for example, references [79], [ ], [81].

Alternatively, the composition of the invention may comprise a live, active bacterial culture.

In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonising the intestine. For example, in some embodiments, the bacterial strain in the composition of the invention is viable and capable of partially or totally colonising the intestine.

In some embodiments, the composition comprises a mixture of live bacterial strains and bacterial strains that have been killed.

In preferred embodiments, the composition of the invention is encapsulated to enable delivery of the bacterial strain and/or the organic acid or a pharmaceutically acceptable salt or ester thereof to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [82] and [83].

The composition may be administered orally and may be in the form of a tablet, capsule or powder. Encapsulated products are preferred because *Megasphaera* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention and/or a therapeutically effective amount an organic acid or a pharmaceutically acceptable salt or ester thereof of the invention. A therapeutically effective amount of a bacterial strain and/or an organic acid of the invention is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU.

In certain embodiments, the composition contains the bacterial strain in an amount of from about $1 \times 10^6$ to about $1 \times 10^{11}$ CFU/g, respect to the weight of the composition; for example, from about $1 \times 10^8$ to about $1 \times 10^{10}$ CFU/g. The dose may be, for example, 1 g, 3 g, 5 g, and 10 g. Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

In some embodiments, the organic acid is provided as a lyophilised salt or ester thereof. The lyophilised organic acid product may be formulated in a single dosage form. The lyophilised organic acid may be formulated in a repeat dosage form. The lyophilised organic acid product may be formulated with the lyophilised bacteria in a single dosage form. Alternatively, the organic acid product may be formulated with the lyophilised bacteria in a repeat dosage form.

In some embodiments, the organic acid product may be formulated as a "slow release" or "fast release" composition. "Slow release" compositions result in lower initial increases in serum plasma concentrations of the organic acid product but have a more sustained effect, with elevated plasma levels of the organic acid remaining longer. By contrast, "fast release" compositions are formulated to provide a high initial dose of the organic acid product, resulting in higher initial plasma concentration but with a shorter duration effect.

In some embodiments, the organic acid is administered intravenously. For example, the organic acid may be sodium valproate and may be administered to a subject in a 60 min infusion at a rate of no more than 20 mg/min. A typical daily dose of the organic acid or a pharmaceutically acceptable salt or ester thereof will vary depending on the physical characteristics of the subject, the route of administration and/or the desired duration of the effect of the composition. In certain embodiments, the compositions of the invention are used in combination with another therapeutic compound for treating or preventing the neurodegenerative disorder.

In some embodiments, the compositions of the invention are administered with nutritional supplements that modulate neuroprotection or neuroproliferation. In preferred embodiments, the nutritional supplements comprise or consist of nutritional vitamins. In certain embodiments, the vitamins are vitamin B6, magnesium, dimethylglycine (vitamin B16) and vitamin C. In certain embodiments, the compositions of the invention are administered in combination with another probiotic.

In certain embodiments, the compositions of the invention are for use in enhancing the effect of a second agent on a neurodegenerative disease. The immune modulatory effects of the compositions of the invention may make the brain more susceptible to conventional therapies such as Levodopa, dopamine agonists, MAO-B inhibitors, COMT inhibitors, Glutamate antagonists, or anticholinergics, which are exemplary secondary agents to be administered in combination (sequentially or contemporaneously) with the compositions of the invention.

The compositions of the invention may comprise pharmaceutically acceptable excipients or carriers. Examples of such suitable excipients may be found in the reference [84]. Acceptable carriers or diluents for therapeutic use are well known in the pharmaceutical art and are described, for example, in reference [85]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In some embodiments, the compositions of the invention comprise one or more bacterial strains of the genus *Megasphaera* and do not contain bacteria from any other genera, or which comprise only de minimis or biologically irrelevant amounts of bacteria from another genera. Thus, in some embodiments, the invention provides a composition comprising one or more bacterial strains of the genus *Megasphaera*, which does not contain bacteria from any other genera or which comprises only de minimis or biologically irrelevant amounts of bacteria from another genera, for use in therapy.

In some embodiments, the compositions of the invention comprise one or more bacterial strains of the species *Megasphaera massiliensis* and do not contain bacteria from any other species, or which comprise only de minimis or biologically irrelevant amounts of bacteria from another species. Thus, in some embodiments, the invention provides a composition comprising one or more bacterial strains of the species *Megasphaera massiliensis*, which does not contain bacteria from any other species or which comprises only de minimis or biologically irrelevant amounts of bacteria from another species, for use in therapy.

In some embodiments, the compositions of the invention comprise one or more bacterial strains of the species *Megasphaera massiliensis* and do not contain bacteria from any other *Megasphaera* species, or which comprise only de minimis or biologically irrelevant amounts of bacteria from another *Megasphaera* species. Thus, in some embodiments, the invention provides a composition comprising one or more bacterial strains of the species *Megasphaera massiliensis*, which does not contain bacteria from any other *Megasphaera* species or which comprises only de minimis or biologically irrelevant amounts of bacteria from another *Megasphaera* species, for use in therapy.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism.

In some embodiments, the invention provides a composition comprising a single bacterial strain of the genus *Megasphaera*, which does not contain bacteria from any other strains or which comprises only de minimis or biologically irrelevant amounts of bacteria from another strain for use in therapy.

In some embodiments, the invention provides a composition comprising a single bacterial strain of the species *Megasphaera massiliensis*, which does not contain bacteria from any other strains or which comprises only de minimis or biologically irrelevant amounts of bacteria from another strain for use in therapy.

In some embodiments, the compositions of the invention comprise more than one bacterial strain. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. The invention comprises any combination of the foregoing.

In some embodiments, the composition comprises a microbial consortium. For example, in some embodiments, the composition comprises the *Megasphaera* commensal bacterial strain as part of a microbial consortium. For example, in some embodiments, the Megasphaera commensal bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a commensal bacterial strain of *Megasphaera* the invention in combination with a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as strain MRX0029, but which is not MRX0029, or which is not a *Megasphaera massiliensis*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human adult faeces. In some embodiments in which the composition of the invention comprises more than one bacterial strain, all of the bacterial strains are obtained from human adult faeces or if other bacterial strains are present they are present only in de minimis amounts. The bacteria may have been cultured subsequent to being obtained from the human adult faeces and being used in a composition of the invention.

As mentioned above, in some embodiments, the one or more *Megasphaera* commensal bacterial strains is/are the only therapeutically active agent(s) in a composition of the invention. In some embodiments, the bacterial strain(s) in the composition is/are the only therapeutically active agent(s) in a composition of the invention.

The compositions for use in accordance with the invention may or may not require marketing approval.

In certain embodiments, the invention provides the above pharmaceutical composition, wherein said bacterial strain is lyophilised. In certain embodiments, the invention provides the above pharmaceutical composition, wherein said bacterial strain is spray dried. In certain embodiments, the invention provides the above pharmaceutical composition, wherein the bacterial strain is lyophilised or spray dried and wherein it is live. In certain embodiments, the invention provides the above pharmaceutical composition, wherein the bacterial strain is lyophilised or spray dried and wherein it is viable. In certain embodiments, the invention provides the above pharmaceutical composition, wherein the bacterial strain is lyophilised or spray dried and wherein it is capable of partially or totally colonising the intestine. In certain embodiments, the invention provides the above pharmaceutical composition, wherein the bacterial strain is lyophilised or spray dried and wherein it is viable and capable of partially or totally colonising the intestine.

In some cases, the lyophilised bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a neurodegenerative disorder when administered to a subject in need thereof.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a neurodegenerative disorder.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4° C. or about 25° C. and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [86]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

Culturing Methods

The bacterial strains for use in the present invention can be cultured using standard microbiology techniques as detailed in, for example, references [87], [ ] and [89].

The solid or liquid medium used for culture may be YCFA agar or YCFA medium. YCFA medium may include (per 100 ml, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH$_4$)$_2$SO$_4$ (0.09 g), MgSO$_4$·7H$_2$O (0.009 g), CaCl$_2$ (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

Bacterial Strains for Use in Vaccine Compositions

The inventors have identified that the bacterial strains of the invention are useful for treating or preventing neurodegenerative disorders. This is likely to be a result of the effect that the bacterial strains of the invention have on the host immune system. Therefore, the compositions of the invention may also be useful for preventing neurodegenerative disorders, when administered as vaccine compositions. In certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [90] and [91, 97], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [98]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [99].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Efficacy of Bacterial Inocula to Act as a Neuroprotectant

Summary

Neuroblastoma cells were treated with compositions comprising bacterial strains according to the invention. The SH-SY5Y neuroblastoma cells used are dopamine producing and well-established as an in vitro model for studying neurodegenerative diseases. The ability of the bacterial strains to increase neuroproliferation was observed. The neuroblastoma cells were treated with dopaminergic neurotoxin 1-methyl-4-phenylpyridinium (MPP), which induces permanent symptoms of Parkinson's disease in neuroblastoma cells. The ability of the bacterial strains to act as a neuroprotectant against MPP was investigated.

Material and Methods

Bacterial Strains

*Megasphaera massiliensis* MRX0029; *Parabacteroides distasonis* MRX0005

Cell Line

SH-SY5Y neuroblastoma cells were purchased from ECCACC (Cat. no: 94030304) and were grown in MEM (Sigma Aldrich, cat n. M2279) supplemented with Nutrient Mixture F-12 Ham (Sigma Aldrich, cat n. N4888).

Method

Once grown the SH-SY5Y neuroblastoma cells were plated on 96-well plate at 11,000 cells/well and incubated for 2 days. The cells were then transferred to differentiation medium (which contains FBS at 1%) and 10 uM retinoic acid (Sigma Aldrich, cat. n. R2625-100MG). Differentiation medium was replaced every other day and cells were harvested at 7 day of differentiation. Cells were pre-treated with or without MPP (Sigma Aldrich, cat. n. D048-1G) for 8 hours. Subsequently, cells were treated with 10% bacterial supernatant and incubated overnight. Cell viability was measured by using CCK-8 reagent (Sigma Aldrich, Cell Counting Kit-8, cat. n. 96992-3000TESTS-F) and read at 450 nm wavelength.

Results

The results of these experiments are shown in FIG. 1. Treatment of neuroblastoma cells with MRX0029 or MRX0005 led to an increase in the proliferation of neurons. Neuroblastoma cells that were treated with MPP together with the bacterial strain had increased cell viability compared to the cells treated with MPP alone (which had decreased viability). The protective effect was greater for MRX0029-treated cells, which rescued viability more than the positive control cells treated with Quercetin. These data show that the bacterial strains can act as a neuroprotectant.

Example 2a—Efficacy of Bacterial Inocula to Reduce IL-6 Secretion

Summary

Activation of proinflammatory cytokines has been associated with neuron damage in neurodegenerative disease. Lipopolysaccharide (LPS) is a known stimulator of the proinflammatory cytokine IL-6. Human glioblastoma astrocytoma cells were treated with compositions comprising bacterial strains according to the invention in combination with LPS to observe their ability to modulate the levels of IL-6.

Material and Methods

Bacterial Strains

*Megasphaera massiliensis* MRX0029; *Parabacteroides distasonis* MRX0005

Cell Line

MG U373 is a human glioblastoma astrocytoma derived from a malignant tumour and were purchased from Sigma-Aldrich (cat n. 08061901-1VL). MG U373 human glioblastoma astrocytoma cells were grown in MEM (Sigma Aldrich, cat n. M-2279) supplemented with 10% FBS, 1% Pen Strep, 4 mM L-Glut, 1× MEM Non essential Amino Acid solution and 1× Sodium Piruvate.

Method

Once grown the MG U373 cells were plated on 24-well plate at 100,000 cells/well. The cells were treated with LPS (1 ug/mL) alone or with 10% of bacteria supernatant from MRX0029 or MRX0005 for 24 h. A control was also performed where the cells were incubated in untreated media. Afterwards the cell free supernatants were collected, centrifuged at 10,000 g for 3 min at 4° C. IL-6 was measured using the Human IL-6 ELISA Kit from Peprotech (cat n.#900-K16) according to manufacturer instructions.

Results

The results of these experiments are shown in FIG. 2. Treatment of neuroblastoma cells with LPS and the bacteria strains led to a decrease in the level of IL-6 secreted.

Example 2b—Efficacy of Bacterial Inocula to Modulate IL-8 Secretion

Summary

As neuro-inflammation plays a pivotal role in neurodegenerative diseases and IL-8 has been shown to have neuro-positive effects, the effect of compositions comprising bacterial strains of the invention and LPS on the activation of IL-8 were assessed. Human glioblastoma astrocytoma cells were treated with compositions comprising bacterial strains according to the invention in combination with LPS to observe their ability to modulate the levels of IL-8.

Material and Methods

Bacterial Strains

*Megasphaera massiliensis* MRX0029; *Parabacteroides distasonis* MRX0005

Cell Line

MG U373 is a human glioblastoma astrocytoma derived from a malignant tumour and were purchased from Sigma-Aldrich (cat n. 08061901-1VL). MG U373 human glioblastoma astrocytoma cells were grown in MEM (Sigma Aldrich, cat n. M-2279) supplemented with 10% FBS, 1% Pen Strep, 4 mM L-Glut, 1× MEM Non essential Amino Acid solution and 1× Sodium Piruvate.

Method

Once grown the MG U373 cells were plated on 24-well plate at 100,000 cells/well. The cells were treated with LPS (1 ug/mL) alone or with 10% of bacteria supernatant from MRX0029 for 24 h. Afterwards the cell free supernatants were collected, centrifuged at 10,000 g for 3 min at 4° C. IL-8 was measured using Human IL-8 ELISA Kit from Peprotech (cat n.#900-K18) according to manufacturer instruction.

Results

The results of these experiments are shown in FIG. 3. Treatment of neuroblastoma cells with the bacteria strains lead to an increase in IL-8 secretion independently of the presence of LPS.

Example 2C—Efficacy of Bacterial Inocula to Reduce α-Synuclein-Induced Inflammation Summary Neuroinflammation plays a pivotal role in Parkinson's disease and α-synuclein has been shown to induce neuroinflammation in vivo. Therefore, the ability of the bacteria strains of the invention to inhibit α-synuclein-induced neuroinflammation was assessed. A co-culture of human glioblastoma astrocytoma cells and neuroblastoma cells were exposed to wild-type α-synuclein and the mutant isoforms E46K and A53T and treated with compositions comprising bacterial strains according to the invention. The ability of the bacteria strains to inhibit α-synuclein-induced secretion of IL-6 was then tested.

Material and Methods

Bacterial Strains

*Megasphaera massiliensis* MRX0029; *Parabacteroides distasonis* MRX0005

Cell Line

MG U373 is a human glioblastoma astrocytoma derived from a malignant tumour and were purchased from Sigma-Aldrich (cat n. 08061901-1VL). MG U373 human glioblastoma astrocytoma cells were grown in MEM (Sigma Aldrich, cat n. M-2279) supplemented with 10% FBS, 1% Pen Strep, 4 mM L-Glut, 1× MEM Non essential Amino Acid solution and 1× Sodium Piruvate.

SH-SY5Y is a human neurobastoma cell line derived from a malignant neuroblastoma and can be purchased from Sigma-Aldrich (cat n. 94030304-1VL). The cells were grown in 50% MEM and 50% Nutrient Mixture F-12 Ham media supplemented with 2 mM L-Glutamine, 10% heat inactivated FBS, 100 U/ml penicillin, 100 μg/ml streptomycin. Cells on growth medium were plated on 96-well plate at 11,000 cells/well and placed in the incubator. After 2 days, media were replaced with differentiation medium (growth medium containing 1% FBS) and 10 μM retinoic acid. Differentiation medium was replaced every other day and cells were used after 7 days of differentiation.

Method

SHSY5Y cells were plated on 12 well plates at a density of 50,000 cells/well. The cells were grown in 50% MEM and 50% Nutrient Mixture F-12 Ham media supplemented with 2 mM L-Glutamine, 10% heat inactivated FBS, 100 U/ml penicillin, 100 μg/ml streptomycin. Cells on growth medium were plated on 96-well plate at 11,000 cells/well and placed in the incubator. After 2 days, media were replaced with differentiation medium (growth medium containing 1% FBS) and 10 μM retinoic acid. Differentiation medium was replaced every other day and cells were used after 7 days of differentiation. U373 were plated on 12 transwell plates (0.4 μm polyester membrane, Costar) at a density of 50,000 cells/well for 72 hrs. Cells were co-cultured together for 24 hrs before treatment in differentiation medium (growth medium containing 1% FBS without retinoic acid).

Thereafter cells were treated with 25 μg/ml α-synuclein (Wt, A53T, E46K) in the presence or absence of 10% bacteria supernatant for 48 hrs. Cell free Supernatants were collected, spun-down at 10000 g for 3 min at 4° C., aliquoted and stored at −80° C. Human IL-6 and IL-8 were measured as described above.

Results

The results of these experiments are shown in FIG. 4. Treatment of cells with wild-type α-synuclein and the mutant isoforms E46K and A53T induced moderate secretion of IL-6 (FIG. 4A). The α-syn-induced secretion of IL-6 was inhibited in cells treated with the bacteria strains (FIG. 4A). The reduction in IL-6 secretion was greatest on administration of MRX0029.

Example 3—Efficacy of Bacterial Inocula to Reduce NFκB Activation

Summary

Activation of the NFκB promoter leads to the production of proinflammatory cytokines including IL-1β, IL-1α, IL-18, TNFα and IL-6. The NFκB promoter can be activated by α-synuclein and LPS by stimulating the TLR4 ligand. Mutations in α-synuclein, such as α-synuclein A53T, are implicated in familial Parkinson's. Treatment of neuronal cells with LPS simulates Parkinson's caused by environmental factors. The ability of compositions comprising bacterial strains according to the invention to inhibit the activation of the NFκB promoter was investigated.
Material and Methods
Bacterial Strain
*Megasphaera massiliensis* MRX0029
Cell Line
Human Hek blue TLR4 were purchased from InvivoGen (cat n. hkb-htlr4). Human Hek blue TLR4 were grown in DMEM high glucose (Sigma Aldrich, cat n. D-6171) supplemented with 10% FBS, 1% Pen Strep, 4 mM L-Glut, Normocin and 1× HEK Blue selection solution.
Method
Once grown the Human Hek blue cells were plated in 96 well plates at 25,000 cells/well in 4 replicates. One set of cells were treated with α-synuclein A53T (1 ug/mL) alone or with 10% of bacteria supernatant from MRX0029 for 22 h. The second set of cells were treated with LPS (10 ng/mL, from Salmonella enterica serotype Typhimurium, Sigma Aldrich, cat n. L6143) alone or with 10% of bacteria supernatant from MR029 for 22 h. The cells were subsequently spun down and 20 ul of the supernatant was mixed with 200 ul of Quanti Blue reagent (InvivoGen, cat n. rep-qb2), incubated for 2 h and absorbance read at 655 nm.
Results
The results of these experiments are shown in FIGS. 5 and 6. FIG. 5 shows that the activation of the NFκB promoter by α-synuclein is not inhibited by MRX0029. FIG. 6 shows that the activation of the NFκB promoter by LPS is inhibited by MRX0029.

Example 4—Efficacy of Bacteria to Alter Neurite Outgrowth

Summary
Neurite outgrowth is an important process for the development of connections between neurons. The ability of bacterial strains and organic acids to induce neurite outgrowth was therefore tested by measuring transcriptional levels of microtubule associated protein MAP2, a specific neuronal differentiation marker.
Bacterial Strain
*Megasphaera massiliensis* MRX0029.
Method
SHSY5Y were plated in 10 cm petri dishes a density of $2 \times 10^6$ cells. After 24 h cells were treated in differentiation medium (growth medium containing 1% FBS without RA) with 10% bacteria supernatants or YCFA+, 10 uM RA, 200 uM hexanoic acid or 200 uM valproic acid, for 17 hrs. There after representative images were taken using phase contrast EVOS XL core microscope at 40×/0.65 magnification. Cells were collected, and total RNA was isolated according to RNeasy mini kit protocol (Qiagen). cDNAs were made using the high capacity cDNA reverse transcription kit (Applied Biosystems). Gene expression was measured using qPCR. GAPDH was used as internal control. Fold change was calculated according to the $2^{(-\Delta\Delta ct)}$ method.
Immunofluorescence and Confocal Microscopy
Cells were seeded onto 8 well chamber slides (Marienfeld Laboratory Glassware) at $5 \times 10^4$ cells/well overnight and were treated with 10% bacterial supernatant for 24 hrs. For differentiation, cells were treated with 10 nM Retinoic acid for 5 days before treating with bacterial supernatant. Cells were then fixed with 4% paraformaldehyde in PBS for 20 minutes at room temperature (RT). Fixed cells were washed with PBS, and permeabilized with 1% Triton X-100 in PBS for 10 minutes. After washing with PBS, the slides were incubated with blocking buffer (4% BSA/PBS) for 1 hr at RT before adding anti-MAP2 antibody (sc-74421, Santa Cruz Biotechnology Inc) diluted in 1% BSA/PBS for 12 hr at 4° C. They were then washed twice with PBS, followed by incubation with Alexa Flour 488 conjugated anti-mouse (Molecular Probes Inc) and Alexa Flour 594 conjugated Phalloidin (ab 176757, Abcam) for 1 hr at RT. After washing 3× with PBS, the slides were mounted with Vectorshield□ containing DAPI (Sigma, Aldrich). Slides were viewed using a Zeiss Axioscope microscope equipped with a 63×/1.2 W Korr objective and filter sets suitable for detection of the fluorochromes used. Manual exposure times for the digital acquisition of images immuno-labelled with MAP-2 were kept constant allowing comparison between different wells and treatments. Phalloidin (F-actin) and DAPI exposure times varied to suit the field of view. Randomised fields of view were acquired using a QImaging camera controlled by Image Pro Plus software. Images were saved as TIFs and opened in Adobe Photoshop CC 2015.1.2 and overlays of the MAP-2, DAPI and Phalloidion images overlaid and merged. Representative images were selected to illustrate the differences in abundance and location of the proteins examined
Results
The results are shown in FIG. 7. FIG. 7A shows representative microscopy images of undifferentiated SHSY-5Y cells incubated with each of the acids and bacteria supernatants. Treatment of cells with MRX0029 induced a neuron-like phenotype, showing similar features to cells treated with retinoic acid (which is used for terminal differentiation of neuroblastoma cells), where cell bodies are bigger and pyramidal-shaped, with neurites and processed branching out to network with neighbour cells. FIG. 7B shows that MRx0029 significantly upregulates MAP2 in undifferentiated neuroblastoma cells. Phalloidin (an actin cytoskeleton-binding agent) staining further proved a different arrangement of cytoskeletal structure in cells treated with MRx0029, further supporting the neuronal differentiation hypothesis for MRx0029 (FIG. 7B)

Example 5—Efficacy of Bacterial Inocula to Alter Antioxidant Capacity

Summary
The ability of compositions comprising bacterial strains according to the invention to alter the antioxidant capacity. The antioxidant capacity of the bacterial strain was established using the well-known ABTS (2,2'-azino-bis(3-ethyl-benzothiazoline-6-sulphonic acid)) assay.
Bacterial Strain
*Megasphaera massiliensis* MRX0029
Method
Bacterial cells ($10^6$ or greater) were collected and centrifuged. They were resuspended in assay buffer (using three times the pellet volume). The suspension was sonicated on ice for 5 minutes and then spun down at 12,000×g for 10 minutes. The supernatant was removed and measured using the ABTS assay kit produced by Sigma Aldrich (code CS0790), in accordance with manufacturer's instructions.
Results
The results of these experiments are shown in FIG. 8. FIG. 8 shows that the MRX0029 has an antioxidant capacity of approximately 2 mM compared to Trolox.

Example 6—Efficacy of Bacterial Inocula to Alter Lipid Peroxidation Levels

Summary

The ability of compositions comprising bacterial strains according to the invention to alter lipid peroxidation levels was investigated. The thiobarbituric reactive substances assay (TBARs) was used to measure the by-products of lipid peroxidation.

Material and Methods

Bacterial Strain

*Megasphaera massiliensis* MRX0029

Method

Bacterial cells ($10^6$ or greater) were collected and centrifuged, a wash step was performed with isotonic saline before the pellet was re-suspended in potassium chloride assay buffer. The suspension was sonicated on ice for 10 minutes and then spun down at 10,000×g for 10 minutes. The supernatant was removed and the level of lipid peroxidation evaluated using the thiobarbituric reactive substances assay.

Results

The results of the experiments are shown in FIG. 9. FIG. 9 shows that MRx0029 is able to inhibit lipid peroxidation by approximately 20%, which is a higher antioxidant capacity than the positive control, butylated hydroxytoluene (1% w/v).

Example 7a—Efficacy of Bacterial Inocula to Reduce Oxidative Levels in Cells Background The generation of reactive oxygen species contributes to the pathology of neurodegenerative diseases. The ability of bacterial strains to protect differentiated SHSY-5Y and U373 cells from reactive oxygen species (ROS) generated by treatment with Tert-Butyl Hydrogen Peroxide (TBHP) was investigated.

Material and Methods

Bacterial Strain

*Megasphaera massiliensis* MRX0029

Method

SHSY-5Y cells were plated in black flat bottom 96 well plate at density of 5000 cells/well and placed in the CO2 incubator. After 24 h, media were replaced with differentiation medium (growth medium containing 1% FBS) and 10 µM retinoic acid. Differentiation medium was replaced every other day. On Day 10 the differentiation medium was removed and cells were washed with pre-warmed PBS and stained with 10 uM DCFDA molecular probe for 20 mins in growth medium containing 1% FBS. Then cells were washed with pre-warmed PBS again and treated with 100 uM TBHP in the presence or absence of 10% bacteria supernatant for 2 h. Fluorescence intensity was measured using TECAN plate reader at Ex/Em 485/530 nm.

Results

The results of the experiments are shown in FIG. 10. FIG. 10b shows that MRX0029 is able to inhibit ROS production in differentiated SHSY-5Y neuroblastoma cells. MRX0029 did not have an effect on the generation of ROS in U373 astroglioblastoma cells (FIG. 10a). This shows that this aspect of the antioxidant effect is neuron-specific.

Example 7b—Neuroprotection

RA-differentiated SHSY-5Y cells were treated with MPP+, the active metabolite of MPTP, a chemical widely used to mimic in vitro and in vivo some of the features of PD pathology. Cell viability was measured as the rate of mitochondria respiration (FIG. 11). Both MRx0005 and MRx0029 showed significant effects and promote per se an increase of the mitochondria metabolic activity in SHSY-5Y cells. MRX0029 showed complete protection from MPP+, restoring cell viability nearly to the same level of untreated cells and higher than quercetin positive control. MRx0005 protection was about 20% compared to YCFA-MPP+ treated sample, about the same observed for the quercetin positive control (FIG. 11).

Example 8—Efficacy of Bacterial Inocula on Histone Deacetylase Activity

Summary

The ability of compositions comprising bacterial strains according to the invention to alter histone deacetylase activity was investigated. Dysregulation of histone deacetylase has been implicated in the pathogenesis associated with age-associated neurodegenerative diseases.

Material and Methods

Bacterial Strain

*Megasphaera massiliensis* MRX0029

Cell Line

The cell line HT-29 was used because histone deacetylase is present.

Method

Cell free supernatants of stationary phase bacterial cultures were isolated by centrifugation and filtering in a 0.22 uM filter. HT-29 cells were used 3 days' post confluence and stepped down in 1 mL DTS 24 hours prior to commencement of the experiment. The HT-29 cells were challenged with 10% cell free supernatant diluted in DTS and this was left to incubate for 48 hours. Nuclease proteins were then extracted using the Sigma Aldrich Nuclease extraction kit and samples were snap frozen prior to HDAC activity measurement. HDAC activity kit was assessed fluorometrically using the Sigma Aldrich (UK) kit.

Results

The results of the experiments are shown in FIG. 12. FIG. 12 shows that MRX0029 is able reduce the levels of histone deacetylase activity.

Example 8a—Further Analysis of the Mechanism of Histone Deacetylation Inhibition Introduction The gut microbiota, with its immense diversity and metabolic capacity, represents a huge metabolic reservoir for production of a vast variety of molecules with potential to influence HDAC activity. Few studies have assessed the HDAC inhibitory activity of microbially-derived metabolites other than butyrate, which has been shown to inhibit HDAC and is associated with improvement of motor function in Huntington's disease [100]. The inventors therefore sought to determine which metabolites are responsible for HDAC inhibition and further elucidate the mechanisms by which inhibition is achieved.

Material and Methods

Bacterial culture and cell-free supernatant collection Pure cultures of bacteria were grown anaerobically in YCFA broth until they reached their stationary growth phase. Cultures were centrifuged at 5,000×g for 5 minutes and the cell-free supernatant (CFS) was filtered using a 0.2 µM filter (Millipore, UK). 1 mL aliquots of the CFS were stored at −80° C. until use. Sodium butyrate, hexanoic and valeric acid were obtained from Sigma Aldrich (UK) and suspensions were prepared in YCFA broth.

SCFA and MCFA Quantification of Bacterial Supernatants

Short chain fatty acids (SCFAs) and medium chain fatty acids (MCFAs) from bacterial supernatants were analysed and quantified by MS Omics APS as follows. Samples were acidified using hydrochloride acid, and deuterium labelled internal standards where added. All samples were analyzed in a randomized order. Analysis was performed using a high polarity column (Zebron™ ZB-FFAP, GC Cap. Column 30 m×0.25 mm×0.25 µm) installed in a GC (7890B, Agilent) coupled with a quadropole detector (59977B, Agilent). The system was controlled by ChemStation (Agilent). Raw data was converted to netCDF format using Chemstation (Agilent), before the data was imported and processed in Matlab R2014b (Mathworks, Inc.) using the PARADISe software described in [101].

Specific HDAC Activity Analysis

Specific HDAC inhibition activity was analysed for HDAC1, 2, 3, 4, 5, 6, 9 using fluorogenic assay kits for each type of HDAC (BPS Bioscience, CA). Assays were conducted according to manufacturer's instructions and each sample were performed in replicates. Cell free supernatants were diluted 1 in 10 and exposed to specific HDAC proteins provided in the kit to maintain consistency between methods.

Results

Figure 13A:
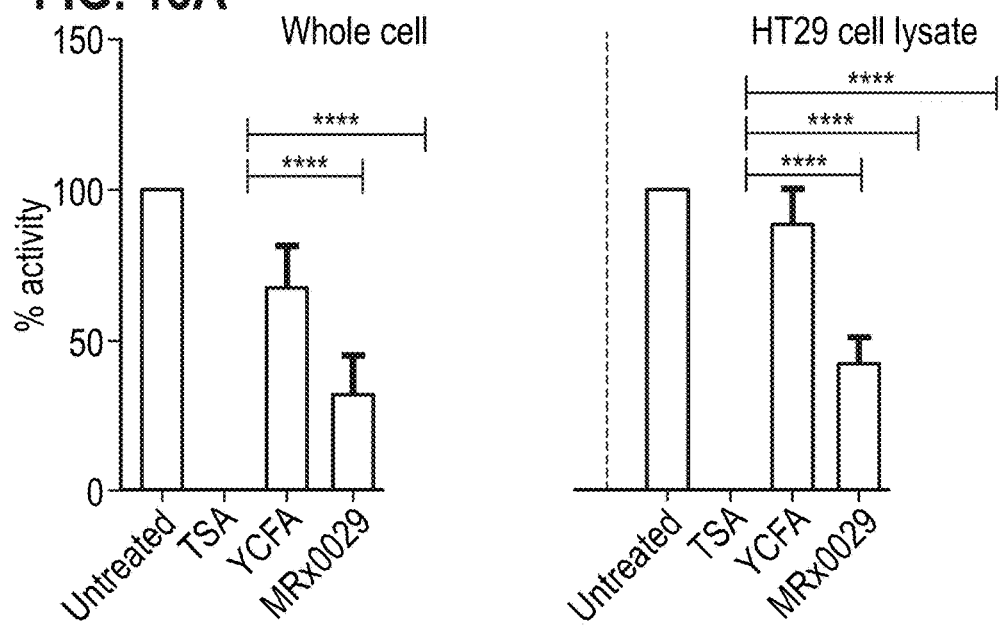
FIGS. 13A-13C: Strain-induced changes in whole cell and cell lysate histone deacetylase activity (FIG. 13A), acid-induced changes in histone deacetylase activity (FIG. 13B), metabolite production by strains (FIG. 13C)

Histone Deacetylase-Inhibiting Gut Commensal Microbial Metabolites are Butyrate and Valeric Acid MRx0029, whose supernatant showed strong HDAC inhibition in assays with either HT29 whole cell or HT29 cell lysate, produced valeric acid and hexanoic acid at mean concentrations of 5.08 mM and 1.60 mM, respectively (FIGS. 13A and C).

Figure 13B:
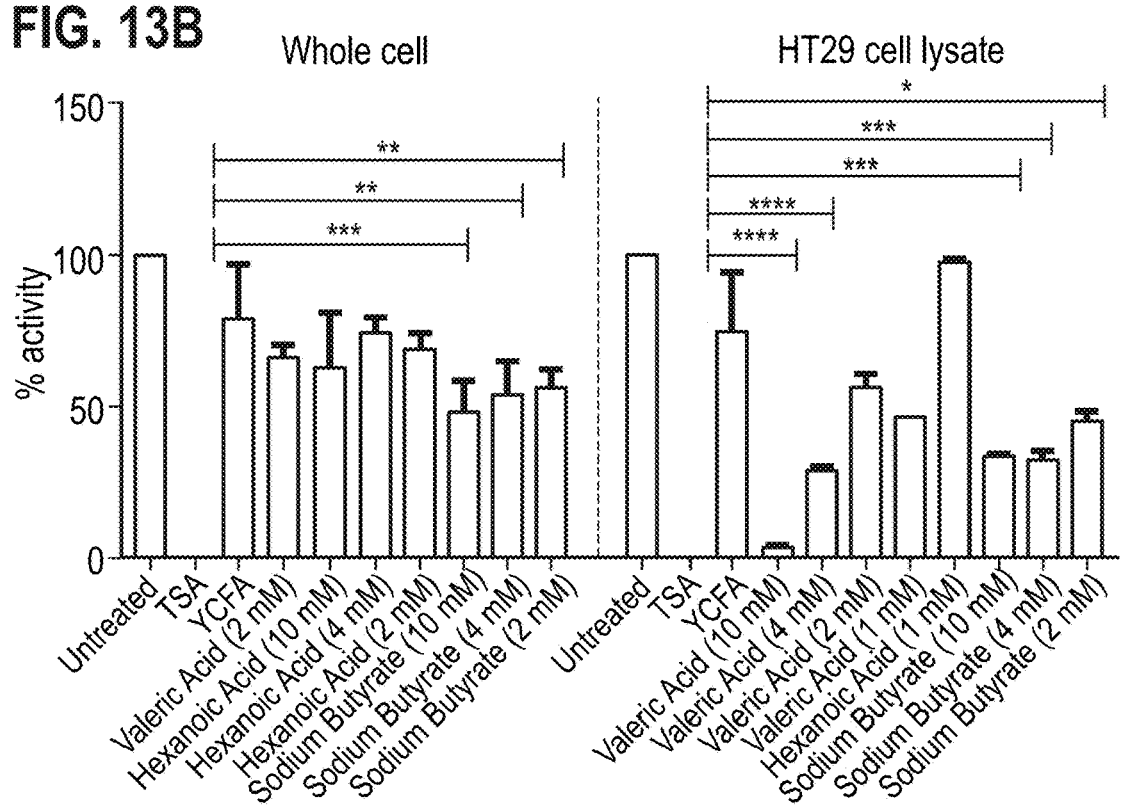

To investigate which metabolites were responsible for the strain-induced HDAC inhibition, different concentrations of hexanoic acid, valeric acid and sodium butyrate were measured for their HDAC inhibition on whole HT-29 cells and on HT-29 cell lysate. The results in FIG. 13B show significant ($P<0.05$) inhibition of HDAC activity by sodium butyrate on whole cells as well as on the cell lysate, while hexanoic acid did not show significant inhibitory activity. Valeric acid inhibited total HDAC activity (*($p<0.05$), ($p<0.005$), *($P<0.001$), ****($p<0.0001$)).

Potent Total HDAC Inhibitors Investigated Target Class I HDACs.

The specific HDAC inhibition profile of the test bacteria strain was investigated. Specific HDAC inhibition assays (BPS Bioscience, CA) were carried out for Class I and Class II HDACs. The ability of the bacterial strain to inhibit HDAC enzymes was compared to butyrate, hexanoic and valeric acid (FIGS. 14 and 15). Our results demonstrate that MRX0029, is a very potent inhibitor of Class 1 HDAC enzymes (HDAC1, 2 and 3). Inhibition of class II HDACs was not as significant (data not shown).

Discussion

Figure 13C:
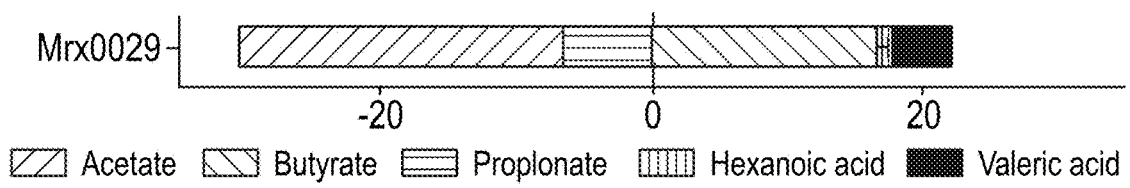
Figure 15A:
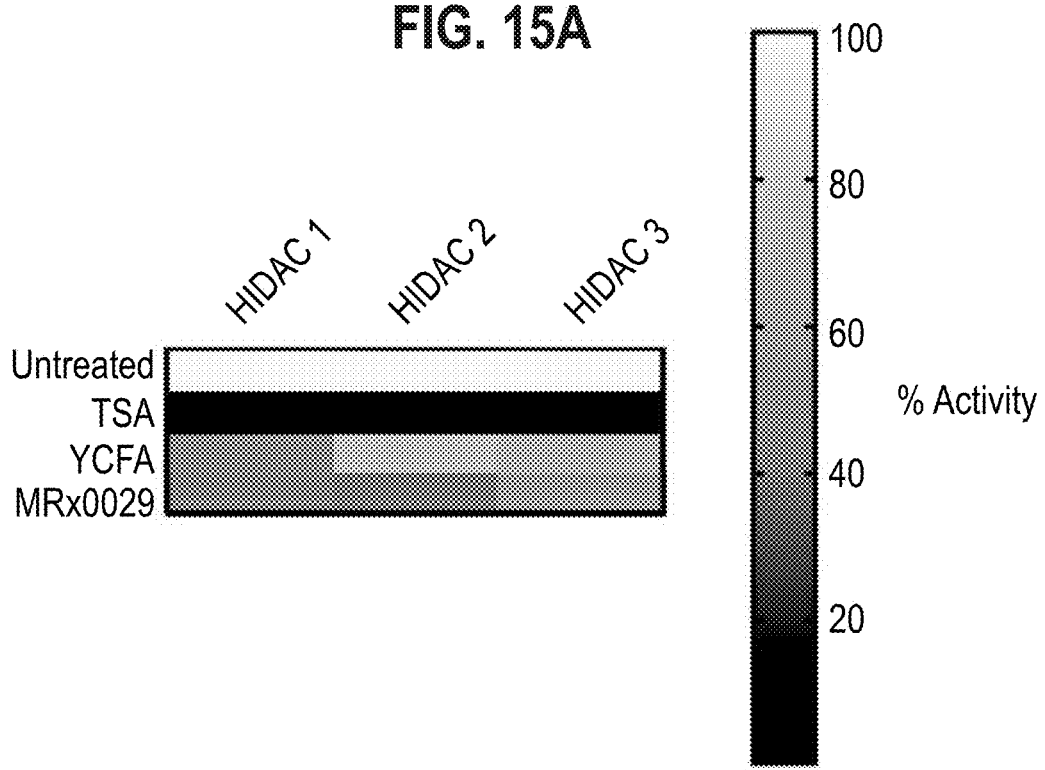
FIGS. 15A-15C: Inhibition of Class I HDACs (FIG. 15A); inhibition of HDAC1 (FIG. 15B); inhibition of HDAC2 (FIG. 15C); inhibition of HDAC3 (FIG. 15D)
Figure 15B:
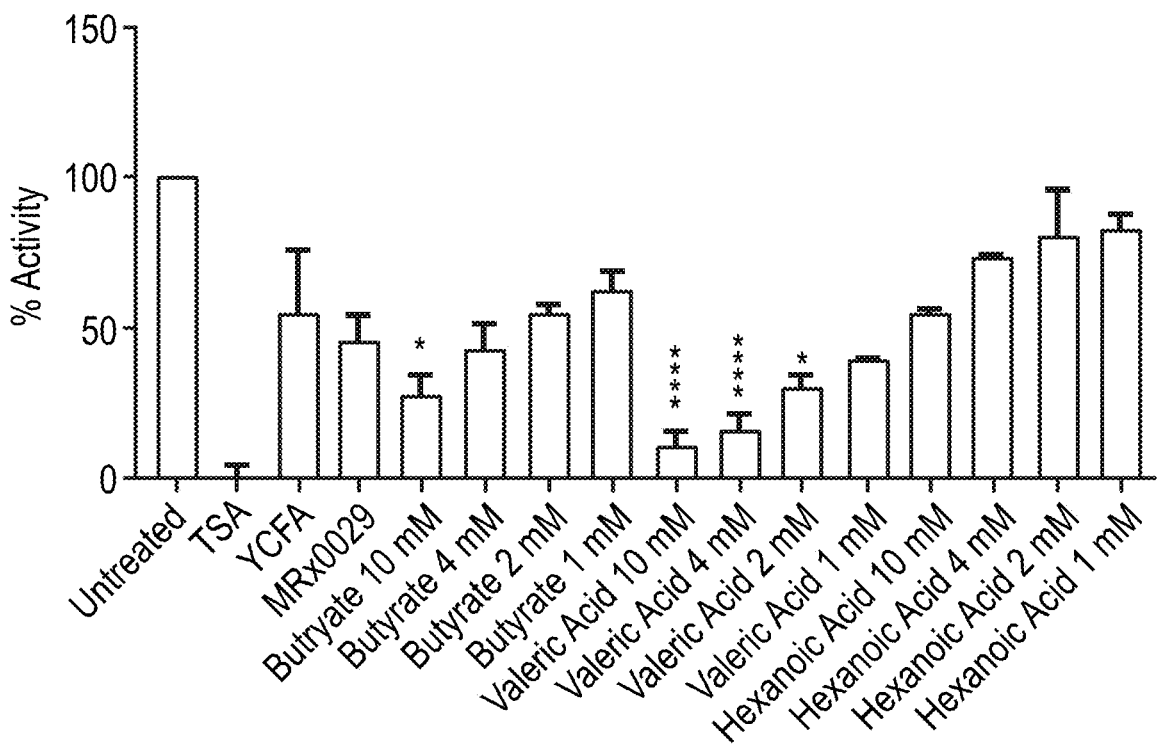
Figure 15C:
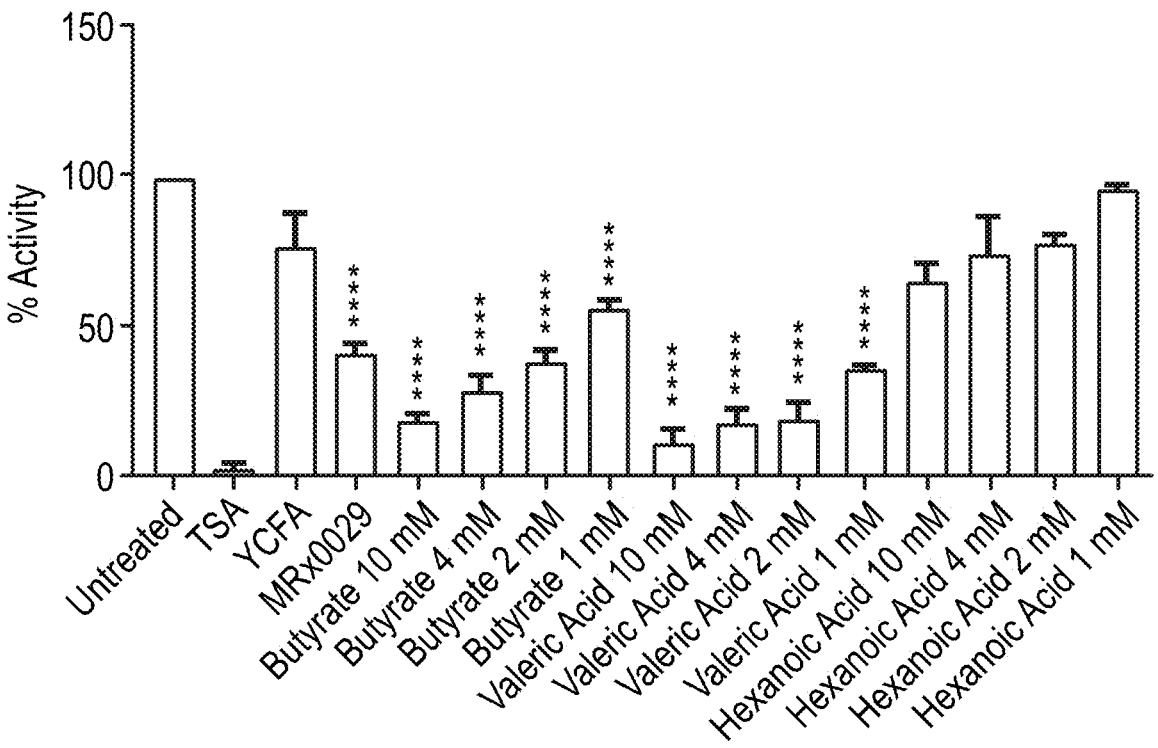
Figure 15D:
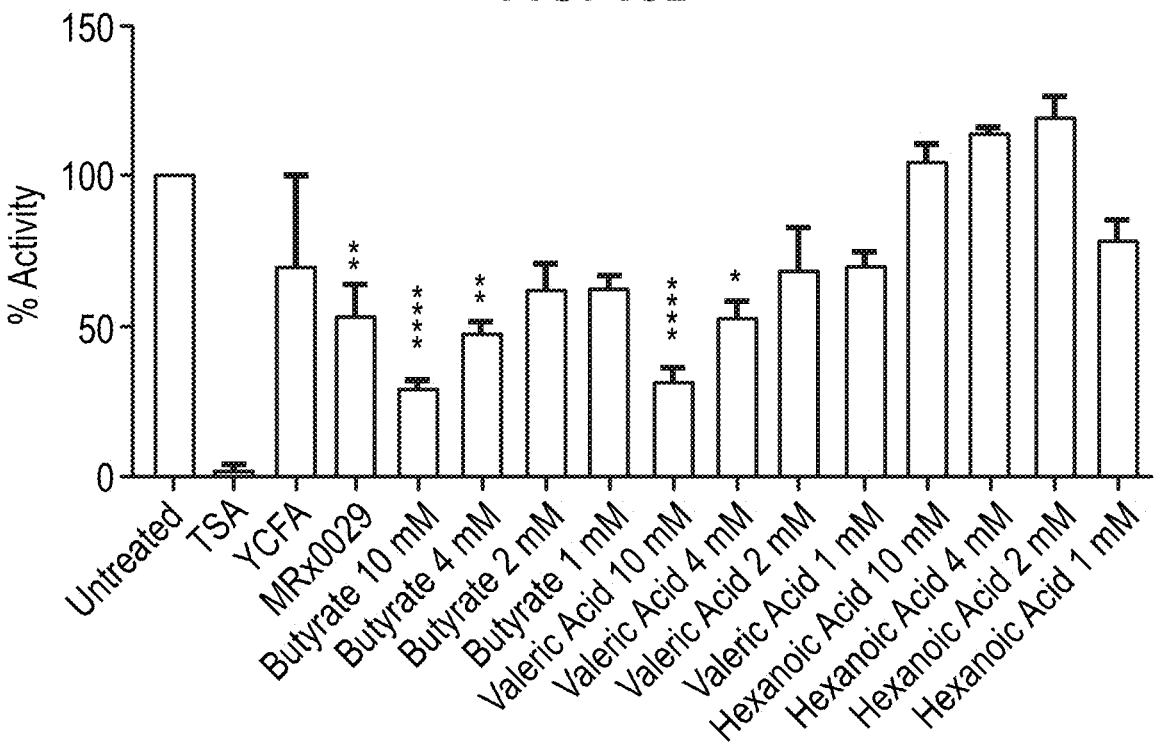

The strain with HDAC inhibitory activity produced significant amounts of valeric acid and hexanoic acid as well as significant amounts of sodium butyrate (FIG. 13C). When tested as pure substances, valeric acid and sodium butyrate resulted in significant HDAC inhibition ($p<0.0001$).

Interestingly, the results for specific HDAC activity show that the tested strain is a potent inhibitor of Class I HDACs, and particularly HDAC2. Class I HDACs (HDAC1, 2, 3 and 8) reside in the nucleus and are ubiquitously expressed in several human cell types. HDACs 1-3 share more than 50% homology, but have distinct structures and cellular functions [102]. They are primarily involved in cell survival, proliferation and differentiation, and thus there inhibition may be useful is wide array of diseases [103]; [104]; [105]; [106]; [107].

Example 9—Level of Indole Production in Bacteria

Summary

The ability of the bacteria of the invention to produce indole was investigated. Indole has been implicated in attenuating inflammation and oxidative stress.

Material and Methods

Bacterial Strain

*Megasphaera massiliensis* MRX0029

ATCC 11775 is a bacterial reference strain that is known to produce indole.

Method

Intact bacterial cells in stationary phase were incubated with 6 mM Tryptophan for 48 hours. Bacterial species which possess the enzyme tryptophanase will utilise tryptophan as a substrate to produce indole. Following the 48 hour incubation period, the supernatant was removed and added to Kovac's reagent for quantification of indole. Standards, stock solutions and reagents were prepared using standardised methods validated in-house.

Results

The results of the experiments are shown in FIG. 16. FIG. 16 shows that MRX0029 has the capacity to produce indole from tryptophan, at concentrations of approximately 0.2 mM.

Example 10—Level of Kynurenine Production in Bacteria

Summary

The ability of the bacteria of the invention to produce kynurenine was investigated. Dysregulation of the kynurenine pathway can lead to activation of the immune system and the accumulation of potentially neurotoxic compounds. Alterations in the kynurenine metabolism may be involved in the development of Parkinson's diseases.

Bacterial Strain

*Megasphaera massiliensis* MRX0029

DSM 17136 is a strain of *Bacteroides copricola* that is known to produce kynurenine.

Method

Cell free supernatants of stationary phase bacterial cultures were isolated by centrifugation and filtering in a 0.22 uM filter and frozen until use. Kynurenine standards, stock solutions and reagents were prepared using standardised methods validated in-house. Sample were treated with trichloroacetic acid and centrifuged at 10,000×g for 10 minutes at 4° C. The supernatant was collected and dispensed into a 96 well plate. Ehrlich's reagent was used for kynurenine detection and added at a ratio of 1:1.

Results

The results of the experiments are shown in FIG. 17. FIG. 17 shows that MRX0029 has the capacity to produce kynurenine at a concentration of approximately 40 µM.

Example 11—Levels of Dopamine, DOPAC and HVA in Striatum in Bacteria-Treated MPTP Mice Parkinson's disease is a common neurodegenerative disorder whose cardinal clinical features include tremor, slowness of movement, stiffness, and postural instability. These symptoms are primarily attributable to the degeneration of dopaminergic neurons in the substantia nigra pars compacta and the consequent loss of their projecting nerve fibers in the striatum [108]. Mice treated with MPTP (1-methyl-4-phenyl-1,2,3,6-tetrahydropyridine) selectively lose significant numbers of nigrostriatal dopaminergic neurons [109]. MPTP induced loss of dopaminergic cells in substantia nigra mimics the clinical condition in Parkinson's disease and is therefore a useful model to test anti-parkinsonian drugs.

The aim of this study was to evaluate the effects of MRX0029 anaerobic bacteria using MPTP lesioned mice. 48 male mice were allocated to 4 different treatment groups (groups A, B, E and I, with n=12 animals in each group). The treatment groups are shown in Table 1 below and the project time course is outlined below.

TABLE 1

Treatment groups

| Group | n | Substance | Safety level | Dose | Route | Schedule | Substance | Dose | Route | Schedule |
|---|---|---|---|---|---|---|---|---|---|---|
| | | Treatment | | | | | Lesion | | | |
| A | 12 | Vehicle (PBS) | — | — | p.o. | 18 days: day (−14)-day 3 | Vehicle (0.9% saline) | | i.p. | day0 |
| B | 12 | Vehicle (PBS) | — | — | p.o. | 18 days: day (−14)-day 3 | MPTP | 4 × 20 mg/kg | i.p. | day0 |
| E | 12 | MR × 0029 Megasphaera sp. (gly) | S1/S2 | 2 × 10^8 bacteria | p.o. | 18 days: day (−14)-day 3 | MPTP | 4 × 20 mg/kg | i.p. | day0 |
| 1 | 12 | Vehicle (PBS) | — | — | p.o. | 18 days: day (−14)-day 3 | MPTP | 4 × 20 mg/kg | i.p. | day0 |
| | | 7-nitroindazole | | 50 mg/kg | i.p. | day0 (2× i.p.) | | | | |

Groups A, B, E and I were treated daily for 18 days via oral gavage with either bacteria (MRx0029-group E), or vehicle (PBS). Oral treatment started 14 days before MPTP lesion. Group I animals received a daily vehicle (PBS) p.o. (per oral) treatment and were injected i.p. (intraperitoneal) with the reference drug 30 min before and 90 min after first MPTP on day 0. The application volume for p.o. and vehicle treatment was 200 µl per mouse. Bacteria strain of group E was from glycerol stocks (gly). For oral treatment, gavages for applications were stored in vial containing 70% Ethanol and were flushed before and after each use with distilled water. Every treatment group had its own gavage and ethanol vial and distilled water vial. The tubes and gavages were not changed between the groups. Directly before treatment each syringe was flushed with N2.

On day 0 MPTP (20 mg/kg bodyweight (b.w.) 4 times, 2 h inter-treatment interval) was injected i.p. in animals of groups B, E and I. One group of animals (A) was sham lesioned by i.p. administration of the MPTP vehicle (0.9% saline). The application volume was 10 µl per g body weight. Weighing of the animals was performed before the MPTP treatment to dose the animals according to their actual body weight. Afterwards animals received the daily p.o. treatment.

Formulation of Preparations for Dosing and Preparation of Glycerol Stocks for Dosing

| | |
|---|---|
| Name of the Bacteria strain: | MRx0029 Megasphaera sp. |
| Storage condition/stability: | −80° C. |
| Vehicle: | 1x PBS |
| Treatment dosages: | 2 × 10^8 bacteria |
| Administration: | 200 µl |
| Lot Number: | n/a |

For Treatment Group E (MRx0029)

1.) 1 glycerol stock was taken from the −80° C. freezer and placed under anaerobic conditions (anaerobic jar with sachet) at 37° C. in order to thaw (this took 30-40 mins).

2.) The completely thawed glycerol stock was centrifuged at 6000×g for 10 min at room temperature.

3.) The supernatant was discarded without disturbing the pellet (e.g. using a pipette).

4.) 4.22 mL of sterile pre-warmed (37° C.) 1×PBS was added and gently mixed using a pipette.

5.) The mice were dosed with 200 µL of the bacterial solution. The animals were dosed within 15 mins after resuspension of the pellet with PBS.

Reference Drug Group Formulation

| | |
|---|---|
| Storage condition/stability: | −20° C. |
| Vehicle: | Peanut oil |
| Treatment dosages: | 50 mg/kg |
| Administration: | i.p. (30 min before and 90 min after 1st MPTP treatment) |
| Batch Number: | MKB56671V |

The appropriate amount of 7-Nitroindazole was dissolved in peanut oil to reach the final concentration of 50 mg/kg.

Materials and Methods

Animals

| | |
|---|---|
| Mouse line: | C57BL/6J (JAX ™ Mice Strain) JAX ™ Mice Stock Number 000664 |
| Provider: | Charles River Laboratories |
| Age at start: | ~10 weeks |
| Sex: | Male |
| Number of animals: | 48 |

Specific Handling of Animals and Randomization

Gloves were changed between each treatment group and sprayed with 70% ethanol solution between each cage of the same group to minimize the risk of contamination whenever animals were handled (e.g.: treatment, behavioural testing, cleaning and tissue sampling).

The treatment was at random and alternated daily so as to prevent the same groups being treated at the same time each day. Animals were randomized per cage at the tissue sampling.

Tissue Sampling and Processing

On day 4 animals of all groups were sacrificed and brains were collected. Therefore, mice were deeply anesthetized by Pentobarbital injection (600 mg/kg).

Blood (approximately 500 µl) was collected by heart puncture. Mice were then transcardially perfused with 0.9% saline and brains were removed and hemisected. The left hemisphere was subdivided into striatal tissue (for HPLC), substantia nigra tissue as well as residual brain, weighed and immediately frozen and stored at −80° C. Instruments and surfaces which were in contact with the animals had to be cleaned with 70% ethanol before the next animal was dissected.

Biochemical Analysis of Dopamine, DOPAC and HVA Levels with HPLC in Striatum

The striatal samples (n=6 from each treatment group; total 24 samples) were mixed at a ratio of 1:10 (w/v) with 0.2 M perchloric acid including 100 M EDTA-2Na and homogenized at 0° C. in a glass-pestlemicro-homogenizer. Following standing for 30 min on ice, the homogenates were centrifuged at 10,000 RPM for 10 minutes in a refrigerated centrifuge Biofuge Fresco (Heraeus Instruments, Germany). The supernatants were carefully aspirated and mixed with 0.4 M Na-acetate buffer, pH 3 at a ratio 1:2 (v/v) and filtered through a 0.22 m centrifugal filter (Merck Millipore, Germany) for 4 min at 14 000 g at 4° C. The filtrates were stored at −80° C. before HPLC analysis.

HPLC Analysis

Concentrations of DA, DOPAC and HVA in the striatal samples were determined by column liquid chromatography with electrochemical detection [110; 111]. The HPLC system (HTEC-500, Eicom Corp., Kyoto, Japan) including a pulse-free microflow pump, a degasser and an amperometric detector equipped with a glassy-carbon electrode operating at +0.45 V vs. an Ag/AgCl ref electrode was used. Samples were injected by use of a CMA/200 Refrigerated Microsampler (CMA/Microdialysis, Stockholm, Sweden). The chromatograms were recorded and integrated by use of a computerized data acquisition system (DataApex, Prague, Czech Republic). DA, DOPAC and HVA were separated on a 150×2.1 i.d. mm column (CA5-ODS, Eicom Corp., Kyoto, Japan). The mobile phase consisted of 0.1 M phosphate buffer at pH 6.0, 0.13 mM EDTA, 2.3 mM sodium-1-octanesulfonate and 20% (v/v) methanol. The detection limit (signal-to-noise ratio=3) for DA was estimated to 0.5 fmol in 15 µl (0.03 nM) injected onto the column.

Results

Administration of bacteria strains was well tolerated by the animals. On the MPTP lesion day and if necessary on the day afterwards a red light was used to warm the animals. If animals were in bad conditions (felt cold, dehydrated, abnormal behaviour), they were supplied with wet food and subcutaneous saline treatment if necessary.

For analysis of Dopamine, DOPAC and HVA levels, striatal tissue of 6 animals per treatment group were used. Data were analyzed by using Kruskal-Wallis test followed by Dunn's multiple comparison post hoc test or One-way analysis of variance followed by Bonferroni post hoc test (A vs. all(*), B vs. all, I vs. all (#)). */#=p<0.05; =p<0.01; *=p<0.001.

The healthy animals in group A had high levels of Dopamine, DOPAC and HVA whereas MPTP treatment in group B reduced this and the positive control (group I) recovered the production to some degree (FIG. 21). Animals of group I tended to have higher Dopamine levels than the bacteria treated group and group B (FIG. 21A). DOPAC (a Dopamine metabolite) levels in general were significantly lower in animals of group B compared to DOPAC levels of unlesioned animals of group A (FIG. 21B).

Significantly, treatment with MRx0029 (group E) was found to recover production of Dopamine and DOPAC (FIGS. 21A and 21B, respectively). Treatment with MRx0029 may therefore be useful for treating or preventing neurodegenerative disorders.

Example 12—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 13—Level of BDNF Secretion in SHSY-5Y Cells

Background

Brain-derived neurotrophic factor (BDNF) is a ubiquitous molecule in the brain associated with neural development, neuro-protection and neuro-regeneration. BDNF not only protects against neurodegeneration but also mental disorders like depression and anxiety, which are quite common amongst patients diagnosed with PD or AD.

Methods

SH-SY5-SY were plated in 24 wells plate at density of 60,000 cells/well and placed in the incubator. After 24 h, media were replaced with differentiation medium (growth medium containing 1% FBS) and 10 µM retinoic acid. Differentiation medium was replaced every other day and cells were used on day 10 of differentiation. For the treatment differentiation medium was removed and replaced with 450 ul of full growth media and 50 µl of bacteria SN was added to the treated wells or YCFA+ was added as negative Control.

Results

The results are shown in FIG. 18, which shows that administration of MRX0029 in combination with retinoic acid increases the secretion of BDNF from differentiated neuroblasoma cells. Compositions comprising commensal bacteria and organic acids may therefore be useful in therapy.

Example 14—Metabolite Production—Metabolites in the Brain

Background

Metabolites present in bacteria supernatants can directly influence the host response to oxidative stress, cell-to-cell communication and neuroprotection. Metabolites that play a key role in neurological processes were measured during the ex vivo screening in brain tissue of mice fed with MRx0005 and MRx0029.

Methods
Animals

BALBc (Envigo, UK) adult male mice were group housed under a 12 h light-dark cycle; standard rodent chow and water were available ad libitum. All experiments were performed in accordance with European guidelines following approval by University College Cork Animal Ethics Experimentation Committee. Animals were 8 weeks old at the start of the experiment.

Study Design

Animals were allowed to habituate to their holding room for one week after arrival into the animal unit. They receive oral gavage (200 µL dose) of live biotherapeutics at a dose of $1\times10^9$ CFU for 6 consecutive days between 15:00 and 17:00. On day 7, the animals are decapitated, and tissues are harvested for experimentation.

Tissue Collection

Animals were sacrificed in a random fashion regarding treatment and testing condition; sampling occurred between 9.00 a.m. and 1:00 p.m. Trunk blood was collected in potassium EDTA (Ethylene Diamine Tetra Acetic Acid) tubes and spun for 15 min at 4000 g. Plasma was isolated and stored at −80° C. for further analysis. The brain was quickly excised, dissected and each brain region was snap-frozen on dry ice and stored at −80° C. for further analysis. Spleen was removed and processed immediately after culls for ex-vivo immune stimulation. Intestinal tissue (2 cm segments of ileum and colon closest to the caecum were excised, and the furthest 1 cm of tissue from the caecum were used) were mounted into the Ussing chambers for intestinal permeability assay. The caecum was removed, weighted and stored at −80° C. for SCFAs analysis.

Monoamine Analysis

Neurotransmitter concentration was analysed by HPLC on samples from the brainstem. Briefly, brainstem tissue was sonicated in 500 µl of chilled mobile phase spiked with 4 ng/40 µl of N-Methyl 5-HT (Sigma Chemical Co., UK) as internal standard. The mobile phase contained 0.1 M citric acid, 5.6 mM octane-1-sulphonic acid (Sigma), 0.1 M sodium dihydrogen phosphate, 0.01 mM EDTA (Alkem/Reagecon, Cork) and 9% (v/v) methanol (Alkem/Reagecon) and was adjusted to pH 2.8 using 4 N sodium hydroxide (Alkem/Reagecon). Homogenates were then centrifuged for 15 min at 22,000×g at 4° C. and 40 µl of the supernatant injected onto the HPLC system which consisted of a SCL 10-Avp system controller, LECD 6A electrochemical detector (Shimadzu), a LC-10AS pump, a CTO-10A oven, a SIL-10A autoinjector (with sample cooler maintained at 40 C) and an online Gastorr Degasser (ISS, UK). A reverse-phase column (Kinetex 2.6 u C18 100×4.6 mm, Phenomenex) maintained at 30° C. was employed in the separation (Flow rate 0.9 ml/min). The glassy carbon working electrode combined with an Ag/AgCl reference electrode (Shimdazu) operated a +0.8 V and the chromatograms generated were analyzed using Class-VP 5 software (Shimadzu). The neurotransmitters were identified by their characteristic retention times as determined by standard injections, which run at regular intervals during the sample analysis. The ratios of peak heights of analyte versus internal standard were measured and compared with standard injection. Results were expressed as ng of neurotransmitter per g fresh weight of tissue.

Metabolite Analysis

For GC-metabolite analysis, samples of bacterial supernatants were derivatized with methyl chloroformate using a slightly modified version of the protocol described in [112]. All samples were analyzed in a randomized order. Analysis was performed using GC (7890B, Agilent) coupled with a quadropole detector (59977B, Agilent). The system was controlled by ChemStation (Agilent). Raw data was converted to netCDF format using Chemstation (Agilent), before the data was imported and processed in Matlab R2014b (Mathworks, Inc.) using the PARADISe software described in [101].

For fatty acid analysis samples were acidified using hydrochloride acid, and deuterium labelled internal standards where added. All samples were analyzed in a randomized order. Analysis was performed using a high polarity column (Zebron™ ZB-FFAP, GC Cap. Column 30 m×0.25 mm×0.25 µm) installed in a GC (7890B, Agilent) coupled with a quadropole detector (59977B, Agilent). The system was controlled by ChemStation (Agilent). Raw data was converted to netCDF format using Chemstation (Agilent), before the data was imported and processed in Matlab R2014b (Mathworks, Inc.) using the PARADISe software described by [101].

Results—Neurotransmitter Production

The results are shown in FIG. 19, which shows that in brains of mice fed with MRx0029, noradrenaline levels are increased (p=0.0507), accompanied with a slight increase of serotonin and 5-HIAA. These data support the metabolite analysis set out below, suggesting that MRx00029 is a major producer of 4-hydroxyphenylacetic acid, a known antioxidant [113]. More importantly, 4-hydroxyphenylacetic acid is a synthetic intermediate of dopamine and norepinephrine and an important bio-active molecule [114]. In fact, in PD, degenerative changes extend beyond the dopaminergic system, affecting equally the serotonergic and noradrenergic systems, which in turn leads to decreased levels of serotonin (5-hydroxytryptamine, 5-HT) and noradrenaline (norepinephrine) in both striatal and extra-striatal structures [115]. L-DOPA targets mainly the dopamine-related features of PD, however it does not address the decreases in both 5-HT and noradrenaline. Adding to this is that the longer is the duration of L-DOPA treatment, the more visible are a range of motor and nonmotor complications (e.g. dyskinesia, psychiatric symptoms) [116]. Therefore, these data demonstrate that bacteria that produce organic acids, such as 4-hydroxyphenylacetic acid, may be useful in therapy, in particular in the treatment of neurodegenerative diseases.

Results—Metabolite Production

Metabolites present in bacteria supernatants can directly influence the host response to oxidative stress, cell-to-cell communication and neuroprotection in the specific. Metabolites in the supernatant of cultures of MRX0029 and MRX0005 were analysed and the results are shown in FIG. 20.

A few metabolites showed a striking difference between the two strains analysed. The concentration of succinic acid was particularly elevated in MRx0005. Interestingly, the ratio sample/media for 4-hydroxyphenylacetic acid was significantly higher in MRx0029 (FIG. 20A).

Fatty acid analysis in the supernatants revealed an interesting dichotomy in the two strains: MRx0005 produced mainly acetic and propanoic acid, while MRx0029 produced butanoic, pentanoic and hexanoic acid, both in the linear and branched forms (FIG. 20B). The two strains looked very different and in particular, the production of succinic acid and 4-hydroxyphenylacetic acid by MRx0005 and MRx0029 respectively was notable (FIG. 20A). Furthermore, MRx0005 seems to produce more C2 and C3 short chain fatty acids, while MRx00029 produced more C4 (butyrate) and both linear and branched medium chain fatty acids, including hexanoic acid.

Succinic acid is a Krebs cycle metabolite involved in oxidative phosphorylation. Oxidative phosphorylation complex is a key step for synaptic trafficking of proteins and vesicles to proximal and distal regions [117]. Its dysfunction has been reported in neurodegenerative disorders including Alzheimer's disease, Parkinson's disease and Spinocerebellar ataxia type 1 [63]. These findings are particularly interesting as succinic acid can augment mitochondrial activity and support vulnerable neurons in neurodegenerative disease related to misfolded proteins including PD [65]. BDNF and succinic acid have both a similar protective activity not only in neuro-degeneration but also in mental disorders like depression and anxiety, which are quite common amongst patients diagnosed with PD or AD.

FIG. 20B also demonstrates that MRX0029 is a butyrate (butanoic acid) producer. This may be significant because butyrate has a known role is reducing impermeability of the blood brain barrier, which has a neuroprotective effect [118]. This property of MRx0029 (and other neuroprotective bacteria) may contribute to its effacy.

Example 15—Modulation of the mRNA Expression of Tight Junction Proteins by MRx0029

Figure 22A:
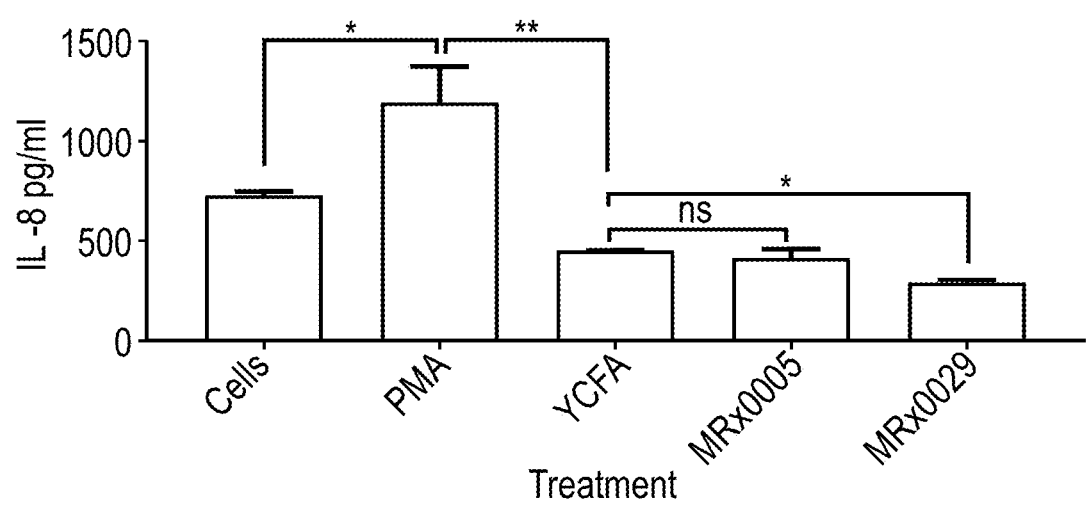

Since recent evidence suggests that intestinal dysfunction and inflammation is a non-motor symptom associated with PD, the ability of the bacterial strains of the invention to cause any intestinal barrier dysfunction was investigated. HT29-mtx epithelial, mucin-producing cell monolayers [119] were used as an in vitro model to evaluate gut barrier disruption and immune stimulation following treatment with MRx0005 and MRx0029. Differentiated HT29-mtx cells exposed to phorbol 12-myristate-13-acetate (PMA) secreted a significant amount of IL-8; in contrast treatment for 24 h with MRx005 and MRx0029 bacterial supernatants, induced an even lower secretion of IL-8 compared than both untreated and YCFA-treated cells (FIG. 22A).

The ability of MRx0005 and MRx0029 to regulate epithelial permeability by modifying intracellular signal transduction involved in the expression and localization of proteins involved in the gut barrier formation was then investigated.

Figure 22B:
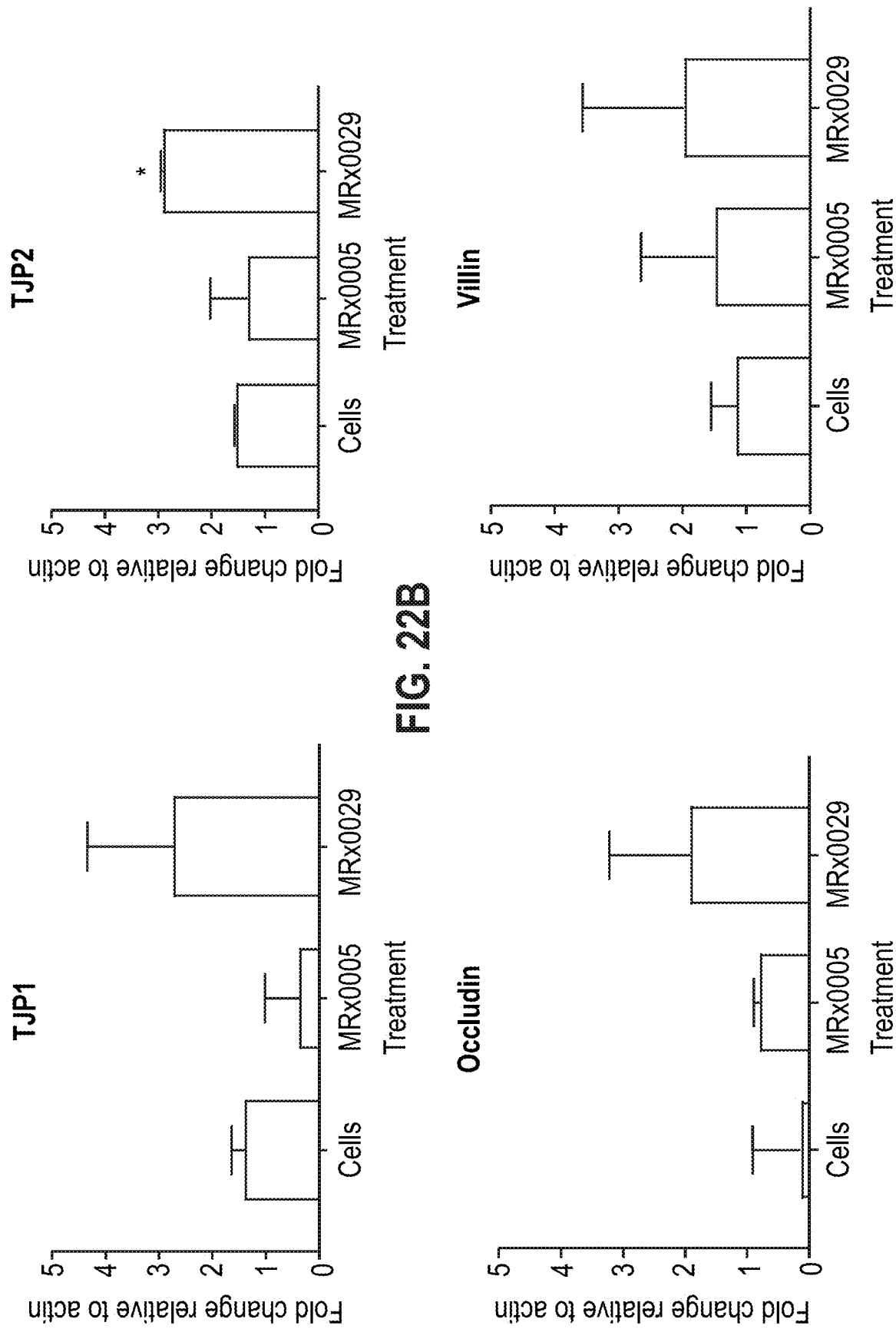
Figure 22D:
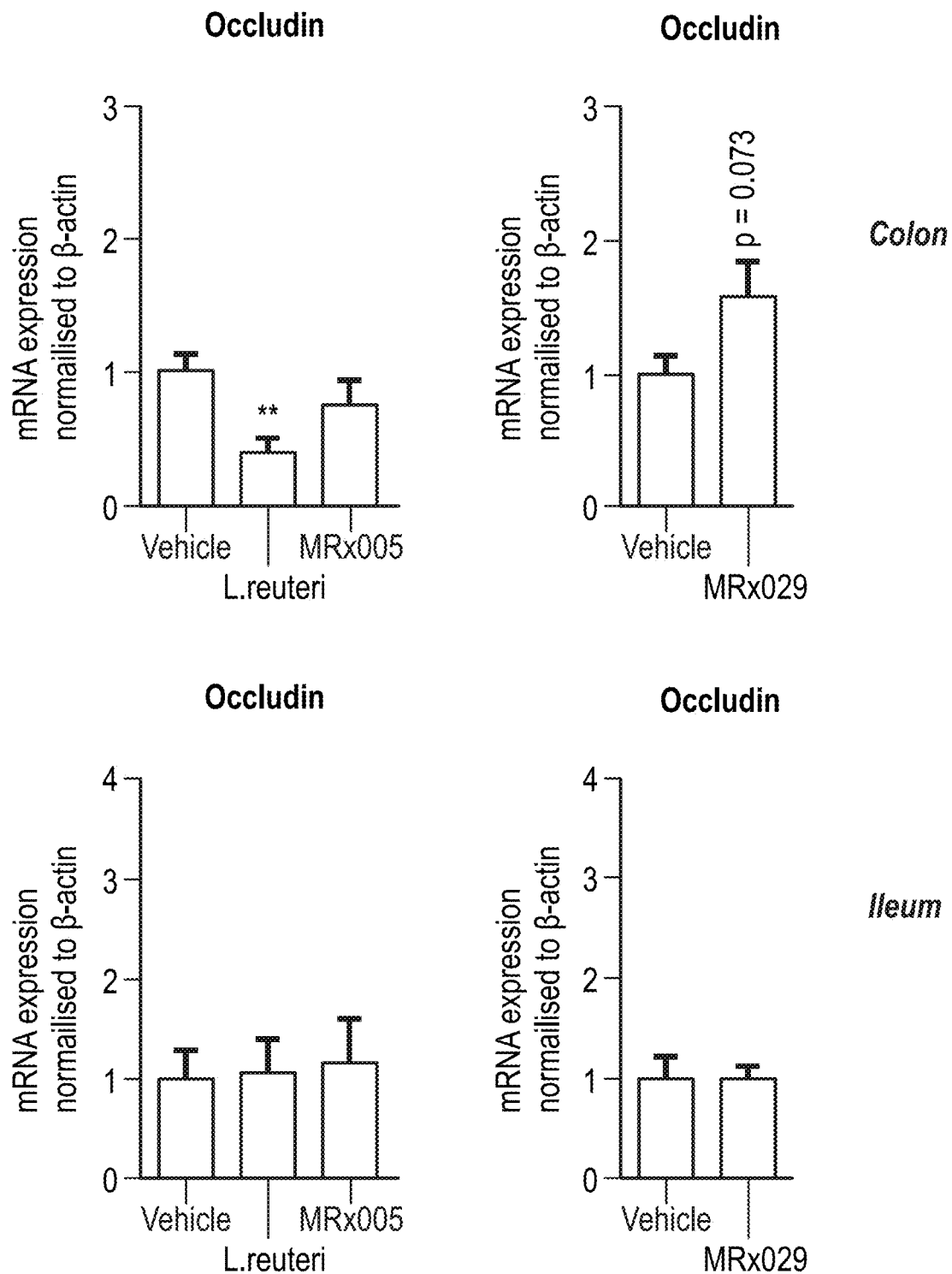

RNA was isolated and Quantitative RT-PCR (qRT-PCR) analysis was performed to characterize the changes in gene expression of tight junction proteins during incubation with MRx0005 and MRx0029. The administration of MRx0029 enhanced Occludin, Vlillin, Tight Junction Protein 1 and 2 (respectively TJP1 and TJP2) mRNA expression after 2 h incubation (FIG. 22B). In contrast, exposure to MRx0005 did not alter the gene expression of tight junction proteins indicating that the two strains act differentially on the intestinal barrier.

The in vitro results were compared with data from the ex vivo parallel analysis on the gut of mice fed with MRx0005 and MRx0029. Gene expression of TJP2 and occludin was quantified in the colon and ileum. The ex vivo data perfectly mirror the in vitro data as MRx0029 was able to significantly up-regulate TJP1 and Occludin (p=0.073) in the colon region of the murine intestine (FIG. 22C+22D). MRx0029 was also able to decrease the permeability function in the colon of the same mice (FIG. 22E+22F).

Materials and Methods—RNA Extraction and gPCR Analysis

Total RNA was extracted using the RNeasy mini kit (Qiagen, Manchester, JUK) according to the manufacturer's instructions, and the RNA concentration determined by absorbance at 260/280 nm using a spectrophotometer (nano-Drop ND-1000; Thermo Scientific, Wilmington, Del.). For mRNA expression analysis, cDNA was prepared from total RNA using the High-Capacity cDNA reverse transcription kit (Applied Biosystems, UK) according to the manufacturer's instructions. The reverse transcription reactions were performed in a Thermo cycler (Biometra, Germany) at 25° C. for 10 min, 37° C. for 120 min, and 85° C. for 5 min, hold on at 4° C. Resulting cDNA was amplified in duplicates by the SYBR-Green PCR assay, and products were detected on QuantStudio 6 flex real-time PCR machine (Applied Biosystems, UK) using a standardised profile (initial denaturation of 95° C. for 10 minutes, followed by 40 cycles of 15 seconds of denaturation at 95° C. and 60 seconds of annealing/extension at 60/65° C., depending on the primers. A dissociation stage was added after the 40 cycles to generate a melting curve. Analysis was performed using the Applied Biosystems QuantStudio Real-Time PCR Software v1.2. The primer sequences for Actin, Villin, Occludin TJP1 and TJP2 are provided in the sequence listing.

Example 16

Methods

Animals

The animals and study design used were the same as for Example 14.

Bacterial Strains

755: *Parabacteroides distasonis* (MRX005)

*Megasphaera massiliensis* (MRX0029)

Tissue Collection

Animals were sacrificed in a random fashion regarding treatment and testing condition; sampling occurred between 9.00 a.m. and 2:30 p.m. Trunk blood was collected in potassium EDTA (Ethylene Diamine Tetra Acetic Acid) tubes and spun for 15 min at 4000 g. Plasma was isolated and stored at −80° C. for further analysis. The brain was quickly excised, dissected and each brain region was snap-frozen on dry ice and stored at −80° C. for further analysis. Spleen was removed, collected in 5 mL RPMI media (with L-glutamine and sodium bicarbonate, R8758 Sigma+10% FBS (F7524, Sigma)+1% Pen/Strep (P4333, Sigma)) and processed immediately after culls for ex-vivo immune stimulation. Intestinal tissue (2 3 cm segments of ileum and colon closest to the caecum were excised, and the furthest 1 cm 2 cm of tissue from the caecum were used) were mounted into the Ussing chambers for intestinal permeability assay. The caecum was removed, weighted and stored at −80° C. for SCFAs analysis.

Monoamine Analysis

The neurotransmitter concentration was analysed as described in Example 10

Spleen Cytokine Assay

Spleens were collected immediately in 5 mL RPMI media following sacrifice and cultured immediately. Spleen cells were first homogenised in this RPMI media, followed by 5 mins incubation with 1 ml of RBC lysis buffer (11814389001 ROCHE, Sigma). A further 10 ml of RPMI media was added, followed by 200G centrifugation for 5 mins. The supernatant was then filtered through 40 um strainer. Cells were counted and seeded (4,000,000/mL media). After 2.5 h of adaptation, cells were stimulated with lipopolysaccharide (LPS-2 µg/ml) or concanavalin A (ConA-2.5 µg/ml) for 24 h. Following stimulation, the supernatants were harvested to assess the cytokine release using Proinflammatory Panel 1 (mouse) V-PLEX Kit (Meso Scale Discovery, Maryland, USA) for TNFα, IL-10, IL-1β, Interferon γ, CXCL2 and IL6. The analyses were performed using MESO QuickPlex SQ 120, SECTOR Imager 2400, SECTOR Imager 6000, SECTOR S 600.

Gene Expression Analysis

Total RNA was extracted using the mirVana™ miRNA Isolation kit (Ambion/Llife technologies, Paisley, UK) and DNase treated (Turbo DNA-free, Ambion/life technologies) according to the manufacturers recommendations. RNA was quantified using NanoDrop™ spectrophotometer (Thermo Fisher Scientific Inc., Wilmington, Del., USA) according to the manufacturer's instructions. RNA quality was assessed using the Agilent Bioanalyzer (Agilent, Stockport, UK) according to the manufacturer's procedure and an RNA integrity number (RIN) was calculated. RNA with RIN value >7 was used for subsequent experiments. RNA was reverse transcribed to cDNA using the Applied Biosystems High Capacity cDNA kit (Applied Biosystems, Warrington, UK) according to manufacturer's instructions. Briefly, Multiscribe Reverse Transcriptase (50 U/μL) (1)(2)(1)(10) was added as part of RT master mix, incubated for 25° C. for 10 min, 37° C. for 2 h, 85° C. for 5 min and stored at 4° C. Quantitative PCR was carried out using probes (6 carboxy fluorescein-FAM) designed by Applied Biosystems to mouse specific targeted genes, while using β-actin as an endogenous control. Amplification reactions contained 1 μl cDNA, 5 μl of the 2× PCR Master mix (Roche), 900 nM of each primer and were brought to a total of 10 μl by the addition of RNase-free water. All reactions were performed in triplicate using 96-well plates on the LightCycler®480 System. Thermal cycling conditions were as recommended by the manufacturer (Roche) for 55 cycles. To check for amplicon contamination, each run contained no template controls in triplicate for each probe used. Cycle threshold (Ct) values were recorded. Data was normalized using β-actin and transformed using the 2-ΔΔCT method and presented as a fold change vs. control group.

Short Chain Fatty Acids Analysis in the Caecal Content

Caecum content was mixed and vortexed with MilliQ water and incubated at room temperature for 10 min. Supernatants were obtained by centrifugation (10000 g, 5 min, 4° C.) to pellet bacteria and other solids and filtration by 0.2 μm. It was transferred to a clear GC vial and 2-Ethylbutyric acid (Sigma) was used as the internal standard. The concentration of SCFA was analyzed using a Varian 3500 GC flame-ionization system, fitted with a with a ZB-FFAP column (30 m×0.32 mm×0.25 mm; Phenomenex). A standard curve was built with different concentrations of a standard mix containing acetate, propionate, iso-butyrate, n-butyrate, isovalerate and valerate (Sigma). Peaks were integrated by using the Varian Star Chromatography Workstation version 6.0 software. All SCFA data are expressed as μmol/g.

Statistical Analysis

Normally distributed data are presented as mean±SEM; Non-parametric datasets are presented as median with interquartile range. Unpaired two-tailed t-test were applied to analyse parametric data and Mann-Whitney test was used for non-parametric. Spearman's rank correlation coefficient was employed for the correlation analysis in the pooled datasets. A p value <0.05 was deemed significant in all cases.

Results—Neurotransmitter Production

Figure 23:
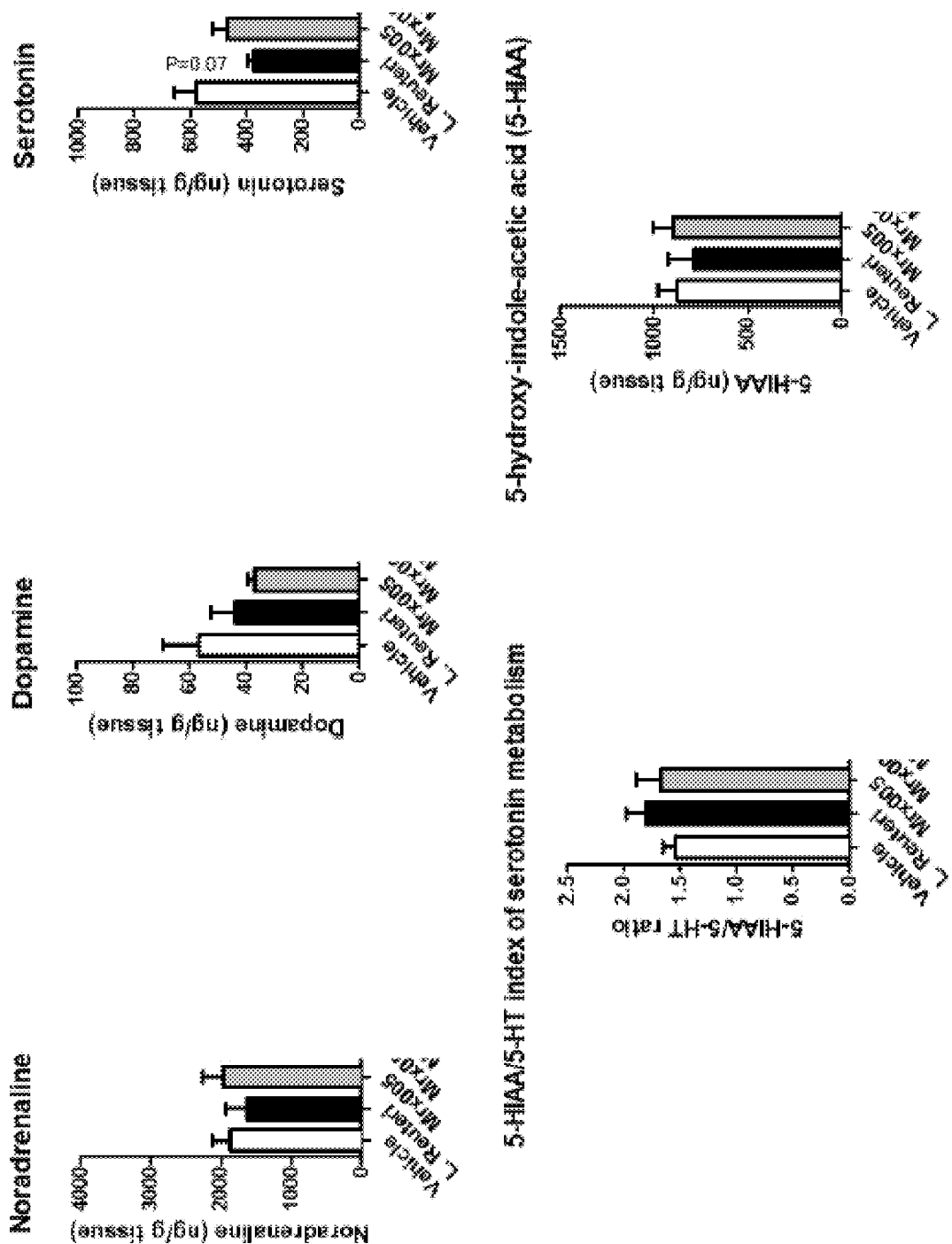
FIG. 23: Production of neurotransmitters in the brain
Figures 26A, 26B:
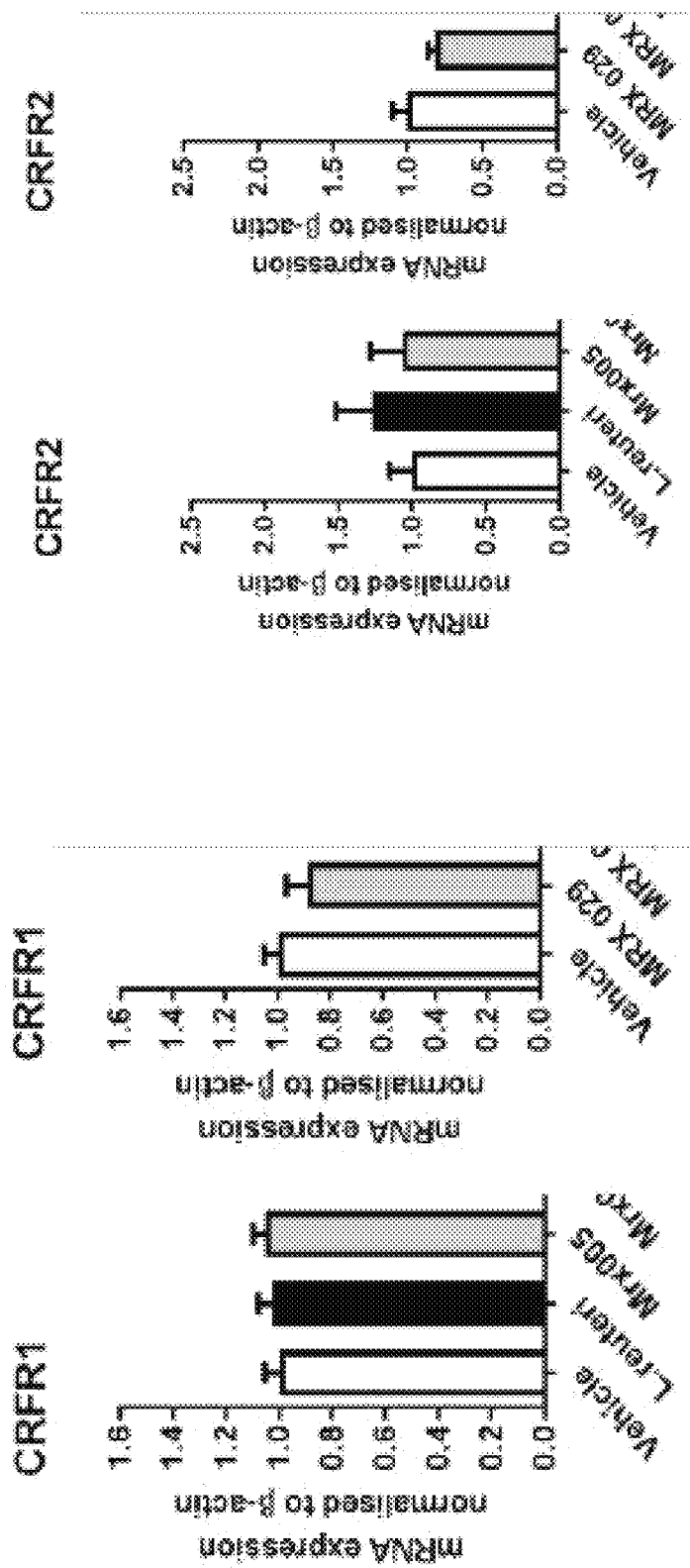
FIGS. 26A-26B.
Figure 27B:
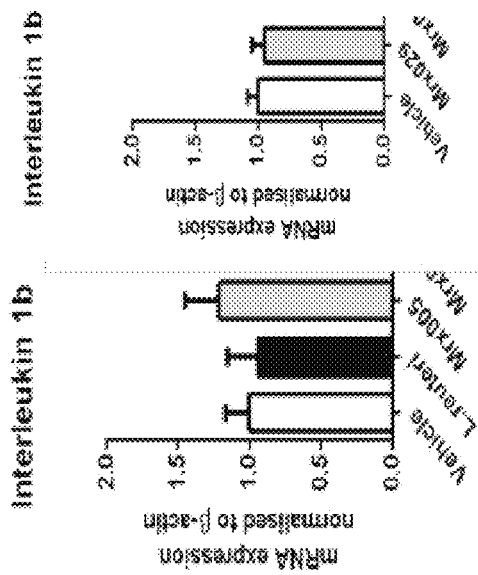
FIGS. 27A-27C: Changes in Hippocampal Expression of FIG. 27A) Tumour Necrosis Factor, FIG. 27B) Interleukin 1b and FIG. 27C) IL-6
Figure 27A:
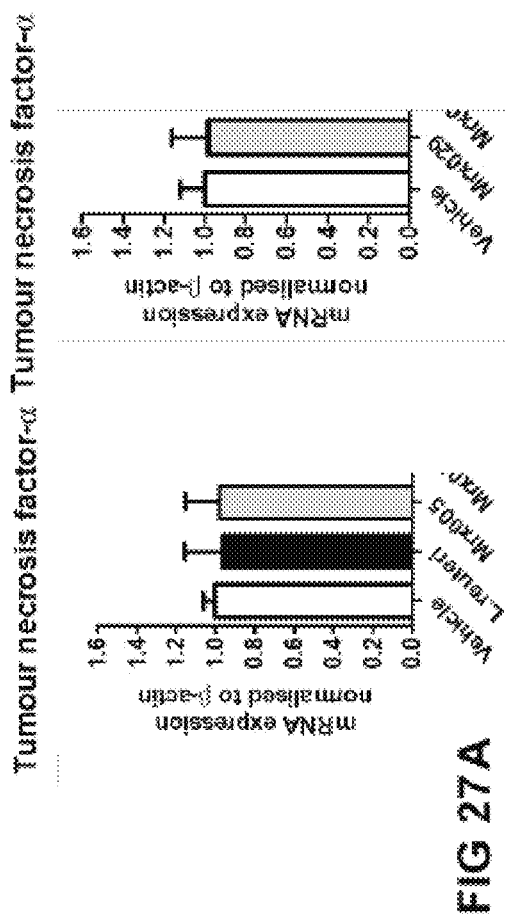
Figure 27C:
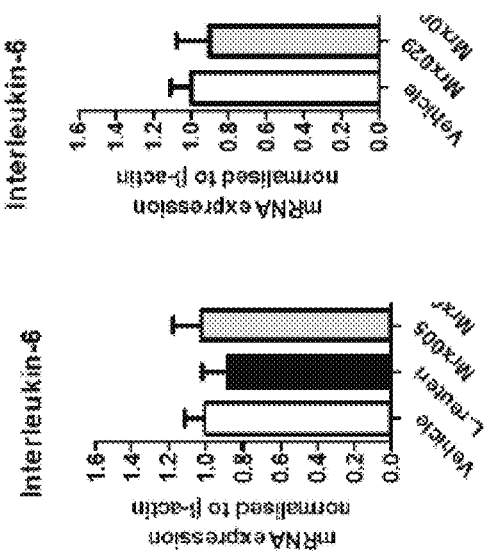
Figures 28A, 28B:
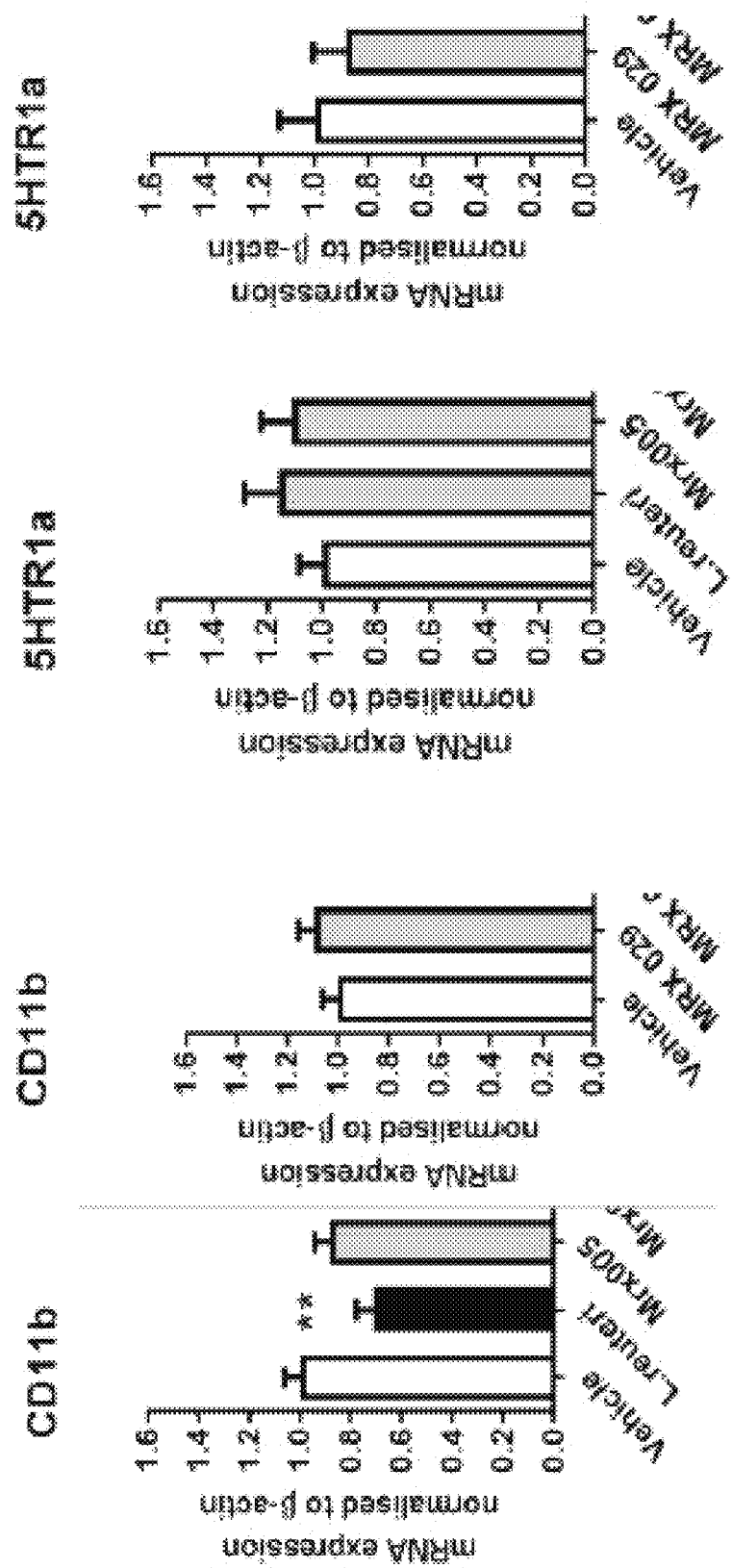
FIGS. 28A-28B.
Figures 29A, 29B:
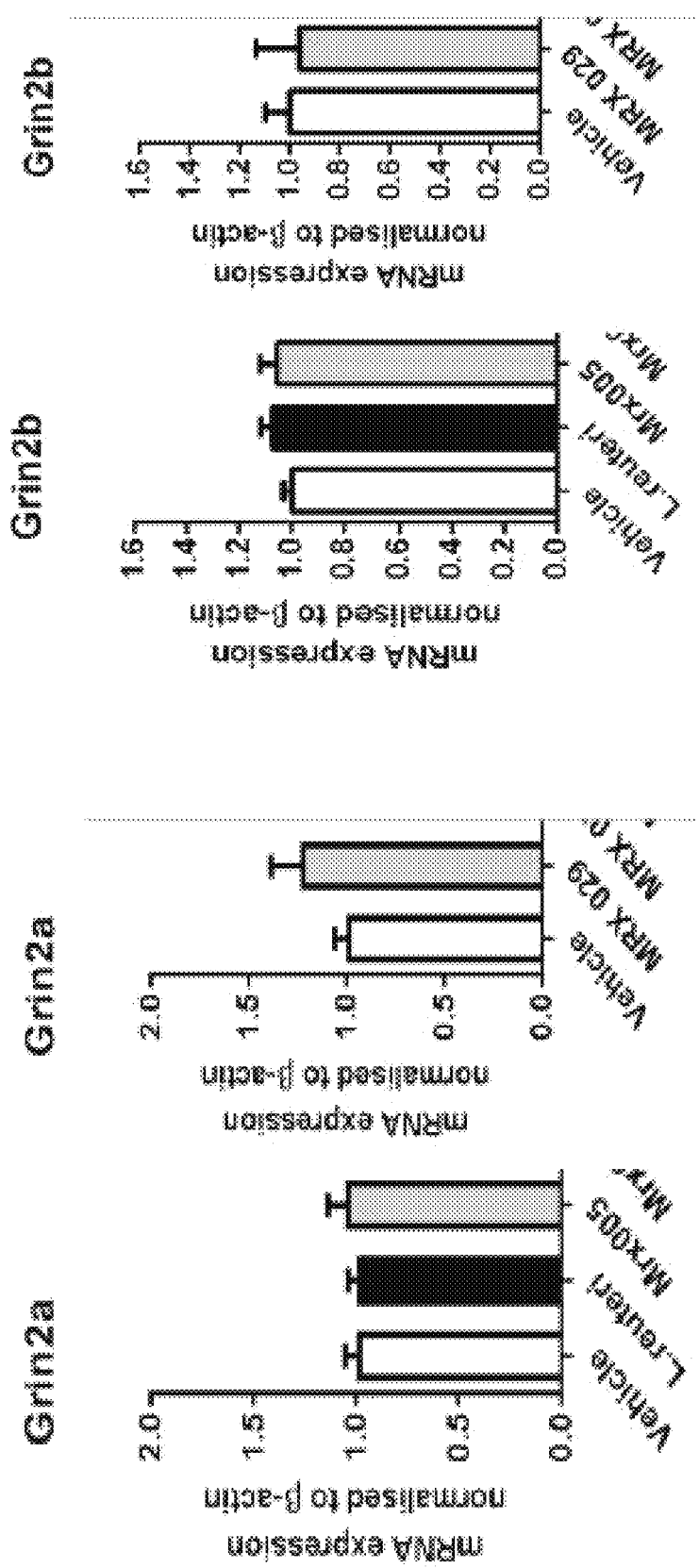
FIGS. 29A-29B.

The results in FIG. 23 show the effect of MRx005 treatment on the concentration of neurotransmitters in the brain of mice. Most notably, treatment with MRx005 leads to a decrease in dopamine.

Results—Gene Expression

Expression of genes for neurotransmitter receptors [serotonin receptor 1a(5-HTR1a), dopamine D1 receptor, GABA receptor subunit B1, GABAA receptor, NMDA2A (Grin2A) and NMDA2B (Grin2b) receptor], inflammatory markers [IL-1β, IL6, CD11b, TNFα and TLR4], and endocrine markers [corticosterone releasing factor (CRF), corticosterone releasing factor receptors 1 and 2 (CRFR1, CRFR2), brain-derived neurotrophin factor (BDNF), vasopressin receptor, oxytocin receptor, glucocorticoid receptor and mineralocorticoid receptor] were analysed in brain tissue from the hippocampus, amygdala and prefrontal cortex.

Figure 32A:
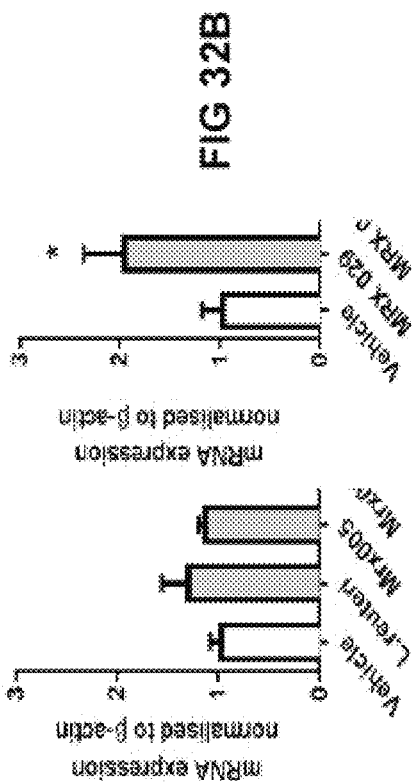
FIGS. 32A-32D: Changes in Amygdala Expression of FIG. 32A) Brain Derived Neurotrophic Factor (BDNF), FIG. 32B) Toll-like Receptor 4 (TLR-4), FIG. 32C) Corticotropin Releasing Hormone Receptor 1 (CRFR1) and FIG. 32D) Corticotropin Releasing Hormone Receptor 2 (CRFR2)
Figure 32B:
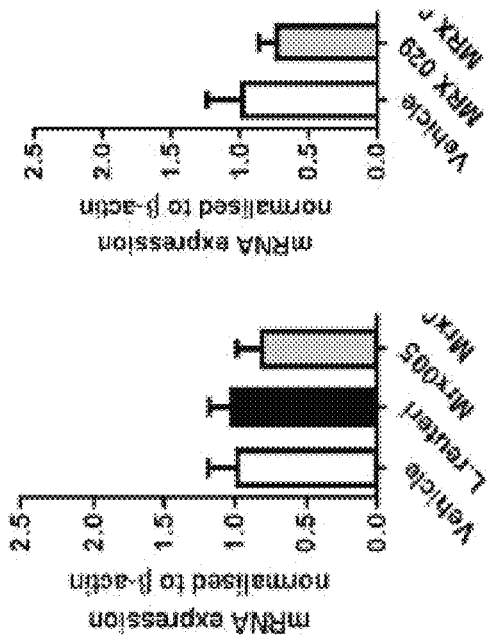
Figure 32C:
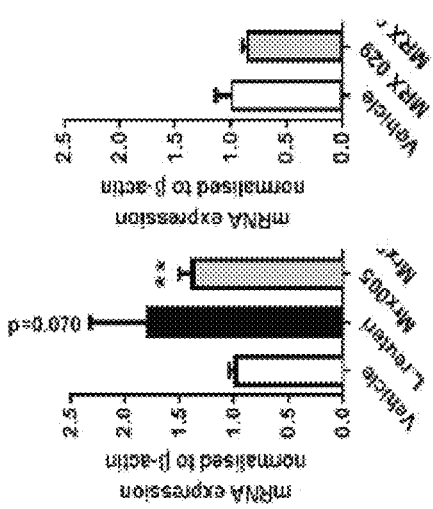
Figure 32D:
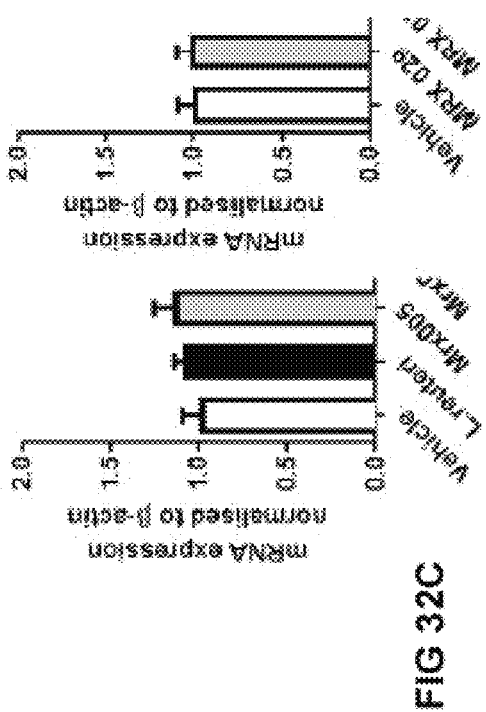
Figure 34A:
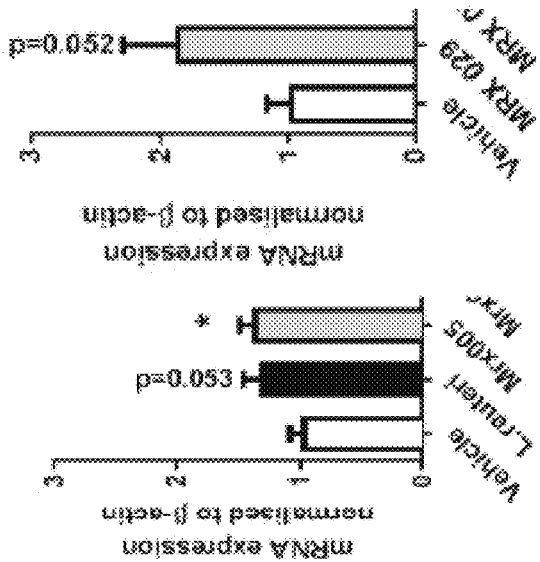
FIGS. 34A-34C: Changes in Amygdala Expression of FIG. 34A) GABA-A Receptor Alpha 2 Subunit (GABRA2), FIG. 34B) GABA-A Type B Receptor 1 Subunit (GABBR1) and FIG. 35C) Dopamine Receptor 1 (DRD1)
Figure 34B:
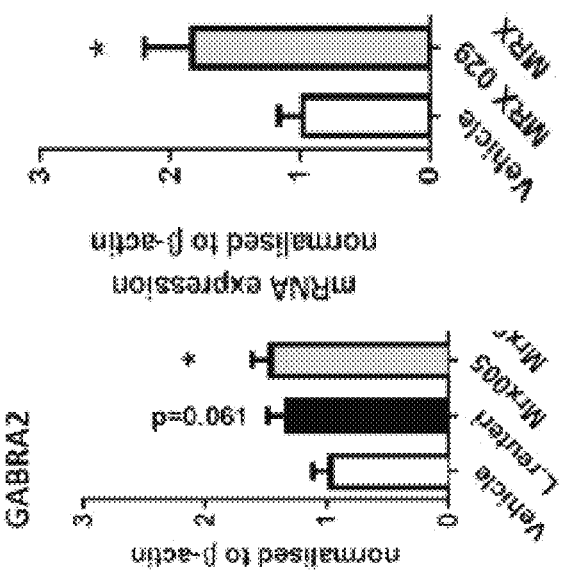
Figure 34C:
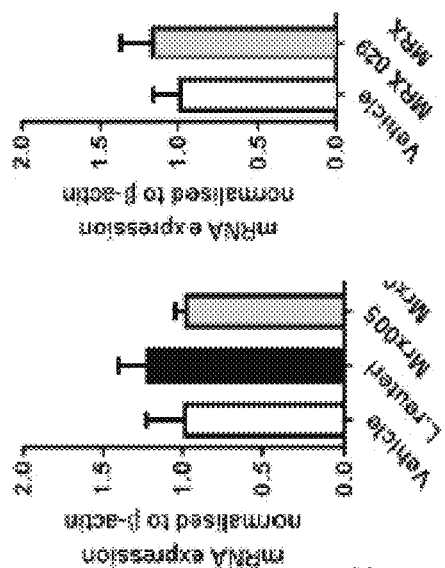

FIGS. 24-38 show the changes in gene expression after MRX005 or MRX0029 treatment in the hippocampal, amygdala and prefrontal cortex. Treatment with MRx0029 led to an increase in glucocorticoid receptor expression in the amygdala (FIG. 31C). FIG. 32A shows that MRx005 significantly increased the expression of BDNF in the amygdala, while treatment with MRx0029 significantly increased the expression of TLR4 in the amygdala (FIG. 32).

Both MRx005 and MRx0029 can increase expression of CD11b in the amygdala (FIG. 33A), while the expression of IL-6, Grin2a and Grin2b is reduced after MRx005 treatment (FIGS. 33B-D). In addition, MRx005 and MRx0029 significantly increased the expression of GABRA2 and increased the expression of GABBR1 in the amygdala.

Figure 35A:
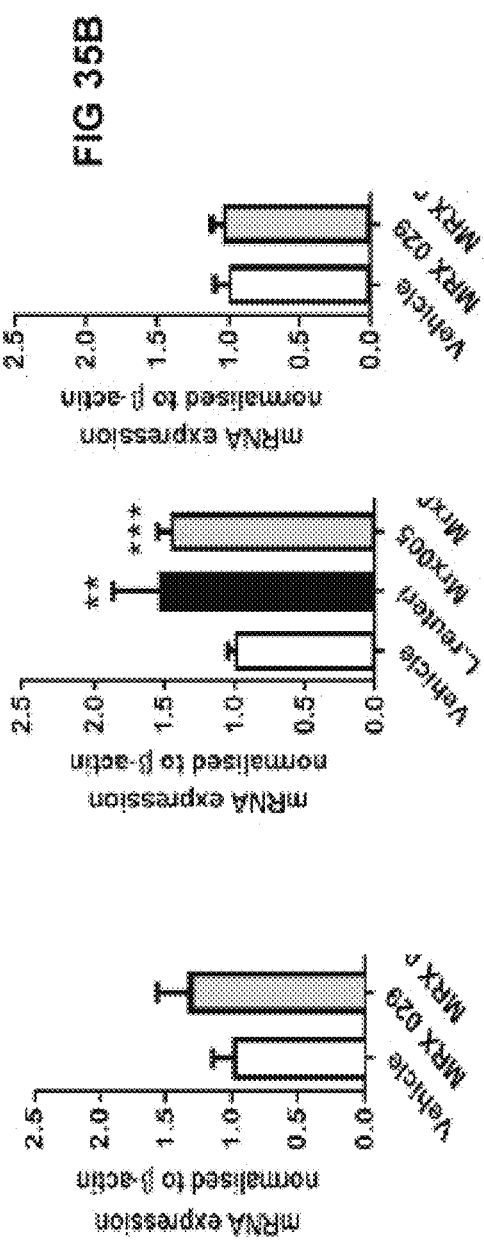
FIGS. 35A-35D: Changes in Prefrontal Cortex Expression of FIG. 35A) Oxytocin Receptor, FIG. 35B) Brain Derived Neurotrophic Factor (BDNF), FIG. 35C) Mineralocorticoid Receptor and FIG. 35D) Glucocorticoid Receptor
Figure 35B:
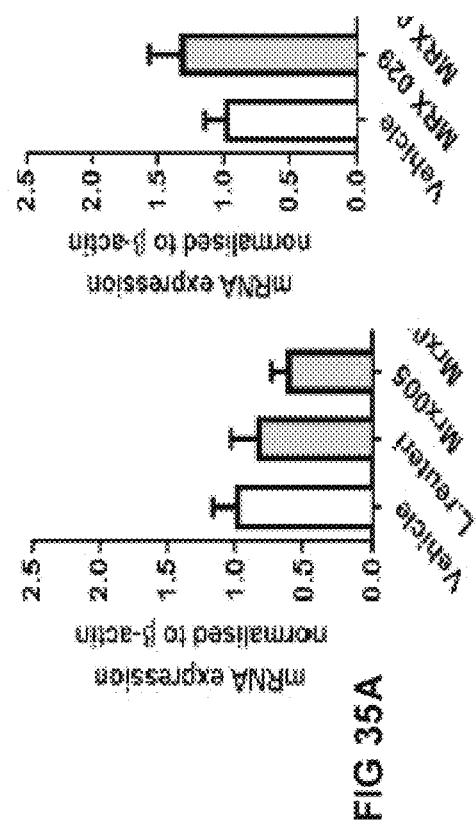
Figure 35C:
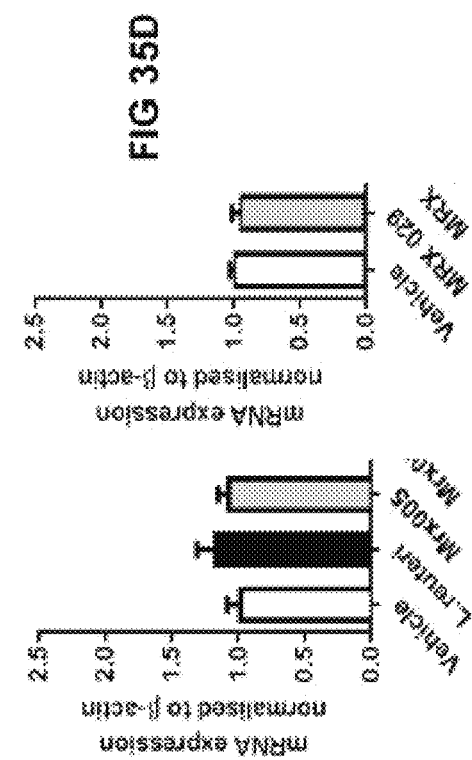
Figure 35D:
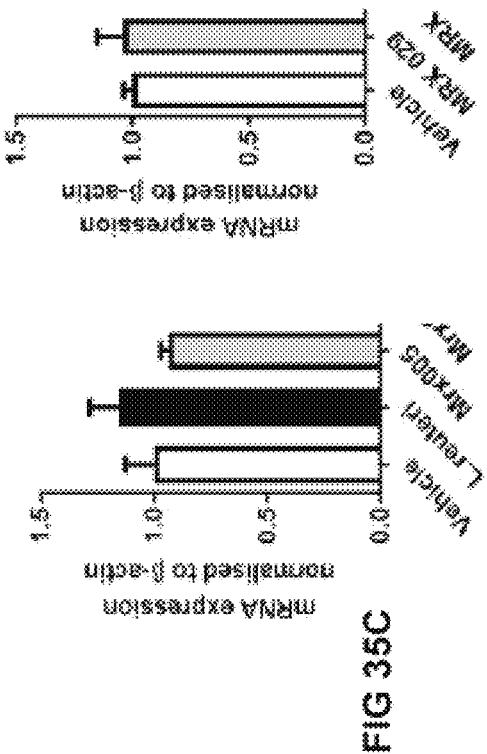

Treatment with MRx005 led to a significant increase in the expression of BDNF in the prefrontal cortex (FIG. 35B).

Discussion

MRx005 and MRx0029 administration caused changes in gene expression, especially in the amygdala.

Results—Effect on Tph1 and IDO-1 Expression

FIG. 39 shows that MRx0029 can significantly increase the expression tryptophan hydroxylase-1 (Tph1) in the colon and that MRX005 treatment can increase IDO-1 expression in the colon. Treatment with MRX005 increased the expression of Tph1 and IDO1 in the ileum (FIG. 40).

Indoleamine-pyrrole 2,3-dioxygenase-1 (IDO-1) the first and rate-limiting enzyme in the tryptophan/kynurenine pathway while tryptophan hydroxylase 1 (Tph1), an isoform of the enzyme tryptophan hydroxylase, responsible for the synthesis of serotonin. These data suggest that MRx0029 and MRx005 may affect serotonin levels and the tryptophan/kynurenine pathway.

Results—Effect on Tryptophan Metabolite Levels

Figures 41A, 41B, 41C:
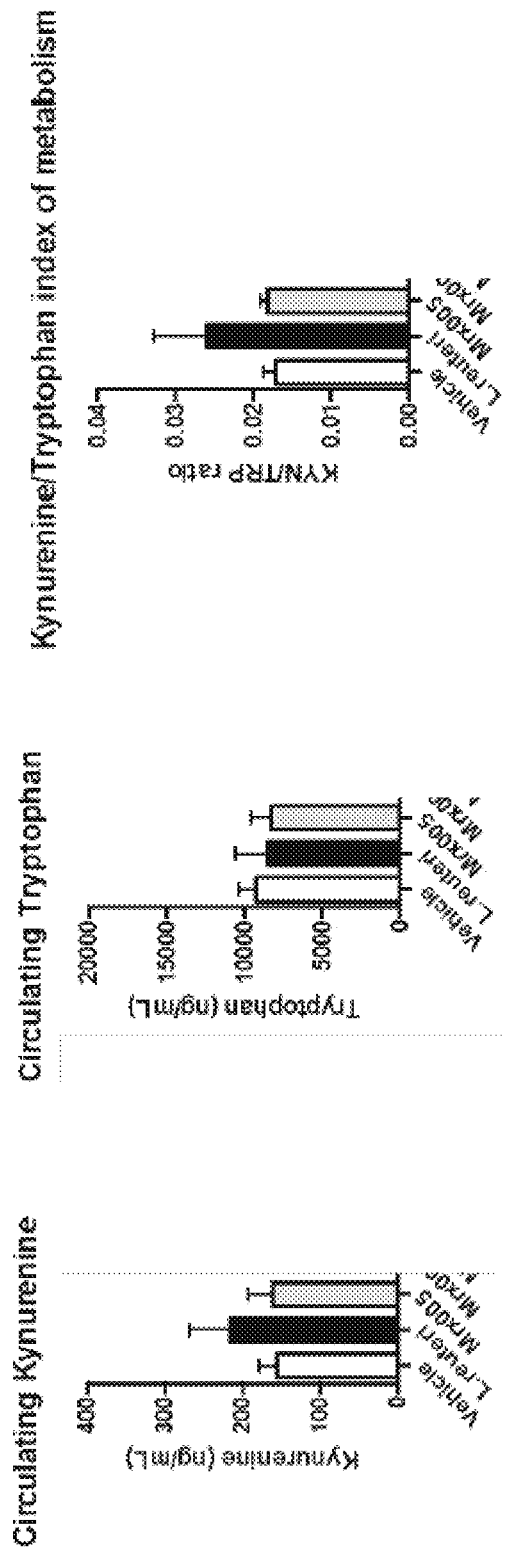
FIGS. 41A-41C: Changes in Circulating Tryptophan Metabolite Levels FIG. 41A) Kynurenine, FIG. 41B) Tryptophan and FIG. 41C) Kynurenine/Tryptophan Index of metabolism

FIG. 41 shows the effect of treatment with MRx005 on the levels of circulating kynurenine and tryptophan.

Results—Effect on Cytokine Expression from Splenocytes

The ex-vivo splenocyte assay involves challenging the splenocytes (cells isolated from the spleen—a main organ involved in immune defense), with a bacterio- or viral-mimetic challenge.

Figure 42:
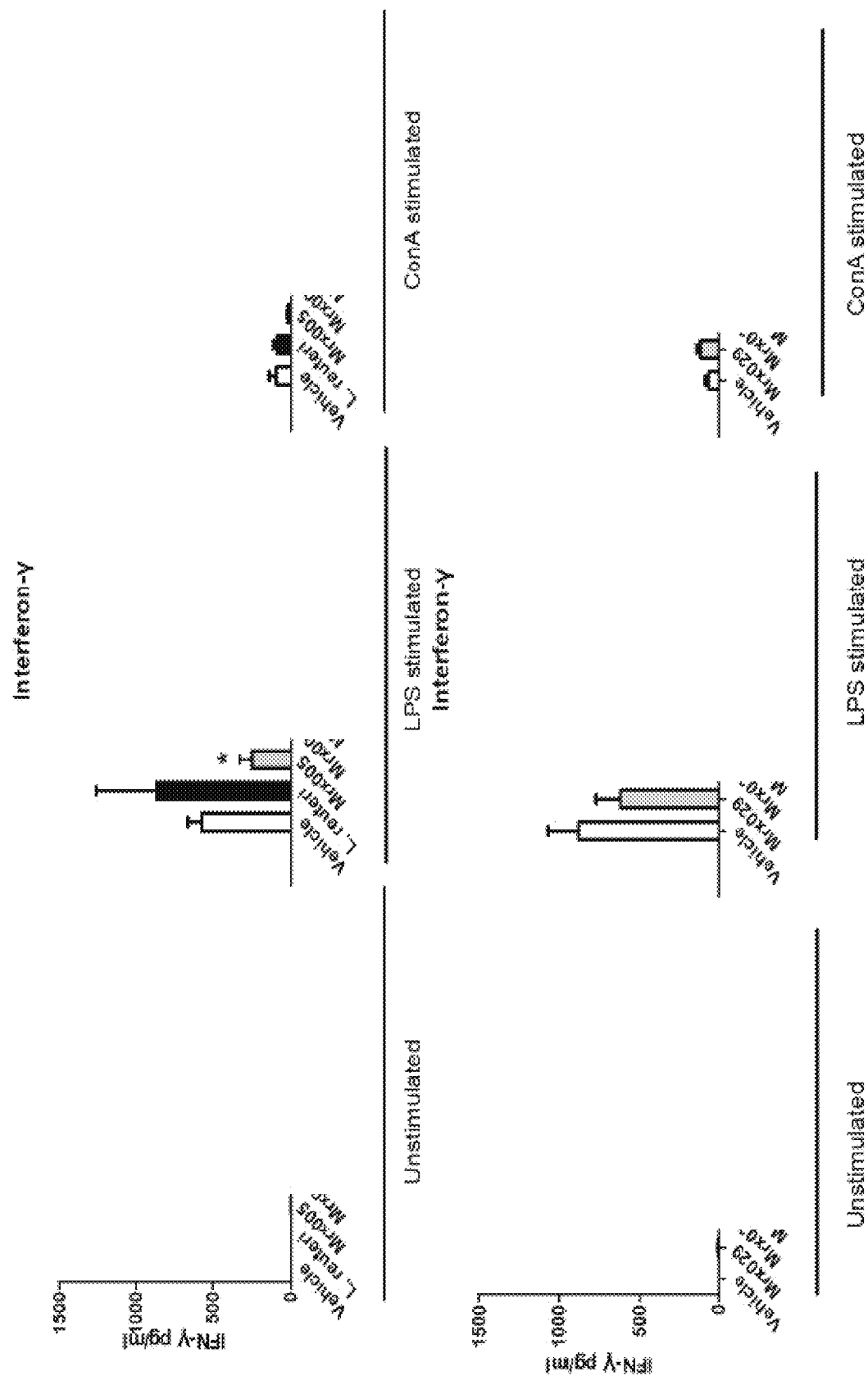
FIG. 42: Effect on Interferon-γ Production from mouse Splenocytes from mice fed with MRx0029
Figure 43:
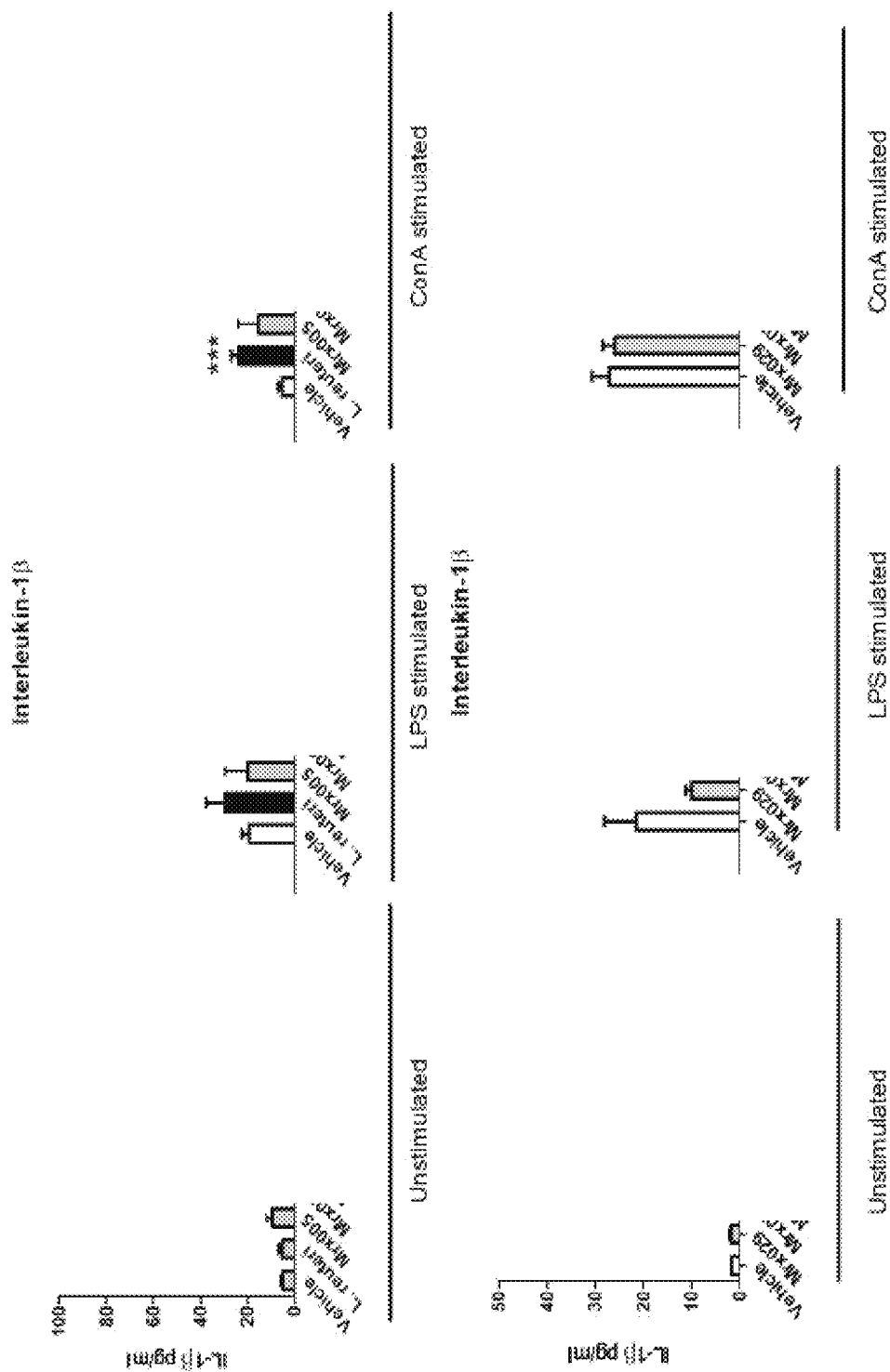
FIG. 43: Effect on Interleukin-1β Production from Splenocytes
Figure 44:
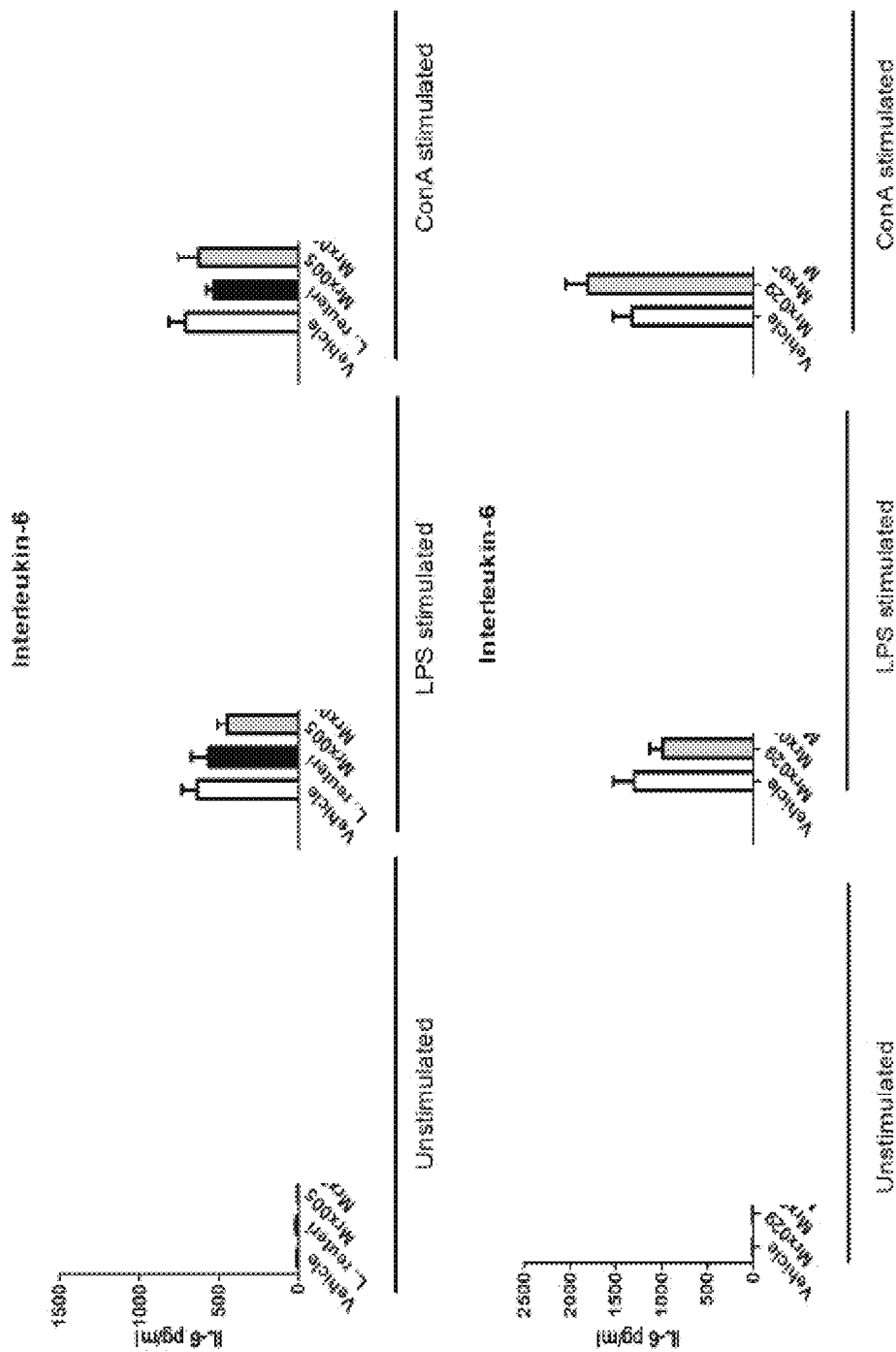
FIG. 44: Effect on Interleukin-6 Production from Splenocytes
Figure 45:
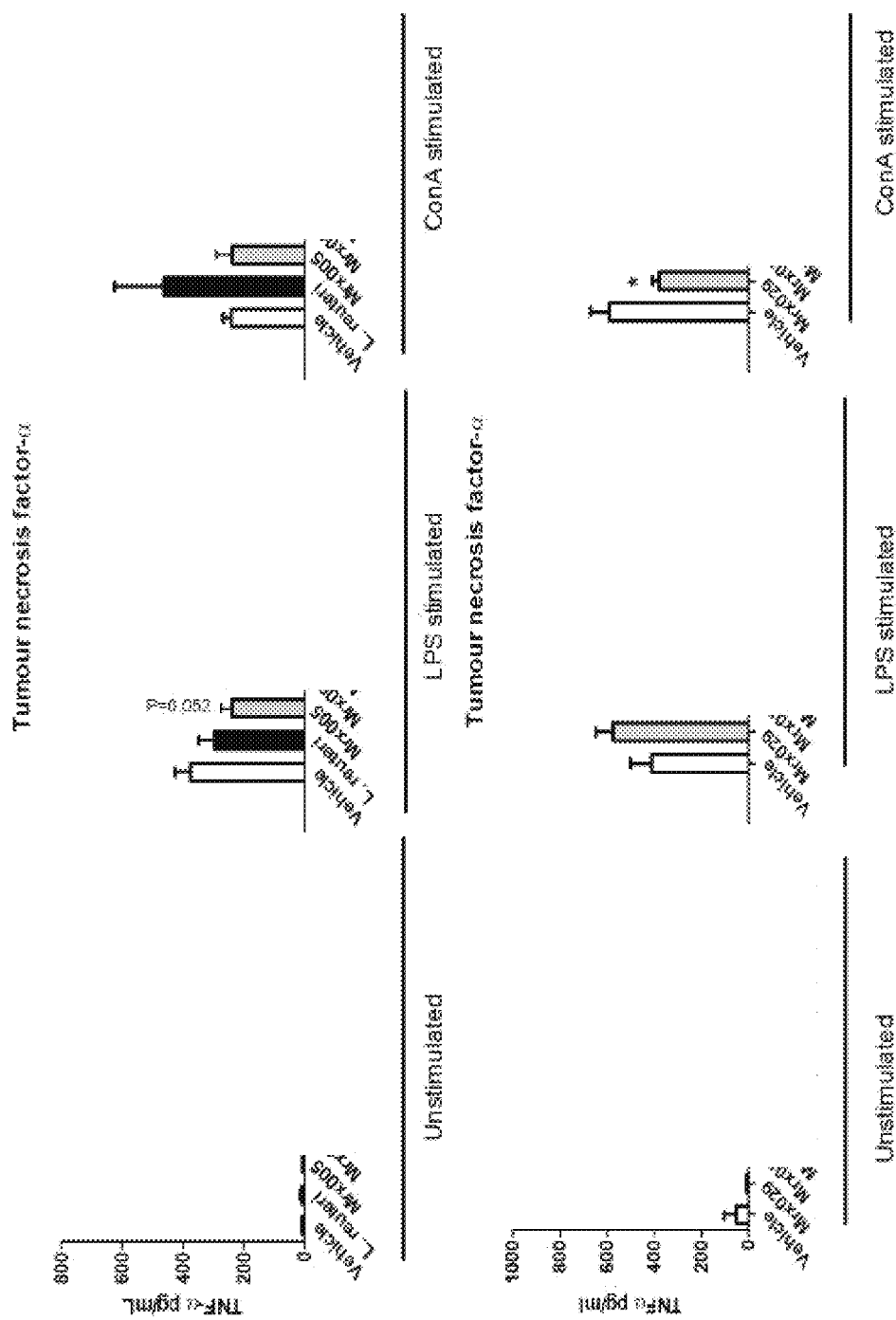
FIG. 45: Effect on Tumour Necrosis Factor Production from Splenocytes
Figure 46:
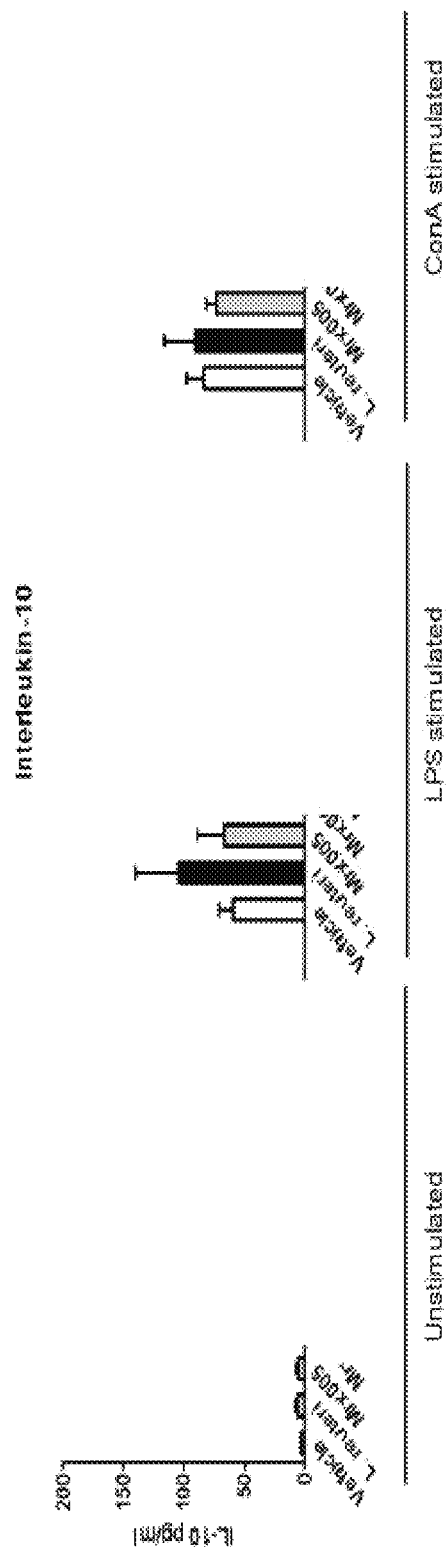
FIG. 46: Effect on Interleukin-10 Production from Splenocytes

MRX005 significantly reduced the levels of interferon-γ in splenocytes following a challenge with LPS (FIG. 42). In addition, MRX005 reduced the levels of interleukin-6 and tumour necrosis factor after a challenge with LPS (FIGS. 44 and 45, respectively). Treatment with MRx0029 led to a reduction in interferon-γ, interleukin-1β and interleukin-6 following a challenge with LPS (FIGS. 42, 43 and 44, respectively).

Figure 47:
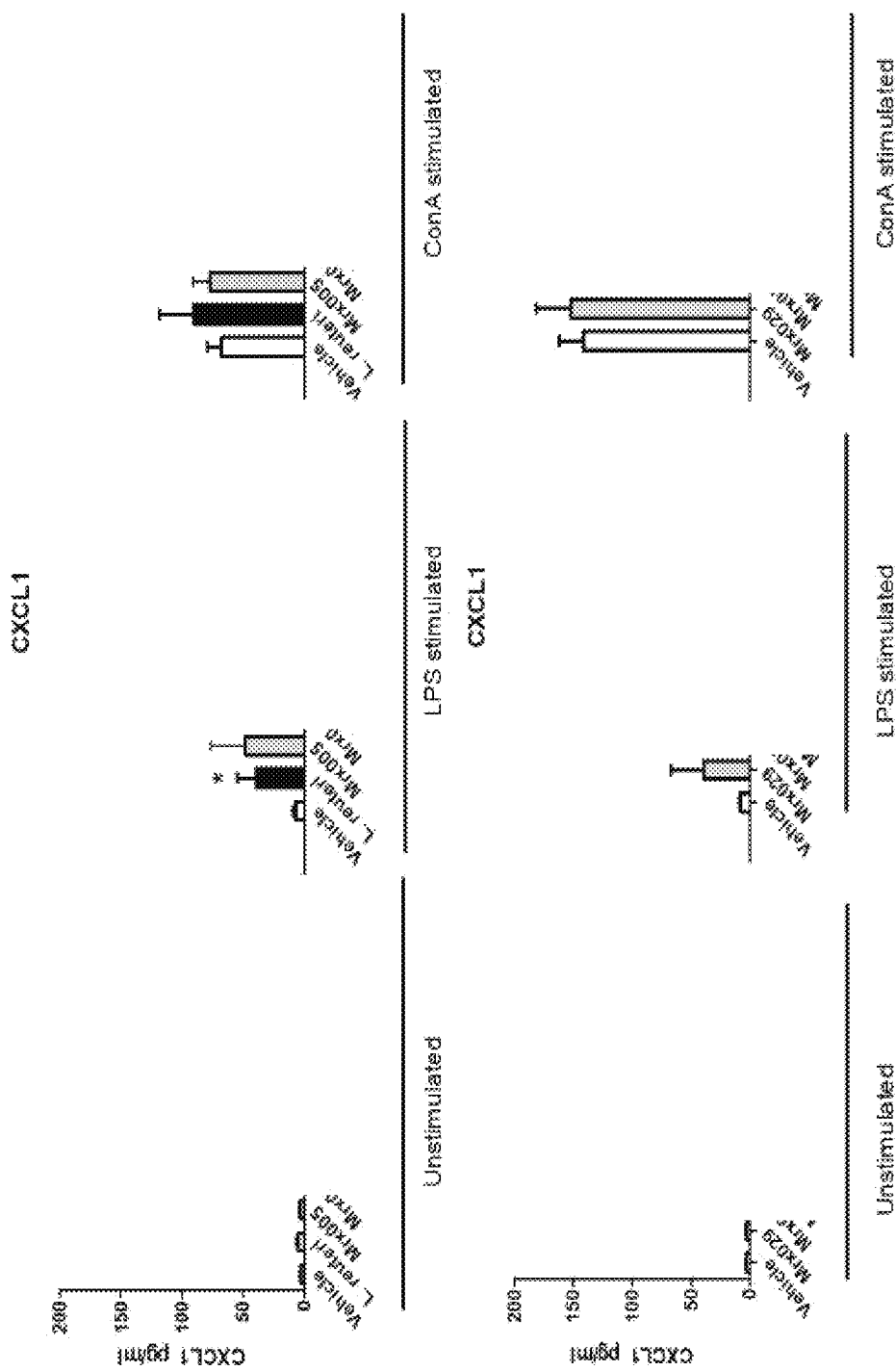
FIG. 47: Effect on Chemoattractant CXCL1 Production from Splenocytes

Treatment with MRx005 and MRx0029 led to an increase in the levels of the chemoattractant CXCL1 (FIG. 47).

Results—Effect on Caecal Short Chain Fatty Acid Levels

Figure 48:
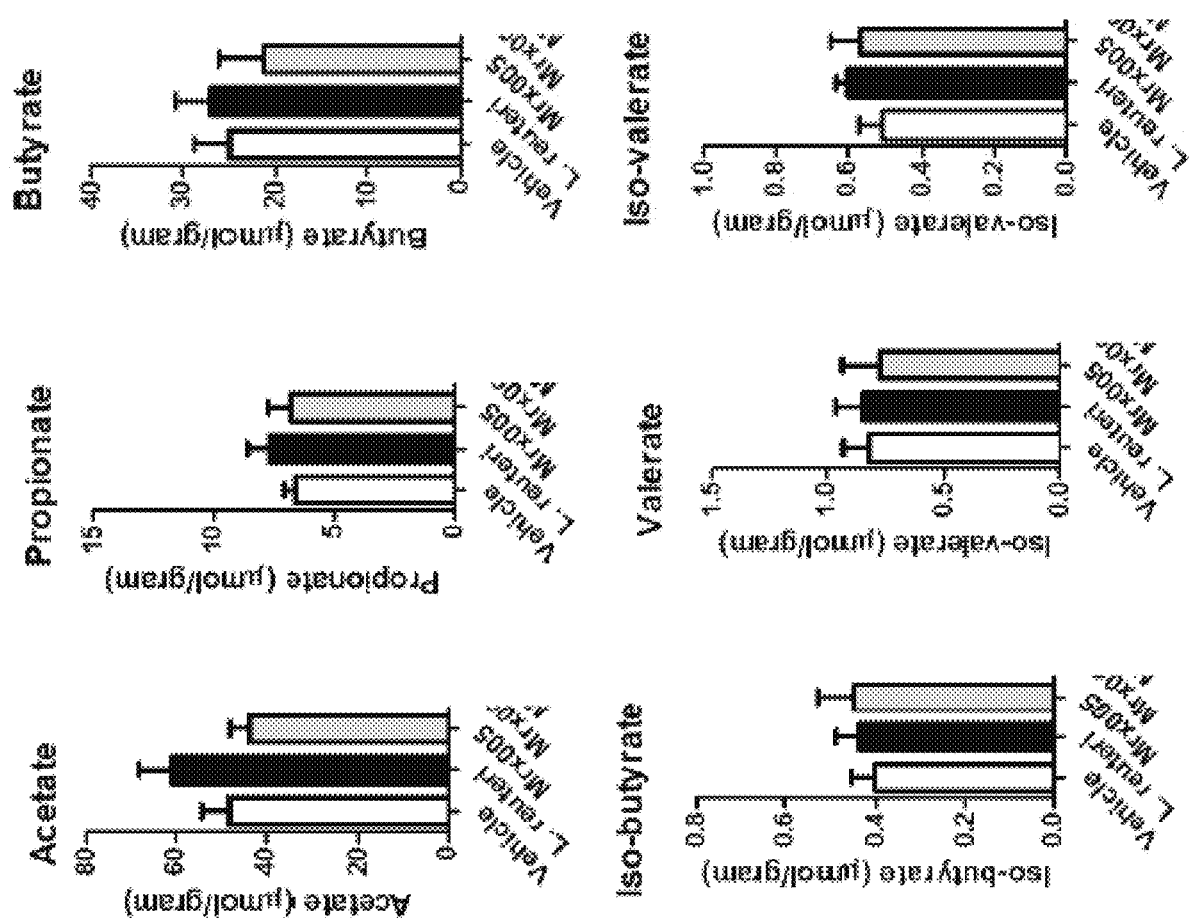
FIG. 48: Changes in Caecal Short Chain Fatty Acid Levels
Figure 49:
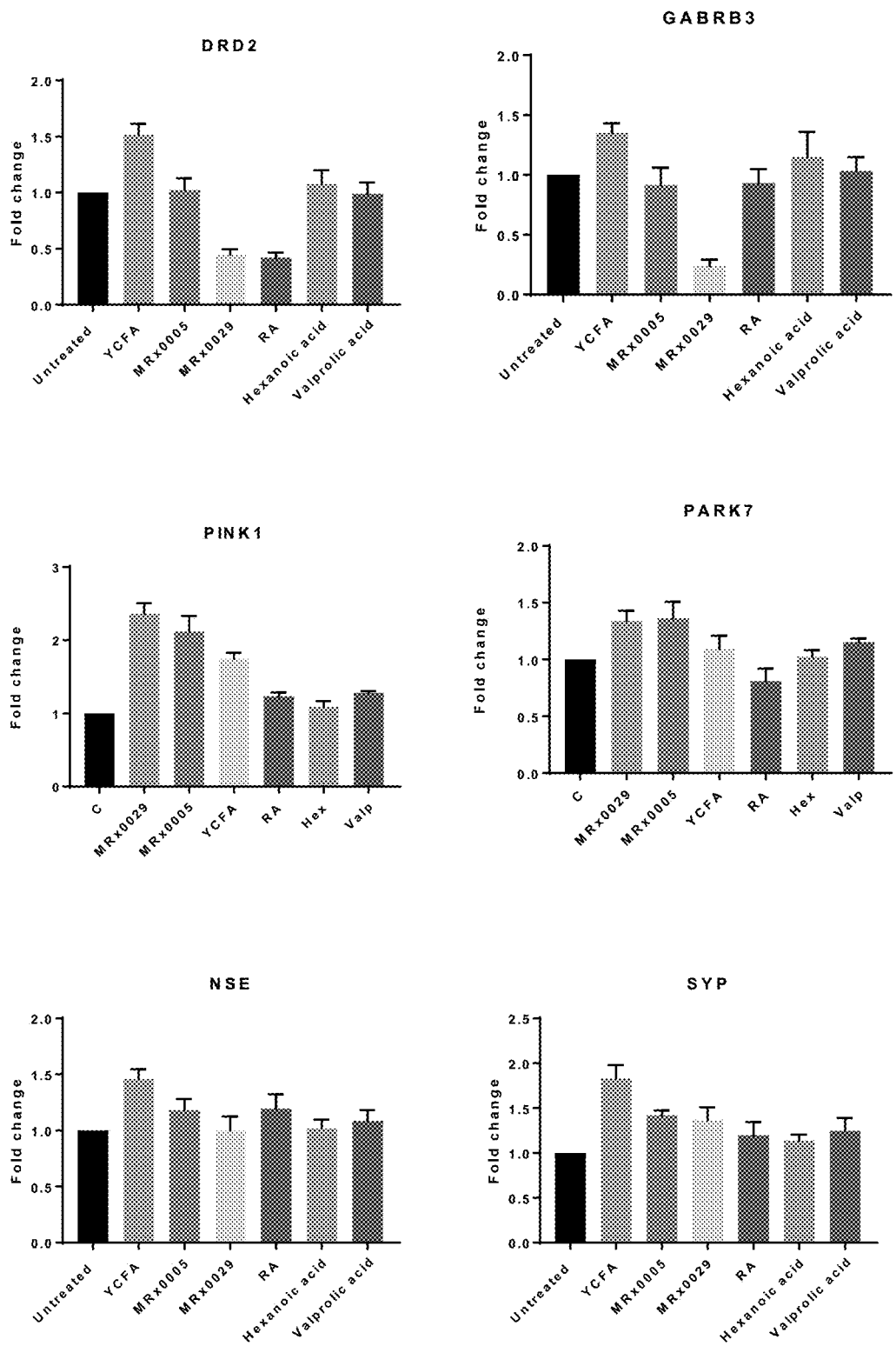
FIG. 49: MRx0029 and MRX005-induced changes in gene expression levels of Actin, Villin, Occludin TJP1, TJP2, MAP2, DRD2, GABRB3, SYP, PINK1, PARK7 and NSE.

Short chain fatty acids (SCFAs) are produced when non-digestible fibres from the diet are fermented by bacteria in the gut. The effects of MRX005 administration are shown in FIG. 48.

Example 17—Further Analysis of MRX029 and MRX005-Induced Changes in Gene Expression Levels Methods
Cell Line
 SH-SY5Y cells
Bacterial Strains
 755: *Parabacteroides distasonis* (MRX005)
 *Megasphaera massiliensis* (MRX0029)
qPCR SHSY5Y were plated in 10 cm petri dishes a density of $2\times10^6$ cells. After 24 h cells were treated in differentiation medium (growth medium containing 1% FBS without RA) with 10% bacteria supernatants or YCFA+, 10 uM RA, 200 uM hexanoic acid or 200 uM valproic acid, for 17 hrs. There after representative images were taken using phase contrast EVOS XL core microscope at 40×/0.65 magnification. Cells were collected, and total RNA was isolated according to RNeasy mini kit protocol (Qiagen). cDNAs were made using the high capacity cDNA reverse transcription kit (Applied Biosystems). Gene expression was measured using qPCR. GAPDH was used as internal control. Fold change was calculated according to the $2^{(-\Delta\Delta ct)}$ method. The primer sequences for MAP2, DRD2, GABRB3, SYP, PINK1, PARK7 and NSE are provided in the sequence listing.

Immuno-Labelling and Cell Imaging

Cells were seeded onto 8-well chamber slides (Marienfeld Laboratory Glassware) at $5\times10^4$ cells/well overnight and were treated with 10% bacterial supernatant for 24 h. For differentiation, cells were treated with 10 nM RA for 5 days before treating with cell-free bacterial supernatant for 24 h. Afterwards, the cells were fixed with 4% paraformaldehyde in PBS for 20 minutes at room temperature (RT). Fixed cells were washed with PBS, and permeabilized with 1% Triton X-100 in PBS for 10 minutes. After washing with PBS, the slides were incubated with blocking buffer (4% BSA/PBS) for 1 h at RT before adding anti-MAP2 antibody or β3-tubulin (sc-74421 and sc-80005 respectively, Santa Cruz Biotechnology Inc) diluted in 1% BSA/PBS for 12 h at 4° C. They were then washed twice with PBS, followed by incubation with Alexa Flour 488 conjugated anti-mouse (Molecular Probes Inc) and Alexa Flour 594 conjugated Phalloidin (ab176757, Abcam) for 1 h at RT. After washing 3× with PBS, the slides were staining with DAPI and mounted with Vectashield® (Vector Laboratories). Slides were viewed using a Axioskop 50 microscope (Zeiss) equipped with a 63×/1.2 W Korr objective and filter sets suitable for detection of the fluorochromes used. Manual exposure times for the digital acquisition of images immuno-labelled with MAP-2 were kept constant allowing comparison between different wells and treatments. Phalloidin (F-actin) and DAPI exposure times varied to suit the field of view. Randomised fields of view were acquired using a QImaging camera controlled by Image Pro Plus software. Images were saved as TIFF files and opened in Adobe Photoshop CC 2015.1.2. Images of the MAP-2, DAPI and Phalloidin images were then overlaid and merged. Representative images were selected to illustrate the differences in abundance and location of the proteins examined.

Immunoblotting

SH-SY5Y cells cultured under the indicated conditions described above, treated with MRx0005 and MRx0029 for 24 h and then lysed in RIPA buffer containing cocktail of protease inhibitors (Roche Diagnostics, UK). Protein concentration was estimated using the BCA protein assay kit (Pierce Biotechnology, Rockford, Ill.), separated by SDS-PAGE and transferred to a PVDF membrane. Membranes were then blocked with 5% non-fat dry milk or 5% BSA and incubated overnight at 4° C. with the primary antibodies (respectively MAP2 and β3-tubulin). The blots were then incubated with the appropriate horseradish peroxidase (HRP)-conjugated secondary antibody, and proteins were detected by chemiluminescence detection kit (Pierce Biotechnology, Rockford, Ill.). For both MAP2 and β3-tubulin, β-actin served as a control to monitor protein loading variability amongst samples.

Results and Discussion
Gene Expression

FIGS. 7a (graph insert) and 49 show the MRx0029 and MRX005-induced changes in expression levels of Actin, Villin, Occludin TJP1, TJP2, MAP2, DRD2, GABRB3, SYP, PINK1, PARK7 and NSE.

Microscopy and Immunoblotting

Figure 50:
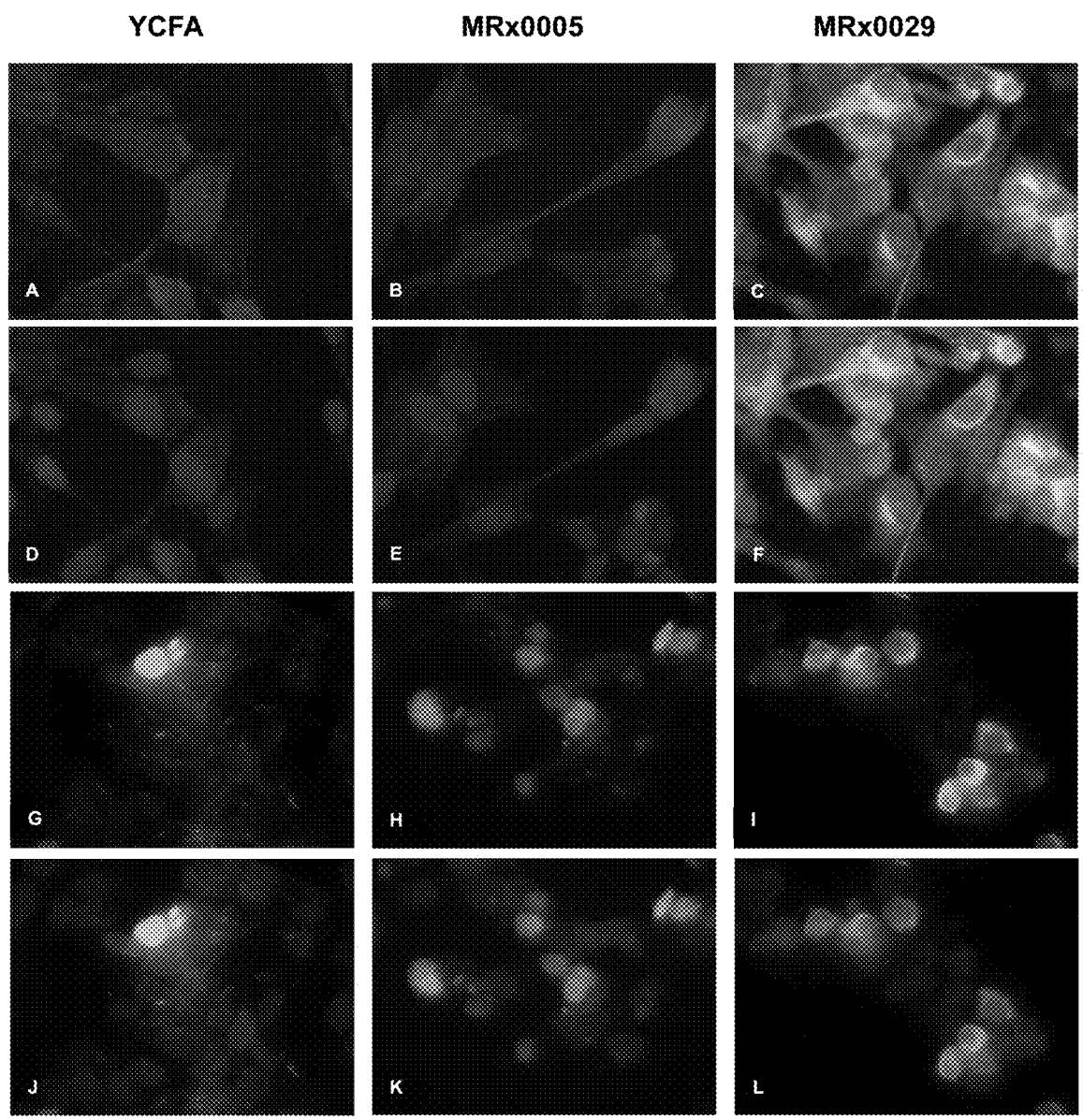
FIG. 50: SHSY5Y cell differentiation induced by MRx0005 and MRx0029. (A-C) Representative images of immuno labelled cells with Phalloidin and MAP2. (D-F) images of A-C merged with DAPI images. (G-I) β3 tubulin immunolabelled cells. (J-L) merged with DAPI images. Magnification ×630. Western blot analysis of effects of MRx0005 and MRx0029 treatment on SHSY5Y cells. Western blot membranes were probed with antibodies to MAP2 (M) and b3 tubulin (N). Actin was used as a loading control. Lower panels: representative blots from one of six separate experiments; upper panels: relative densitometric intensity.

FIG. 50 shows the change in the level of expression of MAP2 in SHSY5Y cells as determined by confocal microscopy. The expression levels of MAP2 and B3-tubulin were also quantified by immunoblot analysis. The results shown in FIGS. 50M and 50N indicate that MRX029 induces an increase in the level expression of MAP2.

Sequences (*Megasphaera massiliensis* gene for 16S ribosomal RNA, partial sequence, strain: NP3-JX424772.1)

SEQ ID NO: 1

```
  1 agagtttgat cctggctcag gacgaacgct ggcggcgtgc ttaacacatg caagtcgaac
 61 gagaagagat gagaagcttg cttcttatca attcgagtgg caaacgggtg agtaacgcgt
121 aagcaacctg cccttcagat ggggacaaca gctggaaacg gctgctaata ccgaatacgt
181 tctttccgcc gcatgacggg aagaagaaag ggaggccttc gggctttcgc tggaggaggg
241 gcttgcgtct gattagctag ttggagggt aacggcccac caaggcgacg atcagtagcc
301 ggtctgagag gatgaacggc cacattggga ctgagacacg gcccagactc ctacgggagg
361 cagcagtggg gaatcttccg caatggacga aagtctgacg gagcaacgcc gcgtgaacga
421 tgacggcctt cgggttgtaa agttctgtta tatgggacga acagggcatc ggttaatacc
```

-continued

```
 481 cggtgtcttt gacggtaccg taagagaaag ccacggctaa ctacgtgcca gcagccgcgg
 541 taatacgtag gtggcaagcg ttgtccggaa ttattgggcg taaagggcgc gcaggcggca
 601 tcgcaagtcg gtcttaaaag tgcggggctt aaccccgtga ggggaccgaa actgtgaagc
 661 tcgagtgtcg gagaggaaag cggaattcct agtgtagcgg tgaaatgcgt agatattagg
 721 aggaacacca gtggcgaaag cggctttctg gacgacaact gacgctgagg cgcgaaagcc
 781 aggggagcaa acgggattag ataccccggt agtcctggcc gtaaacgatg gatactaggt
 841 gtaggaggta tcgactcctt ctgtgccgga gttaacgcaa taagtatccc gcctggggag
 901 tacggccgca aggctgaaac tcaaaggaat tgacggggc ccgcacaagc ggtggagtat
 961 gtggtttaat tcgacgcaac gcgaagaacc ttaccaagcc ttgacattga ttgctacgga
1021 aagagatttc cggttcttct tcggaagaca agaaaacagg tggtgcacgg ctgtcgtcag
1081 ctcgtgtcgt gagatgttgg gttaagtccc gcaacgagcg caacccctat cttctgttgc
1141 cagcacctcg ggtggggact cagaagagac tgccgcagac aatgcggagg aaggcgggga
1201 tgacgtcaag tcatcatgcc ccttatggct gggctacac acgtactaca atggctctta
1261 atagagggac gcgaaggagc gatccggagc aaacccaaaa acagagtcc cagttcggat
1321 tgcaggctgc aactcgcctg catgaagcag gaatcgctag taatcgcagg tcagcatact
1381 gcggtgaata cgttcccggg ccttgtacac accgcccgtc acaccacgaa agtcattcac
1441 acccgaagcc ggtgaggcaa ccgcaaggaa ccagccgtcg aaggtggggg cgatgattgg
1501 ggtgaagtcg taacaaggt
```

(consensus 16S rRNA sequence for *Megasphaera massiliensis* strain MRX0029)

SEQ ID NO: 2

TGAGAAGCTTGCTTCTTATCGATTCTAGTGGCAAACGGGTGAGTAACGCGTAAGCAACCTGCCCTTCAGATGGGGAC
AACAGCTGGAAACGGCTGCTAATACCGAATACGTTCTTTCCGCCGCATGACGGGAAGAAGAAAGGGAGGCCTTCGGG
CTTTCGCTGGAGGAGGGGCTTGCGTCTGATTAGCTAGTTGGAGGGGTAACGGCCCACCAAGGCGACGATCAGTAGCC
GGTCTGAGAGGATGAACGGCCACATTGGGACTGAGACACGGCCCAGACTCCTACGGGAGGCAGCAGTGGGGAATCTT
CCGCAATGGACGAAAGTCTGACGGAGCAACGCCGCGTGAACGATGACGGCCTTCGGGTTGTAAAGTTCTGTTATATG
GGACGAACAGGACATCGGTTAATACCCGGTGTCTTTGACGGTACCGTAAGAGAAAGCCACGGCTAACTACGTGCCAG
CAGCCGCGGTAATACGTAGGTGGCAAGCGTTGTCCGGAATTATTGGGCGTAAAGGGCGCGCAGGCGGCATCGCAAGT
CGGTCTTAAAAGTGCGGGGCTTAACCCCGTGAGGGGACCGAAACTGTGAAGCTCGAGTGTCGGAGAGGAAAGCGGAA
TTCCTAGTGTAGCGGTGAAATGCGTAGATATTAGGAGGAACACCAGTGGCGAAAGCGGCTTTCTGGACGACAACTGA
CGCTGAGGCGCGAAAGCCAGGGGAGCAAACGGGATTAGATACCCCGGTAGTCCTGGCCGTAAACGATGGATACTAGG
TGTAGGAGGTATCGACTCCTTCTGTGCCGGAGTTAACGCAATAAGTATCCCGCCTGGGGAGTACGGCCGCAAGGCTG
AAACTCAAAGGAATTGACGGGGCCCGCACAAGCGGTGGAGTATGTGGTTTAATTCGACGCAACGCGAAGAACCTTA
CCAAGCCTTGACATTGATTGCTACGGAAAGAGATTTCCGGTTCTTCTTCGGAAGACAAGAAAACAGGTGGTGCACGG
CTGTCGTCAGCTCGTGTCGTGAGATGTTGGGTTAAGTCCCGCAACGAGCGCAACCCCTATCTTCTGTTGCCAGCACC
TCGGGTGGGGACTCAGAAGAGACTGCCGCAGACAATGCGGAGGAAGGCGGGGATGACGTCAAGTCATCATGCCCCTT
ATGGCTTGGGCTACACACGTACTACAATGGCTCTTAATAGAGGGAAGCGAAGGAGCGATCCGGAGCAAACCCCAAAA
ACAGAGTCCCAGTTCGGATTGCAGGCTGCAACTCGCCTGCATGAAGCAGGAATCGCTAGTAATCGCAGGTCAGCATA
CTGCGGTGAATACGTTCCCGGGCCTTGTACACACCGCCCGTCACACCACGAAAGTCATTCACACCCGAAGCCGGTGA
GGCAACCGCAAG

Primers used for qPCR (with SEQ ID NO in brackets)

| Name | Forward sequence | Reverse sequence |
|---|---|---|
| ACTB | GATCAAGATCATTGCTCCTC (3) | TTGTCAAGAAAGGGTGTAAC (4) |
| GAPDH | GGTATCGTGGAAGGACTCATG (5) | ATGCCAGTGAGCTTCCCGTT C (6) |
| MAP2 | CTCAGCACCGCTAACAGAGG (7) | CATTGGCGCTTCTCTCCTC (8) |
| Occludin | AAGAGGAATTTTGACACTGG (9) | GCCATGTACTCTTCACTTTC (10) |
| TJ1 | AAGTCACACTGGTGAAATCC (11) | CTCTTGCTGCCAAACTATCT (12) |
| TJP2 | CCCTCCCCTGGATCAGGAT (13) | GCCATCAAACTCGTCCATCA (14) |
| Villin | CATTACCTGCTCTACGTTTG (15) | AGATGGACATAAGATGAGGT G (16) |

(consensus 16S rRNA sequence for *Parabacteroides distasonis* strain MRX0005)

SEQ ID NO: 17
AMCCGGGTGGCGACCGGCGCACGGGTGAGTAACGCGTATGCAACTTGCCTA
TCAGAGGGGGATAACCCGGCGAAAGTCGGACTAATACCGCATGAAGCAGGG
ATCCCGCATGGGAATATTTGCTAAAGATTCATCGCTGATAGATAGGCATGC
GTTCCATTAGGCAGTTGGCGGGGTAACGGCCCACCAAACCGACGATGGATA
AGATATCACGCAGAACCCCGATTGCGAAGGCAGCCTGCCAAGCCATTACTG
ACGCTGATGCACGAAAGCGTGGGGATCAAACAGGATTAGATACCCTGGTAG
TCCACGCAGTAAACGATGATCACTAGCTGTTTGCGATACACTGTAAGCGGC
ACAGCGAAAGCGTTAAGTGATCCACCTGGGGAGTACGCCGGCAACGGTGAA
ACTCAAAGGAATTGACGGGGCCCGCACAAGCGGAGGAACATGTGGTTTAA
TTCGATGATACGCGAGGAACCTTACCCGGGTTTGAACGCATTCGGACMGAK
GTGGAAACACATTTTCTAGCAATAGCCATTTGCGAGGTGCTGCATGGTTGT
CGTCAGCTCGTGCCGTGAGGTGTCGGCTTAAGTGCCATAACGAGCGCAACC
CTTGCCACTAGTTACTAACAGGTAAAGCTGAGGACTCTGGTGGGACTGCCA
GCGTAAGCTGCGAGGAAGGCGGGGATGACGTCAAATCAGCACGGCCCTTAC
ATCCGGGGCGACACACGTGTTACAATGGCGTGGACAAAGGGAAGCCACCTG
GCGACAGGGAGCGAATCCCCAAACCACGTCTCAGTTCGGATCGGAGTCTGC
AACCCGACTCCGTGAAGCTGGATTCGCTAGTAATCGCGCATCAGCCATGGC
GCGGTGAATACGTTCCCGGGCCTTGTACACACCGCCCGTCAAGCCATGGGA
GCCGGGGGTACCTGAAGTCCGTAACCGCGAGGATCGGCCTAGGGTAAAACT
GGTGACTGGGGCTAAGTCGTACGGGG

Primers and probes used for ex vivo qPCR (with SEQ ID NO in brackets)

Ex vivo:

| Name | Forward sequence | Reverse sequence | Probe |
|---|---|---|---|
| ACTB | GAT TAC TGC TCT GGC TCC TAG(18) | GAC TCA TCG TAC TCC TGC TTG(19) | /56-FAM/CTG GCC TCA/ ZEN/CTG TCC ACC TTC C/3IABkFQ/(20) |
| GAPDH | AAT GGT GAA GGT CGG TGT G(21) | GTG GAG TCA TAC TGG AAC ATG TAG(22) | /56-FAM/TGC AAA TGG/ ZEN/CAG CCC TGG TG/ 3IABkFQ/(23) |
| BDNF | GCT GCC TTG ATG TTT ACT TTG AC(24) | GCA ACC GAA GTA TGA AAT AAC CA(25) | /56-FAM/ACC AGG TGA/ ZEN/GAA GAG TGA TGA CCA TCC/3IABkFQ/(26) |
| IL6 | AGC CAG AGT CCT TCA GAG A(27) | TCC TTA GCC ACT CCT TCT GT(28) | /56-FAM/CCT ACC CCA/ ZEN/ATT TCC ATT GCT CTC CT/3IABkFQ/(29) |

-continued
GGGGTTCTGAGAGGAAGGTCCCCCACATTGGTACTGAGACACGGACCAAAC
TCCTACGGGAGGCAGCAGTGAGGAATATTGGTCAATGGGCGTGAGCCTGAA
CCAGCCAAGTCGCGTGAGGGATGAAGGTTCTATGGATCGTAAACCTCTTTT
ATAAGGGAATAAAGTGCGGGACGTGTCCCGTTTTGTATGTACCTTATGAAT
AAGGATCGGCTAACTCCGTGCCAGCAGCCGCGGTAATACGGAGGATCCGAG
CGTTATCCGGATTTATTGGGTTTAAAGGGTGCGTAGGCGGCCTTTTAAGTC
AGCGGTGAAAGTCTGTGGCTCAACCATAGAATTGCCGTTGAAACTGGGAGG
CTTGAGTATGTTTGAGGCAGGCGGAATGCGTGGTGTAGCGGTGAAATGCAT Additional primers used in qPCR (with SEQ ID NO in brackets)

| Gene ID | Forward sequence | Reverse sequence |
|---|---|---|
| NSE | CCCTGTATCGTAAGAACGGT (30) | GCCACCATTGATCACGTTGA (31) |
| PINK1 | CCCAAGCAACTAGCCCCTC (32) | GGCAGCACATCAGGGTAGTC (33) |

-continued

| Gene ID | Forward sequence | Reverse sequence |
|---|---|---|
| PARK7 | GTAGCCGTGATGTGGTCATTT (34) | CTGTGCGCCCAGATTACCT (35) |
| SYP | CTCGGCTTTGTGAAGGTGCT (36) | GGCTTCATGGCATCAACTTCA (37) |

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12):1021-35
[4] Macpherson et al. (2002) *Cell Mol Life Sci.* 59(12):2088-96.
[5] Mazmanian et al. (2005) *Cell* 15; 122(1):107-18.
[6] Frank et al. (2007) *PNAS* 104(34):13780-5.
[7] Scanlan et al. (2006) *J Clin Microbiol.* 44(11):3980-8.
[8] Kang et al. (2010) *Inflamm Bowel Dis.* 16(12):2034-42.
[9] Machiels et al. (2013) Gut. 63(8):1275-83.
[10] WO 2013/050792
[11] WO 03/046580
[12] WO 2013/008039
[13] WO 2014/167338
[14] Goldin and Gorbach (2008) *Clin Infect Dis.* 46 Suppl 2:S96-100.
[15] Azad et al. (2013) *BMJ.* 347:f6471.
[16] Mayer et al (2014) *The Journal of Neuroscience* 34(46): 15490-15496
[17] Cryan and Dinan (2015) *Neuropsychopharmacology,* 40: 241-2.
[18] Zhou and Foster (2015) *Neuropsychiatric Disease and Treatment* 11: 715-723.
[19] Wang and Kasper (2014) *Brain Behav Immun.* 38: 1-12.
[20] US2004/005304
[21] US2004/170617
[22] Kadi et al (2006) *J Neuroimmunol* 174: 133-46
[23] Padmanabhan et al. (2013) Standards in Genomic Sciences 8:525-538
[24] Masco et al. (2003) Systematic and Applied Microbiology, 26:557-563
[25] Jeon, (2017) Int J Syst Evol Microbiol, 67, 2114-2120
[26] Jeon (2016) Biotechnol Biofuels, 9, 129
[27] Nelson (2017) Fermentation, 3, 10
[28] Roddick and Britz (1999) Chem Technol and Biotech, 69 (3), 383
[29] Choi (2013) Apply Biochem Biotechnol, 171 (5), 1094-1107
[30] Kenealy and Weimer 1995) Appl Microbial Cell Physiol, 44, 507-513
[31] Jeon (2010) Appl Microbiol Biotechnol, 88 (5) 1161-1167
[32] Zhu (2017) Biotechnol Biofuels, 10, 102
[33] Corsetti (1998) Appl Microbiol Biotechnol, 50(2), 253-6)
[34] Yuliana and Garcia (2009), Indian J Biotechnol 8 304-310)
[35] Xue (2014) J Chem Pharm Res, 6(7), 2021-2025
[36] Wallace (2004) Microbiology 150, 2921-2930
[37] Hong (2016) Appl Environ Microbiol, 82(13) 3940-3946
[38] Xiong (2016) BioMed Res Int, Article ID 9485412
[39] Shaw (2010) Nutr Neurosci 13(3)
[40] Guerrant (1982) J Clin Microbiol, 16(2) 355-360
[41] Elsden (1976) Arch Microbiol 107(3), 283-288
[42] Moss and Nunez-Montiel (1982) J Clin Microbiol, 15(2) 308-311
[43] Riedel (2017) *Int J Med Microbiol,* 307(6), 311-320
[44] Shaw (2015) *Great Plains Laboratory*
[45] Elsden (1979) Arch Microbiol, 123(2), 137-41
[46] G. E. Lewis Eds (1981), Biomedical Aspects of Botulism, p 211
[47] Shortt (2017) Eur J Nutr, DOI 10.1007/s00394-017-1546-4
[48] Moss (1980) J Clin Microbiol, 11(6), 743-745
[49] Elsden (1979), Arch Microbiol, 123(2), 137-41
[50] Russell (2013) Mol Nutr Food Res, 57(3), 523-535
[51] Guerrant (1982) J Clin Microbiol, 16(2) 355-360
[52] Takahama (2013) Adv Mol Toxicology, 7, 129-177, Section 4.3.3
[53] van den Tweel (1988) Arch Microbiol, 149(3) 207-213
[54] Neilson and Allard (2013) Organic Chemicals in The Environment, Mechanisms of Degradation and Transformation 2nd Ed, p 851
[55] Utkin (1994) Int J Sys Bacteriol 44(4) 612-9
[56] Neilson and Allard, Organic Chemicals in The Environment, Mechanisms of Degradation and Transformation 2nd Ed 2013, p 655
[57] Park et al. (2017) Scientific Reports. DOI 10.1038/s41598-017-15163-57
[58] Sun (2017) *Neurogastroenterology and Motility.* DOI: 10.1111/nmo.13260OI
[59] Tankou et al (2018) *MS Journal* 24(1), 58-63
[60] Bonfili et al. (2018) *Mol Neurobiol* DOI 10.1007/s12035-018-0973-4
[61] Srůtková et al. (2011) *J. Microbiol. Methods,* 87(1):10-6.
[62] Harrison et al. (2015) *British Journal of Pharmacology,* 172:4200-4215
[63] Manczak et al. (2004)
[64] Ebadi et al (2001) *Biol Signals Recept.* 10(3-4):224-253
[65] Ferro et al (2017) *Plos One.* 12(12):e0188425
[66] Pal R et al (2016) *Neurol Res.* 38(12):1111-1122
[67] Daniele et al (2015) *Sci Signal* 8(376):ra45
[68] Ahmed et al, manuscript in preparation
[69] Baraczka et al. (1983) *J Neural Transm.* 58(3-4):299-304
[70] Eldrup et al. (1995) *Acta Neurol Scand.* 92(2):116-21.
[71] Wang et al. (2016) *J Neurogastroenterol Motil* 22: 589-605.
[72] Zadori et al (2012) *Journal of Neural Transmission,* 119, 2, 275-283
[73] Lee et al (2008) *European J. Cell Biology* 87:389-397
[74] Pirooznia and Elefant (2013) *Front Cell Neurosci.* 7: 30.
[75] Tang, et al. (2017) *J Am Heart Assoc,* 6(10).
[76] Wang et al. (2015) PNAS 112(9):2583-2858
[77] Psaty et al. (2003) JAMA, 289(19):2534-44
[78] Lancet. (1995) 346(8991-8992):1647-53
[79] Miyamoto-Shinohara et al. (2008) *J. Gen. Appl. Microbiol.,* 54, 9-24.
[80] Cryopreservation and Freeze-Drying Protocols, ed. by Day and McLellan, Humana Press.
[81] Leslie et al. (1995) *Appl. Environ. Microbiol.* 61, 3592-3597.
[82] Mitropoulou et al. (2013) *J Nutr Metab.* (2013) 716861.
[83] Kailasapathy et al. (2002) *Curr Issues Intest Microbiol.* 3(2):39-48.
[84] Handbook of Pharmaceutical Excipients, 2nd Edition, (1994), Edited by A Wade and P J Weller

[85] Remington's Pharmaceutical Sciences, Mack Publishing Co. (A. R. Gennaro edit. 1985)
[86] US 2016/0067188
[87] *Handbook of Microbiological Media, Fourth Edition* (2010) Ronald Atlas, CRC Press.
[88] *Maintaining Cultures for Biotechnology and Industry* (1996) Jennie C. Hunter-Cevera, Academic Press
[89] Strobel (2009) *Methods Mol Biol.* 581:247-61.
[90] Gennaro (2000) *Remington: The Science and Practice of Pharmacy.* 20th edition, ISBN: 0683306472.
[91] *Molecular Biology Techniques: An Intensive Laboratory Course*, (Ream et al., eds., 1998, Academic Press).
[92] *Methods In Enzymology* (S. Colowick and N. Kaplan, eds., Academic Press, Inc.)
[93] *Handbook of Experimental Immunology*, Vols. I-IV (D. M. Weir and C. C. Blackwell, eds, 1986, Blackwell Scientific Publications)
[94] Sambrook et al. (2001) *Molecular Cloning: A Laboratory Manual*, 3rd edition (Cold Spring Harbor Laboratory Press).
[95] *Handbook of Surface and Colloidal Chemistry* (Birdi, K. S. ed., CRC Press, 1997)
[96] Ausubel et al. (eds) (2002) *Short protocols in molecular biology*, 5th edition (Current Protocols).
[97] PCR (*Introduction to Biotechniques Series*), 2nd ed. (Newton & Graham eds., 1997, Springer Verlag)
[98] *Current Protocols in Molecular Biology* (F. M. Ausubel et al., eds., 1987) Supplement 30
[99] Smith & Waterman (1981) *Adv. Appl. Math.* 2: 482-489.
[100] Abel and Zukin (2008) *Curr Opin Pharmacol*, 2008. 8(1): 57-64
[101] Johnsen et al (2017) *Journal of Chromatography A.* 1503: 57-64
[102] West and Johnstone (2014) *J Clin Invest.* 124, 30-39
[103] Glauben et al. (2006) *J Immunol*, 176: 5015-5022
[104] Angiolilli et al. (2017) *Ann Rheum Dis*, 76: 277-285
[105] Gonneaud et al. (2014) *J Inflamm*, 11: 43
[106] Alenghat et al. (2013) *Nature*, 504: 153-157
[107] Felice et al. (2015) *Ailment Pharmacol Ther*, 41: 26-38
[108] Pakkenberg et al. (1991) *J Neurol Neurosurg Psychiatry*, 54(1):30-3.
[109] Przedborski et al. (2000). *Restor Neurol Neurosci.* 16(2):135-142.
[110] Kehr J. (1999) Monitoring chemistry of brain microenvironment: biosensors, microdialysis and related techniques. Chapter 41. In: Modern techniques in neuroscience research. (Eds. U. Windhorst and H. Johansson) Springer-Verlag GmbH., Heidelberg, Germany. 1149-1198.
[111] Kehr J., and Yoshitake T. (2006) Monitoring brain chemical signals by microdialysis. In: Encyclopedia of Sensors, Vol. 6. (Eds. C. A. Grimes, E. C. Dickey and M. V. Pishko) American Scientific Publishers, USA. 287-312.
[112] Smart et al (2010) *Nature Protocols.* 10:1709-29
[113] Weon et al. (2016)
[114] Huot et al. (2015) *Parkinson's Disease*
[115] Scatton et al. (1983) *Brain Res*, 275(2): 321-8
[116] Helv M A, Morris J G, Reid W G, Trafficante R, Mov Disord. 2005 February; 20(2):190-9
[117] Budd and Nicholls (1998) *Essays Biochem.* 33:43-52
[118] Michel and Prat (2016) *Ann Transl Med.* 4(1): 15.
[119] Gagnon et al (2013) *J Microbiological Methods.* 94: 274-279

---

The invention claimed is:

1. A method of inhibiting histone deacetylase activity in a subject in need thereof comprising: administering to said subject a pharmaceutical composition comprising a bacteria strain that produces a therapeutically effective amount of at least one organic acid of formula Rx-COOH, and a pharmaceutically acceptable excipient, carrier, or diluent, wherein Rx is $C_4$-$C_{11}$ alkyl;

wherein said therapeutically effective amount is effective to inhibit said histone deacetylase activity;

wherein said bacteria strain does not comprise a bacterial strain of the genus *Megasphaera*; and wherein said bacteria strain does not comprise a bacterial strain of the species *Pediococcus acidilactici*, wherein said bacteria strain is lyophilized.

2. The method of claim 1, wherein said organic acid is hexanoic acid, valeric acid, or a combination thereof.

3. The method of claim 1, wherein said bacteria strain further produces a short chain fatty acid.

4. The method of claim 3, wherein said short chain fatty acid is butyric acid.

5. The method of claim 1, wherein said pharmaceutical composition comprises from about $1\times10^3$ to about $1\times10^{11}$ colony forming units (CFU)/g of said bacteria strain with respect to total weight of said pharmaceutical composition.

6. The method of claim 1, wherein said histone deacetylase is a Class I histone deacetylase.

7. The method of claim 1, wherein said pharmaceutical composition is formulated for delivery to an intestine of said subject.

8. The method of claim 1, wherein said administering is oral, rectal, nasal, buccal, sublingual, or subcutaneous.

9. The method of claim 1, wherein said subject is human.

10. The method of claim 1, wherein said bacteria strain is capable of partially or totally colonizing the intestine of said subject.

11. The method of claim 6, wherein said Class I histone deacetylase comprises histone deacetylase 1, histone deacetylase 2, or histone deacetylase 3.

12. The method of claim 1, wherein said pharmaceutical composition comprises no more than de minimis or a biologically irrelevant amount of a bacteria strain that does not produce said at least one organic acid.

13. The method of claim 1, wherein said pharmaceutically acceptable excipient, carrier, or diluent comprises a suitable binder, a lubricant, a suspending agent, a coating agent, a solubilizing agent, or an oxygen scavenger.

14. The method of claim 13, wherein said pharmaceutically acceptable excipient, carrier, or diluent comprises methyl cellulose, magnesium stearate, mannitol, sorbitol, tragacanth or sodium alginate, carboxymethyl cellulose, polyethylene glycol, sodium oleate, sodium stearate, sodium benzoate, sodium acetate, sodium chloride, sorbic acid, or esters of p-hydroxybenzoic acid.

15. The method of claim 1, wherein said subject has been diagnosed with a neurodegenerative disease.

16. The method of claim 15, wherein said neurodegenerative disease comprises Parkinson's disease, Alzheimer's disease, multiple sclerosis, Huntington's disease, amyotrophic lateral sclerosis, Lou Gehrig's disease, motor neuron disease, prion disease, spinocerebellar ataxia, spinal muscular atrophy, dementia, primary progressive aphasia, mild cognitive impairment, human immunodeficiency virus (HIV)-related cognitive impairment, progressive inflammatory neuropathy, or corticobasal degeneration.

17. The method of claim 16, wherein said Parkinson's disease comprises progressive supranuclear palsy, progressive supranuclear palsy, Steele-Richardson-Olszewski syndrome, normal pressure hydrocephalus, vascular or arteriosclerotic parkinsonism, or drug-induced parkinsonism.

18. The method of claim 16, wherein said Alzheimer's disease comprises Benson's syndrome.

19. The method of claim 16, wherein said dementia comprises Lewy body, vascular dementia, or frontotemporal dementia.

\* \* \* \* \*